US012509515B2

(12) United States Patent
Cheung et al.

(10) Patent No.: US 12,509,515 B2
(45) Date of Patent: Dec. 30, 2025

(54) CD22 ANTIBODIES AND METHODS OF USING THE SAME

(71) Applicant: MEMORIAL SLOAN KETTERING CANCER CENTER, New York, NY (US)

(72) Inventors: Nai-Kong V. Cheung, New York, NY (US); Sayed Shahabuddin Hoseini, New York, NY (US); Mahiuddin Ahmed, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 1030 days.

(21) Appl. No.: 17/437,627

(22) PCT Filed: Mar. 10, 2020

(86) PCT No.: PCT/US2020/021866

§ 371 (c)(1),
(2) Date: Sep. 9, 2021

(87) PCT Pub. No.: WO2020/185763

PCT Pub. Date: Sep. 17, 2020

(65) Prior Publication Data

US 2022/0177581 A1 Jun. 9, 2022

Related U.S. Application Data

(60) Provisional application No. 62/816,469, filed on Mar. 11, 2019.

(51) Int. Cl.

| | |
|---|---|
| ***C07K 16/28*** | (2006.01) |
| ***A61P 35/00*** | (2006.01) |
| ***A61P 37/06*** | (2006.01) |

(52) U.S. Cl.

CPC .......... *C07K 16/2809* (2013.01); *A61P 35/00* (2018.01); *A61P 37/06* (2018.01); *C07K 2317/24* (2013.01); *C07K 2317/31* (2013.01); *C07K 2317/622* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 5,789,554 | A * | 8/1998 | Leung | C07K 16/3061 435/328 |
| 9,757,458 | B2 | 9/2017 | Chang et al. | |
| 11,565,005 | B2 | 1/2023 | Cheal et al. | |
| 2010/0143368 | A1 | 6/2010 | King et al. | |
| 2017/0198052 | A1 | 7/2017 | Lin et al. | |

FOREIGN PATENT DOCUMENTS

| | | | |
|---|---|---|---|
| AU | 2018297272 | | 1/2020 |
| EA | 1609803 | | 12/2005 |
| WO | WO-03/104425 | A2 | 12/2003 |
| WO | WO-2004/087763 | A1 | 10/2004 |
| WO | WO-2016/168766 | A1 | 10/2016 |
| WO | WO-2018/064307 | A2 | 4/2018 |
| WO | WO-2018/200562 | A1 | 11/2018 |
| WO | WO-2018/204873 | A1 | 11/2018 |
| WO | WO-2018/232188 | A1 | 12/2018 |

OTHER PUBLICATIONS

International Search Report and Written Opinion on PCT/US2020/021866 dated Aug. 4, 2020 (20 pages).

Request for Submission of an Opinion on KR Appl. No. 10-2021-7032139 dated Aug. 22, 2025 (13 pages).

* cited by examiner

*Primary Examiner* — Daniel E Kolker

*Assistant Examiner* — James Ryland Melchior

(74) *Attorney, Agent, or Firm* — Foley & Lardner LLP

(57) ABSTRACT

The present disclosure relates generally to immunoglobulin-related compositions (e.g., antibodies or antigen binding fragments thereof) that can bind to the CD22 protein. The antibodies of the present technology are useful in methods for detecting and treating a CD22-associated cancer, a CD22-associated autoimmune disease, or a CD22-associated allergy in a subject in need thereof.

19 Claims, 71 Drawing Sheets

Specification includes a Sequence Listing.

FIG. 6

Humanization of Mouse LL2 $V_H$ Domains

*LL2_$V_H$ (murine, humanness 68.4%) (SEQ ID NO: 1)*
QVQLQESGAELSKPGASVKMSCKASGYTFTSYWLHWIKQRPGQGLEWIGYINPRNDYTEYNQ
NFKDKATLTADKSSSTAYMQLSSLTSEDSAVYYCARRDITTFYWGQGTTLTVSS

*VH-1 (humanness 85.7%)(SEQ ID NO: 5)*
QVQLVESGAEVKKPGASVKMSCKASGYTFTSYWLHWIRQAPGQRLEWIGYINPRNDYTKYSQ
KFQGRATITADKSASTAYMELSSLRSEDTAVYYCARRDITTFYWGQGTTLTVSS

*VH-2 (humanness 85.7%)(SEQ ID NO: 6)*
QVQLQESGAEVKKPGASVKMSCKASGYTFTSYWLHWIRQAPGQRLEWIGYINPRNDYTKYSQ
KFQGRVTLTRDKSASTAYMELSSLRSEDTAVYYCARRDITTFYWGQGTTLTVSS

*VH-3 (humanness 85.7%) (SEQ ID NO: 7)*
QVQLQQSGAEVKKPGASVKVSCKASGYTFTSYWLHWIRQAPGQRLEWIGYINPRNDYTEYSQ
KFQGRATLTADTSASTAYMELSSLRSEDTAVYYCARRDITTFYWGQGTTLTVSS

*VH-4 (humanness 84.7%) (SEQ ID NO: 8)*
QVQLQQSGAEVKKPGASVKMSCKASGYTFTSYWLHWIRQAPGQRLEWMGYINPRNDYTEYNQ
KFQGRATITADKSASTAYMELSSLRSEDTAVYYCARRDITTFYWGQGTTLTVSS

*VH-5 (humanness 85.7%) (SEQ ID NO: 9)*
QVQLQESGAEVKKPGASVKVSCKASGYTFTSYWLHWVRQAPGQRLEWIGYINPRNDYTEYSQ
KFQGRATLTADTSASTAYMELSSLRSEDTAVYYCARRDITTFYWGQGTTLTVSS

*VH-6 (humanness 85.7%) (SEQ ID NO: 10)*
QVQLQQSGAEVKKPGASVKVSCKASGYTFTSYWLHWIRQAPGQRLEWMGYINPRNDYTEYNQ
NFKDRVTITRDTSASTAYMELSSLRSEDTAVYYCARRDITTFYWGQGTTLTVSS

*VH-7 (humanness 85.7%)(SEQ ID NO: 11)*
QVQLVESGAEVKKPGASVKVSCKASGYTFTSYWLHWVRQAPGQRLEWMGYINPRNDYTEYNQ
NFKDRATITRDTSASTAYMELSSLRSEDTAVYYCARRDITTFYWGQGTTLTVSS

*VH-8 (humanness 85.7%) (SEQ ID NO: 12)*
QVQLVESGAEVKKPGASVKVSCKASGYTFTSYWLHWIRQAPGQRLEWMGYINPRNDYTEYNQ
NFKDRVTITRDTSASTAYMELSSLRSEDTAVYYCARRDITTFYWGQGTTLTVSS

*VH-9 (humanness 85.7%) (SEQ ID NO: 13)*
QVQLVQSGAEVKKPGASVKVSCKASGYTFTSYWLHWVRQAPGQRLEWIGYINPRNDYTEYNQ
NFKDRVTITADTSASTAYMELSSLRSEDTAVYYCARRDITTFYWGQGTTLTVSS

FIG. 6 (contd.)

*VH-10 (humanness 84.7%) (SEQ ID NO: 14)*
QVQLVQSGAEVKKPGASVKVSCKASGYTFTSYWLHWVRQAPGQRLEWMGYINPRNDYTEYNQ
NFKDRVTLTADKSASTAYMELSSLRSEDTAVYYCARRDITTFYWGQGTTLTVSS

*VH-11 (humanness 84.7%) (SEQ ID NO: 15)*
QVQLVQSGAEVKKPGASVKMSCKASGYTFTSYWLHWVRQAPGQRLEWMGYINPRNDYTEYNQ
NFKDRATITADTSASTAYMELSSLRSEDTAVYYCARRDITTFYWGQGTTLTVSS

*VH-12 (humanness 84.7%) (SEQ ID NO: 16)*
QVQLQQSGAEVKKPGASVKMSCKASGYTFTSYWLHWVRQAPGQRLEWMGYINPRNDYTEYNQ
NFKDRVTITADTSASTAYMELSSLRSEDTAVYYCARRDITTFYWGQGTTLTVSS

FIG. 7

Humanization of Mouse LL2 $V_L$ Domains

*LL2_$V_L$ (murine, humanness 80%)(SEQ ID NO: 17)*
DIQLTQSPSSLAVSAGENVTMSCKSSQSVLYSANHKNYLAWYQQKPGQSPKLLIYWASTRES
GVPDRFTGSGSGTDFTLTISRVQVEDLAIYYCHQYLSSWTFGGGTKLEIK

*VL-1 (humanness 89%) (SEQ ID NO: 21)*
DIVLTQSPDSLAVSAGERVTMNCKSSQSVLYSANHKNYLAWYQQKPGQPPKLLIYWASTRES
GVPDRFSGSGSGTDFTLTISSVQAEDVAIYYCHQYLSSWTFGGGTKLEIK

*VL-2 (humanness 89%) (SEQ ID NO: 22)*
DIVLTQSPDSLAVSLGERVTMNCKSSQSVLYSANHKNYLAWYQQKPGQSPKLLIYWASTRES
GVPDRFSGSGSGTDFTLTISSVQAEDVAIYYCHQYLSSWTFGGGTKLEIK

FIG. 8

Chimeric BsAb (chLL2) – Light chain full amino acid sequence (N to C terminal) [signal peptide-LL2 murine $V_L$-$C_L$-linker-hOKT3 $V_H$-linker-hOKT3 $V_L$] *(SEQ ID NO: 23)*

<u>MGWSCIILFLVATATGVHS</u>*DIQLTQSPSSLAVSAGENVTMSCKSSQSVLYSANHKNYLAW YQQKPGQSPKLLIYWASTRESGVPDRFTGSGSGTDFTLTISRVQVEDLAIYYCHQYLSSWTF GGGTKLEIK*RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKSFNRG ECTS<u>GGGGSGGGGSGGGGS</u>*QVQLVQSGGGVVQPGRSLRLSCKASGYTFTRYTMHWVR QAPGKCLEWIGYINPSRGYTNYNQKFKDRFTISRDNSKNTAFLQMDSLRPEDTGVYFCAR YYDDHYSLDYWGQGTPVTVSS*<u>GGGGSGGGGSGGGGSGGGGSGGGGSGGGGS</u>*DIQ MTQSPSSLSASVGDRVTITCSASSSVSYMNWYQQTPGKAPKRWIYDTSKLASGVPSRFSGSG SGTDYTFTISSLQPEDIATYYCQQWSSNPFTFGCGTKLQITR*

FIG. 9

*Chimeric BsAb (chLL2) – Light chain full nucleotide sequence. (SEQ ID NO: 24)*

ATGGGCTGGTCCTGCATCATCCTGTTCCTGGTGGCCACCGCCACCGGCGTC
CACTCCGACATCCAGCTGACTCAGAGCCCCTCATCACTGGCCGTCTCCGCAGGCG
AAAACGTGACTATGTCTTGTAAATCTTCTCAGTCTGTGCTGTACAGCGCCAACCA
CAAGAATTACCTGGCCTGGTATCAGCAGAAGCCCGGCCAGAGCCCTAAGCTGCT
GATCTATTGGGCCTCCACCAGGGAGTCTGGAGTGCCCGACAGATTCACCGGCAG
CGGCTCCGGAACAGACTTCACCCTGACAATCTCCCGGGTGCAGGTGGAGGACCT
GGCCATCTACTATTGCCATCAGTATCTGTCATCATGGACATTCGGCGGCGGAACA
AAGCTGGAAATCAAG
CGGACCGTGGCCGCCCCCTCCGTGTTCATCTTCCCCCCCTCCGACGAGCAGCTGA
AGTCCGGCACCGCCTCCGTGGTGTGCCTGCTGAACAACTTCTACCCCCGGGAGGC
CAAGGTGCAGTGGAAGGTGGACAACGCCCTGCAGTCCGGCAACTCCCAGGAGTC
CGTGACCGAGCAGGACTCCAAGGACTCCACCTACTCCCTGTCCTCCACCCTGACC
CTGTCCAAGGCCGACTACGAGAAGCACAAGGTGTACGCCTGCGAGGTGACCCAC
CAGGGCCTGTCCTCCCCCGTGACCAAGTCCTTCAACCGGGGCGAGTGCACTAGTG
GCGGCGGAGGATCTGGCGGAGGTGGAAGTGGGGGAGGCGGATCTCAGGTGCAG
CTGGTGCAGAGTGGTGGCGGAGTGGTGCAGCCTGGCAGATCCCTGAGACTGTCT
TGCAAGGCCAGCGGCTACACCTTCACCCGGTACACCATGCACTGGGTGCGACAG
GCCCCTGGCAAGTGCCTGGAATGGATCGGCTACATCAACCCCTCCCGGGGCTAC
ACCAACTACAACCAGAAGTTCAAGGACCGGTTCACCATCAGCCGGGACAACTCC
AAGAACACCGCCTTTCTGCAGATGGACTCCCTGCGGCCTGAGGATACCGGCGTGT
ACTTTTGCGCCCGGTACTACGACG
ACCACTACAGCCTGGACTACTGGGGCCAGGGAACCCCTGTGACAGTGTCTAGCG
GAGGGGGAGGTTCAGGTGGCGGTGGATCAGGGGGCGGAGGAAGTGGCGGGGGA
GGTAGTGGTGGTGGTGGAAGCGGAGGTGGCGGCTCCGATATCCAGATGACCCAG
TCCCCCTCCAGCCTGTCTGCCTCTGTGGGAGACAGAGTGACAATTACATGCTCCG
CCAGCTCCAGCGTGTCCTACATGAATTGGTATCAGCAGACCCCTGGCAAGGCTCC
CAAGCGGTGGATCTACGACACCTCCAAGCTGGCCTCCGGCGTGCCCTCCAGATTT
TCTGGCAGCGGCTCCGGCACAGACTATACCTTTACAATCAGCTCCCTGCAGCCCG
AAGATATCGCCACCTACTACTGCCAGCAGTGGTCCTCCAACCCCTTCACCTTCGG
CTGCGGCACAAAGCTGCAGATCACCAGATAG

FIG. 10

*Chimeric BsAb (chLL2) – Heavy chain full amino acid sequence (N to C terminal) [signal peptide-LL2 murine $V_H$-$C_H$1-3] (SEQ ID NO: 25)*

<u>MGWSCIILFLVATATGVHS</u>*QVQLQESGAELSKPGASVKMSCKASGYTFTSYWLHWIKQR
PGQGLEWIGYINPRNDYTEYNQNFKDKATLTADKSSSTAYMQLSSLTSEDSAVYYCARRDIT
TFYWGQGTTLTVSS*ASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKRVEPKS
CDKTHTCPPCPAPELLGGPSVFLFPPKPKDTLMISRTPEVTCVVVDVSHEDPEVKFNW
YVDGVEVHNAKTKPREEQYASTYRVVSVLTVLHQDWLNGKEYKCAVSNKALPAPI
EKTISKAKGQPREPQVYTLPPSRDELTKNQVSLTCLVKGFYPSDIAVEWESNGQPEN
NYKTTPPVLDSDGSFFLYSKLTVDKSRWQQGNVFSCSVMHEALHNHYTQKSLSLSP
GK

FIG. 11

*Chimeric BsAb (chLL2) – Heavy chain full nucleotide sequence (SEQ ID NO: 26)*

ATGGGCTGGTCCTGCATCATCCTGTTCCTGGTGGCCACCGCCACCGGCGTCCATA
GTCAGGTCCAGCTGCAGGAGAGCGGAGCCGAACTGTCCAAACCCGGAGCATCTG
TCAAAATGTCTTGTAAAGCATCAGGCTACACCTTCACATCCTATTGGCTGCACTG
GATCAAGCAGCGGCCCGGACAGGGCCTGGAGTGGATCGGCTACATCAACCCTAG
AAATGACTACACCGAGTATAACCAGAACTTCAAGGACAAGGCCACCCTGACAGC
CGATAAGAGCTCCTCTACCGCCTATATGCAGCTGAGCTCCCTGACATCTGAGGAT
AGCGCCGTGTACTATTGCGCTCGGCGGGACATCACCACATTCTACTGGGGACAG
GGGACTACACTGACCGTCTCTTCAGCCTCCACCAAGGGCCCATCGGTCTTCCCCC
TGGCACCCTCCTCCAAGAGCACCTCTGGGGGCACAGCGGCCCTGGGCTGCCTGGT
CAAGGACTACTTCCCCGAACCGGTGACGGTGTCGTGGAACTCAGGCGCCCTGAC
CAGCGGCGTGCACACCTTCCCGGCCGTCCTACAGTCCTCAGGACTCTACTCCCTC
AGCAGCGTGGTGACCGTGCCCTCCAGCAGCTTGGGCACCCAGACCTACATCTGC
AACGTGAATCACAAGCCCAGCAACACCAAGGTGGACAAGAGAGTTGAGCCCAA
ATCTTGTGACAAAACTCACACATGCCCACCGTGCCCAGCACCTGAACTCCTGGGG
GGACCGTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGG
TCAAGTTCAACTGGTACGTGGACGGCGTGGAGGTGCATAATGCCAAGACAAAGC
CGCGGGAGGAGCAGTACGCCAGCACGTACCGTGTGGTCAGCGTCCTCACCGTCC
TGCACCAGGACTGGCTGAATGGCAAGGAGTACAAGTGCGCCGTCTCCAACAAAG
CCCTCCCAGCCCCCATCGAGAAAACCATCTCCAAAGCCAAAGGGCAGCCCCGAG
AACCACAGGTGTACACCCTGCCCCCATCCCGGGATGAGCTGACCAAGAACCAGG
TCAGCCTGACCTGCCTGGTCAAAGGCTTCTATCCCAGCGACATCGCCGTGGAGTG
GGAGAGCAATGGGCAGCCGGAGAACAACTACAAGACCACGCCTCCCGTGCTGGA
CTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACT
ACACGCAGAAGAGCCTCTCCCTGTCTCCGGGTAAATGA

FIG. 12

*BC270 (hLL2 L1H4) – Light chain full amino acid sequence (N to C terminal) [signal peptide-hLL2 L1-CL-linker-hOKT3 VH-linker-hOKT3 VL] (SEQ ID NO: 27)*

MGWSCIILFLVATATGVHS*DIVLTQSPDSLAVSAGERVTMNCKSSQSVLYSANHKNYLAW*
*YQQKPGQPPKLLIYWASTRESGVPDRFSGSGSGTDFTLTISSVQAEDVAIYYCHQYLSSWTF*
*GGGTKLEIKR*TVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRG
ECTSGGGGSGGGGSGGGGS*QVQLVQSGGGVVQPGRSLRLSCKASGYTFTRYTMHWVR*
*QAPGKCLEWIGYINPSRGYTNYNQKFKDRFTISRDNSKNTAFLQMDSLRPEDTGVYFCAR*
*YYDDHYSLDYWGQGTPVTVSS*GGGGSGGGGSGGGGSGGGGSGGGGSGGGGS*DIQ*
*MTQSPSSLSASVGDRVTITCSASSSVSYMNWYQQTPGKAPKRWIYDTSKLASGVPSRFSGSG*
*SGTDYTFTISSLQPEDIATYYCQQWSSNPFTFGCGTKLQITR*

FIG. 13

*BC270 (hLL2 L1H4) – Light chain full nucleotide sequence. (SEQ ID NO: 28)*

ATGGGCTGGTCCTGCATCATCCTGTTCCTGGTGGCCACCGCCACCGGCGTG
CACTCCGACATCGTGCTGACCCAGAGCCCAGATTCCCTGGCCGTGAGCGCCGGA
GAGCGGGTGACAATGAACTGCAAGAGCTCCCAGTCTGTGCTGTACAGCGCCAAC
CACAAGAATTACCTGGCCTGGTATCAGCAGAAGCCAGGCCAGCCCCCTAAGCTG
CTGATCTATTGGGCCTCCACCAGGGAGTCTGGAGTGCCCGACAGATTCAGCGGCT
CCGGCTCTGGCACAGACTTCACCCTGACAATCTCTAGCGTGCAGGCCGAGGACGT
GGCCATCTACTATTGTCACCAGTACCTGTCCTCTTGGACCTTCGGCGGCGGCACA
AAGCTGGAGATCAAGCGGACCGTGGCCGCCCCCTCCGTGTTCATCTTCCCCCCCT
CCGACGAGCAGCTGAAGTCCGGCACCGCCTCCGTGGTGTGCCTGCTGAACAACTT
CTACCCCCGGGAGGCCAAGGTGCAGTGGAAGGTGGACAACGCCCTGCAGTCCGG
CAACTCCCAGGAGTCCGTGACCGAGCAGGACTCCAAGGACTCCACCTACTCCCT
GTCCTCCACCCTGACCCTGTCCAAGGCCGACTACGAGAAGCACAAGGTGTACGC
CTGCGAGGTGACCCACCAGGGCCTGTCCTCCCCCGTGACCAAGTCCTTCAACCGG
GGCGAGTGCACTAGTGGCGGCGGAGGATCTGGCGGAGGTGGAAGTGGGGGAGG
CGGATCTCAGGTGCAGCTGGTGCAGAGTGGTGGCGGAGTGGTGCAGCCTGGCAG
ATCCCTGAGACTGTCTTGCAAGGCCAGCGGCTACACCTTCACCCGGTACACCATG
CACTGGGTGCGACAGGCCCCTGGCAAGTGCCTGGAATGGATCGGCTACATCAAC
CCCTCCCGGGGCTACACCAACTACAACCAGAAGTTCAAGGACCGGTTCACCATC
AGCCGGGACAACTCCAAGAACACCGCCTTTCTGCAGA
TGGACTCCCTGCGGCCTGAGGATACCGGCGTGTACTTTTGCGCCCGGTACTACGA
CGACCACTACAGCCTGGACTACTGGGGCCAGGGAACCCCTGTGACAGTGTCTAG
CGGAGGGGGAGGTTCAGGTGGCGGTGGATCAGGGGGCGGAGGAAGTGGCGGGG
GAGGTAGTGGTGGTGGTGGAAGCGGAGGTGGCGGCTCCGATATCCAGATGACCC
AGTCCCCCTCCAGCCTGTCTGCCTCTGTGGGAGACAGAGTGACAATTACATGCTC
CGCCAGCTCCAGCGTGTCCTACATGAATTGGTATCAGCAGACCCCTGGCAAGGCT
CCCAAGCGGTGGATCTACGACACCTCCAAGCTGGCCTCCGGCGTGCCCTCCAGAT
TTTCTGGCAGCGGCTCCGGCACAGACTATACCTTTACAATCAGCTCCCTGCAGCC
CGAAGATATCGCCACCTACTACTGCCAGCAGTGGTCCTCCAACCCCTTCACCTTC
GGCTGCGGCACAAAGCTGCAGATCACCAGATAG

FIG. 14

*BC270 (hLL2 L1H4) – Heavy chain full amino acid sequence (N to C terminal) [signal peptide-hLL2 H4-CH1-3] (SEQ ID NO: 29).*

<u>MGWSCIILFLVATATGVHS</u>*QVQLQQSGAEVKKPGASVKMSCKASGYTFTSYWLHWIRQA PGQRLEWMGYINPRNDYTEYNQKFQGRATITADKSASTAYMELSSLRSEDTAVYYCARRDI TTFYWGQGTTLTVSS*ASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKRVEPK SCDKTHTCPPCPAPELLGGPSVFLFPPKPKDTLMISRTPEVTCVVVDVSHEDPEVKFN WYVDGVEVHNAKTKPREEQYASTYRVVSVLTVLHQDWLNGKEYKCAVSNKALPA PIEKTISKAKGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHYTQKSLSLS PGK

FIG. 15

*BC270 (hLL2 L1H4) – Heavy chain full nucleotide sequence (SEQ ID NO: 30)*

ATGGGCTGGTCCTGCATCATCCTGTTCCTGGTGGCCACCGCCACCGGCGTGCACA
GCCAGGTGCAGCTGCAGCAGTCCGGAGCAGAGGTGAAGAAGCCAGGAGCCAGC
GTGAAGATGTCCTGCAAGGCCTCTGGCTACACCTTCACATCTTATTGGCTGCACT
GGATCAGGCAGGCACCAGGACAGCGCCTGGAGTGGATGGGCTACATCAACCCTC
GGAATGACTACACCGAGTATAACCAGAAGTTTCAGGGCAGGGCCACCATCACAG
CCGATAAGTCCGCCTCTACCGCCTACATGGAGCTGAGCTCCCTGCGGAGCGAGG
ACACAGCCGTGTACTATTGTGCCCGGAGAGATATCACCACATTCTATTGGGGCCA
GGGCACCACACTGACAGTGTCTAGCGCCTCCACCAAGGGCCCATCGGTCTTCCCC
CTGGCACCCTCCTCCAAGAGCACCTCTGGGGGCACAGCGGCCCTGGGCTGCCTG
GTCAAGGACTACTTCCCCGAACCGGTGACGGTGTCGTGGAACTCAGGCGCCCTG
ACCAGCGGCGTGCACACCTTCCCGGCCGTCCTACAGTCCTCAGGACTCTACTCCC
TCAGCAGCGTGGTGACCGTGCCCTCCAGCAGCTTGGGCACCCAGACCTACATCTG
CAACGTGAATCACAAGCCCAGCAACACCAAGGTGGACAAGAGAGTTGAGCCCA
AATCTTGTGACAAAACTCACACATGCCCACCGTGCCCAGCACCTGAACTCCTGGG
GGGACCGTCAGTCTTCCTCTTCCCCCCAAAACCCAAGGACACCCTCATGATCTCC
CGGACCCCTGAGGTCACATGCGTGGTGGTGGACGTGAGCCACGAAGACCCTGAG
GTCAAGTTCAACTGGTACGTGGACGGCGTGGAGGTGCATAATGCCAAGACAAAG
CCGCGGGAGGAGCAGTACGCCAGCACGTACCGTGTGGTCAGCGTCCTCACCGTC
CTGCACCAGGACTGGCTGAATGGCAAGGAGTACAAGTGCGCCGTCTCCAACAAA
GCCCTCCCAGCCCCCATCGAGAAAACCATCTCCAAAG
CCAAAGGGCAGCCCCGAGAACCACAGGTGTACACCCTGCCCCCATCCCGGGATG
AGCTGACCAAGAACCAGGTCAGCCTGACCTGCCTGGTCAAAGGCTTCTATCCCA
GCGACATCGCCGTGGAGTGGGAGAGCAATGGGCAGCCGGAGAACAACTACAAG
ACCACGCCTCCCGTGCTGGACTCCGACGGCTCCTTCTTCCTCTACAGCAAGCTCA
CCGTGGACAAGAGCAGGTGGCAGCAGGGGAACGTCTTCTCATGCTCCGTGATGC
ATGAGGCTCTGCACAACCACTACACGCAGAAGAGCCTCTCCCTGTCTCCGGGTAA
ATGA

FIG. 16

*BC251 (hLL2 L1H10) – Light chain full amino acid sequence (N to C terminal) [signal peptide-hLL2 L1-CL-linker-hOKT3 VH-linker-hOKT3 VL] (SEQ ID NO: 31).*

<u>MGWSCIILFLVATATGVHS</u>*DIVLTQSPDSLAVSAGERVTMNCKSSQSVLYSANHKNYLAW*
*YQQKPGQPPKLLIYWASTRESGVPDRFSGSGSGTDFTLTISSVQAEDVAIYYCHQYLSSWTF*
*GGGTKLEIKR*TVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRG
ECTS<u>GGGGSGGGGSGGGGS</u>*QVQLVQSGGGVVQPGRSLRLSCKASGYTFTRYTMHWVR*
*QAPGKCLEWIGYINPSRGYTNYNQKFKDRFTISRDNSKNTAFLQMDSLRPEDTGVYFCAR*
*YYDDHYSLDYWGQGTPVTVSS*<u>GGGGSGGGGSGGGGSGGGGSGGGGSGGGGS</u>*DIQ*
*MTQSPSSLSASVGDRVTITCSASSSVSYMNWYQQTPGKAPKRWIYDTSKLASGVPSRFSGSG*
*SGTDYTFTISSLQPEDIATYYCQQWSSNPFTFGCGTKLQITR*

FIG. 17

*BC251 (hLL2 L1H10) – Light chain full nucleotide sequence (SEQ ID NO: 32)*

ATGGGCTGGTCCTGCATCATCCTGTTCCTGGTGGCCACCGCCACCGGCGTGCACT
CCGACATCGTGCTGACCCAGAGCCCAGATTCCCTGGCCGTGAGCGCCGGAGAGC
GGGTGACAATGAACTGCAAGAGCTCCCAGTCTGTGCTGTACAGCGCCAACCACA
AGAATTACCTGGCCTGGTATCAGCAGAAGCCAGGCCAGCCCCCTAAGCTGCTGA
TCTATTGGGCCTCCACCAGGGAGTCTGGAGTGCCCGACAGATTCAGCGGCTCCGG
CTCTGGCACAGACTTCACCCTGACAATCTCTAGCGTGCAGGCCGAGGACGTGGCC
ATCTACTATTGTCACCAGTACCTGTCCTCTTGGACCTTCGGCGGCGGCACAAAGC
TGGAGATCAAGCGGACCGTGGCCGCCCCCTCCGTGTTCATCTTCCCCCCCTCCGA
CGAGCAGCTGAAGTCCGGCACCGCCTCCGTGGTGTGCCTGCTGAACAACTTCTAC
CCCCGGGAGGCCAAGGTGCAGTGGAAGGTGGACAACGCCCTGCAGTCCGGCAAC
TCCCAGGAGTCCGTGACCGAGCAGGACTCCAAGGACTCCACCTACTCCCTGTCCT
CCACCCTGACCCTGTCCAAGGCCGACTACGAGAAGCACAAGGTGTACGCCTGCG
AGGTGACCCACCAGGGCCTGTCCTCCCCCGTGACCAAGTCCTTCAACCGGGGCG
AGTGCACTAGTGGCGGCGGAGGATCTGGCGGAGGTGGAAGTGGGGGAGGCGGA
TCTCAGGTGCAGCTGGTGCAGAGTGGTGGCGGAGTGGTGCAGCCTGGCAGATCC
CTGAGACTGTCTTGCAAGGCCAGCGGCTACACCTTCACCCGGTACACCATGCACT
GGGTGCGACAGGCCCCTGGCAAGTGCCTGGAATGGATCGGCTACATCAACCCCT
CCCGGGGCTACACCAACTACAACCAGAAGTTCAAGGACCGGTTCACCATCAGCC
GGGACAACTCCAAGAACACCGCCTTTCTGCAGATGGACTCCCTGCGGCCTGAGG
ATACCGGCGTGTACTTTTGCGCCCGGTACTACGACG
ACCACTACAGCCTGGACTACTGGGGCCAGGGAACCCCTGTGACAGTGTCTAGCG
GAGGGGGAGGTTCAGGTGGCGGTGGATCAGGGGGCGGAGGAAGTGGCGGGGGA
GGTAGTGGTGGTGGTGGAAGCGGAGGTGGCGGCTCCGATATCCAGATGACCCAG
TCCCCCTCCAGCCTGTCTGCCTCTGTGGGAGACAGAGTGACAATTACATGCTCCG
CCAGCTCCAGCGTGTCCTACATGAATTGGTATCAGCAGACCCCTGGCAAGGCTCC
CAAGCGGTGGATCTACGACACCTCCAAGCTGGCCTCCGGCGTGCCCTCCAGATTT
TCTGGCAGCGGCTCCGGCACAGACTATACCTTTACAATCAGCTCCCTGCAGCCCG
AAGATATCGCCACCTACTACTGCCAGCAGTGGTCCTCCAACCCCTTCACCTTCGG
CTGCGGCACAAAGCTGCAGATCACCAGATAG

FIG. 18

*BC251 (hLL2 L1H10) – Heavy chain full amino acid sequence (N to C terminal) [signal peptide-hLL2 H10-CH1-3] (SEQ ID NO: 33)*

<u>MGWSCIILFLVATATGVHS</u>*QVQLVQSGAEVKKPGASVKVSCKASGYTFTSYWLHWVRQA PGQRLEWMGYINPRNDYTEYNQNFKDRVTLTADKSASTAYMELSSLRSEDTAVYYCARRDI TTFYWGQGTTLTVSS*ASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKRVEPK SCDKTHTCPPCPAPELLGGPSVFLFPPKPKDTLMISRTPEVTCVVVDVSHEDPEVKFN WYVDGVEVHNAKTKPREEQYASTYRVVSVLTVLHQDWLNGKEYKCAVSNKALPA PIEKTISKAKGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHYTQKSLSLS PGK

FIG. 19

*BC251 (hLL2 L1H10) – Heavy chain full nucleotide sequence (SEQ ID NO: 34).*

ATGGGCTGGTCCTGCATCATCCTGTTCCTGGTGGCCACCGCCACCGGCGTGCACA
GCCAGGTGCAGCTGGTGCAGTCCGGAGCAGAGGTGAAGAAGCCAGGAGCCAGC
GTGAAGGTGTCCTGCAAGGCCTCTGGCTACACCTTCACATCTTATTGGCTGCACT
GGGTGAGGCAGGCACCAGGACAGCGCCTGGAGTGGATGGGCTACATCAACCCTC
GGAATGACTACACCGAGTATAACCAGAACTTCAAGGACAGGGTGACCCTGACAG
CCGATAAGTCCGCCTCTACCGCCTACATGGAGCTGAGCTCCCTGCGGAGCGAGG
ACACAGCCGTGTACTATTGTGCCCGGAGAGATATCACCACATTCTATTGGGGCCA
GGGCACCACACTGACAGTGTCTAGCGCCTCCACCAAGGGCCCATCGGTCTTCCCC
CTGGCACCCTCCTCCAAGAGCACCTCTGGGGGCACAGCGGCCCTGGGCTGCCTG
GTCAAGGACTACTTCCCCGAACCGGTGACGGTGTCGTGGAACTCAGGCGCCCTG
ACCAGCGGCGTGCACACCTTCCCGGCCGTCCTACAGTCCTCAGGACTCTACTCCC
TCAGCAGCGTGGTGACCGTGCCCTCCAGCAGCTTGGGCACCCAGACCTACATCTG
CAACGTGAATCACAAGCCCAGCAACACCAAGGTGGACAAGAGAGTTGAGCCCA
AATCTTGTGACAAAACTCACACATGCCCACCGTGCCCAGCACCTGAACTCCTGGG
GGGACCGTCAGTCTTCCTCTTCCCCCCAAAACCCAAGGACACCCTCATGATCTCC
CGGACCCCTGAGGTCACATGCGTGGTGGTGGACGTGAGCCACGAAGACCCTGAG
GTCAAGTTCAACTGGTACGTGGACGGCGTGGAGGTGCATAATGCCAAGACAAAG
CCGCGGGAGGAGCAGTACGCCAGCACGTACCGTGTGGTCAGCGTCCTCACCGTC
CTGCACCAGGACTGGCTGAATGGCAAGGAGTACAAGTGCGCCGTCTCCAACAAA
GCCCTCCCAGCCCCCATCGAGAAAACCATCTCCAAAG
CCAAAGGGCAGCCCCGAGAACCACAGGTGTACACCCTGCCCCCATCCCGGGATG
AGCTGACCAAGAACCAGGTCAGCCTGACCTGCCTGGTCAAAGGCTTCTATCCCA
GCGACATCGCCGTGGAGTGGGAGAGCAATGGGCAGCCGGAGAACAACTACAAG
ACCACGCCTCCCGTGCTGGACTCCGACGGCTCCTTCTTCCTCTACAGCAAGCTCA
CCGTGGACAAGAGCAGGTGGCAGCAGGGGAACGTCTTCTCATGCTCCGTGATGC
ATGAGGCTCTGCACAACCACTACACGCAGAAGAGCCTCTCCCTGTCTCCGGGTAA
ATGA

FIG. 20

*Dota-engaging Bispecific antibody for radioimmunotherapy (based on chimeric LL2) – Light chain full amino acid sequence (N to C terminal) anti-CD22 x C825 (CD22-mouseVL-CL-(G4S)3-mouse C825VH-(G4S)6-mouse C825VL) (SEQ ID NO: 35)*

MGWSCIILFLVATATGVHS*DIQLTQSPSSLAVSAGENVTMSCKSSQSVLYSANHKN*

*YLAWYQQKPGQSPKLLIYWASTRESGVPDRFTGSGSGTDFTLTISRVQVEDLAIYYCHQYLS*

*SWTFGGGTKLEIKR*TVAAPSVFIFPPSDEQLKSGTASVVCLLNNFYPREAKVQWKVDN

ALQSGNSQESVTEQDSKDSTYSLSSTLTLSKADYEKHKVYACEVTHQGLSSPVTKSF

NRGECTSGGGGSGGGGSGGGGS*HVKLQESGPGLVQPSQSLSLTCTVSGFSLTDYGVH*

*WVRQSPGKGLEWLGVIWSGGGTAYNTALISRLNIYRDNSKNQVFLEMNSLQAEDTAMYYC*

*ARRGSYPYNYFDAWGCGTTVTVSS*GGGGSGGGGSGGGGSGGGGSGGGGSGGGGS*Q*

*AVVIQESALTTPPGETVTLTCGSSTGAVTASNYANWVQEKPDHCFTGLIGGHNNRPPGVPA*

*RFSGSLIGDKAALTIAGTQTEDEAIYFCALWYSDHWVIGGGTRLTVLG*

FIG. 21

*Dota-engaging Bispecific antibody for radioimmunotherapy (based on chimeric LL2) – Heavy chain full amino acid sequence (N to C terminal) [signal peptide-LL2 mouseVH-CH1-3] (SEQ ID NO: 36)*

MGWSCIILFLVATATGVHS*QVQLQESGAELSKPGASVKMSCKASGYTFTSYWLHWIKQR*
*PGQGLEWIGYINPRNDYTEYNQNFKDKATLTADKSSSTAYMQLSSLTSEDSAVYYCARRDIT*
*TFYWGQGTTLTVSS*ASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKRVEPKS
CDKTHTCPPCPAPELLGGPSVFLFPPKPKDTLMISRTPEVTCVVVDVSHEDPEVKFNW
YVDGVEVHNAKTKPREEQYASTYRVVSVLTVLHQDWLNGKEYKCAVSNKALPAPI
EKTISKAKGQPREPQVYTLPPSRDELTKNQVSLTCLVKGFYPSDIAVEWESNGQPEN
NYKTTPPVLDSDGSFFLYSKLTVDKSRWQQGNVFSCSVMHEALHNHYTQKSLSLSP
GK

FIG. 22

*Dota-engaging Bispecific antibody for radioimmunotherapy (based on chimeric LL2) – Light chain full amino acid sequence (N to C terminal) anti-CD22 x C825 (CD22-mouseVL-CL-(G4S)3- huC825VH-(G4S)6- huC825VL) (SEQ ID NO: 37)*

MGWSCIILFLVATATGVHS*DIQLTQSPSSLAVSAGENVTMSCKSSQSVLYSANHKNYLAWYQQKPGQSPKLLIYWASTRESGVPDRFTGSGSGTDFTLTISRVQVEDLAIYYCHQYLSSWTFGGGTKLEIKR*TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECTSGGGGSGGGGSGGGGS*HVQLVESGGGLVQPGGSLRLSCAASGFSLTDYGVHWVRQAPGKGLEWLGVIWSGGGTAYNTALISRFTISRDNSKNTLYLQMNSLRAEDTAVYYCARRGSYPYNYFDAWGCGTLVTVSS*GGGGSGGGGSGGGGSGGGGSGGGGSGGGGS*QAVVTQEPSLTVSPGGTVTLTCGSSTGAVTASNYANWVQQKPGQCPRGLIGGHNNRPPGVPARFSGSLLGGKAALTLLGAQPEDEAEYYCALWYSDHWVIGGGTKLTVLG*

FIG. 23

*Dota-engaging Bispecific antibody for radioimmunotherapy (based on chimeric LL2) –Heavy chain full amino acid sequence (N to C terminal) [signal peptide-LL2 mouseVH-CH1-3] (SEQ ID NO: 38)*

MGWSCIILFLVATATGVHS*QVQLQESGAELSKPGASVKMSCKASGYTFTSYWLHWIKQRPGQGLEWIGYINPRNDYTEYNQNFKDKATLTADKSSSTAYMQLSSLTSEDSAVYYCARRDITTFYWGQGTTLTVSS*ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCAVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

FIG. 24

*Dota-engaging Bispecific antibody for radioimmunotherapy (based on LL2 L1H4) – Light chain full amino acid sequence (N to C terminal) anti-CD22 x C825 (CD22-VL1-CL-(G4S)3-mouse C825VH-(G4S)6-mouse C825VL) (SEQ ID NO: 39)*

<u>MGWSCIILFLVATATGVHS</u>*DIVLTQSPDSLAVSAGERVTMNCKSSQSVLYSANHKNYLAWYQQKPGQPPKLLIYWASTRESGVPDRFSGSGSGTDFTLTISSVQAEDVAIYYCHQYLSSWTFGGGTKLEIKR*TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECTS<u>GGGGSGGGGSGGGGS</u>*HVKLQESGPGLVQPSQSLSLTCTVSGFSLTDYGVHWVRQSPGKGLEWLGVIWSGGGTAYNTALISRLNIYRDNSKNQVFLEMNSLQAEDTAMYYCARRGSYPYNYFDAWGCGTTVTVSS*<u>GGGGSGGGGSGGGGSGGGGSGGGGSGGGGS</u>*QAVVIQESALTTPPGETVTLTCGSSTGAVTASNYANWVQEKPDHCFTGLIGGHNNRPPGVPARFSGSLIGDKAALTIAGTQTEDEAIYFCALWYSDHWVIGGGTRLTVLG*

FIG. 25

*Dota-engaging Bispecific antibody for radioimmunotherapy (based on LL2 L1H4) –Heavy chain full amino acid sequence (N to C terminal) [signal peptide-hLL2 H4-CH1-3] (SEQ ID NO: 40)*

MGWSCIILFLVATATGVHS*QVQLQQSGAEVKKPGASVKMSCKASGYTFTSYWLH WIRQAPGQRLEWMGYINPRNDYTEYNQKFQGRATITADKSASTAYMELSSLRSEDTAVYYC ARRDITTFYWGQGTTLTVSS*ASTKGPSVFPLAPSSKSTSGGTAALGCLVKDYFPEPVTV SWNSGALTSGVHTFPAVLQSSGLYSLSSVVTVPSSSLGTQTYICNVNHKPSNTKVDK RVEPKSCDKTHTCPPCPAPELLGGPSVFLFPPKPKDTLMISRTPEVTCVVVDVSHEDP EVKFNWYVDGVEVHNAKTKPREEQYASTYRVVSVLTVLHQDWLNGKEYKCAVSN KALPAPIEKTISKAKGQPREPQVYTLPPSRDELTKNQVSLTCLVKGFYPSDIAVEWES NGQPENNYKTTPPVLDSDGSFFLYSKLTVDKSRWQQGNVFSCSVMHEALHNHYTQ KSLSLSPGK

FIG. 26

*Dota-engaging Bispecific antibody for radioimmunotherapy (based on LL2 L1H4) – Light chain full amino acid sequence (N to C terminal) anti-CD22 x C825 (CD22-VL1-CL-(G4S)3- huC825VH-(G4S)6- huC825VL) (SEQ ID NO: 41)*

MGWSCIILFLVATATGVHS*DIVLTQSPDSLAVSAGERVTMNCKSSQSVLYSANHK*
*NYLAWYQQKPGQPPKLLIYWASTRESGVPDRFSGSGSGTDFTLTISSVQAEDVAIYYCHQY*
*LSSWTFGGGTKLEIKR*TVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTK
SFNRGECTSGGGGSGGGGSGGGGS*HVQLVESGGGLVQPGGSLRLSCAASGFSLTDYG*
*VHWVRQAPGKGLEWLGVIWSGGGTAYNTALISRFTISRDNSKNTLYLQMNSLRAEDTAVYY*
*CARRGSYPYNYFDAWGCGTLVTVSS*GGGGSGGGGSGGGGSGGGGSGGGGSGGGGS
*QAVVTQEPSLTVSPGGTVTLTCGSSTGAVTASNYANWVQQKPGQCPRGLIGGHNNRPPGV*
*PARFSGSLLGGKAALTLLGAQPEDEAEYYCALWYSDHWVIGGGTKLTVLG*

FIG. 27

*Dota-engaging Bispecific antibody for radioimmunotherapy (based on LL2 L1H4) –Heavy chain full amino acid sequence (N to C terminal) [signal peptide-hLL2 H4-CH1-3] (SEQ ID NO: 42)*

MGWSCIILFLVATATGVHS*QVQLQQSGAEVKKPGASVKMSCKASGYTFTSYWLHWIRQAPGQRLEWMGYINPRNDYTEYNQKFQGRATITADKSASTAYMELSSLRSEDTAVYYCARRDITTFYWGQGTTLTVSS*ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCAVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK

FIG. 28

*Dota-engaging Bispecific antibody for radioimmunotherapy (based on LL2 L1H10) – Light chain full amino acid sequence (N to C terminal) anti-CD22 x C825 (CD22-VL1-CL-(G4S)3-mouse C825VH-(G4S)6-mouse C825VL) (SEQ ID NO: 43)*

<u>MGWSCIILFLVATATGVHS</u>*DIVLTQSPDSLAVSAGERVTMNCKSSQSVLYSANHK NYLAWYQQKPGQPPKLLIYWASTRESGVPDRFSGSGSGTDFTLTISSVQAEDVAIYYCHQY LSSWTFGGGTKLEIKR*TVAAPSVFIFPPSDEQLKSGTASVVCLLNNFYPREAKVQWKV DNALQSGNSQESVTEQDSKDSTYSLSSTLTLSKADYEKHKVYACEVTHQGLSSPVTK SFNRGECTS<u>GGGGSGGGGSGGGGS</u>*HVKLQESGPGLVQPSQSLSLTCTVSGFSLTDYGV HWVRQSPGKGLEWLGVIWSGGGTAYNTALISRLNIYRDNSKNQVFLEMNSLQAEDTAMYY CARRGSYPYNYFDAWGCGTTVTVSS*<u>GGGGSGGGGSGGGGSGGGGSGGGGSGGGGS</u> *QAVVIQESALTTPPGETVTLTCGSSTGAVTASNYANWVQEKPDHCFTGLIGGHNNRPPGV PARFSGSLIGDKAALTIAGTQTEDEAIYFCALWYSDHWVIGGGTRLTVLG*

FIG. 29

*Dota-engaging Bispecific antibody for radioimmunotherapy (based on LL2 L1H10) –Heavy chain full amino acid sequence (N to C terminal) [signal peptide-hLL2 H10-CH1-3] (SEQ ID NO: 44)*

MGWSCIILFLVATATGVHS*QVQLVQSGAEVKKPGASVKVSCKASGYTFTSYWLH WVRQAPGQRLEWMGYINPRNDYTEYNQNFKDRVTLTADKSASTAYMELSSLRSEDTAVYY CARRDITTFYWGQGTTLTVSS*ASTKGPSVFPLAPSSKSTSGGTAALGCLVKDYFPEPVT VSWNSGALTSGVHTFPAVLQSSGLYSLSSVVTVPSSSLGTQTYICNVNHKPSNTKVD KRVEPKSCDKTHTCPPCPAPELLGGPSVFLFPPKPKDTLMISRTPEVTCVVVDVSHED PEVKFNWYVDGVEVHNAKTKPREEQYASTYRVVSVLTVLHQDWLNGKEYKCAVS NKALPAPIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNHYTQ KSLSLSPGK

FIG. 30

*Dota-engaging Bispecific antibody for radioimmunotherapy (based on LL2 L1H10) – Light chain full amino acid sequence (N to C terminal) anti-CD22 x C825 (CD22-VL1-CL-(G4S)3- huC825VH-(G4S)6- huC825VL) (SEQ ID NO: 45)*

MGWSCIILFLVATATGVHS*DIVLTQSPDSLAVSAGERVTMNCKSSQSVLYSANHK NYLAWYQQKPGQPPKLLIYWASTRESGVPDRFSGSGSGTDFTLTISSVQAEDVAIYYCHQY LSSWTFGGGTKLEIKR*TVAAPSVFIFPPSDEQLKSGTASVVCLLNNFYPREAKVQWKV DNALQSGNSQESVTEQDSKDSTYSLSSTLTLSKADYEKHKVYACEVTHQGLSSPVTK SFNRGECTSGGGGSGGGGSGGGGS*HVQLVESGGGLVQPGGSLRLSCAASGFSLTDYG VHWVRQAPGKGLEWLGVIWSGGGTAYNTALISRFTISRDNSKNTLYLQMNSLRAEDTAVYY CARRGSYPYNYFDAWGCGTLVTVSS*GGGGSGGGGSGGGGSGGGGSGGGGSGGGGS *QAVVTQEPSLTVSPGGTVTLTCGSSTGAVTASNYANWVQQKPGQCPRGLIGGHNNRPPGV PARFSGSLLGGKAALTLLGAQPEDEAEYYCALWYSDHWVIGGGTKLTVLG*

FIG. 31

*Dota-engaging Bispecific antibody for radioimmunotherapy (based on LL2 L1H10) –Heavy chain full amino acid sequence (N to C terminal) [signal peptide-hLL2 H10-CH1-3] (SEQ ID NO: 46)*

<u>MGWSCIILFLVATATGVHS</u>*QVQLVQSGAEVKKPGASVKVSCKASGYTFTSYWLH WVRQAPGQRLEWMGYINPRNDYTEYNQNFKDRVTLTADKSASTAYMELSSLRSEDTAVYY CARRDITTFYWGQGTTLTVSS*ASTKGPSVFPLAPSSKSTSGGTAALGCLVKDYFPEPVT VSWNSGALTSGVHTFPAVLQSSGLYSLSSVVTVPSSSLGTQTYICNVNHKPSNTKVD KRVEPKSCDKTHTCPPCPAPELLGGPSVFLFPPKPKDTLMISRTPEVTCVVVDVSHED PEVKFNWYVDGVEVHNAKTKPREEQYASTYRVVSVLTVLHQDWLNGKEYKCAVS NKALPAPIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNHYTQ KSLSLSPGK

FIG. 32

LL2 MOUSE VL-(G4S)6-LL2 MOUSE VH-(G4S)4-hC825 VH-(G4S)6-hC825 VL-spacer-linker-P53-spacer-H6 *(SEQ ID NO: 47)*

MGWSCIILFLVATATGVHS*DIQLTQSPSSLAVSAGENVTMSCKSSQSVLYSANHKNYLAW YQQKPGQSPKLLIYWASTRESGVPDRFTGSGSGTDFTLTISRVQVEDLAIYYCHQYLSSWTF GGGTKLEIKR*GGGGSGGGGSGGGGSGGGGSGGGGSGGGGS*QVQLQESGAELSKP GASVKMSCKASGYTFTSYWLHWIKQRPGQGLEWIGYINPRNDYTEYNQNFKDKATLTADK SSSTAYMQLSSLTSEDSAVYYCARRDITTFYWGQGTTLTVSS*GGGGSGGGGSGGGGSGG GGS*HVQLVESGGGLVQPGGSLRLSCAASGFSLTDYGVHWVRQAPGKGLEWLGVIWSGG GTAYNTALISRFTISRDNSKNTLYLQMNSLRAEDTAVYYCARRGSYPYNYFDAWGCGTLVTV SS*GGGGSGGGGSGGGGSGGGGSGGGGSGGGGS*QAVVTQEPSLTVSPGGTVTLTCGS STGAVTASNYANWVQQKPGQCPRGLIGGHNNRPPGVPARFSGSLLGGKAALTLLGAQPE DEAEYYCALWYSDHWVIGGGTKLTVLG*TPLGDTTHTSGKPLDGEYFTLQIRGRERFE MFRELNEALELKDAQAGKEPGGSGGAP*HHHHHH

FIG. 33

LL2 MOUSE VL-(G4S)6-LL2 MOUSE VH-(G4S)4-hC825 VH-(G4S)6-hC825 VL-spacer-linker-P53-spacer *(SEQ ID NO: 48)*

MGWSCIILFLVATATGVHS*DIQLTQSPSSLAVSAGENVTMSCKSSQSVLYSANHKNYLAW*
*YQQKPGQSPKLLIYWASTRESGVPDRFTGSGSGTDFTLTISRVQVEDLAIYYCHQYLSSWTF*
*GGGTKLEIKR*GGGGSGGGGSGGGGSGGGGSGGGGSGGGGS*QVQLQESGAELSKP*
*GASVKMSCKASGYTFTSYWLHWIKQRPGQGLEWIGYINPRNDYTEYNQNFKDKATLTADK*
*SSSTAYMQLSSLTSEDSAVYYCARRDITTFYWGQGTTLTVSS*GGGGSGGGGSGGGGSGG
GGS*HVQLVESGGGLVQPGGSLRLSCAASGFSLTDYGVHWVRQAPGKGLEWLGVIWSGG*
*GTAYNTALISRFTISRDNSKNTLYLQMNSLRAEDTAVYYCARRGSYPYNYFDAWGCGTLVTV*
*SS*GGGGSGGGGSGGGGSGGGGSGGGGSGGGGS*QAVVTQEPSLTVSPGGTVTLTCGS*
*STGAVTASNYANWVQQKPGQCPRGLIGGHNNRPPGVPARFSGSLLGGKAALTLLGAQPE*
*DEAEYYCALWYSDHWVIGGGTKLTVLG*TPLGDTTHTSGKPLDGEYFTLQIRGRERFE
MFRELNEALELKDAQAGKEPGGSGGA

FIG. 34

LL2 MOUSE VH-(G4S)6-LL2 MOUSE VL-(G4S)4-hC825 VH-(G4S)6-hC825 VL-spacer-linker-P53-spacer-H6 *(SEQ ID NO: 49)*

MGWSCIILFLVATATGVHS*QVQLQESGAELSKPGASVKMSCKASGYTFTSYWLHWIKQR PGQGLEWIGYINPRNDYTEYNQNFKDKATLTADKSSSTAYMQLSSLTSEDSAVYYCARRDIT TFYWGQGTTLTVSS*GGGGSGGGGSGGGGSGGGGSGGGGSGGGGS*DIQLTQSPSSLA VSAGENVTMSCKSSQSVLYSANHKNYLAWYQQKPGQSPKLLIYWASTRESGVPDRFTGSGS GTDFTLTISRVQVEDLAIYYCHQYLSSWTFGGGTKLEIKR*GGGGSGGGGSGGGGSGGG GS*HVQLVESGGGLVQPGGSLRLSCAASGFSLTDYGVHWVRQAPGKGLEWLGVIWSGGGT AYNTALISRFTISRDNSKNTLYLQMNSLRAEDTAVYYCARRGSYPYNYFDAWGCGTLVTVSS* GGGGSGGGGSGGGGSGGGGSGGGGSGGGGS*QAVVTQEPSLTVSPGGTVTLTCGSS TGAVTASNYANWVQQKPGQCPRGLIGGHNNRPPGVPARFSGSLLGGKAALTLLGAQPED EAEYYCALWYSDHWVIGGGTKLTVLG*TPLGDTTHTSGKPLDGEYFTLQIRGRERFE MFRELNEALELKDAQAGKEPGGSGGAPHHHHHH

FIG. 35

LL2 MOUSE VH-(G4S)6-LL2 MOUSE VL-(G4S)4-hC825 VH-(G4S)6-hC825 VL-spacer-linker-P53-spacer *(SEQ ID NO: 50)*

MGWSCIILFLVATATGVHS*QVQLQESGAELSKPGASVKMSCKASGYTFTSYWLHWIKQR*
*PGQGLEWIGYINPRNDYTEYNQNFKDKATLTADKSSSTAYMQLSSLTSEDSAVYYCARRDIT*
*TFYWGQGTTLTVSS*GGGGSGGGGSGGGGSGGGGSGGGGSGGGGS*DIQLTQSPSSLA*
*VSAGENVTMSCKSSQSVLYSANHKNYLAWYQQKPGQSPKLLIYWASTRESGVPDRFTGSGS*
*GTDFTLTISRVQVEDLAIYYCHQYLSSWTFGGGTKLEIKR*GGGGSGGGGSGGGGSGGG
GS*HVQLVESGGGLVQPGGSLRLSCAASGFSLTDYGVHWVRQAPGKGLEWLGVIWSGGGT*
*AYNTALISRFTISRDNSKNTLYLQMNSLRAEDTAVYYCARRGSYPYNYFDAWGCGTLVTVSS*
GGGGSGGGGSGGGGSGGGGSGGGGSGGGGS*QAVVTQEPSLTVSPGGTVTLTCGSS*
*TGAVTASNYANWVQQKPGQCPRGLIGGHNNRPPGVPARFSGSLLGGKAALTLLGAQPED*
*EAEYYCALWYSDHWVIGGGTKLTVLG*TPLGDTTHTSGKPLDGEYFTLQIRGRERFE
MFRELNEALELKDAQAGKEPGGSGGA

FIG. 36

LL2 MOUSE VL-(G4S)6-LL2 MOUSE VH-(G4S)4-hC825 VH-(G4S)6-hC825 VL-spacer-linker-P63-spacer-H6 *(SEQ ID NO: 51)*

MGWSCIILFLVATATGVHS*DIQLTQSPSSLAVSAGENVTMSCKSSQSVLYSANHKNYLAW*
*YQQKPGQSPKLLIYWASTRESGVPDRFTGSGSGTDFTLTISRVQVEDLAIYYCHQYLSSWTF*
*GGGTKLEIKR*GGGGSGGGGSGGGGSGGGGSGGGGSGGGGS*QVQLQESGAELSKP*
*GASVKMSCKASGYTFTSYWLHWIKQRPGQGLEWIGYINPRNDYTEYNQNFKDKATLTADK*
*SSSTAYMQLSSLTSEDSAVYYCARRDITTFYWGQGTTLTVSS*GGGGSGGGGSGGGGSGG
GGS*HVQLVESGGGLVQPGGSLRLSCAASGFSLTDYGVHWVRQAPGKGLEWLGVIWSGG*
*GTAYNTALISRFTISRDNSKNTLYLQMNSLRAEDTAVYYCARRGSYPYNYFDAWGCGTLVTV*
*SS*GGGGSGGGGSGGGGSGGGGSGGGGSGGGGS*QAVVTQEPSLTVSPGGTVTLTCGS*
*STGAVTASNYANWVQQKPGQCPRGLIGGHNNRPPGVPARFSGSLLGGKAALTLLGAQPE*
*DEAEYYCALWYSDHWVIGGGTKLTVLG*TPLGDTTHTSGRSPDDELLYLPVRGRETYE
MLLKIKESLELMQYLPQHTIETYRQQQQQHQHLLQKQGGSGGAPHHHHHH

FIG. 37

LL2 MOUSE VL-(G4S)6-LL2 MOUSE VH-(G4S)4-hC825 VH-(G4S)6-hC825 VL-spacer-linker-P63-spacer *(SEQ ID NO: 52)*

MGWSCIILFLVATATGVHS*DIQLTQSPSSLAVSAGENVTMSCKSSQSVLYSANHKNYLAW*
*YQQKPGQSPKLLIYWASTRESGVPDRFTGSGSGTDFTLTISRVQVEDLAIYYCHQYLSSWTF*
*GGGTKLEIKR*GGGGSGGGGSGGGGSGGGGSGGGGSGGGGS*QVQLQESGAELSKP*
*GASVKMSCKASGYTFTSYWLHWIKQRPGQGLEWIGYINPRNDYTEYNQNFKDKATLTADK*
*SSSTAYMQLSSLTSEDSAVYYCARRDITTFYWGQGTTLTVSS*GGGGSGGGGSGGGGSGG
GGS*HVQLVESGGGLVQPGGSLRLSCAASGFSLTDYGVHWVRQAPGKGLEWLGVIWSGG*
*GTAYNTALISRFTISRDNSKNTLYLQMNSLRAEDTAVYYCARRGSYPYNYFDAWGCGTLVTV*
*SS*GGGGSGGGGSGGGGSGGGGSGGGGSGGGGS*QAVVTQEPSLTVSPGGTVTLTCGS*
*STGAVTASNYANWVQQKPGQCPRGLIGGHNNRPPGVPARFSGSLLGGKAALTLLGAQPE*
*DEAEYYCALWYSDHWVIGGGTKLTVLG*TPLGDTTHTSGRSPDDELLYLPVRGRETYE
MLLKIKESLELMQYLPQHTIETYRQQQQQHQHLLQKQGGSGGA

FIG. 38

LL2 MOUSE VH-(G4S)6-LL2 MOUSE VL-(G4S)4-hC825 VH-(G4S)6-hC825 VL-spacer-linker-P63-spacer-H6 *(SEQ ID NO: 53)*

MGWSCIILFLVATATGVHS*QVQLQESGAELSKPGASVKMSCKASGYTFTSYWLHWIKQR*
*PGQGLEWIGYINPRNDYTEYNQNFKDKATLTADKSSSTAYMQLSSLTSEDSAVYYCARRDIT*
*TFYWGQGTTLTVSS*GGGGSGGGGSGGGGSGGGGSGGGGSGGGGS*DIQLTQSPSSLA*
*VSAGENVTMSCKSSQSVLYSANHKNYLAWYQQKPGQSPKLLIYWASTRESGVPDRFTGSGS*
*GTDFTLTISRVQVEDLAIYYCHQYLSSWTFGGGTKLEIKR*GGGGSGGGGSGGGGSGGG
GS*HVQLVESGGGLVQPGGSLRLSCAASGFSLTDYGVHWVRQAPGKGLEWLGVIWSGGGT*
*AYNTALISRFTISRDNSKNTLYLQMNSLRAEDTAVYYCARRGSYPYNYFDAWGCGTLVTVSS*
GGGGSGGGGSGGGGSGGGGSGGGGSGGGGS*QAVVTQEPSLTVSPGGTVTLTCGSS*
*TGAVTASNYANWVQQKPGQCPRGLIGGHNNRPPGVPARFSGSLLGGKAALTLLGAQPED*
*EAEYYCALWYSDHWVIGGGTKLTVLG*TPLGDTTHTSGRSPDDELLYLPVRGRETYE
MLLKIKESLELMQYLPQHTIETYRQQQQQHQHLLQKQGGSGGAPHHHHHH

FIG. 39

LL2 MOUSE VH-(G4S)6-LL2 MOUSE VL-(G4S)4-hC825 VH-(G4S)6-hC825 VL-spacer-linker-P63-spacer *(SEQ ID NO: 54)*

MGWSCIILFLVATATGVHS*QVQLQESGAELSKPGASVKMSCKASGYTFTSYWLHWIKQR*
*PGQGLEWIGYINPRNDYTEYNQNFKDKATLTADKSSSTAYMQLSSLTSEDSAVYYCARRDIT*
*TFYWGQGTTLTVSS*GGGGSGGGGSGGGGSGGGGSGGGGSGGGGS*DIQLTQSPSSLA*
*VSAGENVTMSCKSSQSVLYSANHKNYLAWYQQKPGQSPKLLIYWASTRESGVPDRFTGSGS*
*GTDFTLTISRVQVEDLAIYYCHQYLSSWTFGGGTKLEIKR*GGGGSGGGGSGGGGSGGG
GS*HVQLVESGGGLVQPGGSLRLSCAASGFSLTDYGVHWVRQAPGKGLEWLGVIWSGGGT*
*AYNTALISRFTISRDNSKNTLYLQMNSLRAEDTAVYYCARRGSYPYNYFDAWGCGTLVTVSS*
GGGGSGGGGSGGGGSGGGGSGGGGSGGGGS*QAVVTQEPSLTVSPGGTVTLTCGSS*
*TGAVTASNYANWVQQKPGQCPRGLIGGHNNRPPGVPARFSGSLLGGKAALTLLGAQPED*
*EAEYYCALWYSDHWVIGGGTKLTVLG*TPLGDTTHTSGRSPDDELLYLPVRGRETYE
MLLKIKESLELMQYLPQHTIETYRQQQQQHQHLLQKQGGSGGA

FIG. 40

LL2 MOUSE VL-(G4S)6-LL2 MOUSE VH-(G4S)4-hC825 VH-(G4S)6-hC825 VL-spacer-linker-P73-spacer-H6 *(SEQ ID NO: 55)*

MGWSCIILFLVATATGVHS*DIQLTQSPSSLAVSAGENVTMSCKSSQSVLYSANHKNYLAW*
*YQQKPGQSPKLLIYWASTRESGVPDRFTGSGSGTDFTLTISRVQVEDLAIYYCHQYLSSWTF*
*GGGTKLEIKR*__GGGGSGGGGSGGGGSGGGGSGGGGSGGGGS__*QVQLQESGAELSKP*
*GASVKMSCKASGYTFTSYWLHWIKQRPGQGLEWIGYINPRNDYTEYNQNFKDKATLTADK*
*SSSTAYMQLSSLTSEDSAVYYCARRDITTFYWGQGTTLTVSS*__GGGGSGGGGSGGGGSGG__
__GGS__*HVQLVESGGGLVQPGGSLRLSCAASGFSLTDYGVHWVRQAPGKGLEWLGVIWSGG*
*GTAYNTALISRFTISRDNSKNTLYLQMNSLRAEDTAVYYCARRGSYPYNYFDAWGCGTLVTV*
*SS*__GGGGSGGGGSGGGGSGGGGSGGGGSGGGGS__*QAVVTQEPSLTVSPGGTVTLTCGS*
*STGAVTASNYANWVQQKPGQCPRGLIGGHNNRPPGVPARFSGSLLGGKAALTLLGAQPE*
*DEAEYYCALWYSDHWVIGGGTKLTVLG*__TPLGDTTHT__SGRHGDEDTYYLQVRGRENF
EILMKLKESLELMELVPQPLVDSYRQQQLLQRP__GGSGGAP__HHHHHH

FIG. 41

LL2 MOUSE VL-(G4S)6-LL2 MOUSE VH-(G4S)4-hC825 VH-(G4S)6-hC825 VL-spacer-linker-P73-spacer *(SEQ ID NO: 56)*

MGWSCIILFLVATATGVHS*DIQLTQSPSSLAVSAGENVTMSCKSSQSVLYSANHKNYLAW*
*YQQKPGQSPKLLIYWASTRESGVPDRFTGSGSGTDFTLTISRVQVEDLAIYYCHQYLSSWTF*
*GGGTKLEIKR*__GGGGSGGGGSGGGGSGGGGSGGGGSGGGGS__*QVQLQESGAELSKP*
*GASVKMSCKASGYTFTSYWLHWIKQRPGQGLEWIGYINPRNDYTEYNQNFKDKATLTADK*
*SSSTAYMQLSSLTSEDSAVYYCARRDITTFYWGQGTTLTVSS*__GGGGSGGGGSGGGGSGG__
__GGS__*HVQLVESGGGLVQPGGSLRLSCAASGFSLTDYGVHWVRQAPGKGLEWLGVIWSGG*
*GTAYNTALISRFTISRDNSKNTLYLQMNSLRAEDTAVYYCARRGSYPYNYFDAWGCGTLVTV*
*SS*__GGGGSGGGGSGGGGSGGGGSGGGGSGGGGS__*QAVVTQEPSLTVSPGGTVTLTCGS*
*STGAVTASNYANWVQQKPGQCPRGLIGGHNNRPPGVPARFSGSLLGGKAALTLLGAQPE*
*DEAEYYCALWYSDHWVIGGGTKLTVLG*__TPLGDTTHT__SGRHGDEDTYYLQVRGRENF
EILMKLKESLELMELVPQPLVDSYRQQQLLQRP__GGSGGA__

FIG. 42

LL2 MOUSE VH-(G4S)6-LL2 MOUSE VL-(G4S)4-hC825 VH-(G4S)6-hC825 VL-spacer-linker-P73-spacer-H6 *(SEQ ID NO: 57)*

MGWSCIILFLVATATGVHS*QVQLQESGAELSKPGASVKMSCKASGYTFTSYWLHWIKQR*
*PGQGLEWIGYINPRNDYTEYNQNFKDKATLTADKSSSTAYMQLSSLTSEDSAVYYCARRDIT*
*TFYWGQGTTLTVSS*GGGGSGGGGSGGGGSGGGGSGGGGSGGGGS*DIQLTQSPSSLA*
*VSAGENVTMSCKSSQSVLYSANHKNYLAWYQQKPGQSPKLLIYWASTRESGVPDRFTGSGS*
*GTDFTLTISRVQVEDLAIYYCHQYLSSWTFGGGTKLEIKR*GGGGSGGGGSGGGGSGGG
GS*HVQLVESGGGLVQPGGSLRLSCAASGFSLTDYGVHWVRQAPGKGLEWLGVIWSGGGT*
*AYNTALISRFTISRDNSKNTLYLQMNSLRAEDTAVYYCARRGSYPYNYFDAWGCGTLVTVSS*
GGGGSGGGGSGGGGSGGGGSGGGGSGGGGS*QAVVTQEPSLTVSPGGTVTLTCGSS*
*TGAVTASNYANWVQQKPGQCPRGLIGGHNNRPPGVPARFSGSLLGGKAALTLLGAQPED*
*EAEYYCALWYSDHWVIGGGTKLTVLG*TPLGDTTHTSGRHGDEDTYYLQVRGRENFE
ILMKLKESLELMELVPQPLVDSYRQQQLLQRPGGSGGAPHHHHHH

FIG. 43

LL2 MOUSE VH-(G4S)6-LL2 MOUSE VL-(G4S)4-hC825 VH-(G4S)6-hC825 VL-spacer-linker-P73-spacer *(SEQ ID NO: 58)*

MGWSCIILFLVATATGVHS*QVQLQESGAELSKPGASVKMSCKASGYTFTSYWLHWIKQR*
*PGQGLEWIGYINPRNDYTEYNQNFKDKATLTADKSSSTAYMQLSSLTSEDSAVYYCARRDIT*
*TFYWGQGTTLTVSS*GGGGSGGGGSGGGGSGGGGSGGGGSGGGGS*DIQLTQSPSSLA*
*VSAGENVTMSCKSSQSVLYSANHKNYLAWYQQKPGQSPKLLIYWASTRESGVPDRFTGSGS*
*GTDFTLTISRVQVEDLAIYYCHQYLSSWTFGGGTKLEIKR*GGGGSGGGGSGGGGSGGG
GS*HVQLVESGGGLVQPGGSLRLSCAASGFSLTDYGVHWVRQAPGKGLEWLGVIWSGGGT*
*AYNTALISRFTISRDNSKNTLYLQMNSLRAEDTAVYYCARRGSYPYNYFDAWGCGTLVTVSS*
GGGGSGGGGSGGGGSGGGGSGGGGSGGGGS*QAVVTQEPSLTVSPGGTVTLTCGSS*
*TGAVTASNYANWVQQKPGQCPRGLIGGHNNRPPGVPARFSGSLLGGKAALTLLGAQPED*
*EAEYYCALWYSDHWVIGGGTKLTVLG*TPLGDTTHTSGRHGDEDTYYLQVRGRENFE**
ILMKLKESLELMELVPQPLVDSYRQQQLLQRPGGSGGA

FIG. 44 hLL2 VL1-(G4S)6-hLL2 VH4-(G4S)4-hC825 VH-(G4S)6-hC825 VL-spacer-linker-P53-spacer-H6 *(SEQ ID NO: 59)*

MGWSCIILFLVATATGVHS*DIVLTQSPDSLAVSAGERVTMNCKSSQSVLYSANHKNYLAW*
*YQQKPGQPPKLLIYWASTRESGVPDRFSGSGSGTDFTLTISSVQAEDVAIYYCHQYLSSWTF*
*GGGTKLEIKR*GGGGSGGGGSGGGGSGGGGSGGGGSGGGGS*QVQLQQSGAEVKKP*
*GASVKMSCKASGYTFTSYWLHWIRQAPGQRLEWMGYINPRNDYTEYNQKFQGRATITAD*
*KSASTAYMELSSLRSEDTAVYYCARRDITTFYWGQGTTLTVSS*GGGGSGGGGSGGGGSG
GGGS*HVQLVESGGGLVQPGGSLRLSCAASGFSLTDYGVHWVRQAPGKGLEWLGVIWSG*
*GGTAYNTALISRFTISRDNSKNTLYLQMNSLRAEDTAVYYCARRGSYPYNYFDAWGCGTLV*
*TVSS*GGGGSGGGGSGGGGSGGGGSGGGGSGGGGS*QAVVTQEPSLTVSPGGTVTLTC*
*GSSTGAVTASNYANWVQQKPGQCPRGLIGGHNNRPPGVPARFSGSLLGGKAALTLLGAQ*
*PEDEAEYYCALWYSDHWVIGGGTKLTVLG*TPLGDTTHTSGKPLDGEYFTLQIRGRER
FEMFRELNEALELKDAQAGKEPGGSGGAPHHHHHH

FIG. 45 hLL2 VL1-(G4S)6-hLL2 VH4-(G4S)4-hC825 VH-(G4S)6-hC825 VL-spacer-linker-P53-spacer *(SEQ ID NO: 60)*

MGWSCIILFLVATATGVHS*DIVLTQSPDSLAVSAGERVTMNCKSSQSVLYSANHKNYLAW YQQKPGQPPKLLIYWASTRESGVPDRFSGSGSGTDFTLTISSVQAEDVAIYYCHQYLSSWTF GGGTKLEIKR*GGGGSGGGGSGGGGSGGGGSGGGGSGGGGS*QVQLQQSGAEVKKP GASVKMSCKASGYTFTSYWLHWIRQAPGQRLEWMGYINPRNDYTEYNQKFQGRATITAD KSASTAYMELSSLRSEDTAVYYCARRDITTFYWGQGTTLTVSS*GGGGSGGGGSGGGGSG GGGS*HVQLVESGGGLVQPGGSLRLSCAASGFSLTDYGVHWVRQAPGKGLEWLGVIWSG GGTAYNTALISRFTISRDNSKNTLYLQMNSLRAEDTAVYYCARRGSYPYNYFDAWGCGTLV TVSS*GGGGSGGGGSGGGGSGGGGSGGGGSGGGGS*QAVVTQEPSLTVSPGGTVTLTC GSSTGAVTASNYANWVQQKPGQCPRGLIGGHNNRPPGVPARFSGSLLGGKAALTLLGAQ PEDEAEYYCALWYSDHWVIGGGTKLTVLG*TPLGDTTHTSGKPLDGEYFTLQIRGRER FEMFRELNEALELKDAQAGKEPGGSGGA

FIG. 46 hLL2 VH4-(G4S)6-hLL2 VL1-(G4S)4-hC825 VH-(G4S)6-hC825 VL-spacer-linker-P53-spacer-H6 *(SEQ ID NO: 61)*

MGWSCIILFLVATATGVHS*QVQLQQSGAEVKKPGASVKMSCKASGYTFTSYWLHWIRQA*
*PGQRLEWMGYINPRNDYTEYNQKFQGRATITADKSASTAYMELSSLRSEDTAVYYCARRDI*
*TTFYWGQGTTLTVSS*GGGGSGGGGSGGGGSGGGGSGGGGSGGGGS*DIVLTQSPDSL*
*AVSAGERVTMNCKSSQSVLYSANHKNYLAWYQQKPGQPPKLLIYWASTRESGVPDRFSGS*
*GSGTDFTLTISSVQAEDVAIYYCHQYLSSWTFGGGTKLEIKR*GGGGSGGGGSGGGGSG
GGGS*HVQLVESGGGLVQPGGSLRLSCAASGFSLTDYGVHWVRQAPGKGLEWLGVIWSG*
*GGTAYNTALISRFTISRDNSKNTLYLQMNSLRAEDTAVYYCARRGSYPYNYFDAWGCGTLV*
*TVSS*GGGGSGGGGSGGGGSGGGGSGGGGSGGGGS*QAVVTQEPSLTVSPGGTVTLTC*
*GSSTGAVTASNYANWVQQKPGQCPRGLIGGHNNRPPGVPARFSGSLLGGKAALTLLGAQ*
*PEDEAEYYCALWYSDHWVIGGGTKLTVLG*TPLGDTTHTSGKPLDGEYFTLQIRGRER
FEMFRELNEALELKDAQAGKEPGGSGGAPHHHHHH

FIG. 47 hLL2 VH4-(G4S)6-hLL2 VL1-(G4S)4-hC825 VH-(G4S)6-hC825 VL-spacer-linker-P53-spacer *(SEQ ID NO: 62)*

MGWSCIILFLVATATGVHS*QVQLQQSGAEVKKPGASVKMSCKASGYTFTSYWLHWIRQAPGQRLEWMGYINPRNDYTEYNQKFQGRATITADKSASTAYMELSSLRSEDTAVYYCARRDITTFYWGQGTTLTVSS*GGGGSGGGGSGGGGSGGGGSGGGGSGGGGS*DIVLTQSPDSLAVSAGERVTMNCKSSQSVLYSANHKNYLAWYQQKPGQPPKLLIYWASTRESGVPDRFSGSGSGTDFTLTISSVQAEDVAIYYCHQYLSSWTFGGGTKLEIKR*GGGGSGGGGSGGGGSGGGGS*HVQLVESGGGLVQPGGSLRLSCAASGFSLTDYGVHWVRQAPGKGLEWLGVIWSGGGTAYNTALISRFTISRDNSKNTLYLQMNSLRAEDTAVYYCARRGSYPYNYFDAWGCGTLVTVSS*GGGGSGGGGSGGGGSGGGGSGGGGSGGGGS*QAVVTQEPSLTVSPGGTVTLTCGSSTGAVTASNYANWVQQKPGQCPRGLIGGHNNRPPGVPARFSGSLLGGKAALTLLGAQPEDEAEYYCALWYSDHWVIGGGTKLTVLG*TPLGDTTHTSGKPLDGEYFTLQIRGRERFEMFRELNEALELKDAQAGKEPGGSGGA

FIG. 48 hLL2 VL1-(G4S)6-hLL2 VH4-(G4S)4-hC825 VH-(G4S)6-hC825 VL-spacer-linker-P63-spacer-H6 *(SEQ ID NO: 63)*

MGWSCIILFLVATATGVHSDIVLTQSPDSLAVSAGERVTMNCKSSQSVLYSANHKNYLAW
YQQKPGQPPKLLIYWASTRESGVPDRFSGSGSGTDFTLTISSVQAEDVAIYYCHQYLSSWTF
GGGTKLEIKRGGGGSGGGGSGGGGSGGGGSGGGGSGGGGSQVQLQQSGAEVKKP
GASVKMSCKASGYTFTSYWLHWIRQAPGQRLEWMGYINPRNDYTEYNQKFQGRATITAD
KSASTAYMELSSLRSEDTAVYYCARRDITTFYWGQGTTLTVSSGGGGSGGGGSGGGGSG
GGGSHVQLVESGGGLVQPGGSLRLSCAASGFSLTDYGVHWVRQAPGKGLEWLGVIWSG
GGTAYNTALISRFTISRDNSKNTLYLQMNSLRAEDTAVYYCARRGSYPYNYFDAWGCGTLV
TVSSGGGGSGGGGSGGGGSGGGGSGGGGSGGGGSQAVVTQEPSLTVSPGGTVTLTC
GSSTGAVTASNYANWVQQKPGQCPRGLIGGHNNRPPGVPARFSGSLLGGKAALTLLGAQ
PEDEAEYYCALWYSDHWVIGGGTKLTVLGTPLGDTTHTSGRSPDDELLYLPVRGRET
YEMLLKIKESLELMQYLPQHTIETYRQQQQQHQHLLQKQGGSGGAPHHHHH
H

FIG. 49 hLL2 VL1-(G4S)6-hLL2 VH4-(G4S)4-hC825 VH-(G4S)6-hC825 VL-spacer-linker-P63-spacer *(SEQ ID NO: 64)*

MGWSCIILFLVATATGVHS*DIVLTQSPDSLAVSAGERVTMNCKSSQSVLYSANHKNYLAW*
*YQQKPGQPPKLLIYWASTRESGVPDRFSGSGSGTDFTLTISSVQAEDVAIYYCHQYLSSWTF*
*GGGTKLEIKR*__GGGGSGGGGSGGGGSGGGGSGGGGSGGGGS__*QVQLQQSGAEVKKP*
*GASVKMSCKASGYTFTSYWLHWIRQAPGQRLEWMGYINPRNDYTEYNQKFQGRATITAD*
*KSASTAYMELSSLRSEDTAVYYCARRDITTFYWGQGTTLTVSS*__GGGGSGGGGSGGGGSG__
__GGGS__*HVQLVESGGGLVQPGGSLRLSCAASGFSLTDYGVHWVRQAPGKGLEWLGVIWSG*
*GGTAYNTALISRFTISRDNSKNTLYLQMNSLRAEDTAVYYCARRGSYPYNYFDAWGCGTLV*
*TVSS*__GGGGSGGGGSGGGGSGGGGSGGGGSGGGGS__*QAVVTQEPSLTVSPGGTVTLTC*
*GSSTGAVTASNYANWVQQKPGQCPRGLIGGHNNRPPGVPARFSGSLLGGKAALTLLGAQ*
*PEDEAEYYCALWYSDHWVIGGGTKLTVLG*__TPLGDTTHT__SGRSPDDELLYLPVRGRET
YEMLLKIKESLELMQYLPQHTIETYRQQQQQHQHLLQKQGGSGGA

FIG. 50 hLL2 VH4-(G4S)6-hLL2 VL1-(G4S)4-hC825 VH-(G4S)6-hC825 VL-spacer-linker-P63-spacer-H6 *(SEQ ID NO: 65)*

MGWSCIILFLVATATGVHS*QVQLQQSGAEVKKPGASVKMSCKASGYTFTSYWLHWIRQA*
*PGQRLEWMGYINPRNDYTEYNQKFQGRATITADKSASTAYMELSSLRSEDTAVYYCARRDI*
*TTFYWGQGTTLTVSS*GGGGSGGGGSGGGGSGGGGSGGGGSGGGGS*DIVLTQSPDSL*
*AVSAGERVTMNCKSSQSVLYSANHKNYLAWYQQKPGQPPKLLIYWASTRESGVPDRFSGS*
*GSGTDFTLTISSVQAEDVAIYYCHQYLSSWTFGGGTKLEIKR*GGGGSGGGGSGGGGSG
GGGS*HVQLVESGGGLVQPGGSLRLSCAASGFSLTDYGVHWVRQAPGKGLEWLGVIWSG*
*GGTAYNTALISRFTISRDNSKNTLYLQMNSLRAEDTAVYYCARRGSYPYNYFDAWGCGTLV*
*TVSS*GGGGSGGGGSGGGGSGGGGSGGGGSGGGGS*QAVVTQEPSLTVSPGGTVTLTC*
*GSSTGAVTASNYANWVQQKPGQCPRGLIGGHNNRPPGVPARFSGSLLGGKAALTLLGAQ*
*PEDEAEYYCALWYSDHWVIGGGTKLTVLG*TPLGDTTHTSGRSPDDELLYLPVRGRET
YEMLLKIKESLELMQYLPQHTIETYRQQQQQHQHLLQKQGGSGGAPHHHHH
H

FIG. 51 hLL2 VH4-(G4S)6-hLL2 VL1-(G4S)4-hC825 VH-(G4S)6-hC825 VL-spacer-linker-P63-spacer *(SEQ ID NO: 66)*

MGWSCIILFLVATATGVHSQVQLQQSGAEVKKPGASVKMSCKASGYTFTSYWLHWIRQA
PGQRLEWMGYINPRNDYTEYNQKFQGRATITADKSASTAYMELSSLRSEDTAVYYCARRDI
TTFYWGQGTTLTVSSGGGGSGGGGSGGGGSGGGGSGGGGSGGGGSDIVLTQSPDSL
AVSAGERVTMNCKSSQSVLYSANHKNYLAWYQQKPGQPPKLLIYWASTRESGVPDRFSGS
GSGTDFTLTISSVQAEDVAIYYCHQYLSSWTFGGGTKLEIKRGGGGSGGGGSGGGGSG
GGGSHVQLVESGGGLVQPGGSLRLSCAASGFSLTDYGVHWVRQAPGKGLEWLGVIWSG
GGTAYNTALISRFTISRDNSKNTLYLQMNSLRAEDTAVYYCARRGSYPYNYFDAWGCGTLV
TVSSGGGGSGGGGSGGGGSGGGGSGGGGSGGGGSQAVVTQEPSLTVSPGGTVTLTC
GSSTGAVTASNYANWVQQKPGQCPRGLIGGHNNRPPGVPARFSGSLLGGKAALTLLGAQ
PEDEAEYYCALWYSDHWVIGGGTKLTVLGTPLGDTTHTSGRSPDDELLYLPVRGRET
YEMLLKIKESLELMQYLPQHTIETYRQQQQQHQHLLQKQGGSGGA

FIG. 52 hLL2 VL1-(G4S)6-hLL2 VH4-(G4S)4-hC825 VH-(G4S)6-hC825 VL-spacer-linker-P73-spacer-H6 *(SEQ ID NO: 67)*

MGWSCIILFLVATATGVHS*DIVLTQSPDSLAVSAGERVTMNCKSSQSVLYSANHKNYLAW YQQKPGQPPKLLIYWASTRESGVPDRFSGSGSGTDFTLTISSVQAEDVAIYYCHQYLSSWTF GGGTKLEIKR*GGGGSGGGGSGGGGSGGGGSGGGGSGGGGS*QVQLQQSGAEVKKP GASVKMSCKASGYTFTSYWLHWIRQAPGQRLEWMGYINPRNDYTEYNQKFQGRATITAD KSASTAYMELSSLRSEDTAVYYCARRDITTFYWGQGTTLTVSS*GGGGSGGGGSGGGGSG GGGS*HVQLVESGGGLVQPGGSLRLSCAASGFSLTDYGVHWVRQAPGKGLEWLGVIWSG GGTAYNTALISRFTISRDNSKNTLYLQMNSLRAEDTAVYYCARRGSYPYNYFDAWGCGTLV TVSS*GGGGSGGGGSGGGGSGGGGSGGGGSGGGGS*QAVVTQEPSLTVSPGGTVTLTC GSSTGAVTASNYANWVQQKPGQCPRGLIGGHNNRPPGVPARFSGSLLGGKAALTLLGAQ PEDEAEYYCALWYSDHWVIGGGTKLTVLG*TPLGDTTHTSGRHGDEDTYYLQVRGRE NFEILMKLKESLELMELVPQPLVDSYRQQQQLLQRPGGSGGAPHHHHHH

FIG. 53 hLL2 VL1-(G4S)6-hLL2 VH4-(G4S)4-hC825 VH-(G4S)6-hC825 VL-spacer-linker-P73-spacer *(SEQ ID NO: 68)*

MGWSCIILFLVATATGVHS*DIVLTQSPDSLAVSAGERVTMNCKSSQSVLYSANHKNYLAW*
*YQQKPGQPPKLLIYWASTRESGVPDRFSGSGSGTDFTLTISSVQAEDVAIYYCHQYLSSWTF*
*GGGTKLEIKR*__GGGGSGGGGSGGGGSGGGGSGGGGSGGGGS__*QVQLQQSGAEVKKP*
*GASVKMSCKASGYTFTSYWLHWIRQAPGQRLEWMGYINPRNDYTEYNQKFQGRATITAD*
*KSASTAYMELSSLRSEDTAVYYCARRDITTFYWGQGTTLTVSS*__GGGGSGGGGSGGGGSG__
__GGGS__*HVQLVESGGGLVQPGGSLRLSCAASGFSLTDYGVHWVRQAPGKGLEWLGVIWSG*
*GGTAYNTALISRFTISRDNSKNTLYLQMNSLRAEDTAVYYCARRGSYPYNYFDAWGCGTLV*
*TVSS*__GGGGSGGGGSGGGGSGGGGSGGGGSGGGGS__*QAVVTQEPSLTVSPGGTVTLTC*
*GSSTGAVTASNYANWVQQKPGQCPRGLIGGHNNRPPGVPARFSGSLLGGKAALTLLGAQ*
*PEDEAEYYCALWYSDHWVIGGGTKLTVLG*__TPLGDTTHT__SGRHGDEDTYYLQVRGRE
NFEILMKLKESLELMELVPQPLVDSYRQQQLLQRP__GGSGGA__

FIG. 54 hLL2 VH4-(G4S)6-hLL2 VL1-(G4S)4-hC825 VH-(G4S)6-hC825 VL-spacer-linker-P73-spacer-H6 *(SEQ ID NO: 69)*

MGWSCIILFLVATATGVHS*QVQLQQSGAEVKKPGASVKMSCKASGYTFTSYWLHWIRQA*
*PGQRLEWMGYINPRNDYTEYNQKFQGRATITADKSASTAYMELSSLRSEDTAVYYCARRDI*
*TTFYWGQGTTLTVSS*GGGGSGGGGSGGGGSGGGGSGGGGSGGGGS*DIVLTQSPDSL*
*AVSAGERVTMNCKSSQSVLYSANHKNYLAWYQQKPGQPPKLLIYWASTRESGVPDRFSGS*
*GSGTDFTLTISSVQAEDVAIYYCHQYLSSWTFGGGTKLEIKR*GGGGSGGGGSGGGGSG
GGGS*HVQLVESGGGLVQPGGSLRLSCAASGFSLTDYGVHWVRQAPGKGLEWLGVIWSG*
*GGTAYNTALISRFTISRDNSKNTLYLQMNSLRAEDTAVYYCARRGSYPYNYFDAWGCGTLV*
*TVSS*GGGGSGGGGSGGGGSGGGGSGGGGSGGGGS*QAVVTQEPSLTVSPGGTVTLTC*
*GSSTGAVTASNYANWVQQKPGQCPRGLIGGHNNRPPGVPARFSGSLLGGKAALTLLGAQ*
*PEDEAEYYCALWYSDHWVIGGGTKLTVLG*TPLGDTTHTSGRHGDEDTYYLQVRGRE
NFEILMKLKESLELMELVPQPLVDSYRQQQLLQRPGGSGGAPHHHHHH

FIG. 55

**hLL2 VH4-(G4S)6-hLL2 VL1-(G4S)4-hC825 VH-(G4S)6-hC825 VL-spacer-linker-P73-spacer *(SEQ ID NO: 70)***

MGWSCIILFLVATATGVHS*QVQLQQSGAEVKKPGASVKMSCKASGYTFTSYWLHWIRQA*
*PGQRLEWMGYINPRNDYTEYNQKFQGRATITADKSASTAYMELSSLRSEDTAVYYCARRDI*
*TTFYWGQGTTLTVSS*GGGGSGGGGSGGGGSGGGGSGGGGSGGGGS*DIVLTQSPDSL*
*AVSAGERVTMNCKSSQSVLYSANHKNYLAWYQQKPGQPPKLLIYWASTRESGVPDRFSGS*
*GSGTDFTLTISSVQAEDVAIYYCHQYLSSWTFGGGTKLEIKR*GGGGSGGGGSGGGGSG
GGGS*HVQLVESGGGLVQPGGSLRLSCAASGFSLTDYGVHWVRQAPGKGLEWLGVIWSG*
*GGTAYNTALISRFTISRDNSKNTLYLQMNSLRAEDTAVYYCARRGSYPYNYFDAWGCGTLV*
*TVSS*GGGGSGGGGSGGGGSGGGGSGGGGSGGGGS*QAVVTQEPSLTVSPGGTVTLTC*
*GSSTGAVTASNYANWVQQKPGQCPRGLIGGHNNRPPGVPARFSGSLLGGKAALTLLGAQ*
*PEDEAEYYCALWYSDHWVIGGGTKLTVLG*TPLGDTTHTSGRHGDEDTYYLQVRGRE
NFEILMKLKESLELMELVPQPLVDSYRQQQLLQRPGGSGGA

FIG. 56 hLL2 VL1-(G4S)6-hLL2 VH10-(G4S)4-hC825 VH-(G4S)6-hC825 VL-spacer-linker-P53-spacer-H6 *(SEQ ID NO: 71)*

<u>MGWSCIILFLVATATGVHS</u>*DIVLTQSPDSLAVSAGERVTMNCKSSQSVLYSANHKNYLAWYQQKPGQPPKLLIYWASTRESGVPDRFSGSGSGTDFTLTISSVQAEDVAIYYCHQYLSSWTFGGGTKLEIKR*<u>GGGGSGGGGSGGGGSGGGGSGGGGSGGGGS</u>*QVQLVQSGAEVKKPGASVKVSCKASGYTFTSYWLHWVRQAPGQRLEWMGYINPRNDYTEYNQNFKDRVTLTADKSASTAYMELSSLRSEDTAVYYCARRDITTFYWGQGTTLTVSS*<u>GGGGSGGGGSGGGGSGGGGS</u>*HVQLVESGGGLVQPGGSLRLSCAASGFSLTDYGVHWVRQAPGKGLEWLGVIWSGGGTAYNTALISRFTISRDNSKNTLYLQMNSLRAEDTAVYYCARRGSYPYNYFDAWGCGTLVTVSS*<u>GGGGSGGGGSGGGGSGGGGSGGGGSGGGGS</u>*QAVVTQEPSLTVSPGGTVTLTCGSSTGAVTASNYANWVQQKPGQCPRGLIGGHNNRPPGVPARFSGSLLGGKAALTLLGAQPEDEAEYYCALWYSDHWVIGGGTKLTVLG*<u>TPLGDTTHT</u>SGKPLDGEYFTLQIRGRERFEMFRELNEALELKDAQAGKEP<u>GGSGGAP</u>HHHHHH

FIG. 57 hLL2 VL1-(G4S)6-hLL2 VH10-(G4S)4-hC825 VH-(G4S)6-hC825 VL-spacer-linker-P53-spacer *(SEQ ID NO: 72)*

MGWSCIILFLVATATGVHS*DIVLTQSPDSLAVSAGERVTMNCKSSQSVLYSANHKNYLAWYQQKPGQPPKLLIYWASTRESGVPDRFSGSGSGTDFTLTISSVQAEDVAIYYCHQYLSSWTFGGGTKLEIKR*GGGGSGGGGSGGGGSGGGGSGGGGSGGGGS*QVQLVQSGAEVKKPGASVKVSCKASGYTFTSYWLHWVRQAPGQRLEWMGYINPRNDYTEYNQNFKDRVTLTADKSASTAYMELSSLRSEDTAVYYCARRDITTFYWGQGTTLTVSS*GGGGSGGGGSGGGGSGGGGS*HVQLVESGGGLVQPGGSLRLSCAASGFSLTDYGVHWVRQAPGKGLEWLGVIWSGGGTAYNTALISRFTISRDNSKNTLYLQMNSLRAEDTAVYYCARRGSYPYNYFDAWGCGTLVTVSS*GGGGSGGGGSGGGGSGGGGSGGGGSGGGGS*QAVVTQEPSLTVSPGGTVTLTCGSSTGAVTASNYANWVQQKPGQCPRGLIGGHNNRPPGVPARFSGSLLGGKAALTLLGAQPEDEAEYYCALWYSDHWVIGGGTKLTVLG*TPLGDTTHTSGKPLDGEYFTLQIRGRERFEMFRELNEALELKDAQAGKEPGGSGGA

FIG. 58 hLL2 VH10-(G4S)6-hLL2 VL1-(G4S)4-hC825 VH-(G4S)6-hC825 VL-spacer-linker-P53-spacer-H6 *(SEQ ID NO: 73)*

MGWSCIILFLVATATGVHS*QVQLVQSGAEVKKPGASVKVSCKASGYTFTSYWLHWVRQA*
*PGQRLEWMGYINPRNDYTEYNQNFKDRVTLTADKSASTAYMELSSLRSEDTAVYYCARRDI*
*TTFYWGQGTTLTVSS*GGGGSGGGGSGGGGSGGGGSGGGGSGGGGS*DIVLTQSPDSL*
*AVSAGERVTMNCKSSQSVLYSANHKNYLAWYQQKPGQPPKLLIYWASTRESGVPDRFSGS*
*GSGTDFTLTISSVQAEDVAIYYCHQYLSSWTFGGGTKLEIKR*GGGGSGGGGSGGGGSG
GGGS*HVQLVESGGGLVQPGGSLRLSCAASGFSLTDYGVHWVRQAPGKGLEWLGVIWSG*
*GGTAYNTALISRFTISRDNSKNTLYLQMNSLRAEDTAVYYCARRGSYPYNYFDAWGCGTLV*
*TVSS*GGGGSGGGGSGGGGSGGGGSGGGGSGGGGS*QAVVTQEPSLTVSPGGTVTLTC*
*GSSTGAVTASNYANWVQQKPGQCPRGLIGGHNNRPPGVPARFSGSLLGGKAALTLLGAQ*
*PEDEAEYYCALWYSDHWVIGGGTKLTVLG*TPLGDTTHTSGKPLDGEYFTLQIRGRER
FEMFRELNEALELKDAQAGKEPGGSGGAPHHHHHH

FIG. 59 hLL2 VH10-(G4S)6-hLL2 VL1-(G4S)4-hC825 VH-(G4S)6-hC825 VL-spacer-linker-P53-spacer *(SEQ ID NO: 74)*

MGWSCIILFLVATATGVHS*QVQLVQSGAEVKKPGASVKVSCKASGYTFTSYWLHWVRQAPGQRLEWMGYINPRNDYTEYNQNFKDRVTLTADKSASTAYMELSSLRSEDTAVYYCARRDITTFYWGQGTTLTVSS*GGGGSGGGGSGGGGSGGGGSGGGGSGGGGS*DIVLTQSPDSLAVSAGERVTMNCKSSQSVLYSANHKNYLAWYQQKPGQPPKLLIYWASTRESGVPDRFSGSGSGTDFTLTISSVQAEDVAIYYCHQYLSSWTFGGGTKLEIKR*GGGGSGGGGSGGGGSGGGGS*HVQLVESGGGLVQPGGSLRLSCAASGFSLTDYGVHWVRQAPGKGLEWLGVIWSGGGTAYNTALISRFTISRDNSKNTLYLQMNSLRAEDTAVYYCARRGSYPYNYFDAWGCGTLVTVSS*GGGGSGGGGSGGGGSGGGGSGGGGSGGGGS*QAVVTQEPSLTVSPGGTVTLTCGSSTGAVTASNYANWVQQKPGQCPRGLIGGHNNRPPGVPARFSGSLLGGKAALTLLGAQPEDEAEYYCALWYSDHWVIGGGTKLTVLG*TPLGDTTHTSGKPLDGEYFTLQIRGRERFEMFRELNEALELKDAQAGKEPGGSGGA

FIG. 60 hLL2 VL1-(G4S)6-hLL2 VH10-(G4S)4-hC825 VH-(G4S)6-hC825 VL-spacer-linker-P63-spacer-H6 *(SEQ ID NO: 75)*

MGWSCIILFLVATATGVHS*DIVLTQSPDSLAVSAGERVTMNCKSSQSVLYSANHKNYLAW*
*YQQKPGQPPKLLIYWASTRESGVPDRFSGSGSGTDFTLTISSVQAEDVAIYYCHQYLSSWTF*
*GGGTKLEIKR*GGGGSGGGGSGGGGSGGGGSGGGGSGGGGS*QVQLVQSGAEVKKP*
*GASVKVSCKASGYTFTSYWLHWVRQAPGQRLEWMGYINPRNDYTEYNQNFKDRVTLTAD*
*KSASTAYMELSSLRSEDTAVYYCARRDITTFYWGQGTTLTVSS*GGGGSGGGGSGGGGSG
GGGS*HVQLVESGGGLVQPGGSLRLSCAASGFSLTDYGVHWVRQAPGKGLEWLGVIWSG*
*GGTAYNTALISRFTISRDNSKNTLYLQMNSLRAEDTAVYYCARRGSYPYNYFDAWGCGTLV*
*TVSS*GGGGSGGGGSGGGGSGGGGSGGGGSGGGGS*QAVVTQEPSLTVSPGGTVTLTC*
*GSSTGAVTASNYANWVQQKPGQCPRGLIGGHNNRPPGVPARFSGSLLGGKAALTLLGAQ*
*PEDEAEYYCALWYSDHWVIGGGTKLTVLG*TPLGDTTHTSGRSPDDELLYLPVRGRET
YEMLLKIKESLELMQYLPQHTIETYRQQQQQHQHLLQKQGGSGGAPHHHHH
H

FIG. 61 hLL2 VL1-(G4S)6-hLL2 VH10-(G4S)4-hC825 VH-(G4S)6-hC825 VL-spacer-linker-P63-spacer *(SEQ ID NO: 76)*

MGWSCIILFLVATATGVHS*DIVLTQSPDSLAVSAGERVTMNCKSSQSVLYSANHKNYLAW YQQKPGQPPKLLIYWASTRESGVPDRFSGSGSGTDFTLTISSVQAEDVAIYYCHQYLSSWTF GGGTKLEIKR*__GGGGSGGGGSGGGGSGGGGSGGGGSGGGGS__*QVQLVQSGAEVKKP GASVKVSCKASGYTFTSYWLHWVRQAPGQRLEWMGYINPRNDYTEYNQNFKDRVTLTAD KSASTAYMELSSLRSEDTAVYYCARRDITTFYWGQGTTLTVSS*__GGGGSGGGGSGGGGSG GGGS__*HVQLVESGGGLVQPGGSLRLSCAASGFSLTDYGVHWVRQAPGKGLEWLGVIWSG GGTAYNTALISRFTISRDNSKNTLYLQMNSLRAEDTAVYYCARRGSYPYNYFDAWGCGTLV TVSS*__GGGGSGGGGSGGGGSGGGGSGGGGSGGGGS__*QAVVTQEPSLTVSPGGTVTLTC GSSTGAVTASNYANWVQQKPGQCPRGLIGGHNNRPPGVPARFSGSLLGGKAALTLLGAQ PEDEAEYYCALWYSDHWVIGGGTKLTVLG*__TPLGDTTHT__SGRSPDDELLYLPVRGRET YEMLLKIKESLELMQYLPQHTIETYRQQQQQHQHLLQKQ__GGSGGA__

FIG. 62 hLL2 VH10-(G4S)6-hLL2 VL1-(G4S)4-hC825 VH-(G4S)6-hC825 VL-spacer-linker-P63-spacer-H6 *(SEQ ID NO: 77)*

MGWSCIILFLVATATGVHS*QVQLVQSGAEVKKPGASVKVSCKASGYTFTSYWLHWVRQA*
*PGQRLEWMGYINPRNDYTEYNQNFKDRVTLTADKSASTAYMELSSLRSEDTAVYYCARRDI*
*TTFYWGQGTTLTVSS*GGGGSGGGGSGGGGSGGGGSGGGGSGGGGS*DIVLTQSPDSL*
*AVSAGERVTMNCKSSQSVLYSANHKNYLAWYQQKPGQPPKLLIYWASTRESGVPDRFSGS*
*GSGTDFTLTISSVQAEDVAIYYCHQYLSSWTFGGGTKLEIKR*GGGGSGGGGSGGGGSG
GGGS*HVQLVESGGGLVQPGGSLRLSCAASGFSLTDYGVHWVRQAPGKGLEWLGVIWSG*
*GGTAYNTALISRFTISRDNSKNTLYLQMNSLRAEDTAVYYCARRGSYPYNYFDAWGCGTLV*
*TVSS*GGGGSGGGGSGGGGSGGGGSGGGGSGGGGS*QAVVTQEPSLTVSPGGTVTLTC*
*GSSTGAVTASNYANWVQQKPGQCPRGLIGGHNNRPPGVPARFSGSLLGGKAALTLLGAQ*
*PEDEAEYYCALWYSDHWVIGGGTKLTVLG*TPLGDTTHTSGRSPDDELLYLPVRGRET
YEMLLKIKESLELMQYLPQHTIETYRQQQQQHQHLLQKQGGSGGAPHHHHH
H

FIG. 63 hLL2 VH10-(G4S)6-hLL2 VL1-(G4S)4-hC825 VH-(G4S)6-hC825 VL-spacer-linker-P63-spacer *(SEQ ID NO: 78)*

MGWSCIILFLVATATGVHS*QVQLVQSGAEVKKPGASVKVSCKASGYTFTSYWLHWVRQAPGQRLEWMGYINPRNDYTEYNQNFKDRVTLTADKSASTAYMELSSLRSEDTAVYYCARRDITTFYWGQGTTLTVSS*GGGGSGGGGSGGGGSGGGGSGGGGSGGGGS*DIVLTQSPDSLAVSAGERVTMNCKSSQSVLYSANHKNYLAWYQQKPGQPPKLLIYWASTRESGVPDRFSGSGSGTDFTLTISSVQAEDVAIYYCHQYLSSWTFGGGTKLEIKR*GGGGSGGGGSGGGGSGGGGS*HVQLVESGGGLVQPGGSLRLSCAASGFSLTDYGVHWVRQAPGKGLEWLGVIWSGGGTAYNTALISRFTISRDNSKNTLYLQMNSLRAEDTAVYYCARRGSYPYNYFDAWGCGTLVTVSS*GGGGSGGGGSGGGGSGGGGSGGGGSGGGGS*QAVVTQEPSLTVSPGGTVTLTCGSSTGAVTASNYANWVQQKPGQCPRGLIGGHNNRPPGVPARFSGSLLGGKAALTLLGAQPEDEAEYYCALWYSDHWVIGGGTKLTVLG*TPLGDTTHTSGRSPDDELLYLPVRGRETYEMLLKIKESLELMQYLPQHTIETYRQQQQQHQHLLQKQGGSGGA

FIG. 64 hLL2 VL1-(G4S)6-hLL2 VH10-(G4S)4-hC825 VH-(G4S)6-hC825 VL-spacer-linker-P73-spacer-H6 *(SEQ ID NO: 79)*

MGWSCIILFLVATATGVHS*DIVLTQSPDSLAVSAGERVTMNCKSSQSVLYSANHKNYLAW YQQKPGQPPKLLIYWASTRESGVPDRFSGSGSGTDFTLTISSVQAEDVAIYYCHQYLSSWTF GGGTKLEIKR*__GGGGSGGGGSGGGGSGGGGSGGGGSGGGGS__*QVQLVQSGAEVKKP GASVKVSCKASGYTFTSYWLHWVRQAPGQRLEWMGYINPRNDYTEYNQNFKDRVTLTAD KSASTAYMELSSLRSEDTAVYYCARRDITTFYWGQGTTLTVSS*__GGGGSGGGGSGGGGSG GGGS__*HVQLVESGGGLVQPGGSLRLSCAASGFSLTDYGVHWVRQAPGKGLEWLGVIWSG GGTAYNTALISRFTISRDNSKNTLYLQMNSLRAEDTAVYYCARRGSYPYNYFDAWGCGTLV TVSS*__GGGGSGGGGSGGGGSGGGGSGGGGSGGGGS__*QAVVTQEPSLTVSPGGTVTLTC GSSTGAVTASNYANWVQQKPGQCPRGLIGGHNNRPPGVPARFSGSLLGGKAALTLLGAQ PEDEAEYYCALWYSDHWVIGGGTKLTVLG*__TPLGDTTHT__SGRHGDEDTYYLQVRGRE NFEILMKLKESLELMELVPQPLVDSYRQQQLLQRP__GGSGGAP__HHHHHH

FIG. 65 hLL2 VL1-(G4S)6-hLL2 VH10-(G4S)4-hC825 VH-(G4S)6-hC825 VL-spacer-linker-P73-spacer *(SEQ ID NO: 80)*

MGWSCIILFLVATATGVHS*DIVLTQSPDSLAVSAGERVTMNCKSSQSVLYSANHKNYLAW*
*YQQKPGQPPKLLIYWASTRESGVPDRFSGSGSGTDFTLTISSVQAEDVAIYYCHQYLSSWTF*
*GGGTKLEIKR*GGGGSGGGGSGGGGSGGGGSGGGGSGGGGS*QVQLVQSGAEVKKP*
*GASVKVSCKASGYTFTSYWLHWVRQAPGQRLEWMGYINPRNDYTEYNQNFKDRVTLTAD*
*KSASTAYMELSSLRSEDTAVYYCARRDITTFYWGQGTTLTVSS*GGGGSGGGGSGGGGSG
GGGS*HVQLVESGGGLVQPGGSLRLSCAASGFSLTDYGVHWVRQAPGKGLEWLGVIWSG*
*GGTAYNTALISRFTISRDNSKNTLYLQMNSLRAEDTAVYYCARRGSYPYNYFDAWGCGTLV*
*TVSS*GGGGSGGGGSGGGGSGGGGSGGGGSGGGGS*QAVVTQEPSLTVSPGGTVTLTC*
*GSSTGAVTASNYANWVQQKPGQCPRGLIGGHNNRPPGVPARFSGSLLGGKAALTLLGAQ*
*PEDEAEYYCALWYSDHWVIGGGTKLTVLG*TPLGDTTHTSGRHGDEDTYYLQVRGRE
NFEILMKLKESLELMELVPQPLVDSYRQQQLLQRPGGSGGA

FIG. 66 hLL2 VH10-(G4S)6-hLL2 VL1-(G4S)4-hC825 VH-(G4S)6-hC825 VL-spacer-linker-P73-spacer-H6 *(SEQ ID NO: 81)*

MGWSCIILFLVATATGVHS*QVQLVQSGAEVKKPGASVKVSCKASGYTFTSYWLHWVRQA*
*PGQRLEWMGYINPRNDYTEYNQNFKDRVTLTADKSASTAYMELSSLRSEDTAVYYCARRDI*
*TTFYWGQGTTLTVSS*GGGGSGGGGSGGGGSGGGGSGGGGSGGGGS*DIVLTQSPDSL*
*AVSAGERVTMNCKSSQSVLYSANHKNYLAWYQQKPGQPPKLLIYWASTRESGVPDRFSGS*
*GSGTDFTLTISSVQAEDVAIYYCHQYLSSWTFGGGTKLEIKR*GGGGSGGGGSGGGGSG
GGGS*HVQLVESGGGLVQPGGSLRLSCAASGFSLTDYGVHWVRQAPGKGLEWLGVIWSG*
*GGTAYNTALISRFTISRDNSKNTLYLQMNSLRAEDTAVYYCARRGSYPYNYFDAWGCGTLV*
*TVSS*GGGGSGGGGSGGGGSGGGGSGGGGSGGGGS*QAVVTQEPSLTVSPGGTVTLTC*
*GSSTGAVTASNYANWVQQKPGQCPRGLIGGHNNRPPGVPARFSGSLLGGKAALTLLGAQ*
*PEDEAEYYCALWYSDHWVIGGGTKLTVLG*TPLGDTTHTSGRHGDEDTYYLQVRGRE
NFEILMKLKESLELMELVPQPLVDSYRQQQLLQRPGGSGGAPHHHHHH

FIG. 67 hLL2 VH10-(G4S)6-hLL2 VL1-(G4S)4-hC825 VH-(G4S)6-hC825 VL-spacer-linker-P73-spacer *(SEQ ID NO: 82)*

MGWSCIILFLVATATGVHS*QVQLVQSGAEVKKPGASVKVSCKASGYTFTSYWLHWVRQA*
*PGQRLEWMGYINPRNDYTEYNQNFKDRVTLTADKSASTAYMELSSLRSEDTAVYYCARRDI*
*TTFYWGQGTTLTVSS*GGGGSGGGGSGGGGSGGGGSGGGGSGGGGS*DIVLTQSPDSL*
*AVSAGERVTMNCKSSQSVLYSANHKNYLAWYQQKPGQPPKLLIYWASTRESGVPDRFSGS*
*GSGTDFTLTISSVQAEDVAIYYCHQYLSSWTFGGGTKLEIKR*GGGGSGGGGSGGGGSG
GGGS*HVQLVESGGGLVQPGGSLRLSCAASGFSLTDYGVHWVRQAPGKGLEWLGVIWSG*
*GGTAYNTALISRFTISRDNSKNTLYLQMNSLRAEDTAVYYCARRGSYPYNYFDAWGCGTLV*
*TVSS*GGGGSGGGGSGGGGSGGGGSGGGGSGGGGS*QAVVTQEPSLTVSPGGTVTLTC*
*GSSTGAVTASNYANWVQQKPGQCPRGLIGGHNNRPPGVPARFSGSLLGGKAALTLLGAQ*
*PEDEAEYYCALWYSDHWVIGGGTKLTVLG*TPLGDTTHTSGRHGDEDTYYLQVRGRE
NFEILMKLKESLELMELVPQPLVDSYRQQQLLQRPGGSGGA

SEQUENCE LISTING

```
<160> NUMBER OF SEQ ID NOS: 108

<210> SEQ ID NO 1
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Glu Ser Gly Ala Glu Leu Ser Lys Pro Gly Ala
1               5                   10                  15

Ser Val Lys Met Ser Cys Lys Ala Ser Gly Tyr Thr Phe Thr Ser Tyr
            20                  25                  30

Trp Leu His Trp Ile Lys Gln Arg Pro Gly Gln Gly Leu Glu Trp Ile
        35                  40                  45

Gly Tyr Ile Asn Pro Arg Asn Asp Tyr Thr Glu Tyr Asn Gln Asn Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Asp Ile Thr Thr Phe Tyr Trp Gly Gln Gly Thr Thr Leu
            100                 105                 110

Thr Val Ser Ser
        115


<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Tyr Thr Phe Thr Ser Tyr Trp
1               5


<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ile Asn Pro Arg Asn Asp Tyr Thr
1               5
```

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 4

Ala Arg Arg Asp Ile Thr Thr Phe Tyr
1 5

<210> SEQ ID NO 5
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 5

Gln Val Gln Leu Val Glu Ser Gly Ala Glu Val Lys Lys Pro Gly Ala
1 5 10 15

Ser Val Lys Met Ser Cys Lys Ala Ser Gly Tyr Thr Phe Thr Ser Tyr
20 25 30

Trp Leu His Trp Ile Arg Gln Ala Pro Gly Gln Arg Leu Glu Trp Ile
35 40 45

Gly Tyr Ile Asn Pro Arg Asn Asp Tyr Thr Lys Tyr Ser Gln Lys Phe
50 55 60

Gln Gly Arg Ala Thr Ile Thr Ala Asp Lys Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Arg Asp Ile Thr Thr Phe Tyr Trp Gly Gln Gly Thr Thr Leu
100 105 110

Thr Val Ser Ser
115

<210> SEQ ID NO 6
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 6

Gln Val Gln Leu Gln Glu Ser Gly Ala Glu Val Lys Lys Pro Gly Ala
1 5 10 15

Ser Val Lys Met Ser Cys Lys Ala Ser Gly Tyr Thr Phe Thr Ser Tyr
20 25 30

Trp Leu His Trp Ile Arg Gln Ala Pro Gly Gln Arg Leu Glu Trp Ile
35 40 45

Gly Tyr Ile Asn Pro Arg Asn Asp Tyr Thr Lys Tyr Ser Gln Lys Phe
50 55 60

Gln Gly Arg Val Thr Leu Thr Arg Asp Lys Ser Ala Ser Thr Ala Tyr
65 70 75 80

Met Glu Leu Ser Ser Leu Arg Ser Glu Asp Thr Ala Val Tyr Tyr Cys
85 90 95

```
Ala Arg Arg Asp Ile Thr Thr Phe Tyr Trp Gly Gln Gly Thr Thr Leu
            100                 105                 110

Thr Val Ser Ser
        115


<210> SEQ ID NO 7
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Leu His Trp Ile Arg Gln Ala Pro Gly Gln Arg Leu Glu Trp Ile
        35                  40                  45

Gly Tyr Ile Asn Pro Arg Asn Asp Tyr Thr Glu Tyr Ser Gln Lys Phe
    50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Asp Ile Thr Thr Phe Tyr Trp Gly Gln Gly Thr Thr Leu
            100                 105                 110

Thr Val Ser Ser
        115


<210> SEQ ID NO 8
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Gln Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Trp Leu His Trp Ile Arg Gln Ala Pro Gly Gln Arg Leu Glu Trp Met
        35                  40                  45

Gly Tyr Ile Asn Pro Arg Asn Asp Tyr Thr Glu Tyr Asn Gln Lys Phe
    50                  55                  60

Gln Gly Arg Ala Thr Ile Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Asp Ile Thr Thr Phe Tyr Trp Gly Gln Gly Thr Thr Leu
            100                 105                 110

Thr Val Ser Ser
        115


<210> SEQ ID NO 9
<211> LENGTH: 116
```

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 9

Gln Val Gln Leu Gln Glu Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Leu His Trp Val Arg Gln Ala Pro Gly Gln Arg Leu Glu Trp Ile
35 40 45

Gly Tyr Ile Asn Pro Arg Asn Asp Tyr Thr Glu Tyr Ser Gln Lys Phe
50 55 60

Gln Gly Arg Ala Thr Leu Thr Ala Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Arg Asp Ile Thr Thr Phe Tyr Trp Gly Gln Gly Thr Thr Leu
100 105 110

Thr Val Ser Ser
115

<210> SEQ ID NO 10
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 10

Gln Val Gln Leu Gln Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Leu His Trp Ile Arg Gln Ala Pro Gly Gln Arg Leu Glu Trp Met
35 40 45

Gly Tyr Ile Asn Pro Arg Asn Asp Tyr Thr Glu Tyr Asn Gln Asn Phe
50 55 60

Lys Asp Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Arg Asp Ile Thr Thr Phe Tyr Trp Gly Gln Gly Thr Thr Leu
100 105 110

Thr Val Ser Ser
115

<210> SEQ ID NO 11
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 11

Gln Val Gln Leu Val Glu Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Leu His Trp Val Arg Gln Ala Pro Gly Gln Arg Leu Glu Trp Met
35 40 45

Gly Tyr Ile Asn Pro Arg Asn Asp Tyr Thr Glu Tyr Asn Gln Asn Phe
50 55 60

Lys Asp Arg Ala Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Arg Asp Ile Thr Thr Phe Tyr Trp Gly Gln Gly Thr Thr Leu
100 105 110

Thr Val Ser Ser
115

<210> SEQ ID NO 12
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

Gln Val Gln Leu Val Glu Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Leu His Trp Ile Arg Gln Ala Pro Gly Gln Arg Leu Glu Trp Met
35 40 45

Gly Tyr Ile Asn Pro Arg Asn Asp Tyr Thr Glu Tyr Asn Gln Asn Phe
50 55 60

Lys Asp Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Arg Asp Ile Thr Thr Phe Tyr Trp Gly Gln Gly Thr Thr Leu
100 105 110

Thr Val Ser Ser
115

<210> SEQ ID NO 13
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

```
Trp Leu His Trp Val Arg Gln Ala Pro Gly Gln Arg Leu Glu Trp Ile
        35                  40                  45

Gly Tyr Ile Asn Pro Arg Asn Asp Tyr Thr Glu Tyr Asn Gln Asn Phe
    50                  55                  60

Lys Asp Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Asp Ile Thr Thr Phe Tyr Trp Gly Gln Gly Thr Thr Leu
            100                 105                 110

Thr Val Ser Ser
        115


<210> SEQ ID NO 14
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Leu His Trp Val Arg Gln Ala Pro Gly Gln Arg Leu Glu Trp Met
        35                  40                  45

Gly Tyr Ile Asn Pro Arg Asn Asp Tyr Thr Glu Tyr Asn Gln Asn Phe
    50                  55                  60

Lys Asp Arg Val Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Asp Ile Thr Thr Phe Tyr Trp Gly Gln Gly Thr Thr Leu
            100                 105                 110

Thr Val Ser Ser
        115


<210> SEQ ID NO 15
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Trp Leu His Trp Val Arg Gln Ala Pro Gly Gln Arg Leu Glu Trp Met
        35                  40                  45

Gly Tyr Ile Asn Pro Arg Asn Asp Tyr Thr Glu Tyr Asn Gln Asn Phe
    50                  55                  60

Lys Asp Arg Ala Thr Ile Thr Ala Asp Thr Ser Ala Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Arg Asp Ile Thr Thr Phe Tyr Trp Gly Gln Gly Thr Thr Leu
            100                 105                 110

Thr Val Ser Ser
        115


<210> SEQ ID NO 16
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Gln Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Trp Leu His Trp Val Arg Gln Ala Pro Gly Gln Arg Leu Glu Trp Met
        35                  40                  45

Gly Tyr Ile Asn Pro Arg Asn Asp Tyr Thr Glu Tyr Asn Gln Asn Phe
    50                  55                  60

Lys Asp Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Asp Ile Thr Thr Phe Tyr Trp Gly Gln Gly Thr Thr Leu
            100                 105                 110

Thr Val Ser Ser
        115


<210> SEQ ID NO 17
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Gln Leu Thr Gln Ser Pro Ser Ser Leu Ala Val Ser Ala Gly
1               5                   10                  15

Glu Asn Val Thr Met Ser Cys Lys Ser Ser Gln Ser Val Leu Tyr Ser
            20                  25                  30

Ala Asn His Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Arg Val Gln Val Glu Asp Leu Ala Ile Tyr Tyr Cys His Gln
                85                  90                  95

Tyr Leu Ser Ser Trp Thr Phe Gly Gly Gly Thr Lys Leu Glu Ile Lys
            100                 105                 110


<210> SEQ ID NO 18
<211> LENGTH: 12
```

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Gln Ser Val Leu Tyr Ser Ala Asn His Lys Asn Tyr
1 5 10

<210> SEQ ID NO 19
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 19

Trp Ala Ser
1

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

His Gln Tyr Leu Ser Ser Trp Thr
1 5

<210> SEQ ID NO 21
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 21

Asp Ile Val Leu Thr Gln Ser Pro Asp Ser Leu Ala Val Ser Ala Gly
1 5 10 15

Glu Arg Val Thr Met Asn Cys Lys Ser Ser Gln Ser Val Leu Tyr Ser
20 25 30

Ala Asn His Lys Asn Tyr Leu Ala Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Val Gln Ala Glu Asp Val Ala Ile Tyr Tyr Cys His Gln
85 90 95

Tyr Leu Ser Ser Trp Thr Phe Gly Gly Gly Thr Lys Leu Glu Ile Lys
100 105 110

<210> SEQ ID NO 22
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 22

```
Asp Ile Val Leu Thr Gln Ser Pro Asp Ser Leu Ala Val Ser Leu Gly
1               5                   10                  15

Glu Arg Val Thr Met Asn Cys Lys Ser Ser Gln Ser Val Leu Tyr Ser
            20                  25                  30

Ala Asn His Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Ile Tyr Tyr Cys His Gln
                85                  90                  95

Tyr Leu Ser Ser Trp Thr Phe Gly Gly Gly Thr Lys Leu Glu Ile Lys
            100                 105                 110
```

<210> SEQ ID NO 23
<211> LENGTH: 511
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Met Gly Trp Ser Cys Ile Ile Leu Phe Leu Val Ala Thr Ala Thr Gly
1               5                   10                  15

Val His Ser Asp Ile Gln Leu Thr Gln Ser Pro Ser Ser Leu Ala Val
            20                  25                  30

Ser Ala Gly Glu Asn Val Thr Met Ser Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Ser Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Arg Val Gln Val Glu Asp Leu Ala Ile Tyr Tyr
            100                 105                 110

Cys His Gln Tyr Leu Ser Ser Trp Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys Thr Ser
225                 230                 235                 240
```

```
Gly Gly Gly Gly Ser Gly Gly Gly Gly Ser Gly Gly Gly Gly Ser Gln
                245                 250                 255

Val Gln Leu Val Gln Ser Gly Gly Gly Val Val Gln Pro Gly Arg Ser
            260                 265                 270

Leu Arg Leu Ser Cys Lys Ala Ser Gly Tyr Thr Phe Thr Arg Tyr Thr
        275                 280                 285

Met His Trp Val Arg Gln Ala Pro Gly Lys Cys Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Arg Phe Thr Ile Ser Arg Asp Asn Ser Lys Asn Thr Ala Phe Leu
                325                 330                 335

Gln Met Asp Ser Leu Arg Pro Glu Asp Thr Gly Val Tyr Phe Cys Ala
            340                 345                 350

Arg Tyr Tyr Asp Asp His Tyr Ser Leu Asp Tyr Trp Gly Gln Gly Thr
        355                 360                 365

Pro Val Thr Val Ser Ser Gly Gly Gly Gly Ser Gly Gly Gly Gly Ser
    370                 375                 380

Gly Gly Gly Gly Ser Gly Gly Gly Gly Ser Gly Gly Gly Gly Ser Gly
385                 390                 395                 400

Gly Gly Gly Ser Asp Ile Gln Met Thr Gln Ser Pro Ser Ser Leu Ser
                405                 410                 415

Ala Ser Val Gly Asp Arg Val Thr Ile Thr Cys Ser Ala Ser Ser Ser
            420                 425                 430

Val Ser Tyr Met Asn Trp Tyr Gln Gln Thr Pro Gly Lys Ala Pro Lys
        435                 440                 445

Arg Trp Ile Tyr Asp Thr Ser Lys Leu Ala Ser Gly Val Pro Ser Arg
    450                 455                 460

Phe Ser Gly Ser Gly Ser Gly Thr Asp Tyr Thr Phe Thr Ile Ser Ser
465                 470                 475                 480

Leu Gln Pro Glu Asp Ile Ala Thr Tyr Tyr Cys Gln Gln Trp Ser Ser
                485                 490                 495

Asn Pro Phe Thr Phe Gly Cys Gly Thr Lys Leu Gln Ile Thr Arg
            500                 505                 510
```

<210> SEQ ID NO 24
<211> LENGTH: 1536
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 24

```
atgggctggt cctgcatcat cctgttcctg gtggccaccg ccaccggcgt ccactccgac      60

atccagctga ctcagagccc ctcatcactg gccgtctccg caggcgaaaa cgtgactatg     120

tcttgtaaat cttctcagtc tgtgctgtac agcgccaacc acaagaatta cctggcctgg     180

tatcagcaga agcccggcca gagccctaag ctgctgatct attgggcctc caccagggag     240

tctggagtgc ccgacagatt caccggcagc ggctccggaa cagacttcac cctgacaatc     300

tcccgggtgc aggtggagga cctggccatc tactattgcc atcagtatct gtcatcatgg     360

acattcggcg gcggaacaaa gctggaaatc aagcggaccg tggccgcccc ctccgtgttc     420

atcttccccc cctccgacga gcagctgaag tccggcaccg cctccgtggt gtgcctgctg     480
```

```
aacaacttct acccccggga ggccaaggtg cagtggaagg tggacaacgc cctgcagtcc    540

ggcaactccc aggagtccgt gaccgagcag gactccaagg actccaccta ctccctgtcc    600

tccaccctga ccctgtccaa ggccgactac gagaagcaca aggtgtacgc ctgcgaggtg    660

acccaccagg gcctgtcctc ccccgtgacc aagtccttca accggggcga gtgcactagt    720

ggcggcggag gatctggcgg aggtggaagt gggggaggcg gatctcaggt gcagctggtg    780

cagagtggtg gcggagtggt gcagcctggc agatccctga gactgtcttg caaggccagc    840

ggctacacct tcacccggta caccatgcac tgggtgcgac aggcccctgg caagtgcctg    900

gaatggatcg gctacatcaa cccctcccgg ggctacacca actacaacca gaagttcaag    960

gaccggttca ccatcagccg ggacaactcc aagaacaccg cctttctgca gatggactcc   1020

ctgcggcctg aggataccgg cgtgtacttt tgcgcccggt actacgacga ccactacagc   1080

ctggactact ggggccaggg aacccctgtg acagtgtcta gcggaggggg aggttcaggt   1140

ggcggtggat caggggggcgg aggaagtggc gggggaggta gtggtggtgg tggaagcgga   1200

ggtggcggct ccgatatcca gatgacccag tccccctcca gcctgtctgc ctctgtggga   1260

gacagagtga caattacatg ctccgccagc tccagcgtgt cctacatgaa ttggtatcag   1320

cagacccctg gcaaggctcc caagcggtgg atctacgaca cctccaagct ggcctccggc   1380

gtgccctcca gattttctgg cagcggctcc ggcacagact atacctttac aatcagctcc   1440

ctgcagcccg aagatatcgc cacctactac tgccagcagt ggtcctccaa ccccttcacc   1500

ttcggctgcg gcacaaagct gcagatcacc agatag                              1536
```

<210> SEQ ID NO 25
<211> LENGTH: 465
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Met Gly Trp Ser Cys Ile Ile Leu Phe Leu Val Ala Thr Ala Thr Gly
1               5                   10                  15

Val His Ser Gln Val Gln Leu Gln Glu Ser Gly Ala Glu Leu Ser Lys
            20                  25                  30

Pro Gly Ala Ser Val Lys Met Ser Cys Lys Ala Ser Gly Tyr Thr Phe
        35                  40                  45

Thr Ser Tyr Trp Leu His Trp Ile Lys Gln Arg Pro Gly Gln Gly Leu
    50                  55                  60

Glu Trp Ile Gly Tyr Ile Asn Pro Arg Asn Asp Tyr Thr Glu Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175
```

```
Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Ala Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Ala Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465
```

<210> SEQ ID NO 26
<211> LENGTH: 1398
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26

```
atgggctggt cctgcatcat cctgttcctg gtggccaccg ccaccggcgt ccatagtcag     60

gtccagctgc aggagagcgg agccgaactg tccaaacccg gagcatctgt caaaatgtct    120

tgtaaagcat caggctacac cttcacatcc tattggctgc actggatcaa gcagcggccc    180

ggacagggcc tggagtggat cggctacatc aaccctagaa atgactacac cgagtataac    240

cagaacttca aggacaaggc caccctgaca gccgataaga gctcctctac cgcctatatg    300
```

```
cagctgagct ccctgacatc tgaggatagc gccgtgtact attgcgctcg gcgggacatc    360

accacattct actggggaca ggggactaca ctgaccgtct cttcagcctc caccaagggc    420

ccatcggtct tcccccctggc accctcctcc aagagcacct ctgggggcac agcggccctg    480

ggctgcctgg tcaaggacta cttccccgaa ccggtgacgg tgtcgtggaa ctcaggcgcc    540

ctgaccagcg gcgtgcacac cttcccggcc gtcctacagt cctcaggact ctactccctc    600

agcagcgtgg tgaccgtgcc ctccagcagc ttgggcaccc agacctacat ctgcaacgtg    660

aatcacaagc ccagcaacac caaggtggac aagagagttg agcccaaatc ttgtgacaaa    720

actcacacat gcccaccgtg cccagcacct gaactcctgg ggggaccgtc agtcttcctc    780

ttccccccaa aacccaagga caccctcatg atctcccgga cccctgaggt cacatgcgtg    840

gtggtggacg tgagccacga agaccctgag gtcaagttca actggtacgt ggacggcgtg    900

gaggtgcata atgccaagac aaagccgcgg gaggagcagt acgccagcac gtaccgtgtg    960

gtcagcgtcc tcaccgtcct gcaccaggac tggctgaatg gcaaggagta caagtgcgcc   1020

gtctccaaca aagccctccc agcccccatc gagaaaacca tctccaaagc caaagggcag   1080

ccccgagaac cacaggtgta caccctgccc ccatcccggg atgagctgac caagaaccag   1140

gtcagcctga cctgcctggt caaaggcttc tatcccagcg acatcgccgt ggagtgggag   1200

agcaatgggc agccggagaa caactacaag accacgcctc ccgtgctgga ctccgacggc   1260

tccttcttcc tctacagcaa gctcaccgtg gacaagagca ggtggcagca ggggaacgtc   1320

ttctcatgct ccgtgatgca tgaggctctg cacaaccact acacgcagaa gagcctctcc   1380

ctgtctccgg gtaaatga                                                 1398
```

```
<210> SEQ ID NO 27
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Gly Trp Ser Cys Ile Ile Leu Phe Leu Val Ala Thr Ala Thr Gly
1               5                   10                  15

Val His Ser Asp Ile Val Leu Thr Gln Ser Pro Asp Ser Leu Ala Val
            20                  25                  30

Ser Ala Gly Glu Arg Val Thr Met Asn Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Val Gln Ala Glu Asp Val Ala Ile Tyr Tyr
            100                 105                 110

Cys His Gln Tyr Leu Ser Ser Trp Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160
```

```
Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys Thr Ser
225                 230                 235                 240

Gly Gly Gly Gly Ser Gly Gly Gly Gly Ser Gly Gly Gly Gly Ser Gln
                245                 250                 255

Val Gln Leu Val Gln Ser Gly Gly Gly Val Val Gln Pro Gly Arg Ser
            260                 265                 270

Leu Arg Leu Ser Cys Lys Ala Ser Gly Tyr Thr Phe Thr Arg Tyr Thr
        275                 280                 285

Met His Trp Val Arg Gln Ala Pro Gly Lys Cys Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Arg Phe Thr Ile Ser Arg Asp Asn Ser Lys Asn Thr Ala Phe Leu
                325                 330                 335

Gln Met Asp Ser Leu Arg Pro Glu Asp Thr Gly Val Tyr Phe Cys Ala
            340                 345                 350

Arg Tyr Tyr Asp Asp His Tyr Ser Leu Asp Tyr Trp Gly Gln Gly Thr
        355                 360                 365

Pro Val Thr Val Ser Ser Gly Gly Gly Gly Ser Gly Gly Gly Gly Ser
    370                 375                 380

Gly Gly Gly Gly Ser Gly Gly Gly Gly Ser Gly Gly Gly Gly Ser Gly
385                 390                 395                 400

Gly Gly Gly Ser Asp Ile Gln Met Thr Gln Ser Pro Ser Ser Leu Ser
                405                 410                 415

Ala Ser Val Gly Asp Arg Val Thr Ile Thr Cys Ser Ala Ser Ser Ser
            420                 425                 430

Val Ser Tyr Met Asn Trp Tyr Gln Gln Thr Pro Gly Lys Ala Pro Lys
        435                 440                 445

Arg Trp Ile Tyr Asp Thr Ser Lys Leu Ala Ser Gly Val Pro Ser Arg
    450                 455                 460

Phe Ser Gly Ser Gly Ser Gly Thr Asp Tyr Thr Phe Thr Ile Ser Ser
465                 470                 475                 480

Leu Gln Pro Glu Asp Ile Ala Thr Tyr Tyr Cys Gln Gln Trp Ser Ser
                485                 490                 495

Asn Pro Phe Thr Phe Gly Cys Gly Thr Lys Leu Gln Ile Thr Arg
            500                 505                 510
```

<210> SEQ ID NO 28
<211> LENGTH: 1536
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
atgggctggt cctgcatcat cctgttcctg gtggccaccg ccaccggcgt gcactccgac     60
atcgtgctga cccagagccc agattccctg gccgtgagcg ccggagagcg ggtgacaatg    120
aactgcaaga gctcccagtc tgtgctgtac agcgccaacc acaagaatta cctggcctgg    180
tatcagcaga agccaggcca gccccctaag ctgctgatct attgggcctc caccagggag    240
tctggagtgc ccgacagatt cagcggctcc ggctctggca cagacttcac cctgacaatc    300
tctagcgtgc aggccgagga cgtggccatc tactattgtc accagtacct gtcctcttgg    360
accttcggcg gcggcacaaa gctggagatc aagcggaccg tggccgcccc ctccgtgttc    420
atcttccccc cctccgacga gcagctgaag tccggcaccg cctccgtggt gtgcctgctg    480
aacaacttct acccccggga ggccaaggtg cagtggaagg tggacaacgc cctgcagtcc    540
ggcaactccc aggagtccgt gaccgagcag gactccaagg actccaccta ctccctgtcc    600
tccaccctga ccctgtccaa ggccgactac gagaagcaca aggtgtacgc ctgcgaggtg    660
acccaccagg gcctgtcctc ccccgtgacc aagtccttca accggggcga gtgcactagt    720
ggcggcggag gatctggcgg aggtggaagt gggggaggcg gatctcaggt gcagctggtg    780
cagagtggtg gcggagtggt gcagcctggc agatccctga gactgtcttg caaggccagc    840
ggctacacct tcacccggta caccatgcac tgggtgcgac aggcccctgg caagtgcctg    900
gaatggatcg gctacatcaa cccctcccgg ggctacacca actacaacca gaagttcaag    960
gaccggttca ccatcagccg ggacaactcc aagaacaccg cctttctgca gatggactcc   1020
ctgcggcctg aggataccgg cgtgtacttt tgcgcccggt actacgacga ccactacagc   1080
ctggactact ggggccaggg aacccctgtg acagtgtcta gcggaggggg aggttcaggt   1140
ggcggtggat caggggggcgg aggaagtggc gggggaggta gtggtggtgg tggaagcgga   1200
ggtggcggct ccgatatcca gatgacccag tccccctcca gcctgtctgc ctctgtggga   1260
gacagagtga caattacatg ctccgccagc tccagcgtgt cctacatgaa ttggtatcag   1320
cagacccctg gcaaggctcc caagcggtgg atctacgaca cctccaagct ggcctccggc   1380
gtgccctcca gattttctgg cagcggctcc ggcacagact ataccttac aatcagctcc    1440
ctgcagcccg aagatatcgc cacctactac tgccagcagt ggtcctccaa cccccttcacc   1500
ttcggctgcg gcacaaagct gcagatcacc agatag                             1536
```

<210> SEQ ID NO 29
<211> LENGTH: 465
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

```
Met Gly Trp Ser Cys Ile Ile Leu Phe Leu Val Ala Thr Ala Thr Gly
1               5                   10                  15

Val His Ser Gln Val Gln Leu Gln Gln Ser Gly Ala Glu Val Lys Lys
            20                  25                  30

Pro Gly Ala Ser Val Lys Met Ser Cys Lys Ala Ser Gly Tyr Thr Phe
        35                  40                  45

Thr Ser Tyr Trp Leu His Trp Ile Arg Gln Ala Pro Gly Gln Arg Leu
    50                  55                  60
```

Glu Trp Met Gly Tyr Ile Asn Pro Arg Asn Asp Tyr Thr Glu Tyr Asn
65 70 75 80

Gln Lys Phe Gln Gly Arg Ala Thr Ile Thr Ala Asp Lys Ser Ala Ser
85 90 95

Thr Ala Tyr Met Glu Leu Ser Ser Leu Arg Ser Glu Asp Thr Ala Val
100 105 110

Tyr Tyr Cys Ala Arg Arg Asp Ile Thr Thr Phe Tyr Trp Gly Gln Gly
115 120 125

Thr Thr Leu Thr Val Ser Ser Ala Ser Thr Lys Gly Pro Ser Val Phe
130 135 140

Pro Leu Ala Pro Ser Ser Lys Ser Thr Ser Gly Gly Thr Ala Ala Leu
145 150 155 160

Gly Cys Leu Val Lys Asp Tyr Phe Pro Glu Pro Val Thr Val Ser Trp
165 170 175

Asn Ser Gly Ala Leu Thr Ser Gly Val His Thr Phe Pro Ala Val Leu
180 185 190

Gln Ser Ser Gly Leu Tyr Ser Leu Ser Ser Val Val Thr Val Pro Ser
195 200 205

Ser Ser Leu Gly Thr Gln Thr Tyr Ile Cys Asn Val Asn His Lys Pro
210 215 220

Ser Asn Thr Lys Val Asp Lys Arg Val Glu Pro Lys Ser Cys Asp Lys
225 230 235 240

Thr His Thr Cys Pro Pro Cys Pro Ala Pro Glu Leu Leu Gly Gly Pro
245 250 255

Ser Val Phe Leu Phe Pro Pro Lys Pro Lys Asp Thr Leu Met Ile Ser
260 265 270

Arg Thr Pro Glu Val Thr Cys Val Val Val Asp Val Ser His Glu Asp
275 280 285

Pro Glu Val Lys Phe Asn Trp Tyr Val Asp Gly Val Glu Val His Asn
290 295 300

Ala Lys Thr Lys Pro Arg Glu Glu Gln Tyr Ala Ser Thr Tyr Arg Val
305 310 315 320

Val Ser Val Leu Thr Val Leu His Gln Asp Trp Leu Asn Gly Lys Glu
325 330 335

Tyr Lys Cys Ala Val Ser Asn Lys Ala Leu Pro Ala Pro Ile Glu Lys
340 345 350

Thr Ile Ser Lys Ala Lys Gly Gln Pro Arg Glu Pro Gln Val Tyr Thr
355 360 365

Leu Pro Pro Ser Arg Asp Glu Leu Thr Lys Asn Gln Val Ser Leu Thr
370 375 380

Cys Leu Val Lys Gly Phe Tyr Pro Ser Asp Ile Ala Val Glu Trp Glu
385 390 395 400

Ser Asn Gly Gln Pro Glu Asn Asn Tyr Lys Thr Thr Pro Pro Val Leu
405 410 415

Asp Ser Asp Gly Ser Phe Phe Leu Tyr Ser Lys Leu Thr Val Asp Lys
420 425 430

Ser Arg Trp Gln Gln Gly Asn Val Phe Ser Cys Ser Val Met His Glu
435 440 445

Ala Leu His Asn His Tyr Thr Gln Lys Ser Leu Ser Leu Ser Pro Gly
450 455 460

Lys
465

<210> SEQ ID NO 30
<211> LENGTH: 1398
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 30
atgggctggt cctgcatcat cctgttcctg gtggccaccg ccaccggcgt gcacagccag 60
gtgcagctgc agcagtccgg agcagaggtg aagaagccag gagccagcgt gaagatgtcc 120
tgcaaggcct ctggctacac cttcacatct tattggctgc actggatcag gcaggcacca 180
ggacagcgcc tggagtggat gggctacatc aaccctcgga atgactacac cgagtataac 240
cagaagtttc agggcagggc caccatcaca gccgataagt ccgcctctac cgcctacatg 300
gagctgagct ccctgcggag cgaggacaca gccgtgtact attgtgcccg gagagatatc 360
accacattct attggggcca gggcaccaca ctgacagtgt ctagcgcctc caccaagggc 420
ccatcggtct tccccctggc accctcctcc aagagcacct ctgggggcac agcggccctg 480
ggctgcctgg tcaaggacta cttccccgaa ccggtgacgg tgtcgtggaa ctcaggcgcc 540
ctgaccagcg gcgtgcacac cttcccggcc gtcctacagt cctcaggact ctactccctc 600
agcagcgtgg tgaccgtgcc ctccagcagc ttgggcaccc agacctacat ctgcaacgtg 660
aatcacaagc ccagcaacac caaggtggac aagagagttg agcccaaatc ttgtgacaaa 720
actcacacat gcccaccgtg cccagcacct gaactcctgg ggggaccgtc agtcttcctc 780
ttccccccaa aacccaagga caccctcatg atctcccgga cccctgaggt cacatgcgtg 840
gtggtggacg tgagccacga agaccctgag gtcaagttca actggtacgt ggacggcgtg 900
gaggtgcata atgccaagac aaagccgcgg gaggagcagt acgccagcac gtaccgtgtg 960
gtcagcgtcc tcaccgtcct gcaccaggac tggctgaatg gcaaggagta caagtgcgcc 1020
gtctccaaca aagccctccc agcccccatc gagaaaacca tctccaaagc caaagggcag 1080
ccccgagaac cacaggtgta caccctgccc ccatcccggg atgagctgac caagaaccag 1140
gtcagcctga cctgcctggt caaaggcttc tatcccagcg acatcgccgt ggagtgggag 1200
agcaatgggc agccggagaa caactacaag accacgcctc ccgtgctgga ctccgacggc 1260
tccttcttcc tctacagcaa gctcaccgtg gacaagagca ggtggcagca ggggaacgtc 1320
ttctcatgct ccgtgatgca tgaggctctg cacaaccact acacgcagaa gagcctctcc 1380
ctgtctccgg gtaaatga 1398

<210> SEQ ID NO 31
<211> LENGTH: 511
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 31

Met Gly Trp Ser Cys Ile Ile Leu Phe Leu Val Ala Thr Ala Thr Gly
1 5 10 15

Val His Ser Asp Ile Val Leu Thr Gln Ser Pro Asp Ser Leu Ala Val
20 25 30

Ser Ala Gly Glu Arg Val Thr Met Asn Cys Lys Ser Ser Gln Ser Val
35 40 45

-continued

```
Leu Tyr Ser Ala Asn His Lys Asn Tyr Leu Ala Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Val Gln Ala Glu Asp Val Ala Ile Tyr Tyr
            100                 105                 110

Cys His Gln Tyr Leu Ser Ser Trp Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys Thr Ser
225                 230                 235                 240

Gly Gly Gly Gly Ser Gly Gly Gly Gly Ser Gly Gly Gly Gly Ser Gln
                245                 250                 255

Val Gln Leu Val Gln Ser Gly Gly Gly Val Val Gln Pro Gly Arg Ser
            260                 265                 270

Leu Arg Leu Ser Cys Lys Ala Ser Gly Tyr Thr Phe Thr Arg Tyr Thr
        275                 280                 285

Met His Trp Val Arg Gln Ala Pro Gly Lys Cys Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Arg Phe Thr Ile Ser Arg Asp Asn Ser Lys Asn Thr Ala Phe Leu
                325                 330                 335

Gln Met Asp Ser Leu Arg Pro Glu Asp Thr Gly Val Tyr Phe Cys Ala
            340                 345                 350

Arg Tyr Tyr Asp Asp His Tyr Ser Leu Asp Tyr Trp Gly Gln Gly Thr
        355                 360                 365

Pro Val Thr Val Ser Ser Gly Gly Gly Gly Ser Gly Gly Gly Gly Ser
    370                 375                 380

Gly Gly Gly Gly Ser Gly Gly Gly Gly Ser Gly Gly Gly Gly Ser Gly
385                 390                 395                 400

Gly Gly Gly Ser Asp Ile Gln Met Thr Gln Ser Pro Ser Ser Leu Ser
                405                 410                 415

Ala Ser Val Gly Asp Arg Val Thr Ile Thr Cys Ser Ala Ser Ser Ser
            420                 425                 430

Val Ser Tyr Met Asn Trp Tyr Gln Gln Thr Pro Gly Lys Ala Pro Lys
        435                 440                 445

Arg Trp Ile Tyr Asp Thr Ser Lys Leu Ala Ser Gly Val Pro Ser Arg
    450                 455                 460
```

```
Phe Ser Gly Ser Gly Ser Gly Thr Asp Tyr Thr Phe Thr Ile Ser Ser
465                 470                 475                 480

Leu Gln Pro Glu Asp Ile Ala Thr Tyr Tyr Cys Gln Gln Trp Ser Ser
                485                 490                 495

Asn Pro Phe Thr Phe Gly Cys Gly Thr Lys Leu Gln Ile Thr Arg
            500                 505                 510


<210> SEQ ID NO 32
<211> LENGTH: 1536
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

atgggctggt cctgcatcat cctgttcctg gtggccaccg ccaccggcgt gcactccgac     60

atcgtgctga cccagagccc agattccctg gccgtgagcg ccggagagcg ggtgacaatg    120

aactgcaaga gctcccagtc tgtgctgtac agcgccaacc acaagaatta cctggcctgg    180

tatcagcaga agccaggcca gccccctaag ctgctgatct attgggcctc caccagggag    240

tctggagtgc ccgacagatt cagcggctcc ggctctggca cagacttcac cctgacaatc    300

tctagcgtgc aggccgagga cgtggccatc tactattgtc accagtacct gtcctcttgg    360

accttcggcg gcggcacaaa gctggagatc aagcggaccg tggccgcccc ctccgtgttc    420

atcttccccc cctccgacga gcagctgaag tccggcaccg cctccgtggt gtgcctgctg    480

aacaacttct acccccggga ggccaaggtg cagtggaagg tggacaacgc cctgcagtcc    540

ggcaactccc aggagtccgt gaccgagcag gactccaagg actccaccta ctccctgtcc    600

tccaccctga ccctgtccaa ggccgactac gagaagcaca aggtgtacgc ctgcgaggtg    660

acccaccagg gcctgtcctc ccccgtgacc aagtccttca accggggcga gtgcactagt    720

ggcggcggag gatctggcgg aggtggaagt gggggaggcg gatctcaggt gcagctggtg    780

cagagtggtg gcggagtggt gcagcctggc agatccctga gactgtcttg caaggccagc    840

ggctacacct tcacccggta caccatgcac tgggtgcgac aggcccctgg caagtgcctg    900

gaatggatcg gctacatcaa cccctcccgg ggctacacca actacaacca gaagttcaag    960

gaccggttca ccatcagccg ggacaactcc aagaacaccg cctttctgca gatggactcc   1020

ctgcggcctg aggataccgg cgtgtacttt tgcgcccggt actacgacga ccactacagc   1080

ctggactact ggggccaggg aacccctgtg acagtgtcta gcggaggggg aggttcaggt   1140

ggcggtggat caggggggcgg aggaagtggc gggggaggta gtggtggtgg tggaagcgga   1200

ggtggcggct ccgatatcca gatgacccag tccccctcca gcctgtctgc ctctgtggga   1260

gacagagtga caattacatg ctccgccagc tccagcgtgt cctacatgaa ttggtatcag   1320

cagacccctg gcaaggctcc caagcggtgg atctacgaca cctccaagct ggcctccggc   1380

gtgccctcca gattttctgg cagcggctcc ggcacagact atacctttac aatcagctcc   1440

ctgcagcccg aagatatcgc cacctactac tgccagcagt ggtcctccaa ccccttcacc   1500

ttcggctgcg gcacaaagct gcagatcacc agatag                             1536


<210> SEQ ID NO 33
<211> LENGTH: 465
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 33

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Leu His Trp Val Arg Gln Ala Pro Gly Gln Arg Leu
    50                  55                  60

Glu Trp Met Gly Tyr Ile Asn Pro Arg Asn Asp Tyr Thr Glu Tyr Asn
65                  70                  75                  80

Gln Asn Phe Lys Asp Arg Val Thr Leu Thr Ala Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Ala Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Ala Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400
```

```
Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465


<210> SEQ ID NO 34
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

atgggctggt cctgcatcat cctgttcctg gtggccaccg ccaccggcgt gcacagccag     60

gtgcagctgg tgcagtccgg agcagaggtg aagaagccag gagccagcgt gaaggtgtcc    120

tgcaaggcct ctggctacac cttcacatct tattggctgc actgggtgag gcaggcacca    180

ggacagcgcc tggagtggat gggctacatc aaccctcgga atgactacac cgagtataac    240

cagaacttca aggacagggt gaccctgaca gccgataagt ccgcctctac cgcctacatg    300

gagctgagct ccctgcggag cgaggacaca gccgtgtact attgtgcccg gagagatatc    360

accacattct attggggcca gggcaccaca ctgacagtgt ctagcgcctc caccaagggc    420

ccatcggtct tccccctggc accctcctcc aagagcacct ctgggggcac agcggccctg    480

ggctgcctgg tcaaggacta cttccccgaa ccggtgacgg tgtcgtggaa ctcaggcgcc    540

ctgaccagcg gcgtgcacac cttcccggcc gtcctacagt cctcaggact ctactccctc    600

agcagcgtgg tgaccgtgcc ctccagcagc ttgggcaccc agacctacat ctgcaacgtg    660

aatcacaagc ccagcaacac caaggtggac aagagagttg agcccaaatc ttgtgacaaa    720

actcacacat gcccaccgtg cccagcacct gaactcctgg ggggaccgtc agtcttcctc    780

ttccccccaa aacccaagga caccctcatg atctcccgga cccctgaggt cacatgcgtg    840

gtggtggacg tgagccacga agaccctgag gtcaagttca actggtacgt ggacggcgtg    900

gaggtgcata atgccaagac aaagccgcgg gaggagcagt acgccagcac gtaccgtgtg    960

gtcagcgtcc tcaccgtcct gcaccaggac tggctgaatg gcaaggagta caagtgcgcc   1020

gtctccaaca aagccctccc agcccccatc gagaaaacca tctccaaagc caaagggcag   1080

ccccgagaac cacaggtgta caccctgccc ccatcccggg atgagctgac caagaaccag   1140

gtcagcctga cctgcctggt caaaggcttc tatcccagcg acatcgccgt ggagtgggag   1200

agcaatgggc agccggagaa caactacaag accacgcctc ccgtgctgga ctccgacggc   1260

tccttcttcc tctacagcaa gctcaccgtg gacaagagca ggtggcagca ggggaacgtc   1320

ttctcatgct ccgtgatgca tgaggctctg cacaaccact acacgcagaa gagcctctcc   1380

ctgtctccgg gtaaatga                                                 1398


<210> SEQ ID NO 35
<211> LENGTH: 514
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 35

```
Met Gly Trp Ser Cys Ile Ile Leu Phe Leu Val Ala Thr Ala Thr Gly
1               5                   10                  15

Val His Ser Asp Ile Gln Leu Thr Gln Ser Pro Ser Ser Leu Ala Val
            20                  25                  30

Ser Ala Gly Glu Asn Val Thr Met Ser Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Ser Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Arg Val Gln Val Glu Asp Leu Ala Ile Tyr Tyr
            100                 105                 110

Cys His Gln Tyr Leu Ser Ser Trp Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys Thr Ser
225                 230                 235                 240

Gly Gly Gly Gly Ser Gly Gly Gly Gly Ser Gly Gly Gly Gly Ser His
                245                 250                 255

Val Lys Leu Gln Glu Ser Gly Pro Gly Leu Val Gln Pro Ser Gln Ser
            260                 265                 270

Leu Ser Leu Thr Cys Thr Val Ser Gly Phe Ser Leu Thr Asp Tyr Gly
        275                 280                 285

Val His Trp Val Arg Gln Ser Pro Gly Lys Gly Leu Glu Trp Leu Gly
    290                 295                 300

Val Ile Trp Ser Gly Gly Gly Thr Ala Tyr Asn Thr Ala Leu Ile Ser
305                 310                 315                 320

Arg Leu Asn Ile Tyr Arg Asp Asn Ser Lys Asn Gln Val Phe Leu Glu
                325                 330                 335

Met Asn Ser Leu Gln Ala Glu Asp Thr Ala Met Tyr Tyr Cys Ala Arg
            340                 345                 350

Arg Gly Ser Tyr Pro Tyr Asn Tyr Phe Asp Ala Trp Gly Cys Gly Thr
        355                 360                 365

Thr Val Thr Val Ser Ser Gly Gly Gly Gly Ser Gly Gly Gly Gly Ser
    370                 375                 380
```

```
Gly Gly Gly Gly Ser Gly Gly Gly Gly Ser Gly Gly Gly Gly Ser Gly
385                 390                 395                 400

Gly Gly Gly Ser Gln Ala Val Val Ile Gln Glu Ser Ala Leu Thr Thr
                405                 410                 415

Pro Pro Gly Glu Thr Val Thr Leu Thr Cys Gly Ser Ser Thr Gly Ala
            420                 425                 430

Val Thr Ala Ser Asn Tyr Ala Asn Trp Val Gln Glu Lys Pro Asp His
        435                 440                 445

Cys Phe Thr Gly Leu Ile Gly Gly His Asn Asn Arg Pro Pro Gly Val
    450                 455                 460

Pro Ala Arg Phe Ser Gly Ser Leu Ile Gly Asp Lys Ala Ala Leu Thr
465                 470                 475                 480

Ile Ala Gly Thr Gln Thr Glu Asp Glu Ala Ile Tyr Phe Cys Ala Leu
                485                 490                 495

Trp Tyr Ser Asp His Trp Val Ile Gly Gly Gly Thr Arg Leu Thr Val
            500                 505                 510

Leu Gly
```

<210> SEQ ID NO 36
<211> LENGTH: 465
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

```
Met Gly Trp Ser Cys Ile Ile Leu Phe Leu Val Ala Thr Ala Thr Gly
1               5                   10                  15

Val His Ser Gln Val Gln Leu Gln Glu Ser Gly Ala Glu Leu Ser Lys
            20                  25                  30

Pro Gly Ala Ser Val Lys Met Ser Cys Lys Ala Ser Gly Tyr Thr Phe
        35                  40                  45

Thr Ser Tyr Trp Leu His Trp Ile Lys Gln Arg Pro Gly Gln Gly Leu
    50                  55                  60

Glu Trp Ile Gly Tyr Ile Asn Pro Arg Asn Asp Tyr Thr Glu Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220
```

```
Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Ala Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Ala Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465


<210> SEQ ID NO 37
<211> LENGTH: 514
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Gly Trp Ser Cys Ile Ile Leu Phe Leu Val Ala Thr Ala Thr Gly
1               5                   10                  15

Val His Ser Asp Ile Gln Leu Thr Gln Ser Pro Ser Ser Leu Ala Val
            20                  25                  30

Ser Ala Gly Glu Asn Val Thr Met Ser Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Ser Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Arg Val Gln Val Glu Asp Leu Ala Ile Tyr Tyr
            100                 105                 110
```

```
Cys His Gln Tyr Leu Ser Ser Trp Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys Thr Ser
225                 230                 235                 240

Gly Gly Gly Gly Ser Gly Gly Gly Gly Ser Gly Gly Gly Gly Ser His
                245                 250                 255

Val Gln Leu Val Glu Ser Gly Gly Gly Leu Val Gln Pro Gly Gly Ser
            260                 265                 270

Leu Arg Leu Ser Cys Ala Ala Ser Gly Phe Ser Leu Thr Asp Tyr Gly
        275                 280                 285

Val His Trp Val Arg Gln Ala Pro Gly Lys Gly Leu Glu Trp Leu Gly
    290                 295                 300

Val Ile Trp Ser Gly Gly Gly Thr Ala Tyr Asn Thr Ala Leu Ile Ser
305                 310                 315                 320

Arg Phe Thr Ile Ser Arg Asp Asn Ser Lys Asn Thr Leu Tyr Leu Gln
                325                 330                 335

Met Asn Ser Leu Arg Ala Glu Asp Thr Ala Val Tyr Tyr Cys Ala Arg
            340                 345                 350

Arg Gly Ser Tyr Pro Tyr Asn Tyr Phe Asp Ala Trp Gly Cys Gly Thr
        355                 360                 365

Leu Val Thr Val Ser Ser Gly Gly Gly Gly Ser Gly Gly Gly Gly Ser
    370                 375                 380

Gly Gly Gly Gly Ser Gly Gly Gly Gly Ser Gly Gly Gly Gly Ser Gly
385                 390                 395                 400

Gly Gly Gly Ser Gln Ala Val Val Thr Gln Glu Pro Ser Leu Thr Val
                405                 410                 415

Ser Pro Gly Gly Thr Val Thr Leu Thr Cys Gly Ser Ser Thr Gly Ala
            420                 425                 430

Val Thr Ala Ser Asn Tyr Ala Asn Trp Val Gln Gln Lys Pro Gly Gln
        435                 440                 445

Cys Pro Arg Gly Leu Ile Gly Gly His Asn Asn Arg Pro Pro Gly Val
    450                 455                 460

Pro Ala Arg Phe Ser Gly Ser Leu Leu Gly Gly Lys Ala Ala Leu Thr
465                 470                 475                 480

Leu Leu Gly Ala Gln Pro Glu Asp Glu Ala Glu Tyr Tyr Cys Ala Leu
                485                 490                 495

Trp Tyr Ser Asp His Trp Val Ile Gly Gly Gly Thr Lys Leu Thr Val
            500                 505                 510

Leu Gly
```

```
<210> SEQ ID NO 38
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Gly Trp Ser Cys Ile Ile Leu Phe Leu Val Ala Thr Ala Thr Gly
1               5                   10                  15

Val His Ser Gln Val Gln Leu Gln Glu Ser Gly Ala Glu Leu Ser Lys
            20                  25                  30

Pro Gly Ala Ser Val Lys Met Ser Cys Lys Ala Ser Gly Tyr Thr Phe
        35                  40                  45

Thr Ser Tyr Trp Leu His Trp Ile Lys Gln Arg Pro Gly Gln Gly Leu
    50                  55                  60

Glu Trp Ile Gly Tyr Ile Asn Pro Arg Asn Asp Tyr Thr Glu Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Ala Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Ala Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365
```

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 39
<211> LENGTH: 514
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Gly Trp Ser Cys Ile Ile Leu Phe Leu Val Ala Thr Ala Thr Gly
1               5                   10                  15

Val His Ser Asp Ile Val Leu Thr Gln Ser Pro Asp Ser Leu Ala Val
            20                  25                  30

Ser Ala Gly Glu Arg Val Thr Met Asn Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Val Gln Ala Glu Asp Val Ala Ile Tyr Tyr
            100                 105                 110

Cys His Gln Tyr Leu Ser Ser Trp Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys Thr Ser
225                 230                 235                 240

Gly Gly Gly Gly Ser Gly Gly Gly Gly Ser Gly Gly Gly Gly Ser His
                245                 250                 255

```
Val Lys Leu Gln Glu Ser Gly Pro Gly Leu Val Gln Pro Ser Gln Ser
            260                 265                 270

Leu Ser Leu Thr Cys Thr Val Ser Gly Phe Ser Leu Thr Asp Tyr Gly
        275                 280                 285

Val His Trp Val Arg Gln Ser Pro Gly Lys Gly Leu Glu Trp Leu Gly
    290                 295                 300

Val Ile Trp Ser Gly Gly Gly Thr Ala Tyr Asn Thr Ala Leu Ile Ser
305                 310                 315                 320

Arg Leu Asn Ile Tyr Arg Asp Asn Ser Lys Asn Gln Val Phe Leu Glu
                325                 330                 335

Met Asn Ser Leu Gln Ala Glu Asp Thr Ala Met Tyr Tyr Cys Ala Arg
            340                 345                 350

Arg Gly Ser Tyr Pro Tyr Asn Tyr Phe Asp Ala Trp Gly Cys Gly Thr
        355                 360                 365

Thr Val Thr Val Ser Ser Gly Gly Gly Gly Ser Gly Gly Gly Gly Ser
    370                 375                 380

Gly Gly Gly Gly Ser Gly Gly Gly Gly Ser Gly Gly Gly Gly Ser Gly
385                 390                 395                 400

Gly Gly Gly Ser Gln Ala Val Val Ile Gln Glu Ser Ala Leu Thr Thr
                405                 410                 415

Pro Pro Gly Glu Thr Val Thr Leu Thr Cys Gly Ser Ser Thr Gly Ala
            420                 425                 430

Val Thr Ala Ser Asn Tyr Ala Asn Trp Val Gln Glu Lys Pro Asp His
        435                 440                 445

Cys Phe Thr Gly Leu Ile Gly Gly His Asn Asn Arg Pro Pro Gly Val
    450                 455                 460

Pro Ala Arg Phe Ser Gly Ser Leu Ile Gly Asp Lys Ala Ala Leu Thr
465                 470                 475                 480

Ile Ala Gly Thr Gln Thr Glu Asp Glu Ala Ile Tyr Phe Cys Ala Leu
                485                 490                 495

Trp Tyr Ser Asp His Trp Val Ile Gly Gly Gly Thr Arg Leu Thr Val
            500                 505                 510

Leu Gly
```

```
<210> SEQ ID NO 40
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Gly Trp Ser Cys Ile Ile Leu Phe Leu Val Ala Thr Ala Thr Gly
1               5                   10                  15

Val His Ser Gln Val Gln Leu Gln Gln Ser Gly Ala Glu Val Lys Lys
            20                  25                  30

Pro Gly Ala Ser Val Lys Met Ser Cys Lys Ala Ser Gly Tyr Thr Phe
        35                  40                  45

Thr Ser Tyr Trp Leu His Trp Ile Arg Gln Ala Pro Gly Gln Arg Leu
    50                  55                  60

Glu Trp Met Gly Tyr Ile Asn Pro Arg Asn Asp Tyr Thr Glu Tyr Asn
65                  70                  75                  80

Gln Lys Phe Gln Gly Arg Ala Thr Ile Thr Ala Asp Lys Ser Ala Ser
                85                  90                  95
```

```
Thr Ala Tyr Met Glu Leu Ser Ser Leu Arg Ser Glu Asp Thr Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Ala Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Ala Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465
```

<210> SEQ ID NO 41
<211> LENGTH: 514
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 41

Met Gly Trp Ser Cys Ile Ile Leu Phe Leu Val Ala Thr Ala Thr Gly
1 5 10 15

Val His Ser Asp Ile Val Leu Thr Gln Ser Pro Asp Ser Leu Ala Val
20 25 30

Ser Ala Gly Glu Arg Val Thr Met Asn Cys Lys Ser Ser Gln Ser Val
35 40 45

Leu Tyr Ser Ala Asn His Lys Asn Tyr Leu Ala Trp Tyr Gln Gln Lys
50 55 60

Pro Gly Gln Pro Pro Lys Leu Leu Ile Tyr Trp Ala Ser Thr Arg Glu
65 70 75 80

Ser Gly Val Pro Asp Arg Phe Ser Gly Ser Gly Ser Gly Thr Asp Phe
85 90 95

Thr Leu Thr Ile Ser Ser Val Gln Ala Glu Asp Val Ala Ile Tyr Tyr
100 105 110

Cys His Gln Tyr Leu Ser Ser Trp Thr Phe Gly Gly Gly Thr Lys Leu
115 120 125

Glu Ile Lys Arg Thr Val Ala Ala Pro Ser Val Phe Ile Phe Pro Pro
130 135 140

Ser Asp Glu Gln Leu Lys Ser Gly Thr Ala Ser Val Val Cys Leu Leu
145 150 155 160

Asn Asn Phe Tyr Pro Arg Glu Ala Lys Val Gln Trp Lys Val Asp Asn
165 170 175

Ala Leu Gln Ser Gly Asn Ser Gln Glu Ser Val Thr Glu Gln Asp Ser
180 185 190

Lys Asp Ser Thr Tyr Ser Leu Ser Ser Thr Leu Thr Leu Ser Lys Ala
195 200 205

Asp Tyr Glu Lys His Lys Val Tyr Ala Cys Glu Val Thr His Gln Gly
210 215 220

Leu Ser Ser Pro Val Thr Lys Ser Phe Asn Arg Gly Glu Cys Thr Ser
225 230 235 240

Gly Gly Gly Gly Ser Gly Gly Gly Gly Ser Gly Gly Gly Gly Ser His
245 250 255

Val Gln Leu Val Glu Ser Gly Gly Gly Leu Val Gln Pro Gly Gly Ser
260 265 270

Leu Arg Leu Ser Cys Ala Ala Ser Gly Phe Ser Leu Thr Asp Tyr Gly
275 280 285

Val His Trp Val Arg Gln Ala Pro Gly Lys Gly Leu Glu Trp Leu Gly
290 295 300

Val Ile Trp Ser Gly Gly Gly Thr Ala Tyr Asn Thr Ala Leu Ile Ser
305 310 315 320

Arg Phe Thr Ile Ser Arg Asp Asn Ser Lys Asn Thr Leu Tyr Leu Gln
325 330 335

Met Asn Ser Leu Arg Ala Glu Asp Thr Ala Val Tyr Tyr Cys Ala Arg
340 345 350

Arg Gly Ser Tyr Pro Tyr Asn Tyr Phe Asp Ala Trp Gly Cys Gly Thr
355 360 365

Leu Val Thr Val Ser Ser Gly Gly Gly Gly Ser Gly Gly Gly Gly Ser
370 375 380

Gly Gly Gly Gly Ser Gly Gly Gly Gly Ser Gly Gly Gly Gly Ser Gly
385 390 395 400

```
Gly Gly Gly Ser Gln Ala Val Val Thr Gln Glu Pro Ser Leu Thr Val
                405                 410                 415

Ser Pro Gly Gly Thr Val Thr Leu Thr Cys Gly Ser Ser Thr Gly Ala
            420                 425                 430

Val Thr Ala Ser Asn Tyr Ala Asn Trp Val Gln Gln Lys Pro Gly Gln
        435                 440                 445

Cys Pro Arg Gly Leu Ile Gly Gly His Asn Asn Arg Pro Pro Gly Val
    450                 455                 460

Pro Ala Arg Phe Ser Gly Ser Leu Leu Gly Gly Lys Ala Ala Leu Thr
465                 470                 475                 480

Leu Leu Gly Ala Gln Pro Glu Asp Glu Ala Glu Tyr Tyr Cys Ala Leu
                485                 490                 495

Trp Tyr Ser Asp His Trp Val Ile Gly Gly Gly Thr Lys Leu Thr Val
            500                 505                 510

Leu Gly


<210> SEQ ID NO 42
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Gly Trp Ser Cys Ile Ile Leu Phe Leu Val Ala Thr Ala Thr Gly
1               5                   10                  15

Val His Ser Gln Val Gln Leu Gln Gln Ser Gly Ala Glu Val Lys Lys
            20                  25                  30

Pro Gly Ala Ser Val Lys Met Ser Cys Lys Ala Ser Gly Tyr Thr Phe
        35                  40                  45

Thr Ser Tyr Trp Leu His Trp Ile Arg Gln Ala Pro Gly Gln Arg Leu
    50                  55                  60

Glu Trp Met Gly Tyr Ile Asn Pro Arg Asn Asp Tyr Thr Glu Tyr Asn
65                  70                  75                  80

Gln Lys Phe Gln Gly Arg Ala Thr Ile Thr Ala Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240
```

```
Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Ala Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Ala Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465
```

<210> SEQ ID NO 43
<211> LENGTH: 514
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

```
Met Gly Trp Ser Cys Ile Ile Leu Phe Leu Val Ala Thr Ala Thr Gly
1               5                   10                  15

Val His Ser Asp Ile Val Leu Thr Gln Ser Pro Asp Ser Leu Ala Val
            20                  25                  30

Ser Ala Gly Glu Arg Val Thr Met Asn Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Val Gln Ala Glu Asp Val Ala Ile Tyr Tyr
            100                 105                 110
```

```
Cys His Gln Tyr Leu Ser Ser Trp Thr Phe Gly Gly Gly Thr Lys Leu
      115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys Thr Ser
225                 230                 235                 240

Gly Gly Gly Gly Ser Gly Gly Gly Gly Ser Gly Gly Gly Gly Ser His
                245                 250                 255

Val Lys Leu Gln Glu Ser Gly Pro Gly Leu Val Gln Pro Ser Gln Ser
            260                 265                 270

Leu Ser Leu Thr Cys Thr Val Ser Gly Phe Ser Leu Thr Asp Tyr Gly
        275                 280                 285

Val His Trp Val Arg Gln Ser Pro Gly Lys Gly Leu Glu Trp Leu Gly
    290                 295                 300

Val Ile Trp Ser Gly Gly Gly Thr Ala Tyr Asn Thr Ala Leu Ile Ser
305                 310                 315                 320

Arg Leu Asn Ile Tyr Arg Asp Asn Ser Lys Asn Gln Val Phe Leu Glu
                325                 330                 335

Met Asn Ser Leu Gln Ala Glu Asp Thr Ala Met Tyr Tyr Cys Ala Arg
            340                 345                 350

Arg Gly Ser Tyr Pro Tyr Asn Tyr Phe Asp Ala Trp Gly Cys Gly Thr
        355                 360                 365

Thr Val Thr Val Ser Ser Gly Gly Gly Gly Ser Gly Gly Gly Gly Ser
    370                 375                 380

Gly Gly Gly Gly Ser Gly Gly Gly Gly Ser Gly Gly Gly Gly Ser Gly
385                 390                 395                 400

Gly Gly Gly Ser Gln Ala Val Val Ile Gln Glu Ser Ala Leu Thr Thr
                405                 410                 415

Pro Pro Gly Glu Thr Val Thr Leu Thr Cys Gly Ser Ser Thr Gly Ala
            420                 425                 430

Val Thr Ala Ser Asn Tyr Ala Asn Trp Val Gln Glu Lys Pro Asp His
        435                 440                 445

Cys Phe Thr Gly Leu Ile Gly Gly His Asn Asn Arg Pro Pro Gly Val
    450                 455                 460

Pro Ala Arg Phe Ser Gly Ser Leu Ile Gly Asp Lys Ala Ala Leu Thr
465                 470                 475                 480

Ile Ala Gly Thr Gln Thr Glu Asp Glu Ala Ile Tyr Phe Cys Ala Leu
                485                 490                 495

Trp Tyr Ser Asp His Trp Val Ile Gly Gly Gly Thr Arg Leu Thr Val
            500                 505                 510

Leu Gly
```

<210> SEQ ID NO 44
<211> LENGTH: 465
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 44

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Leu His Trp Val Arg Gln Ala Pro Gly Gln Arg Leu
    50                  55                  60

Glu Trp Met Gly Tyr Ile Asn Pro Arg Asn Asp Tyr Thr Glu Tyr Asn
65                  70                  75                  80

Gln Asn Phe Lys Asp Arg Val Thr Leu Thr Ala Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Ala Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Ala Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365
```

```
Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465


<210> SEQ ID NO 45
<211> LENGTH: 514
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Gly Trp Ser Cys Ile Ile Leu Phe Leu Val Ala Thr Ala Thr Gly
1               5                   10                  15

Val His Ser Asp Ile Val Leu Thr Gln Ser Pro Asp Ser Leu Ala Val
            20                  25                  30

Ser Ala Gly Glu Arg Val Thr Met Asn Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Val Gln Ala Glu Asp Val Ala Ile Tyr Tyr
            100                 105                 110

Cys His Gln Tyr Leu Ser Ser Trp Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys Thr Ser
225                 230                 235                 240

Gly Gly Gly Gly Ser Gly Gly Gly Gly Ser Gly Gly Gly Gly Ser His
                245                 250                 255
```

```
Val Gln Leu Val Glu Ser Gly Gly Gly Leu Val Gln Pro Gly Gly Ser
            260                 265                 270

Leu Arg Leu Ser Cys Ala Ala Ser Gly Phe Ser Leu Thr Asp Tyr Gly
        275                 280                 285

Val His Trp Val Arg Gln Ala Pro Gly Lys Gly Leu Glu Trp Leu Gly
    290                 295                 300

Val Ile Trp Ser Gly Gly Gly Thr Ala Tyr Asn Thr Ala Leu Ile Ser
305                 310                 315                 320

Arg Phe Thr Ile Ser Arg Asp Asn Ser Lys Asn Thr Leu Tyr Leu Gln
                325                 330                 335

Met Asn Ser Leu Arg Ala Glu Asp Thr Ala Val Tyr Tyr Cys Ala Arg
            340                 345                 350

Arg Gly Ser Tyr Pro Tyr Asn Tyr Phe Asp Ala Trp Gly Cys Gly Thr
        355                 360                 365

Leu Val Thr Val Ser Ser Gly Gly Gly Gly Ser Gly Gly Gly Gly Ser
    370                 375                 380

Gly Gly Gly Gly Ser Gly Gly Gly Gly Ser Gly Gly Gly Gly Ser Gly
385                 390                 395                 400

Gly Gly Gly Ser Gln Ala Val Val Thr Gln Glu Pro Ser Leu Thr Val
                405                 410                 415

Ser Pro Gly Gly Thr Val Thr Leu Thr Cys Gly Ser Ser Thr Gly Ala
            420                 425                 430

Val Thr Ala Ser Asn Tyr Ala Asn Trp Val Gln Gln Lys Pro Gly Gln
        435                 440                 445

Cys Pro Arg Gly Leu Ile Gly Gly His Asn Asn Arg Pro Pro Gly Val
    450                 455                 460

Pro Ala Arg Phe Ser Gly Ser Leu Leu Gly Gly Lys Ala Ala Leu Thr
465                 470                 475                 480

Leu Leu Gly Ala Gln Pro Glu Asp Glu Ala Glu Tyr Tyr Cys Ala Leu
                485                 490                 495

Trp Tyr Ser Asp His Trp Val Ile Gly Gly Gly Thr Lys Leu Thr Val
            500                 505                 510

Leu Gly
```

<210> SEQ ID NO 46
<211> LENGTH: 465
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Leu His Trp Val Arg Gln Ala Pro Gly Gln Arg Leu
    50                  55                  60

Glu Trp Met Gly Tyr Ile Asn Pro Arg Asn Asp Tyr Thr Glu Tyr Asn
65                  70                  75                  80

Gln Asn Phe Lys Asp Arg Val Thr Leu Thr Ala Asp Lys Ser Ala Ser
                85                  90                  95
```

```
Thr Ala Tyr Met Glu Leu Ser Ser Leu Arg Ser Glu Asp Thr Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Ala Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Ala Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465
```

<210> SEQ ID NO 47
<211> LENGTH: 620
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 47

Met Gly Trp Ser Cys Ile Ile Leu Phe Leu Val Ala Thr Ala Thr Gly
1               5                   10                  15

Val His Ser Asp Ile Gln Leu Thr Gln Ser Pro Ser Ser Leu Ala Val
            20                  25                  30

Ser Ala Gly Glu Asn Val Thr Met Ser Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Ser Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Arg Val Gln Val Glu Asp Leu Ala Ile Tyr Tyr
            100                 105                 110

Cys His Gln Tyr Leu Ser Ser Trp Thr Phe Gly Gly Gly Thr Lys Leu
        115                 120                 125

Glu Ile Lys Arg Gly Gly Gly Gly Ser Gly Gly Gly Gly Ser Gly Gly
    130                 135                 140

Gly Gly Ser Gly Gly Gly Gly Ser Gly Gly Gly Gly Ser Gly Gly Gly
145                 150                 155                 160

Gly Ser Gln Val Gln Leu Gln Glu Ser Gly Ala Glu Leu Ser Lys Pro
                165                 170                 175

Gly Ala Ser Val Lys Met Ser Cys Lys Ala Ser Gly Tyr Thr Phe Thr
            180                 185                 190

Ser Tyr Trp Leu His Trp Ile Lys Gln Arg Pro Gly Gln Gly Leu Glu
        195                 200                 205

Trp Ile Gly Tyr Ile Asn Pro Arg Asn Asp Tyr Thr Glu Tyr Asn Gln
    210                 215                 220

Asn Phe Lys Asp Lys Ala Thr Leu Thr Ala Asp Lys Ser Ser Ser Thr
225                 230                 235                 240

Ala Tyr Met Gln Leu Ser Ser Leu Thr Ser Glu Asp Ser Ala Val Tyr
                245                 250                 255

Tyr Cys Ala Arg Arg Asp Ile Thr Thr Phe Tyr Trp Gly Gln Gly Thr
            260                 265                 270

Thr Leu Thr Val Ser Ser Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400
```

```
Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Lys Pro Leu Asp Gly Glu Tyr Phe
                565                 570                 575

Thr Leu Gln Ile Arg Gly Arg Glu Arg Phe Glu Met Phe Arg Glu Leu
            580                 585                 590

Asn Glu Ala Leu Glu Leu Lys Asp Ala Gln Ala Gly Lys Glu Pro Gly
        595                 600                 605

Gly Ser Gly Gly Ala Pro His His His His His His
    610                 615                 620


<210> SEQ ID NO 48
<211> LENGTH: 613
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Gly Trp Ser Cys Ile Ile Leu Phe Leu Val Ala Thr Ala Thr Gly
1               5                   10                  15

Val His Ser Asp Ile Gln Leu Thr Gln Ser Pro Ser Ser Leu Ala Val
            20                  25                  30

Ser Ala Gly Glu Asn Val Thr Met Ser Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Ser Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Arg Val Gln Val Glu Asp Leu Ala Ile Tyr Tyr
            100                 105                 110

Cys His Gln Tyr Leu Ser Ser Trp Thr Phe Gly Gly Gly Thr Lys Leu
        115                 120                 125
```

```
Glu Ile Lys Arg Gly Gly Gly Gly Ser Gly Gly Gly Gly Ser Gly Gly
    130                 135                 140

Gly Gly Ser Gly Gly Gly Gly Ser Gly Gly Gly Gly Ser Gly Gly Gly
145                 150                 155                 160

Gly Ser Gln Val Gln Leu Gln Glu Ser Gly Ala Glu Leu Ser Lys Pro
                165                 170                 175

Gly Ala Ser Val Lys Met Ser Cys Lys Ala Ser Gly Tyr Thr Phe Thr
            180                 185                 190

Ser Tyr Trp Leu His Trp Ile Lys Gln Arg Pro Gly Gln Gly Leu Glu
        195                 200                 205

Trp Ile Gly Tyr Ile Asn Pro Arg Asn Asp Tyr Thr Glu Tyr Asn Gln
    210                 215                 220

Asn Phe Lys Asp Lys Ala Thr Leu Thr Ala Asp Lys Ser Ser Ser Thr
225                 230                 235                 240

Ala Tyr Met Gln Leu Ser Ser Leu Thr Ser Glu Asp Ser Ala Val Tyr
                245                 250                 255

Tyr Cys Ala Arg Arg Asp Ile Thr Thr Phe Tyr Trp Gly Gln Gly Thr
            260                 265                 270

Thr Leu Thr Val Ser Ser Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540
```

Trp Val Ile Gly Gly Gly Thr Lys Leu Thr Val Leu Gly Thr Pro Leu
545 550 555 560

Gly Asp Thr Thr His Thr Ser Gly Lys Pro Leu Asp Gly Glu Tyr Phe
565 570 575

Thr Leu Gln Ile Arg Gly Arg Glu Arg Phe Glu Met Phe Arg Glu Leu
580 585 590

Asn Glu Ala Leu Glu Leu Lys Asp Ala Gln Ala Gly Lys Glu Pro Gly
595 600 605

Gly Ser Gly Gly Ala
610

<210> SEQ ID NO 49
<211> LENGTH: 620
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 49

Met Gly Trp Ser Cys Ile Ile Leu Phe Leu Val Ala Thr Ala Thr Gly
1 5 10 15

Val His Ser Gln Val Gln Leu Gln Glu Ser Gly Ala Glu Leu Ser Lys
20 25 30

Pro Gly Ala Ser Val Lys Met Ser Cys Lys Ala Ser Gly Tyr Thr Phe
35 40 45

Thr Ser Tyr Trp Leu His Trp Ile Lys Gln Arg Pro Gly Gln Gly Leu
50 55 60

Glu Trp Ile Gly Tyr Ile Asn Pro Arg Asn Asp Tyr Thr Glu Tyr Asn
65 70 75 80

Gln Asn Phe Lys Asp Lys Ala Thr Leu Thr Ala Asp Lys Ser Ser Ser
85 90 95

Thr Ala Tyr Met Gln Leu Ser Ser Leu Thr Ser Glu Asp Ser Ala Val
100 105 110

Tyr Tyr Cys Ala Arg Arg Asp Ile Thr Thr Phe Tyr Trp Gly Gln Gly
115 120 125

Thr Thr Leu Thr Val Ser Ser Gly Gly Gly Gly Ser Gly Gly Gly Gly
130 135 140

Ser Gly Gly Gly Gly Ser Gly Gly Gly Gly Ser Gly Gly Gly Gly Ser
145 150 155 160

Gly Gly Gly Gly Ser Asp Ile Gln Leu Thr Gln Ser Pro Ser Ser Leu
165 170 175

Ala Val Ser Ala Gly Glu Asn Val Thr Met Ser Cys Lys Ser Ser Gln
180 185 190

Ser Val Leu Tyr Ser Ala Asn His Lys Asn Tyr Leu Ala Trp Tyr Gln
195 200 205

Gln Lys Pro Gly Gln Ser Pro Lys Leu Leu Ile Tyr Trp Ala Ser Thr
210 215 220

Arg Glu Ser Gly Val Pro Asp Arg Phe Thr Gly Ser Gly Ser Gly Thr
225 230 235 240

Asp Phe Thr Leu Thr Ile Ser Arg Val Gln Val Glu Asp Leu Ala Ile
245 250 255

Tyr Tyr Cys His Gln Tyr Leu Ser Ser Trp Thr Phe Gly Gly Gly Thr
260 265 270

Lys Leu Glu Ile Lys Arg Gly Gly Gly Gly Ser Gly Gly Gly Ser
275 280 285

Gly Gly Gly Gly Ser Gly Gly Gly Gly Ser His Val Gln Leu Val Glu
290 295 300

Ser Gly Gly Gly Leu Val Gln Pro Gly Gly Ser Leu Arg Leu Ser Cys
305 310 315 320

Ala Ala Ser Gly Phe Ser Leu Thr Asp Tyr Gly Val His Trp Val Arg
325 330 335

Gln Ala Pro Gly Lys Gly Leu Glu Trp Leu Gly Val Ile Trp Ser Gly
340 345 350

Gly Gly Thr Ala Tyr Asn Thr Ala Leu Ile Ser Arg Phe Thr Ile Ser
355 360 365

Arg Asp Asn Ser Lys Asn Thr Leu Tyr Leu Gln Met Asn Ser Leu Arg
370 375 380

Ala Glu Asp Thr Ala Val Tyr Tyr Cys Ala Arg Arg Gly Ser Tyr Pro
385 390 395 400

Tyr Asn Tyr Phe Asp Ala Trp Gly Cys Gly Thr Leu Val Thr Val Ser
405 410 415

Ser Gly Gly Gly Gly Ser Gly Gly Gly Gly Ser Gly Gly Gly Gly Ser
420 425 430

Gly Gly Gly Gly Ser Gly Gly Gly Gly Ser Gly Gly Gly Gly Ser Gln
435 440 445

Ala Val Val Thr Gln Glu Pro Ser Leu Thr Val Ser Pro Gly Gly Thr
450 455 460

Val Thr Leu Thr Cys Gly Ser Ser Thr Gly Ala Val Thr Ala Ser Asn
465 470 475 480

Tyr Ala Asn Trp Val Gln Gln Lys Pro Gly Gln Cys Pro Arg Gly Leu
485 490 495

Ile Gly Gly His Asn Asn Arg Pro Pro Gly Val Pro Ala Arg Phe Ser
500 505 510

Gly Ser Leu Leu Gly Gly Lys Ala Ala Leu Thr Leu Leu Gly Ala Gln
515 520 525

Pro Glu Asp Glu Ala Glu Tyr Tyr Cys Ala Leu Trp Tyr Ser Asp His
530 535 540

Trp Val Ile Gly Gly Gly Thr Lys Leu Thr Val Leu Gly Thr Pro Leu
545 550 555 560

Gly Asp Thr Thr His Thr Ser Gly Lys Pro Leu Asp Gly Glu Tyr Phe
565 570 575

Thr Leu Gln Ile Arg Gly Arg Glu Arg Phe Glu Met Phe Arg Glu Leu
580 585 590

Asn Glu Ala Leu Glu Leu Lys Asp Ala Gln Ala Gly Lys Glu Pro Gly
595 600 605

Gly Ser Gly Gly Ala Pro His His His His His His
610 615 620

<210> SEQ ID NO 50
<211> LENGTH: 613
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 50

Met Gly Trp Ser Cys Ile Ile Leu Phe Leu Val Ala Thr Ala Thr Gly
1 5 10 15

```
Val His Ser Gln Val Gln Leu Gln Glu Ser Gly Ala Glu Leu Ser Lys
            20                  25                  30

Pro Gly Ala Ser Val Lys Met Ser Cys Lys Ala Ser Gly Tyr Thr Phe
        35                  40                  45

Thr Ser Tyr Trp Leu His Trp Ile Lys Gln Arg Pro Gly Gln Gly Leu
    50                  55                  60

Glu Trp Ile Gly Tyr Ile Asn Pro Arg Asn Asp Tyr Thr Glu Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Asp Ile Gln Leu Thr Gln Ser Pro Ser Ser Leu
                165                 170                 175

Ala Val Ser Ala Gly Glu Asn Val Thr Met Ser Cys Lys Ser Ser Gln
            180                 185                 190

Ser Val Leu Tyr Ser Ala Asn His Lys Asn Tyr Leu Ala Trp Tyr Gln
        195                 200                 205

Gln Lys Pro Gly Gln Ser Pro Lys Leu Leu Ile Tyr Trp Ala Ser Thr
    210                 215                 220

Arg Glu Ser Gly Val Pro Asp Arg Phe Thr Gly Ser Gly Ser Gly Thr
225                 230                 235                 240

Asp Phe Thr Leu Thr Ile Ser Arg Val Gln Val Glu Asp Leu Ala Ile
                245                 250                 255

Tyr Tyr Cys His Gln Tyr Leu Ser Ser Trp Thr Phe Gly Gly Gly Thr
            260                 265                 270

Lys Leu Glu Ile Lys Arg Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430
```

```
Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Lys Pro Leu Asp Gly Glu Tyr Phe
                565                 570                 575

Thr Leu Gln Ile Arg Gly Arg Glu Arg Phe Glu Met Phe Arg Glu Leu
            580                 585                 590

Asn Glu Ala Leu Glu Leu Lys Asp Ala Gln Ala Gly Lys Glu Pro Gly
        595                 600                 605

Gly Ser Gly Gly Ala
    610
```

<210> SEQ ID NO 51
<211> LENGTH: 638
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 51

```
Met Gly Trp Ser Cys Ile Ile Leu Phe Leu Val Ala Thr Ala Thr Gly
1               5                   10                  15

Val His Ser Asp Ile Gln Leu Thr Gln Ser Pro Ser Ser Leu Ala Val
            20                  25                  30

Ser Ala Gly Glu Asn Val Thr Met Ser Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Ser Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Arg Val Gln Val Glu Asp Leu Ala Ile Tyr Tyr
            100                 105                 110

Cys His Gln Tyr Leu Ser Ser Trp Thr Phe Gly Gly Gly Thr Lys Leu
        115                 120                 125

Glu Ile Lys Arg Gly Gly Gly Gly Ser Gly Gly Gly Gly Ser Gly Gly
    130                 135                 140

Gly Gly Ser Gly Gly Gly Gly Ser Gly Gly Gly Gly Ser Gly Gly Gly
145                 150                 155                 160

Gly Ser Gln Val Gln Leu Gln Glu Ser Gly Ala Glu Leu Ser Lys Pro
                165                 170                 175
```

```
Gly Ala Ser Val Lys Met Ser Cys Lys Ala Ser Gly Tyr Thr Phe Thr
            180                 185                 190

Ser Tyr Trp Leu His Trp Ile Lys Gln Arg Pro Gly Gln Gly Leu Glu
        195                 200                 205

Trp Ile Gly Tyr Ile Asn Pro Arg Asn Asp Tyr Thr Glu Tyr Asn Gln
    210                 215                 220

Asn Phe Lys Asp Lys Ala Thr Leu Thr Ala Asp Lys Ser Ser Ser Thr
225                 230                 235                 240

Ala Tyr Met Gln Leu Ser Ser Leu Thr Ser Glu Asp Ser Ala Val Tyr
                245                 250                 255

Tyr Cys Ala Arg Arg Asp Ile Thr Thr Phe Tyr Trp Gly Gln Gly Thr
            260                 265                 270

Thr Leu Thr Val Ser Ser Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Arg Ser Pro Asp Asp Glu Leu Leu
                565                 570                 575

Tyr Leu Pro Val Arg Gly Arg Glu Thr Tyr Glu Met Leu Leu Lys Ile
            580                 585                 590
```

Lys Glu Ser Leu Glu Leu Met Gln Tyr Leu Pro Gln His Thr Ile Glu
595 600 605

Thr Tyr Arg Gln Gln Gln Gln Gln Gln His Gln His Leu Leu Gln Lys
610 615 620

Gln Gly Gly Ser Gly Gly Ala Pro His His His His His His
625 630 635

<210> SEQ ID NO 52
<211> LENGTH: 631
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

Met Gly Trp Ser Cys Ile Ile Leu Phe Leu Val Ala Thr Ala Thr Gly
1 5 10 15

Val His Ser Asp Ile Gln Leu Thr Gln Ser Pro Ser Ser Leu Ala Val
20 25 30

Ser Ala Gly Glu Asn Val Thr Met Ser Cys Lys Ser Ser Gln Ser Val
35 40 45

Leu Tyr Ser Ala Asn His Lys Asn Tyr Leu Ala Trp Tyr Gln Gln Lys
50 55 60

Pro Gly Gln Ser Pro Lys Leu Leu Ile Tyr Trp Ala Ser Thr Arg Glu
65 70 75 80

Ser Gly Val Pro Asp Arg Phe Thr Gly Ser Gly Ser Gly Thr Asp Phe
85 90 95

Thr Leu Thr Ile Ser Arg Val Gln Val Glu Asp Leu Ala Ile Tyr Tyr
100 105 110

Cys His Gln Tyr Leu Ser Ser Trp Thr Phe Gly Gly Gly Thr Lys Leu
115 120 125

Glu Ile Lys Arg Gly Gly Gly Gly Ser Gly Gly Gly Gly Ser Gly Gly
130 135 140

Gly Gly Ser Gly Gly Gly Gly Ser Gly Gly Gly Gly Ser Gly Gly Gly
145 150 155 160

Gly Ser Gln Val Gln Leu Gln Glu Ser Gly Ala Glu Leu Ser Lys Pro
165 170 175

Gly Ala Ser Val Lys Met Ser Cys Lys Ala Ser Gly Tyr Thr Phe Thr
180 185 190

Ser Tyr Trp Leu His Trp Ile Lys Gln Arg Pro Gly Gln Gly Leu Glu
195 200 205

Trp Ile Gly Tyr Ile Asn Pro Arg Asn Asp Tyr Thr Glu Tyr Asn Gln
210 215 220

Asn Phe Lys Asp Lys Ala Thr Leu Thr Ala Asp Lys Ser Ser Ser Thr
225 230 235 240

Ala Tyr Met Gln Leu Ser Ser Leu Thr Ser Glu Asp Ser Ala Val Tyr
245 250 255

Tyr Cys Ala Arg Arg Asp Ile Thr Thr Phe Tyr Trp Gly Gln Gly Thr
260 265 270

Thr Leu Thr Val Ser Ser Gly Gly Gly Gly Ser Gly Gly Gly Gly Ser
275 280 285

Gly Gly Gly Gly Ser Gly Gly Gly Gly Ser His Val Gln Leu Val Glu
290 295 300

Ser Gly Gly Gly Leu Val Gln Pro Gly Gly Ser Leu Arg Leu Ser Cys
305 310 315 320

Ala Ala Ser Gly Phe Ser Leu Thr Asp Tyr Gly Val His Trp Val Arg
325 330 335

Gln Ala Pro Gly Lys Gly Leu Glu Trp Leu Gly Val Ile Trp Ser Gly
340 345 350

Gly Gly Thr Ala Tyr Asn Thr Ala Leu Ile Ser Arg Phe Thr Ile Ser
355 360 365

Arg Asp Asn Ser Lys Asn Thr Leu Tyr Leu Gln Met Asn Ser Leu Arg
370 375 380

Ala Glu Asp Thr Ala Val Tyr Tyr Cys Ala Arg Arg Gly Ser Tyr Pro
385 390 395 400

Tyr Asn Tyr Phe Asp Ala Trp Gly Cys Gly Thr Leu Val Thr Val Ser
405 410 415

Ser Gly Gly Gly Gly Ser Gly Gly Gly Gly Ser Gly Gly Gly Gly Ser
420 425 430

Gly Gly Gly Gly Ser Gly Gly Gly Gly Ser Gly Gly Gly Gly Ser Gln
435 440 445

Ala Val Val Thr Gln Glu Pro Ser Leu Thr Val Ser Pro Gly Gly Thr
450 455 460

Val Thr Leu Thr Cys Gly Ser Ser Thr Gly Ala Val Thr Ala Ser Asn
465 470 475 480

Tyr Ala Asn Trp Val Gln Gln Lys Pro Gly Gln Cys Pro Arg Gly Leu
485 490 495

Ile Gly Gly His Asn Asn Arg Pro Pro Gly Val Pro Ala Arg Phe Ser
500 505 510

Gly Ser Leu Leu Gly Gly Lys Ala Ala Leu Thr Leu Leu Gly Ala Gln
515 520 525

Pro Glu Asp Glu Ala Glu Tyr Tyr Cys Ala Leu Trp Tyr Ser Asp His
530 535 540

Trp Val Ile Gly Gly Gly Thr Lys Leu Thr Val Leu Gly Thr Pro Leu
545 550 555 560

Gly Asp Thr Thr His Thr Ser Gly Arg Ser Pro Asp Asp Glu Leu Leu
565 570 575

Tyr Leu Pro Val Arg Gly Arg Glu Thr Tyr Glu Met Leu Leu Lys Ile
580 585 590

Lys Glu Ser Leu Glu Leu Met Gln Tyr Leu Pro Gln His Thr Ile Glu
595 600 605

Thr Tyr Arg Gln Gln Gln Gln Gln Gln His Gln His Leu Leu Gln Lys
610 615 620

Gln Gly Gly Ser Gly Gly Ala
625 630

<210> SEQ ID NO 53
<211> LENGTH: 638
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 53

Met Gly Trp Ser Cys Ile Ile Leu Phe Leu Val Ala Thr Ala Thr Gly
1 5 10 15

Val His Ser Gln Val Gln Leu Gln Glu Ser Gly Ala Glu Leu Ser Lys
20 25 30

```
Pro Gly Ala Ser Val Lys Met Ser Cys Lys Ala Ser Gly Tyr Thr Phe
        35                  40                  45

Thr Ser Tyr Trp Leu His Trp Ile Lys Gln Arg Pro Gly Gln Gly Leu
    50                  55                  60

Glu Trp Ile Gly Tyr Ile Asn Pro Arg Asn Asp Tyr Thr Glu Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Asp Ile Gln Leu Thr Gln Ser Pro Ser Ser Leu
                165                 170                 175

Ala Val Ser Ala Gly Glu Asn Val Thr Met Ser Cys Lys Ser Ser Gln
            180                 185                 190

Ser Val Leu Tyr Ser Ala Asn His Lys Asn Tyr Leu Ala Trp Tyr Gln
        195                 200                 205

Gln Lys Pro Gly Gln Ser Pro Lys Leu Leu Ile Tyr Trp Ala Ser Thr
    210                 215                 220

Arg Glu Ser Gly Val Pro Asp Arg Phe Thr Gly Ser Gly Ser Gly Thr
225                 230                 235                 240

Asp Phe Thr Leu Thr Ile Ser Arg Val Gln Val Glu Asp Leu Ala Ile
                245                 250                 255

Tyr Tyr Cys His Gln Tyr Leu Ser Ser Trp Thr Phe Gly Gly Gly Thr
            260                 265                 270

Lys Leu Glu Ile Lys Arg Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445
```

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Arg Ser Pro Asp Asp Glu Leu Leu
                565                 570                 575

Tyr Leu Pro Val Arg Gly Arg Glu Thr Tyr Glu Met Leu Leu Lys Ile
            580                 585                 590

Lys Glu Ser Leu Glu Leu Met Gln Tyr Leu Pro Gln His Thr Ile Glu
        595                 600                 605

Thr Tyr Arg Gln Gln Gln Gln Gln Gln His Gln His Leu Leu Gln Lys
    610                 615                 620

Gln Gly Gly Ser Gly Gly Ala Pro His His His His His His
625                 630                 635

<210> SEQ ID NO 54
<211> LENGTH: 631
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Gly Trp Ser Cys Ile Ile Leu Phe Leu Val Ala Thr Ala Thr Gly
1               5                   10                  15

Val His Ser Gln Val Gln Leu Gln Glu Ser Gly Ala Glu Leu Ser Lys
            20                  25                  30

Pro Gly Ala Ser Val Lys Met Ser Cys Lys Ala Ser Gly Tyr Thr Phe
        35                  40                  45

Thr Ser Tyr Trp Leu His Trp Ile Lys Gln Arg Pro Gly Gln Gly Leu
    50                  55                  60

Glu Trp Ile Gly Tyr Ile Asn Pro Arg Asn Asp Tyr Thr Glu Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Asp Ile Gln Leu Thr Gln Ser Pro Ser Ser Leu
                165                 170                 175

```
Ala Val Ser Ala Gly Glu Asn Val Thr Met Ser Cys Lys Ser Ser Gln
            180                 185                 190

Ser Val Leu Tyr Ser Ala Asn His Lys Asn Tyr Leu Ala Trp Tyr Gln
        195                 200                 205

Gln Lys Pro Gly Gln Ser Pro Lys Leu Leu Ile Tyr Trp Ala Ser Thr
    210                 215                 220

Arg Glu Ser Gly Val Pro Asp Arg Phe Thr Gly Ser Gly Ser Gly Thr
225                 230                 235                 240

Asp Phe Thr Leu Thr Ile Ser Arg Val Gln Val Glu Asp Leu Ala Ile
                245                 250                 255

Tyr Tyr Cys His Gln Tyr Leu Ser Ser Trp Thr Phe Gly Gly Gly Thr
            260                 265                 270

Lys Leu Glu Ile Lys Arg Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Arg Ser Pro Asp Asp Glu Leu Leu
                565                 570                 575

Tyr Leu Pro Val Arg Gly Arg Glu Thr Tyr Glu Met Leu Leu Lys Ile
            580                 585                 590
```

```
Lys Glu Ser Leu Glu Leu Met Gln Tyr Leu Pro Gln His Thr Ile Glu
        595                 600                 605

Thr Tyr Arg Gln Gln Gln Gln Gln Gln His Gln His Leu Leu Gln Lys
    610                 615                 620

Gln Gly Gly Ser Gly Gly Ala
625                 630


<210> SEQ ID NO 55
<211> LENGTH: 633
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Gly Trp Ser Cys Ile Ile Leu Phe Leu Val Ala Thr Ala Thr Gly
1               5                   10                  15

Val His Ser Asp Ile Gln Leu Thr Gln Ser Pro Ser Ser Leu Ala Val
            20                  25                  30

Ser Ala Gly Glu Asn Val Thr Met Ser Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Ser Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Arg Val Gln Val Glu Asp Leu Ala Ile Tyr Tyr
            100                 105                 110

Cys His Gln Tyr Leu Ser Ser Trp Thr Phe Gly Gly Gly Thr Lys Leu
        115                 120                 125

Glu Ile Lys Arg Gly Gly Gly Gly Ser Gly Gly Gly Gly Ser Gly Gly
    130                 135                 140

Gly Gly Ser Gly Gly Gly Gly Ser Gly Gly Gly Gly Ser Gly Gly Gly
145                 150                 155                 160

Gly Ser Gln Val Gln Leu Gln Glu Ser Gly Ala Glu Leu Ser Lys Pro
                165                 170                 175

Gly Ala Ser Val Lys Met Ser Cys Lys Ala Ser Gly Tyr Thr Phe Thr
            180                 185                 190

Ser Tyr Trp Leu His Trp Ile Lys Gln Arg Pro Gly Gln Gly Leu Glu
        195                 200                 205

Trp Ile Gly Tyr Ile Asn Pro Arg Asn Asp Tyr Thr Glu Tyr Asn Gln
    210                 215                 220

Asn Phe Lys Asp Lys Ala Thr Leu Thr Ala Asp Lys Ser Ser Ser Thr
225                 230                 235                 240

Ala Tyr Met Gln Leu Ser Ser Leu Thr Ser Glu Asp Ser Ala Val Tyr
                245                 250                 255

Tyr Cys Ala Arg Arg Asp Ile Thr Thr Phe Tyr Trp Gly Gln Gly Thr
            260                 265                 270

Thr Leu Thr Val Ser Ser Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320
```

Ala Ala Ser Gly Phe Ser Leu Thr Asp Tyr Gly Val His Trp Val Arg
325 330 335

Gln Ala Pro Gly Lys Gly Leu Glu Trp Leu Gly Val Ile Trp Ser Gly
340 345 350

Gly Gly Thr Ala Tyr Asn Thr Ala Leu Ile Ser Arg Phe Thr Ile Ser
355 360 365

Arg Asp Asn Ser Lys Asn Thr Leu Tyr Leu Gln Met Asn Ser Leu Arg
370 375 380

Ala Glu Asp Thr Ala Val Tyr Tyr Cys Ala Arg Arg Gly Ser Tyr Pro
385 390 395 400

Tyr Asn Tyr Phe Asp Ala Trp Gly Cys Gly Thr Leu Val Thr Val Ser
405 410 415

Ser Gly Gly Gly Gly Ser Gly Gly Gly Gly Ser Gly Gly Gly Gly Ser
420 425 430

Gly Gly Gly Gly Ser Gly Gly Gly Gly Ser Gly Gly Gly Gly Ser Gln
435 440 445

Ala Val Val Thr Gln Glu Pro Ser Leu Thr Val Ser Pro Gly Gly Thr
450 455 460

Val Thr Leu Thr Cys Gly Ser Ser Thr Gly Ala Val Thr Ala Ser Asn
465 470 475 480

Tyr Ala Asn Trp Val Gln Gln Lys Pro Gly Gln Cys Pro Arg Gly Leu
485 490 495

Ile Gly Gly His Asn Asn Arg Pro Pro Gly Val Pro Ala Arg Phe Ser
500 505 510

Gly Ser Leu Leu Gly Gly Lys Ala Ala Leu Thr Leu Leu Gly Ala Gln
515 520 525

Pro Glu Asp Glu Ala Glu Tyr Tyr Cys Ala Leu Trp Tyr Ser Asp His
530 535 540

Trp Val Ile Gly Gly Gly Thr Lys Leu Thr Val Leu Gly Thr Pro Leu
545 550 555 560

Gly Asp Thr Thr His Thr Ser Gly Arg His Gly Asp Glu Asp Thr Tyr
565 570 575

Tyr Leu Gln Val Arg Gly Arg Glu Asn Phe Glu Ile Leu Met Lys Leu
580 585 590

Lys Glu Ser Leu Glu Leu Met Glu Leu Val Pro Gln Pro Leu Val Asp
595 600 605

Ser Tyr Arg Gln Gln Gln Gln Leu Leu Gln Arg Pro Gly Gly Ser Gly
610 615 620

Gly Ala Pro His His His His His His
625 630

<210> SEQ ID NO 56
<211> LENGTH: 626
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 56

Met Gly Trp Ser Cys Ile Ile Leu Phe Leu Val Ala Thr Ala Thr Gly
1 5 10 15

Val His Ser Asp Ile Gln Leu Thr Gln Ser Pro Ser Ser Leu Ala Val
20 25 30

```
Ser Ala Gly Glu Asn Val Thr Met Ser Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Ser Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Arg Val Gln Val Glu Asp Leu Ala Ile Tyr Tyr
            100                 105                 110

Cys His Gln Tyr Leu Ser Ser Trp Thr Phe Gly Gly Gly Thr Lys Leu
        115                 120                 125

Glu Ile Lys Arg Gly Gly Gly Gly Ser Gly Gly Gly Gly Ser Gly Gly
    130                 135                 140

Gly Gly Ser Gly Gly Gly Gly Ser Gly Gly Gly Gly Ser Gly Gly Gly
145                 150                 155                 160

Gly Ser Gln Val Gln Leu Gln Glu Ser Gly Ala Glu Leu Ser Lys Pro
                165                 170                 175

Gly Ala Ser Val Lys Met Ser Cys Lys Ala Ser Gly Tyr Thr Phe Thr
            180                 185                 190

Ser Tyr Trp Leu His Trp Ile Lys Gln Arg Pro Gly Gln Gly Leu Glu
        195                 200                 205

Trp Ile Gly Tyr Ile Asn Pro Arg Asn Asp Tyr Thr Glu Tyr Asn Gln
    210                 215                 220

Asn Phe Lys Asp Lys Ala Thr Leu Thr Ala Asp Lys Ser Ser Ser Thr
225                 230                 235                 240

Ala Tyr Met Gln Leu Ser Ser Leu Thr Ser Glu Asp Ser Ala Val Tyr
                245                 250                 255

Tyr Cys Ala Arg Arg Asp Ile Thr Thr Phe Tyr Trp Gly Gln Gly Thr
            260                 265                 270

Thr Leu Thr Val Ser Ser Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445
```

```
Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Arg His Gly Asp Glu Asp Thr Tyr
                565                 570                 575

Tyr Leu Gln Val Arg Gly Arg Glu Asn Phe Glu Ile Leu Met Lys Leu
            580                 585                 590

Lys Glu Ser Leu Glu Leu Met Glu Leu Val Pro Gln Pro Leu Val Asp
        595                 600                 605

Ser Tyr Arg Gln Gln Gln Gln Leu Leu Gln Arg Pro Gly Gly Ser Gly
    610                 615                 620

Gly Ala
625


<210> SEQ ID NO 57
<211> LENGTH: 633
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Gly Trp Ser Cys Ile Ile Leu Phe Leu Val Ala Thr Ala Thr Gly
1               5                   10                  15

Val His Ser Gln Val Gln Leu Gln Glu Ser Gly Ala Glu Leu Ser Lys
            20                  25                  30

Pro Gly Ala Ser Val Lys Met Ser Cys Lys Ala Ser Gly Tyr Thr Phe
        35                  40                  45

Thr Ser Tyr Trp Leu His Trp Ile Lys Gln Arg Pro Gly Gln Gly Leu
    50                  55                  60

Glu Trp Ile Gly Tyr Ile Asn Pro Arg Asn Asp Tyr Thr Glu Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Asp Ile Gln Leu Thr Gln Ser Pro Ser Ser Leu
                165                 170                 175
```

```
Ala Val Ser Ala Gly Glu Asn Val Thr Met Ser Cys Lys Ser Ser Gln
            180                 185                 190

Ser Val Leu Tyr Ser Ala Asn His Lys Asn Tyr Leu Ala Trp Tyr Gln
        195                 200                 205

Gln Lys Pro Gly Gln Ser Pro Lys Leu Leu Ile Tyr Trp Ala Ser Thr
    210                 215                 220

Arg Glu Ser Gly Val Pro Asp Arg Phe Thr Gly Ser Gly Ser Gly Thr
225                 230                 235                 240

Asp Phe Thr Leu Thr Ile Ser Arg Val Gln Val Glu Asp Leu Ala Ile
                245                 250                 255

Tyr Tyr Cys His Gln Tyr Leu Ser Ser Trp Thr Phe Gly Gly Gly Thr
            260                 265                 270

Lys Leu Glu Ile Lys Arg Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Arg His Gly Asp Glu Asp Thr Tyr
                565                 570                 575

Tyr Leu Gln Val Arg Gly Arg Glu Asn Phe Glu Ile Leu Met Lys Leu
            580                 585                 590
```

Lys Glu Ser Leu Glu Leu Met Glu Leu Val Pro Gln Pro Leu Val Asp
595 600 605

Ser Tyr Arg Gln Gln Gln Gln Leu Leu Gln Arg Pro Gly Gly Ser Gly
610 615 620

Gly Ala Pro His His His His His His
625 630

<210> SEQ ID NO 58
<211> LENGTH: 626
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

Met Gly Trp Ser Cys Ile Ile Leu Phe Leu Val Ala Thr Ala Thr Gly
1 5 10 15

Val His Ser Gln Val Gln Leu Gln Glu Ser Gly Ala Glu Leu Ser Lys
20 25 30

Pro Gly Ala Ser Val Lys Met Ser Cys Lys Ala Ser Gly Tyr Thr Phe
35 40 45

Thr Ser Tyr Trp Leu His Trp Ile Lys Gln Arg Pro Gly Gln Gly Leu
50 55 60

Glu Trp Ile Gly Tyr Ile Asn Pro Arg Asn Asp Tyr Thr Glu Tyr Asn
65 70 75 80

Gln Asn Phe Lys Asp Lys Ala Thr Leu Thr Ala Asp Lys Ser Ser Ser
85 90 95

Thr Ala Tyr Met Gln Leu Ser Ser Leu Thr Ser Glu Asp Ser Ala Val
100 105 110

Tyr Tyr Cys Ala Arg Arg Asp Ile Thr Thr Phe Tyr Trp Gly Gln Gly
115 120 125

Thr Thr Leu Thr Val Ser Ser Gly Gly Gly Gly Ser Gly Gly Gly Gly
130 135 140

Ser Gly Gly Gly Gly Ser Gly Gly Gly Gly Ser Gly Gly Gly Gly Ser
145 150 155 160

Gly Gly Gly Gly Ser Asp Ile Gln Leu Thr Gln Ser Pro Ser Ser Leu
165 170 175

Ala Val Ser Ala Gly Glu Asn Val Thr Met Ser Cys Lys Ser Ser Gln
180 185 190

Ser Val Leu Tyr Ser Ala Asn His Lys Asn Tyr Leu Ala Trp Tyr Gln
195 200 205

Gln Lys Pro Gly Gln Ser Pro Lys Leu Leu Ile Tyr Trp Ala Ser Thr
210 215 220

Arg Glu Ser Gly Val Pro Asp Arg Phe Thr Gly Ser Gly Ser Gly Thr
225 230 235 240

Asp Phe Thr Leu Thr Ile Ser Arg Val Gln Val Glu Asp Leu Ala Ile
245 250 255

Tyr Tyr Cys His Gln Tyr Leu Ser Ser Trp Thr Phe Gly Gly Gly Thr
260 265 270

Lys Leu Glu Ile Lys Arg Gly Gly Gly Gly Ser Gly Gly Gly Gly Ser
275 280 285

Gly Gly Gly Gly Ser Gly Gly Gly Gly Ser His Val Gln Leu Val Glu
290 295 300

Ser Gly Gly Gly Leu Val Gln Pro Gly Gly Ser Leu Arg Leu Ser Cys
305 310 315 320

```
Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Arg His Gly Asp Glu Asp Thr Tyr
                565                 570                 575

Tyr Leu Gln Val Arg Gly Arg Glu Asn Phe Glu Ile Leu Met Lys Leu
            580                 585                 590

Lys Glu Ser Leu Glu Leu Met Glu Leu Val Pro Gln Pro Leu Val Asp
        595                 600                 605

Ser Tyr Arg Gln Gln Gln Gln Leu Leu Gln Arg Pro Gly Gly Ser Gly
    610                 615                 620

Gly Ala
625


<210> SEQ ID NO 59
<211> LENGTH: 620
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Gly Trp Ser Cys Ile Ile Leu Phe Leu Val Ala Thr Ala Thr Gly
1               5                   10                  15

Val His Ser Asp Ile Val Leu Thr Gln Ser Pro Asp Ser Leu Ala Val
            20                  25                  30
```

```
Ser Ala Gly Glu Arg Val Thr Met Asn Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Val Gln Ala Glu Asp Val Ala Ile Tyr Tyr
            100                 105                 110

Cys His Gln Tyr Leu Ser Ser Trp Thr Phe Gly Gly Gly Thr Lys Leu
        115                 120                 125

Glu Ile Lys Arg Gly Gly Gly Gly Ser Gly Gly Gly Gly Ser Gly Gly
    130                 135                 140

Gly Gly Ser Gly Gly Gly Gly Ser Gly Gly Gly Gly Ser Gly Gly Gly
145                 150                 155                 160

Gly Ser Gln Val Gln Leu Gln Gln Ser Gly Ala Glu Val Lys Lys Pro
                165                 170                 175

Gly Ala Ser Val Lys Met Ser Cys Lys Ala Ser Gly Tyr Thr Phe Thr
            180                 185                 190

Ser Tyr Trp Leu His Trp Ile Arg Gln Ala Pro Gly Gln Arg Leu Glu
        195                 200                 205

Trp Met Gly Tyr Ile Asn Pro Arg Asn Asp Tyr Thr Glu Tyr Asn Gln
    210                 215                 220

Lys Phe Gln Gly Arg Ala Thr Ile Thr Ala Asp Lys Ser Ala Ser Thr
225                 230                 235                 240

Ala Tyr Met Glu Leu Ser Ser Leu Arg Ser Glu Asp Thr Ala Val Tyr
                245                 250                 255

Tyr Cys Ala Arg Arg Asp Ile Thr Thr Phe Tyr Trp Gly Gln Gly Thr
            260                 265                 270

Thr Leu Thr Val Ser Ser Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445
```

```
Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Lys Pro Leu Asp Gly Glu Tyr Phe
                565                 570                 575

Thr Leu Gln Ile Arg Gly Arg Glu Arg Phe Glu Met Phe Arg Glu Leu
            580                 585                 590

Asn Glu Ala Leu Glu Leu Lys Asp Ala Gln Ala Gly Lys Glu Pro Gly
        595                 600                 605

Gly Ser Gly Gly Ala Pro His His His His His His
    610                 615                 620
```

<210> SEQ ID NO 60
<211> LENGTH: 613
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Met Gly Trp Ser Cys Ile Ile Leu Phe Leu Val Ala Thr Ala Thr Gly
1               5                   10                  15

Val His Ser Asp Ile Val Leu Thr Gln Ser Pro Asp Ser Leu Ala Val
            20                  25                  30

Ser Ala Gly Glu Arg Val Thr Met Asn Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Val Gln Ala Glu Asp Val Ala Ile Tyr Tyr
            100                 105                 110

Cys His Gln Tyr Leu Ser Ser Trp Thr Phe Gly Gly Gly Thr Lys Leu
        115                 120                 125

Glu Ile Lys Arg Gly Gly Gly Gly Ser Gly Gly Gly Gly Ser Gly Gly
    130                 135                 140

Gly Gly Ser Gly Gly Gly Gly Ser Gly Gly Gly Gly Ser Gly Gly Gly
145                 150                 155                 160

Gly Ser Gln Val Gln Leu Gln Gln Ser Gly Ala Glu Val Lys Lys Pro
                165                 170                 175

Gly Ala Ser Val Lys Met Ser Cys Lys Ala Ser Gly Tyr Thr Phe Thr
            180                 185                 190
```

```
Ser Tyr Trp Leu His Trp Ile Arg Gln Ala Pro Gly Gln Arg Leu Glu
        195                 200                 205

Trp Met Gly Tyr Ile Asn Pro Arg Asn Asp Tyr Thr Glu Tyr Asn Gln
    210                 215                 220

Lys Phe Gln Gly Arg Ala Thr Ile Thr Ala Asp Lys Ser Ala Ser Thr
225                 230                 235                 240

Ala Tyr Met Glu Leu Ser Ser Leu Arg Ser Glu Asp Thr Ala Val Tyr
                245                 250                 255

Tyr Cys Ala Arg Arg Asp Ile Thr Thr Phe Tyr Trp Gly Gln Gly Thr
            260                 265                 270

Thr Leu Thr Val Ser Ser Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Lys Pro Leu Asp Gly Glu Tyr Phe
                565                 570                 575

Thr Leu Gln Ile Arg Gly Arg Glu Arg Phe Glu Met Phe Arg Glu Leu
            580                 585                 590

Asn Glu Ala Leu Glu Leu Lys Asp Ala Gln Ala Gly Lys Glu Pro Gly
        595                 600                 605
```

```
Gly Ser Gly Gly Ala
    610


<210> SEQ ID NO 61
<211> LENGTH: 620
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Gly Trp Ser Cys Ile Ile Leu Phe Leu Val Ala Thr Ala Thr Gly
1               5                   10                  15

Val His Ser Gln Val Gln Leu Gln Gln Ser Gly Ala Glu Val Lys Lys
            20                  25                  30

Pro Gly Ala Ser Val Lys Met Ser Cys Lys Ala Ser Gly Tyr Thr Phe
        35                  40                  45

Thr Ser Tyr Trp Leu His Trp Ile Arg Gln Ala Pro Gly Gln Arg Leu
    50                  55                  60

Glu Trp Met Gly Tyr Ile Asn Pro Arg Asn Asp Tyr Thr Glu Tyr Asn
65                  70                  75                  80

Gln Lys Phe Gln Gly Arg Ala Thr Ile Thr Ala Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Asp Ile Val Leu Thr Gln Ser Pro Asp Ser Leu
                165                 170                 175

Ala Val Ser Ala Gly Glu Arg Val Thr Met Asn Cys Lys Ser Ser Gln
            180                 185                 190

Ser Val Leu Tyr Ser Ala Asn His Lys Asn Tyr Leu Ala Trp Tyr Gln
        195                 200                 205

Gln Lys Pro Gly Gln Pro Pro Lys Leu Leu Ile Tyr Trp Ala Ser Thr
    210                 215                 220

Arg Glu Ser Gly Val Pro Asp Arg Phe Ser Gly Ser Gly Ser Gly Thr
225                 230                 235                 240

Asp Phe Thr Leu Thr Ile Ser Ser Val Gln Ala Glu Asp Val Ala Ile
                245                 250                 255

Tyr Tyr Cys His Gln Tyr Leu Ser Ser Trp Thr Phe Gly Gly Gly Thr
            260                 265                 270

Lys Leu Glu Ile Lys Arg Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350
```

Gly Gly Thr Ala Tyr Asn Thr Ala Leu Ile Ser Arg Phe Thr Ile Ser
355 360 365

Arg Asp Asn Ser Lys Asn Thr Leu Tyr Leu Gln Met Asn Ser Leu Arg
370 375 380

Ala Glu Asp Thr Ala Val Tyr Tyr Cys Ala Arg Arg Gly Ser Tyr Pro
385 390 395 400

Tyr Asn Tyr Phe Asp Ala Trp Gly Cys Gly Thr Leu Val Thr Val Ser
405 410 415

Ser Gly Gly Gly Gly Ser Gly Gly Gly Gly Ser Gly Gly Gly Gly Ser
420 425 430

Gly Gly Gly Gly Ser Gly Gly Gly Gly Ser Gly Gly Gly Gly Ser Gln
435 440 445

Ala Val Val Thr Gln Glu Pro Ser Leu Thr Val Ser Pro Gly Gly Thr
450 455 460

Val Thr Leu Thr Cys Gly Ser Ser Thr Gly Ala Val Thr Ala Ser Asn
465 470 475 480

Tyr Ala Asn Trp Val Gln Gln Lys Pro Gly Gln Cys Pro Arg Gly Leu
485 490 495

Ile Gly Gly His Asn Asn Arg Pro Pro Gly Val Pro Ala Arg Phe Ser
500 505 510

Gly Ser Leu Leu Gly Gly Lys Ala Ala Leu Thr Leu Leu Gly Ala Gln
515 520 525

Pro Glu Asp Glu Ala Glu Tyr Tyr Cys Ala Leu Trp Tyr Ser Asp His
530 535 540

Trp Val Ile Gly Gly Gly Thr Lys Leu Thr Val Leu Gly Thr Pro Leu
545 550 555 560

Gly Asp Thr Thr His Thr Ser Gly Lys Pro Leu Asp Gly Glu Tyr Phe
565 570 575

Thr Leu Gln Ile Arg Gly Arg Glu Arg Phe Glu Met Phe Arg Glu Leu
580 585 590

Asn Glu Ala Leu Glu Leu Lys Asp Ala Gln Ala Gly Lys Glu Pro Gly
595 600 605

Gly Ser Gly Gly Ala Pro His His His His His His
610 615 620

<210> SEQ ID NO 62
<211> LENGTH: 613
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 62

Met Gly Trp Ser Cys Ile Ile Leu Phe Leu Val Ala Thr Ala Thr Gly
1 5 10 15

Val His Ser Gln Val Gln Leu Gln Gln Ser Gly Ala Glu Val Lys Lys
20 25 30

Pro Gly Ala Ser Val Lys Met Ser Cys Lys Ala Ser Gly Tyr Thr Phe
35 40 45

Thr Ser Tyr Trp Leu His Trp Ile Arg Gln Ala Pro Gly Gln Arg Leu
50 55 60

Glu Trp Met Gly Tyr Ile Asn Pro Arg Asn Asp Tyr Thr Glu Tyr Asn
65 70 75 80

```
Gln Lys Phe Gln Gly Arg Ala Thr Ile Thr Ala Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Asp Ile Val Leu Thr Gln Ser Pro Asp Ser Leu
                165                 170                 175

Ala Val Ser Ala Gly Glu Arg Val Thr Met Asn Cys Lys Ser Ser Gln
            180                 185                 190

Ser Val Leu Tyr Ser Ala Asn His Lys Asn Tyr Leu Ala Trp Tyr Gln
        195                 200                 205

Gln Lys Pro Gly Gln Pro Pro Lys Leu Leu Ile Tyr Trp Ala Ser Thr
    210                 215                 220

Arg Glu Ser Gly Val Pro Asp Arg Phe Ser Gly Ser Gly Ser Gly Thr
225                 230                 235                 240

Asp Phe Thr Leu Thr Ile Ser Ser Val Gln Ala Glu Asp Val Ala Ile
                245                 250                 255

Tyr Tyr Cys His Gln Tyr Leu Ser Ser Trp Thr Phe Gly Gly Gly Thr
            260                 265                 270

Lys Leu Glu Ile Lys Arg Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495
```

```
Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Lys Pro Leu Asp Gly Glu Tyr Phe
                565                 570                 575

Thr Leu Gln Ile Arg Gly Arg Glu Arg Phe Glu Met Phe Arg Glu Leu
            580                 585                 590

Asn Glu Ala Leu Glu Leu Lys Asp Ala Gln Ala Gly Lys Glu Pro Gly
        595                 600                 605

Gly Ser Gly Gly Ala
    610


<210> SEQ ID NO 63
<211> LENGTH: 638
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Gly Trp Ser Cys Ile Ile Leu Phe Leu Val Ala Thr Ala Thr Gly
1               5                   10                  15

Val His Ser Asp Ile Val Leu Thr Gln Ser Pro Asp Ser Leu Ala Val
            20                  25                  30

Ser Ala Gly Glu Arg Val Thr Met Asn Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Val Gln Ala Glu Asp Val Ala Ile Tyr Tyr
            100                 105                 110

Cys His Gln Tyr Leu Ser Ser Trp Thr Phe Gly Gly Gly Thr Lys Leu
        115                 120                 125

Glu Ile Lys Arg Gly Gly Gly Gly Ser Gly Gly Gly Gly Ser Gly Gly
    130                 135                 140

Gly Gly Ser Gly Gly Gly Gly Ser Gly Gly Gly Gly Ser Gly Gly Gly
145                 150                 155                 160

Gly Ser Gln Val Gln Leu Gln Gln Ser Gly Ala Glu Val Lys Lys Pro
                165                 170                 175

Gly Ala Ser Val Lys Met Ser Cys Lys Ala Ser Gly Tyr Thr Phe Thr
            180                 185                 190

Ser Tyr Trp Leu His Trp Ile Arg Gln Ala Pro Gly Gln Arg Leu Glu
        195                 200                 205

Trp Met Gly Tyr Ile Asn Pro Arg Asn Asp Tyr Thr Glu Tyr Asn Gln
    210                 215                 220

Lys Phe Gln Gly Arg Ala Thr Ile Thr Ala Asp Lys Ser Ala Ser Thr
225                 230                 235                 240
```

```
Ala Tyr Met Glu Leu Ser Ser Leu Arg Ser Glu Asp Thr Ala Val Tyr
                245                 250                 255

Tyr Cys Ala Arg Arg Asp Ile Thr Thr Phe Tyr Trp Gly Gln Gly Thr
            260                 265                 270

Thr Leu Thr Val Ser Ser Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Arg Ser Pro Asp Asp Glu Leu Leu
                565                 570                 575

Tyr Leu Pro Val Arg Gly Arg Glu Thr Tyr Glu Met Leu Leu Lys Ile
            580                 585                 590

Lys Glu Ser Leu Glu Leu Met Gln Tyr Leu Pro Gln His Thr Ile Glu
        595                 600                 605

Thr Tyr Arg Gln Gln Gln Gln Gln Gln His Gln His Leu Leu Gln Lys
    610                 615                 620

Gln Gly Gly Ser Gly Gly Ala Pro His His His His His His
625                 630                 635
```

<210> SEQ ID NO 64
<211> LENGTH: 631

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 64

```
Met Gly Trp Ser Cys Ile Ile Leu Phe Leu Val Ala Thr Ala Thr Gly
1               5                   10                  15

Val His Ser Asp Ile Val Leu Thr Gln Ser Pro Asp Ser Leu Ala Val
            20                  25                  30

Ser Ala Gly Glu Arg Val Thr Met Asn Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Val Gln Ala Glu Asp Val Ala Ile Tyr Tyr
            100                 105                 110

Cys His Gln Tyr Leu Ser Ser Trp Thr Phe Gly Gly Gly Thr Lys Leu
        115                 120                 125

Glu Ile Lys Arg Gly Gly Gly Gly Ser Gly Gly Gly Gly Ser Gly Gly
    130                 135                 140

Gly Gly Ser Gly Gly Gly Gly Ser Gly Gly Gly Ser Gly Gly Gly
145                 150                 155                 160

Gly Ser Gln Val Gln Leu Gln Gln Ser Gly Ala Glu Val Lys Lys Pro
                165                 170                 175

Gly Ala Ser Val Lys Met Ser Cys Lys Ala Ser Gly Tyr Thr Phe Thr
            180                 185                 190

Ser Tyr Trp Leu His Trp Ile Arg Gln Ala Pro Gly Gln Arg Leu Glu
        195                 200                 205

Trp Met Gly Tyr Ile Asn Pro Arg Asn Asp Tyr Thr Glu Tyr Asn Gln
    210                 215                 220

Lys Phe Gln Gly Arg Ala Thr Ile Thr Ala Asp Lys Ser Ala Ser Thr
225                 230                 235                 240

Ala Tyr Met Glu Leu Ser Ser Leu Arg Ser Glu Asp Thr Ala Val Tyr
                245                 250                 255

Tyr Cys Ala Arg Arg Asp Ile Thr Thr Phe Tyr Trp Gly Gln Gly Thr
            260                 265                 270

Thr Leu Thr Val Ser Ser Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380
```

Ala Glu Asp Thr Ala Val Tyr Tyr Cys Ala Arg Arg Gly Ser Tyr Pro
385 390 395 400

Tyr Asn Tyr Phe Asp Ala Trp Gly Cys Gly Thr Leu Val Thr Val Ser
405 410 415

Ser Gly Gly Gly Gly Ser Gly Gly Gly Gly Ser Gly Gly Gly Gly Ser
420 425 430

Gly Gly Gly Gly Ser Gly Gly Gly Gly Ser Gly Gly Gly Gly Ser Gln
435 440 445

Ala Val Val Thr Gln Glu Pro Ser Leu Thr Val Ser Pro Gly Gly Thr
450 455 460

Val Thr Leu Thr Cys Gly Ser Ser Thr Gly Ala Val Thr Ala Ser Asn
465 470 475 480

Tyr Ala Asn Trp Val Gln Gln Lys Pro Gly Gln Cys Pro Arg Gly Leu
485 490 495

Ile Gly Gly His Asn Asn Arg Pro Pro Gly Val Pro Ala Arg Phe Ser
500 505 510

Gly Ser Leu Leu Gly Gly Lys Ala Ala Leu Thr Leu Leu Gly Ala Gln
515 520 525

Pro Glu Asp Glu Ala Glu Tyr Tyr Cys Ala Leu Trp Tyr Ser Asp His
530 535 540

Trp Val Ile Gly Gly Gly Thr Lys Leu Thr Val Leu Gly Thr Pro Leu
545 550 555 560

Gly Asp Thr Thr His Thr Ser Gly Arg Ser Pro Asp Asp Glu Leu Leu
565 570 575

Tyr Leu Pro Val Arg Gly Arg Glu Thr Tyr Glu Met Leu Leu Lys Ile
580 585 590

Lys Glu Ser Leu Glu Leu Met Gln Tyr Leu Pro Gln His Thr Ile Glu
595 600 605

Thr Tyr Arg Gln Gln Gln Gln Gln Gln His Gln His Leu Leu Gln Lys
610 615 620

Gln Gly Gly Ser Gly Gly Ala
625 630

<210> SEQ ID NO 65
<211> LENGTH: 638
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 65

Met Gly Trp Ser Cys Ile Ile Leu Phe Leu Val Ala Thr Ala Thr Gly
1 5 10 15

Val His Ser Gln Val Gln Leu Gln Gln Ser Gly Ala Glu Val Lys Lys
20 25 30

Pro Gly Ala Ser Val Lys Met Ser Cys Lys Ala Ser Gly Tyr Thr Phe
35 40 45

Thr Ser Tyr Trp Leu His Trp Ile Arg Gln Ala Pro Gly Gln Arg Leu
50 55 60

Glu Trp Met Gly Tyr Ile Asn Pro Arg Asn Asp Tyr Thr Glu Tyr Asn
65 70 75 80

Gln Lys Phe Gln Gly Arg Ala Thr Ile Thr Ala Asp Lys Ser Ala Ser
85 90 95

```
Thr Ala Tyr Met Glu Leu Ser Ser Leu Arg Ser Glu Asp Thr Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Asp Ile Val Leu Thr Gln Ser Pro Asp Ser Leu
                165                 170                 175

Ala Val Ser Ala Gly Glu Arg Val Thr Met Asn Cys Lys Ser Ser Gln
            180                 185                 190

Ser Val Leu Tyr Ser Ala Asn His Lys Asn Tyr Leu Ala Trp Tyr Gln
        195                 200                 205

Gln Lys Pro Gly Gln Pro Pro Lys Leu Leu Ile Tyr Trp Ala Ser Thr
    210                 215                 220

Arg Glu Ser Gly Val Pro Asp Arg Phe Ser Gly Ser Gly Ser Gly Thr
225                 230                 235                 240

Asp Phe Thr Leu Thr Ile Ser Ser Val Gln Ala Glu Asp Val Ala Ile
                245                 250                 255

Tyr Tyr Cys His Gln Tyr Leu Ser Ser Trp Thr Phe Gly Gly Gly Thr
            260                 265                 270

Lys Leu Glu Ile Lys Arg Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510
```

Gly Ser Leu Leu Gly Gly Lys Ala Ala Leu Thr Leu Leu Gly Ala Gln
515 520 525

Pro Glu Asp Glu Ala Glu Tyr Tyr Cys Ala Leu Trp Tyr Ser Asp His
530 535 540

Trp Val Ile Gly Gly Gly Thr Lys Leu Thr Val Leu Gly Thr Pro Leu
545 550 555 560

Gly Asp Thr Thr His Thr Ser Gly Arg Ser Pro Asp Asp Glu Leu Leu
565 570 575

Tyr Leu Pro Val Arg Gly Arg Glu Thr Tyr Glu Met Leu Leu Lys Ile
580 585 590

Lys Glu Ser Leu Glu Leu Met Gln Tyr Leu Pro Gln His Thr Ile Glu
595 600 605

Thr Tyr Arg Gln Gln Gln Gln Gln Gln His Gln His Leu Leu Gln Lys
610 615 620

Gln Gly Gly Ser Gly Gly Ala Pro His His His His His His
625 630 635

<210> SEQ ID NO 66
<211> LENGTH: 631
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

Met Gly Trp Ser Cys Ile Ile Leu Phe Leu Val Ala Thr Ala Thr Gly
1 5 10 15

Val His Ser Gln Val Gln Leu Gln Gln Ser Gly Ala Glu Val Lys Lys
20 25 30

Pro Gly Ala Ser Val Lys Met Ser Cys Lys Ala Ser Gly Tyr Thr Phe
35 40 45

Thr Ser Tyr Trp Leu His Trp Ile Arg Gln Ala Pro Gly Gln Arg Leu
50 55 60

Glu Trp Met Gly Tyr Ile Asn Pro Arg Asn Asp Tyr Thr Glu Tyr Asn
65 70 75 80

Gln Lys Phe Gln Gly Arg Ala Thr Ile Thr Ala Asp Lys Ser Ala Ser
85 90 95

Thr Ala Tyr Met Glu Leu Ser Ser Leu Arg Ser Glu Asp Thr Ala Val
100 105 110

Tyr Tyr Cys Ala Arg Arg Asp Ile Thr Thr Phe Tyr Trp Gly Gln Gly
115 120 125

Thr Thr Leu Thr Val Ser Ser Gly Gly Gly Gly Ser Gly Gly Gly Gly
130 135 140

Ser Gly Gly Gly Gly Ser Gly Gly Gly Gly Ser Gly Gly Gly Gly Ser
145 150 155 160

Gly Gly Gly Gly Ser Asp Ile Val Leu Thr Gln Ser Pro Asp Ser Leu
165 170 175

Ala Val Ser Ala Gly Glu Arg Val Thr Met Asn Cys Lys Ser Ser Gln
180 185 190

Ser Val Leu Tyr Ser Ala Asn His Lys Asn Tyr Leu Ala Trp Tyr Gln
195 200 205

Gln Lys Pro Gly Gln Pro Pro Lys Leu Leu Ile Tyr Trp Ala Ser Thr
210 215 220

Arg Glu Ser Gly Val Pro Asp Arg Phe Ser Gly Ser Gly Ser Gly Thr
225 230 235 240

```
Asp Phe Thr Leu Thr Ile Ser Ser Val Gln Ala Glu Asp Val Ala Ile
                245                 250                 255

Tyr Tyr Cys His Gln Tyr Leu Ser Ser Trp Thr Phe Gly Gly Gly Thr
            260                 265                 270

Lys Leu Glu Ile Lys Arg Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Arg Ser Pro Asp Asp Glu Leu Leu
                565                 570                 575

Tyr Leu Pro Val Arg Gly Arg Glu Thr Tyr Glu Met Leu Leu Lys Ile
            580                 585                 590

Lys Glu Ser Leu Glu Leu Met Gln Tyr Leu Pro Gln His Thr Ile Glu
        595                 600                 605

Thr Tyr Arg Gln Gln Gln Gln Gln Gln His Gln His Leu Leu Gln Lys
    610                 615                 620

Gln Gly Gly Ser Gly Gly Ala
625                 630
```

<210> SEQ ID NO 67
<211> LENGTH: 633

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 67

Met Gly Trp Ser Cys Ile Ile Leu Phe Leu Val Ala Thr Ala Thr Gly
1 5 10 15

Val His Ser Asp Ile Val Leu Thr Gln Ser Pro Asp Ser Leu Ala Val
20 25 30

Ser Ala Gly Glu Arg Val Thr Met Asn Cys Lys Ser Ser Gln Ser Val
35 40 45

Leu Tyr Ser Ala Asn His Lys Asn Tyr Leu Ala Trp Tyr Gln Gln Lys
50 55 60

Pro Gly Gln Pro Pro Lys Leu Leu Ile Tyr Trp Ala Ser Thr Arg Glu
65 70 75 80

Ser Gly Val Pro Asp Arg Phe Ser Gly Ser Gly Ser Gly Thr Asp Phe
85 90 95

Thr Leu Thr Ile Ser Ser Val Gln Ala Glu Asp Val Ala Ile Tyr Tyr
100 105 110

Cys His Gln Tyr Leu Ser Ser Trp Thr Phe Gly Gly Gly Thr Lys Leu
115 120 125

Glu Ile Lys Arg Gly Gly Gly Gly Ser Gly Gly Gly Gly Ser Gly Gly
130 135 140

Gly Gly Ser Gly Gly Gly Gly Ser Gly Gly Gly Ser Gly Gly Gly
145 150 155 160

Gly Ser Gln Val Gln Leu Gln Gln Ser Gly Ala Glu Val Lys Lys Pro
165 170 175

Gly Ala Ser Val Lys Met Ser Cys Lys Ala Ser Gly Tyr Thr Phe Thr
180 185 190

Ser Tyr Trp Leu His Trp Ile Arg Gln Ala Pro Gly Gln Arg Leu Glu
195 200 205

Trp Met Gly Tyr Ile Asn Pro Arg Asn Asp Tyr Thr Glu Tyr Asn Gln
210 215 220

Lys Phe Gln Gly Arg Ala Thr Ile Thr Ala Asp Lys Ser Ala Ser Thr
225 230 235 240

Ala Tyr Met Glu Leu Ser Ser Leu Arg Ser Glu Asp Thr Ala Val Tyr
245 250 255

Tyr Cys Ala Arg Arg Asp Ile Thr Thr Phe Tyr Trp Gly Gln Gly Thr
260 265 270

Thr Leu Thr Val Ser Ser Gly Gly Gly Gly Ser Gly Gly Gly Gly Ser
275 280 285

Gly Gly Gly Gly Ser Gly Gly Gly Gly Ser His Val Gln Leu Val Glu
290 295 300

Ser Gly Gly Gly Leu Val Gln Pro Gly Gly Ser Leu Arg Leu Ser Cys
305 310 315 320

Ala Ala Ser Gly Phe Ser Leu Thr Asp Tyr Gly Val His Trp Val Arg
325 330 335

Gln Ala Pro Gly Lys Gly Leu Glu Trp Leu Gly Val Ile Trp Ser Gly
340 345 350

Gly Gly Thr Ala Tyr Asn Thr Ala Leu Ile Ser Arg Phe Thr Ile Ser
355 360 365

Arg Asp Asn Ser Lys Asn Thr Leu Tyr Leu Gln Met Asn Ser Leu Arg
370 375 380

```
Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Arg His Gly Asp Glu Asp Thr Tyr
                565                 570                 575

Tyr Leu Gln Val Arg Gly Arg Glu Asn Phe Glu Ile Leu Met Lys Leu
            580                 585                 590

Lys Glu Ser Leu Glu Leu Met Glu Leu Val Pro Gln Pro Leu Val Asp
        595                 600                 605

Ser Tyr Arg Gln Gln Gln Gln Leu Leu Gln Arg Pro Gly Gly Ser Gly
    610                 615                 620

Gly Ala Pro His His His His His His
625                 630
```

```
<210> SEQ ID NO 68
<211> LENGTH: 626
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Gly Trp Ser Cys Ile Ile Leu Phe Leu Val Ala Thr Ala Thr Gly
1               5                   10                  15

Val His Ser Asp Ile Val Leu Thr Gln Ser Pro Asp Ser Leu Ala Val
            20                  25                  30

Ser Ala Gly Glu Arg Val Thr Met Asn Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95
```

```
Thr Leu Thr Ile Ser Ser Val Gln Ala Glu Asp Val Ala Ile Tyr Tyr
            100                 105                 110

Cys His Gln Tyr Leu Ser Ser Trp Thr Phe Gly Gly Gly Thr Lys Leu
        115                 120                 125

Glu Ile Lys Arg Gly Gly Gly Gly Ser Gly Gly Gly Gly Ser Gly Gly
    130                 135                 140

Gly Gly Ser Gly Gly Gly Gly Ser Gly Gly Gly Gly Ser Gly Gly Gly
145                 150                 155                 160

Gly Ser Gln Val Gln Leu Gln Gln Ser Gly Ala Glu Val Lys Lys Pro
                165                 170                 175

Gly Ala Ser Val Lys Met Ser Cys Lys Ala Ser Gly Tyr Thr Phe Thr
            180                 185                 190

Ser Tyr Trp Leu His Trp Ile Arg Gln Ala Pro Gly Gln Arg Leu Glu
        195                 200                 205

Trp Met Gly Tyr Ile Asn Pro Arg Asn Asp Tyr Thr Glu Tyr Asn Gln
    210                 215                 220

Lys Phe Gln Gly Arg Ala Thr Ile Thr Ala Asp Lys Ser Ala Ser Thr
225                 230                 235                 240

Ala Tyr Met Glu Leu Ser Ser Leu Arg Ser Glu Asp Thr Ala Val Tyr
                245                 250                 255

Tyr Cys Ala Arg Arg Asp Ile Thr Thr Phe Tyr Trp Gly Gln Gly Thr
            260                 265                 270

Thr Leu Thr Val Ser Ser Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510
```

```
Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Arg His Gly Asp Glu Asp Thr Tyr
                565                 570                 575

Tyr Leu Gln Val Arg Gly Arg Glu Asn Phe Glu Ile Leu Met Lys Leu
            580                 585                 590

Lys Glu Ser Leu Glu Leu Met Glu Leu Val Pro Gln Pro Leu Val Asp
        595                 600                 605

Ser Tyr Arg Gln Gln Gln Gln Leu Leu Gln Arg Pro Gly Gly Ser Gly
    610                 615                 620

Gly Ala
625
```

```
<210> SEQ ID NO 69
<211> LENGTH: 633
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Met Gly Trp Ser Cys Ile Ile Leu Phe Leu Val Ala Thr Ala Thr Gly
1               5                   10                  15

Val His Ser Gln Val Gln Leu Gln Gln Ser Gly Ala Glu Val Lys Lys
            20                  25                  30

Pro Gly Ala Ser Val Lys Met Ser Cys Lys Ala Ser Gly Tyr Thr Phe
        35                  40                  45

Thr Ser Tyr Trp Leu His Trp Ile Arg Gln Ala Pro Gly Gln Arg Leu
    50                  55                  60

Glu Trp Met Gly Tyr Ile Asn Pro Arg Asn Asp Tyr Thr Glu Tyr Asn
65                  70                  75                  80

Gln Lys Phe Gln Gly Arg Ala Thr Ile Thr Ala Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Asp Ile Val Leu Thr Gln Ser Pro Asp Ser Leu
                165                 170                 175

Ala Val Ser Ala Gly Glu Arg Val Thr Met Asn Cys Lys Ser Ser Gln
            180                 185                 190

Ser Val Leu Tyr Ser Ala Asn His Lys Asn Tyr Leu Ala Trp Tyr Gln
        195                 200                 205

Gln Lys Pro Gly Gln Pro Pro Lys Leu Leu Ile Tyr Trp Ala Ser Thr
    210                 215                 220

Arg Glu Ser Gly Val Pro Asp Arg Phe Ser Gly Ser Gly Ser Gly Thr
225                 230                 235                 240
```

```
Asp Phe Thr Leu Thr Ile Ser Ser Val Gln Ala Glu Asp Val Ala Ile
                245                 250                 255

Tyr Tyr Cys His Gln Tyr Leu Ser Ser Trp Thr Phe Gly Gly Gly Thr
            260                 265                 270

Lys Leu Glu Ile Lys Arg Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Arg His Gly Asp Glu Asp Thr Tyr
                565                 570                 575

Tyr Leu Gln Val Arg Gly Arg Glu Asn Phe Glu Ile Leu Met Lys Leu
            580                 585                 590

Lys Glu Ser Leu Glu Leu Met Glu Leu Val Pro Gln Pro Leu Val Asp
        595                 600                 605

Ser Tyr Arg Gln Gln Gln Gln Leu Leu Gln Arg Pro Gly Gly Ser Gly
    610                 615                 620

Gly Ala Pro His His His His His His
625                 630
```

<210> SEQ ID NO 70
<211> LENGTH: 626

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 70

Met Gly Trp Ser Cys Ile Ile Leu Phe Leu Val Ala Thr Ala Thr Gly
1 5 10 15

Val His Ser Gln Val Gln Leu Gln Gln Ser Gly Ala Glu Val Lys Lys
20 25 30

Pro Gly Ala Ser Val Lys Met Ser Cys Lys Ala Ser Gly Tyr Thr Phe
35 40 45

Thr Ser Tyr Trp Leu His Trp Ile Arg Gln Ala Pro Gly Gln Arg Leu
50 55 60

Glu Trp Met Gly Tyr Ile Asn Pro Arg Asn Asp Tyr Thr Glu Tyr Asn
65 70 75 80

Gln Lys Phe Gln Gly Arg Ala Thr Ile Thr Ala Asp Lys Ser Ala Ser
85 90 95

Thr Ala Tyr Met Glu Leu Ser Ser Leu Arg Ser Glu Asp Thr Ala Val
100 105 110

Tyr Tyr Cys Ala Arg Arg Asp Ile Thr Thr Phe Tyr Trp Gly Gln Gly
115 120 125

Thr Thr Leu Thr Val Ser Ser Gly Gly Gly Gly Ser Gly Gly Gly Gly
130 135 140

Ser Gly Gly Gly Gly Ser Gly Gly Gly Gly Ser Gly Gly Gly Gly Ser
145 150 155 160

Gly Gly Gly Gly Ser Asp Ile Val Leu Thr Gln Ser Pro Asp Ser Leu
165 170 175

Ala Val Ser Ala Gly Glu Arg Val Thr Met Asn Cys Lys Ser Ser Gln
180 185 190

Ser Val Leu Tyr Ser Ala Asn His Lys Asn Tyr Leu Ala Trp Tyr Gln
195 200 205

Gln Lys Pro Gly Gln Pro Pro Lys Leu Leu Ile Tyr Trp Ala Ser Thr
210 215 220

Arg Glu Ser Gly Val Pro Asp Arg Phe Ser Gly Ser Gly Ser Gly Thr
225 230 235 240

Asp Phe Thr Leu Thr Ile Ser Ser Val Gln Ala Glu Asp Val Ala Ile
245 250 255

Tyr Tyr Cys His Gln Tyr Leu Ser Ser Trp Thr Phe Gly Gly Gly Thr
260 265 270

Lys Leu Glu Ile Lys Arg Gly Gly Gly Gly Ser Gly Gly Gly Gly Ser
275 280 285

Gly Gly Gly Gly Ser Gly Gly Gly Gly Ser His Val Gln Leu Val Glu
290 295 300

Ser Gly Gly Gly Leu Val Gln Pro Gly Gly Ser Leu Arg Leu Ser Cys
305 310 315 320

Ala Ala Ser Gly Phe Ser Leu Thr Asp Tyr Gly Val His Trp Val Arg
325 330 335

Gln Ala Pro Gly Lys Gly Leu Glu Trp Leu Gly Val Ile Trp Ser Gly
340 345 350

Gly Gly Thr Ala Tyr Asn Thr Ala Leu Ile Ser Arg Phe Thr Ile Ser
355 360 365

Arg Asp Asn Ser Lys Asn Thr Leu Tyr Leu Gln Met Asn Ser Leu Arg
370 375 380

Ala Glu Asp Thr Ala Val Tyr Tyr Cys Ala Arg Arg Gly Ser Tyr Pro
385 390 395 400

Tyr Asn Tyr Phe Asp Ala Trp Gly Cys Gly Thr Leu Val Thr Val Ser
405 410 415

Ser Gly Gly Gly Gly Ser Gly Gly Gly Gly Ser Gly Gly Gly Gly Ser
420 425 430

Gly Gly Gly Gly Ser Gly Gly Gly Gly Ser Gly Gly Gly Gly Ser Gln
435 440 445

Ala Val Val Thr Gln Glu Pro Ser Leu Thr Val Ser Pro Gly Gly Thr
450 455 460

Val Thr Leu Thr Cys Gly Ser Ser Thr Gly Ala Val Thr Ala Ser Asn
465 470 475 480

Tyr Ala Asn Trp Val Gln Gln Lys Pro Gly Gln Cys Pro Arg Gly Leu
485 490 495

Ile Gly Gly His Asn Asn Arg Pro Pro Gly Val Pro Ala Arg Phe Ser
500 505 510

Gly Ser Leu Leu Gly Gly Lys Ala Ala Leu Thr Leu Leu Gly Ala Gln
515 520 525

Pro Glu Asp Glu Ala Glu Tyr Tyr Cys Ala Leu Trp Tyr Ser Asp His
530 535 540

Trp Val Ile Gly Gly Gly Thr Lys Leu Thr Val Leu Gly Thr Pro Leu
545 550 555 560

Gly Asp Thr Thr His Thr Ser Gly Arg His Gly Asp Glu Asp Thr Tyr
565 570 575

Tyr Leu Gln Val Arg Gly Arg Glu Asn Phe Glu Ile Leu Met Lys Leu
580 585 590

Lys Glu Ser Leu Glu Leu Met Glu Leu Val Pro Gln Pro Leu Val Asp
595 600 605

Ser Tyr Arg Gln Gln Gln Gln Leu Leu Gln Arg Pro Gly Gly Ser Gly
610 615 620

Gly Ala
625

<210> SEQ ID NO 71
<211> LENGTH: 620
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 71

Met Gly Trp Ser Cys Ile Ile Leu Phe Leu Val Ala Thr Ala Thr Gly
1 5 10 15

Val His Ser Asp Ile Val Leu Thr Gln Ser Pro Asp Ser Leu Ala Val
20 25 30

Ser Ala Gly Glu Arg Val Thr Met Asn Cys Lys Ser Ser Gln Ser Val
35 40 45

Leu Tyr Ser Ala Asn His Lys Asn Tyr Leu Ala Trp Tyr Gln Gln Lys
50 55 60

Pro Gly Gln Pro Pro Lys Leu Leu Ile Tyr Trp Ala Ser Thr Arg Glu
65 70 75 80

Ser Gly Val Pro Asp Arg Phe Ser Gly Ser Gly Ser Gly Thr Asp Phe
85 90 95

```
Thr Leu Thr Ile Ser Ser Val Gln Ala Glu Asp Val Ala Ile Tyr Tyr
            100                 105                 110

Cys His Gln Tyr Leu Ser Ser Trp Thr Phe Gly Gly Gly Thr Lys Leu
        115                 120                 125

Glu Ile Lys Arg Gly Gly Gly Gly Ser Gly Gly Gly Gly Ser Gly Gly
    130                 135                 140

Gly Gly Ser Gly Gly Gly Gly Ser Gly Gly Gly Gly Ser Gly Gly Gly
145                 150                 155                 160

Gly Ser Gln Val Gln Leu Val Gln Ser Gly Ala Glu Val Lys Lys Pro
                165                 170                 175

Gly Ala Ser Val Lys Val Ser Cys Lys Ala Ser Gly Tyr Thr Phe Thr
            180                 185                 190

Ser Tyr Trp Leu His Trp Val Arg Gln Ala Pro Gly Gln Arg Leu Glu
        195                 200                 205

Trp Met Gly Tyr Ile Asn Pro Arg Asn Asp Tyr Thr Glu Tyr Asn Gln
    210                 215                 220

Asn Phe Lys Asp Arg Val Thr Leu Thr Ala Asp Lys Ser Ala Ser Thr
225                 230                 235                 240

Ala Tyr Met Glu Leu Ser Ser Leu Arg Ser Glu Asp Thr Ala Val Tyr
                245                 250                 255

Tyr Cys Ala Arg Arg Asp Ile Thr Thr Phe Tyr Trp Gly Gln Gly Thr
            260                 265                 270

Thr Leu Thr Val Ser Ser Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510
```

```
Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Lys Pro Leu Asp Gly Glu Tyr Phe
                565                 570                 575

Thr Leu Gln Ile Arg Gly Arg Glu Arg Phe Glu Met Phe Arg Glu Leu
            580                 585                 590

Asn Glu Ala Leu Glu Leu Lys Asp Ala Gln Ala Gly Lys Glu Pro Gly
        595                 600                 605

Gly Ser Gly Gly Ala Pro His His His His His His
    610                 615                 620


<210> SEQ ID NO 72
<211> LENGTH: 613
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Gly Trp Ser Cys Ile Ile Leu Phe Leu Val Ala Thr Ala Thr Gly
1               5                   10                  15

Val His Ser Asp Ile Val Leu Thr Gln Ser Pro Asp Ser Leu Ala Val
            20                  25                  30

Ser Ala Gly Glu Arg Val Thr Met Asn Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Val Gln Ala Glu Asp Val Ala Ile Tyr Tyr
            100                 105                 110

Cys His Gln Tyr Leu Ser Ser Trp Thr Phe Gly Gly Gly Thr Lys Leu
        115                 120                 125

Glu Ile Lys Arg Gly Gly Gly Gly Ser Gly Gly Gly Gly Ser Gly Gly
    130                 135                 140

Gly Gly Ser Gly Gly Gly Gly Ser Gly Gly Gly Gly Ser Gly Gly Gly
145                 150                 155                 160

Gly Ser Gln Val Gln Leu Val Gln Ser Gly Ala Glu Val Lys Lys Pro
                165                 170                 175

Gly Ala Ser Val Lys Val Ser Cys Lys Ala Ser Gly Tyr Thr Phe Thr
            180                 185                 190

Ser Tyr Trp Leu His Trp Val Arg Gln Ala Pro Gly Gln Arg Leu Glu
        195                 200                 205

Trp Met Gly Tyr Ile Asn Pro Arg Asn Asp Tyr Thr Glu Tyr Asn Gln
    210                 215                 220

Asn Phe Lys Asp Arg Val Thr Leu Thr Ala Asp Lys Ser Ala Ser Thr
225                 230                 235                 240

Ala Tyr Met Glu Leu Ser Ser Leu Arg Ser Glu Asp Thr Ala Val Tyr
                245                 250                 255
```

```
Tyr Cys Ala Arg Arg Asp Ile Thr Thr Phe Tyr Trp Gly Gln Gly Thr
            260                 265                 270

Thr Leu Thr Val Ser Ser Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Lys Pro Leu Asp Gly Glu Tyr Phe
                565                 570                 575

Thr Leu Gln Ile Arg Gly Arg Glu Arg Phe Glu Met Phe Arg Glu Leu
            580                 585                 590

Asn Glu Ala Leu Glu Leu Lys Asp Ala Gln Ala Gly Lys Glu Pro Gly
        595                 600                 605

Gly Ser Gly Gly Ala
    610
```

<210> SEQ ID NO 73
<211> LENGTH: 620
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Leu His Trp Val Arg Gln Ala Pro Gly Gln Arg Leu
    50                  55                  60

Glu Trp Met Gly Tyr Ile Asn Pro Arg Asn Asp Tyr Thr Glu Tyr Asn
65                  70                  75                  80

Gln Asn Phe Lys Asp Arg Val Thr Leu Thr Ala Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Asp Ile Val Leu Thr Gln Ser Pro Asp Ser Leu
                165                 170                 175

Ala Val Ser Ala Gly Glu Arg Val Thr Met Asn Cys Lys Ser Ser Gln
            180                 185                 190

Ser Val Leu Tyr Ser Ala Asn His Lys Asn Tyr Leu Ala Trp Tyr Gln
        195                 200                 205

Gln Lys Pro Gly Gln Pro Pro Lys Leu Leu Ile Tyr Trp Ala Ser Thr
    210                 215                 220

Arg Glu Ser Gly Val Pro Asp Arg Phe Ser Gly Ser Gly Ser Gly Thr
225                 230                 235                 240

Asp Phe Thr Leu Thr Ile Ser Ser Val Gln Ala Glu Asp Val Ala Ile
                245                 250                 255

Tyr Tyr Cys His Gln Tyr Leu Ser Ser Trp Thr Phe Gly Gly Gly Thr
            260                 265                 270

Lys Leu Glu Ile Lys Arg Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415
```

```
Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Lys Pro Leu Asp Gly Glu Tyr Phe
                565                 570                 575

Thr Leu Gln Ile Arg Gly Arg Glu Arg Phe Glu Met Phe Arg Glu Leu
            580                 585                 590

Asn Glu Ala Leu Glu Leu Lys Asp Ala Gln Ala Gly Lys Glu Pro Gly
        595                 600                 605

Gly Ser Gly Gly Ala Pro His His His His His His
    610                 615                 620
```

<210> SEQ ID NO 74
<211> LENGTH: 613
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Leu His Trp Val Arg Gln Ala Pro Gly Gln Arg Leu
    50                  55                  60

Glu Trp Met Gly Tyr Ile Asn Pro Arg Asn Asp Tyr Thr Glu Tyr Asn
65                  70                  75                  80

Gln Asn Phe Lys Asp Arg Val Thr Leu Thr Ala Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Gly Gly Gly Gly Ser Gly Gly Gly Gly
    130                 135                 140
```

```
Ser Gly Gly Gly Gly Ser Gly Gly Gly Gly Ser Gly Gly Gly Gly Ser
145                 150                 155                 160

Gly Gly Gly Gly Ser Asp Ile Val Leu Thr Gln Ser Pro Asp Ser Leu
                165                 170                 175

Ala Val Ser Ala Gly Glu Arg Val Thr Met Asn Cys Lys Ser Ser Gln
            180                 185                 190

Ser Val Leu Tyr Ser Ala Asn His Lys Asn Tyr Leu Ala Trp Tyr Gln
        195                 200                 205

Gln Lys Pro Gly Gln Pro Pro Lys Leu Leu Ile Tyr Trp Ala Ser Thr
    210                 215                 220

Arg Glu Ser Gly Val Pro Asp Arg Phe Ser Gly Ser Gly Ser Gly Thr
225                 230                 235                 240

Asp Phe Thr Leu Thr Ile Ser Ser Val Gln Ala Glu Asp Val Ala Ile
                245                 250                 255

Tyr Tyr Cys His Gln Tyr Leu Ser Ser Trp Thr Phe Gly Gly Gly Thr
            260                 265                 270

Lys Leu Glu Ile Lys Arg Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560
```

```
Gly Asp Thr Thr His Thr Ser Gly Lys Pro Leu Asp Gly Glu Tyr Phe
                565                 570                 575

Thr Leu Gln Ile Arg Gly Arg Glu Arg Phe Glu Met Phe Arg Glu Leu
            580                 585                 590

Asn Glu Ala Leu Glu Leu Lys Asp Ala Gln Ala Gly Lys Glu Pro Gly
        595                 600                 605

Gly Ser Gly Gly Ala
    610
```

<210> SEQ ID NO 75
<211> LENGTH: 638
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

```
Met Gly Trp Ser Cys Ile Ile Leu Phe Leu Val Ala Thr Ala Thr Gly
1               5                   10                  15

Val His Ser Asp Ile Val Leu Thr Gln Ser Pro Asp Ser Leu Ala Val
            20                  25                  30

Ser Ala Gly Glu Arg Val Thr Met Asn Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Val Gln Ala Glu Asp Val Ala Ile Tyr Tyr
            100                 105                 110

Cys His Gln Tyr Leu Ser Ser Trp Thr Phe Gly Gly Gly Thr Lys Leu
        115                 120                 125

Glu Ile Lys Arg Gly Gly Gly Gly Ser Gly Gly Gly Gly Ser Gly Gly
    130                 135                 140

Gly Gly Ser Gly Gly Gly Gly Ser Gly Gly Gly Gly Ser Gly Gly Gly
145                 150                 155                 160

Gly Ser Gln Val Gln Leu Val Gln Ser Gly Ala Glu Val Lys Lys Pro
                165                 170                 175

Gly Ala Ser Val Lys Val Ser Cys Lys Ala Ser Gly Tyr Thr Phe Thr
            180                 185                 190

Ser Tyr Trp Leu His Trp Val Arg Gln Ala Pro Gly Gln Arg Leu Glu
        195                 200                 205

Trp Met Gly Tyr Ile Asn Pro Arg Asn Asp Tyr Thr Glu Tyr Asn Gln
    210                 215                 220

Asn Phe Lys Asp Arg Val Thr Leu Thr Ala Asp Lys Ser Ala Ser Thr
225                 230                 235                 240

Ala Tyr Met Glu Leu Ser Ser Leu Arg Ser Glu Asp Thr Ala Val Tyr
                245                 250                 255

Tyr Cys Ala Arg Arg Asp Ile Thr Thr Phe Tyr Trp Gly Gln Gly Thr
            260                 265                 270

Thr Leu Thr Val Ser Ser Gly Gly Gly Gly Ser Gly Gly Gly Ser
        275                 280                 285

Gly Gly Gly Gly Ser Gly Gly Gly Gly Ser His Val Gln Leu Val Glu
    290                 295                 300
```

```
Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Arg Ser Pro Asp Asp Glu Leu Leu
                565                 570                 575

Tyr Leu Pro Val Arg Gly Arg Glu Thr Tyr Glu Met Leu Leu Lys Ile
            580                 585                 590

Lys Glu Ser Leu Glu Leu Met Gln Tyr Leu Pro Gln His Thr Ile Glu
        595                 600                 605

Thr Tyr Arg Gln Gln Gln Gln Gln Gln His Gln His Leu Leu Gln Lys
    610                 615                 620

Gln Gly Gly Ser Gly Gly Ala Pro His His His His His His
625                 630                 635
```

<210> SEQ ID NO 76
<211> LENGTH: 631
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

```
Met Gly Trp Ser Cys Ile Ile Leu Phe Leu Val Ala Thr Ala Thr Gly
1               5                   10                  15
```

```
Val His Ser Asp Ile Val Leu Thr Gln Ser Pro Asp Ser Leu Ala Val
            20                  25                  30

Ser Ala Gly Glu Arg Val Thr Met Asn Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Val Gln Ala Glu Asp Val Ala Ile Tyr Tyr
            100                 105                 110

Cys His Gln Tyr Leu Ser Ser Trp Thr Phe Gly Gly Gly Thr Lys Leu
        115                 120                 125

Glu Ile Lys Arg Gly Gly Gly Gly Ser Gly Gly Gly Gly Ser Gly Gly
    130                 135                 140

Gly Gly Ser Gly Gly Gly Gly Ser Gly Gly Gly Gly Ser Gly Gly Gly
145                 150                 155                 160

Gly Ser Gln Val Gln Leu Val Gln Ser Gly Ala Glu Val Lys Lys Pro
                165                 170                 175

Gly Ala Ser Val Lys Val Ser Cys Lys Ala Ser Gly Tyr Thr Phe Thr
            180                 185                 190

Ser Tyr Trp Leu His Trp Val Arg Gln Ala Pro Gly Gln Arg Leu Glu
        195                 200                 205

Trp Met Gly Tyr Ile Asn Pro Arg Asn Asp Tyr Thr Glu Tyr Asn Gln
    210                 215                 220

Asn Phe Lys Asp Arg Val Thr Leu Thr Ala Asp Lys Ser Ala Ser Thr
225                 230                 235                 240

Ala Tyr Met Glu Leu Ser Ser Leu Arg Ser Glu Asp Thr Ala Val Tyr
                245                 250                 255

Tyr Cys Ala Arg Arg Asp Ile Thr Thr Phe Tyr Trp Gly Gln Gly Thr
            260                 265                 270

Thr Leu Thr Val Ser Ser Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430
```

```
Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Arg Ser Pro Asp Asp Glu Leu Leu
                565                 570                 575

Tyr Leu Pro Val Arg Gly Arg Glu Thr Tyr Glu Met Leu Leu Lys Ile
            580                 585                 590

Lys Glu Ser Leu Glu Leu Met Gln Tyr Leu Pro Gln His Thr Ile Glu
        595                 600                 605

Thr Tyr Arg Gln Gln Gln Gln Gln Gln His Gln His Leu Leu Gln Lys
    610                 615                 620

Gln Gly Gly Ser Gly Gly Ala
625                 630
```

<210> SEQ ID NO 77
<211> LENGTH: 638
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 77

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Leu His Trp Val Arg Gln Ala Pro Gly Gln Arg Leu
    50                  55                  60

Glu Trp Met Gly Tyr Ile Asn Pro Arg Asn Asp Tyr Thr Glu Tyr Asn
65                  70                  75                  80

Gln Asn Phe Lys Asp Arg Val Thr Leu Thr Ala Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160
```

```
Gly Gly Gly Gly Ser Asp Ile Val Leu Thr Gln Ser Pro Asp Ser Leu
                165                 170                 175

Ala Val Ser Ala Gly Glu Arg Val Thr Met Asn Cys Lys Ser Ser Gln
            180                 185                 190

Ser Val Leu Tyr Ser Ala Asn His Lys Asn Tyr Leu Ala Trp Tyr Gln
        195                 200                 205

Gln Lys Pro Gly Gln Pro Pro Lys Leu Leu Ile Tyr Trp Ala Ser Thr
    210                 215                 220

Arg Glu Ser Gly Val Pro Asp Arg Phe Ser Gly Ser Gly Ser Gly Thr
225                 230                 235                 240

Asp Phe Thr Leu Thr Ile Ser Ser Val Gln Ala Glu Asp Val Ala Ile
                245                 250                 255

Tyr Tyr Cys His Gln Tyr Leu Ser Ser Trp Thr Phe Gly Gly Gly Thr
            260                 265                 270

Lys Leu Glu Ile Lys Arg Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Arg Ser Pro Asp Asp Glu Leu Leu
                565                 570                 575
```

```
Tyr Leu Pro Val Arg Gly Arg Glu Thr Tyr Glu Met Leu Leu Lys Ile
            580                 585                 590

Lys Glu Ser Leu Glu Leu Met Gln Tyr Leu Pro Gln His Thr Ile Glu
        595                 600                 605

Thr Tyr Arg Gln Gln Gln Gln Gln Gln His Gln His Leu Leu Gln Lys
    610                 615                 620

Gln Gly Gly Ser Gly Gly Ala Pro His His His His His His
625                 630                 635


<210> SEQ ID NO 78
<211> LENGTH: 631
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Leu His Trp Val Arg Gln Ala Pro Gly Gln Arg Leu
    50                  55                  60

Glu Trp Met Gly Tyr Ile Asn Pro Arg Asn Asp Tyr Thr Glu Tyr Asn
65                  70                  75                  80

Gln Asn Phe Lys Asp Arg Val Thr Leu Thr Ala Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Asp Ile Val Leu Thr Gln Ser Pro Asp Ser Leu
                165                 170                 175

Ala Val Ser Ala Gly Glu Arg Val Thr Met Asn Cys Lys Ser Ser Gln
            180                 185                 190

Ser Val Leu Tyr Ser Ala Asn His Lys Asn Tyr Leu Ala Trp Tyr Gln
        195                 200                 205

Gln Lys Pro Gly Gln Pro Pro Lys Leu Leu Ile Tyr Trp Ala Ser Thr
    210                 215                 220

Arg Glu Ser Gly Val Pro Asp Arg Phe Ser Gly Ser Gly Ser Gly Thr
225                 230                 235                 240

Asp Phe Thr Leu Thr Ile Ser Ser Val Gln Ala Glu Asp Val Ala Ile
                245                 250                 255

Tyr Tyr Cys His Gln Tyr Leu Ser Ser Trp Thr Phe Gly Gly Gly Thr
            260                 265                 270

Lys Leu Glu Ile Lys Arg Gly Gly Gly Gly Ser Gly Gly Gly Ser
        275                 280                 285

Gly Gly Gly Gly Ser Gly Gly Gly Gly Ser His Val Gln Leu Val Glu
    290                 295                 300
```

```
Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Arg Ser Pro Asp Asp Glu Leu Leu
                565                 570                 575

Tyr Leu Pro Val Arg Gly Arg Glu Thr Tyr Glu Met Leu Leu Lys Ile
            580                 585                 590

Lys Glu Ser Leu Glu Leu Met Gln Tyr Leu Pro Gln His Thr Ile Glu
        595                 600                 605

Thr Tyr Arg Gln Gln Gln Gln Gln Gln His Gln His Leu Leu Gln Lys
    610                 615                 620

Gln Gly Gly Ser Gly Gly Ala
625                 630
```

<210> SEQ ID NO 79
<211> LENGTH: 633
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 79

```
Met Gly Trp Ser Cys Ile Ile Leu Phe Leu Val Ala Thr Ala Thr Gly
1               5                   10                  15
```

```
Val His Ser Asp Ile Val Leu Thr Gln Ser Pro Asp Ser Leu Ala Val
            20                  25                  30

Ser Ala Gly Glu Arg Val Thr Met Asn Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Val Gln Ala Glu Asp Val Ala Ile Tyr Tyr
            100                 105                 110

Cys His Gln Tyr Leu Ser Ser Trp Thr Phe Gly Gly Gly Thr Lys Leu
        115                 120                 125

Glu Ile Lys Arg Gly Gly Gly Gly Ser Gly Gly Gly Gly Ser Gly Gly
    130                 135                 140

Gly Gly Ser Gly Gly Gly Gly Ser Gly Gly Gly Gly Ser Gly Gly Gly
145                 150                 155                 160

Gly Ser Gln Val Gln Leu Val Gln Ser Gly Ala Glu Val Lys Lys Pro
                165                 170                 175

Gly Ala Ser Val Lys Val Ser Cys Lys Ala Ser Gly Tyr Thr Phe Thr
            180                 185                 190

Ser Tyr Trp Leu His Trp Val Arg Gln Ala Pro Gly Gln Arg Leu Glu
        195                 200                 205

Trp Met Gly Tyr Ile Asn Pro Arg Asn Asp Tyr Thr Glu Tyr Asn Gln
    210                 215                 220

Asn Phe Lys Asp Arg Val Thr Leu Thr Ala Asp Lys Ser Ala Ser Thr
225                 230                 235                 240

Ala Tyr Met Glu Leu Ser Ser Leu Arg Ser Glu Asp Thr Ala Val Tyr
                245                 250                 255

Tyr Cys Ala Arg Arg Asp Ile Thr Thr Phe Tyr Trp Gly Gln Gly Thr
            260                 265                 270

Thr Leu Thr Val Ser Ser Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430
```

```
Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Arg His Gly Asp Glu Asp Thr Tyr
                565                 570                 575

Tyr Leu Gln Val Arg Gly Arg Glu Asn Phe Glu Ile Leu Met Lys Leu
            580                 585                 590

Lys Glu Ser Leu Glu Leu Met Glu Leu Val Pro Gln Pro Leu Val Asp
        595                 600                 605

Ser Tyr Arg Gln Gln Gln Gln Leu Leu Gln Arg Pro Gly Gly Ser Gly
    610                 615                 620

Gly Ala Pro His His His His His His
625                 630


<210> SEQ ID NO 80
<211> LENGTH: 626
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Gly Trp Ser Cys Ile Ile Leu Phe Leu Val Ala Thr Ala Thr Gly
1               5                   10                  15

Val His Ser Asp Ile Val Leu Thr Gln Ser Pro Asp Ser Leu Ala Val
            20                  25                  30

Ser Ala Gly Glu Arg Val Thr Met Asn Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Val Gln Ala Glu Asp Val Ala Ile Tyr Tyr
            100                 105                 110

Cys His Gln Tyr Leu Ser Ser Trp Thr Phe Gly Gly Gly Thr Lys Leu
        115                 120                 125

Glu Ile Lys Arg Gly Gly Gly Gly Ser Gly Gly Gly Gly Ser Gly Gly
    130                 135                 140

Gly Gly Ser Gly Gly Gly Gly Ser Gly Gly Gly Gly Ser Gly Gly Gly
145                 150                 155                 160
```

```
Gly Ser Gln Val Gln Leu Val Gln Ser Gly Ala Glu Val Lys Lys Pro
                165                 170                 175

Gly Ala Ser Val Lys Val Ser Cys Lys Ala Ser Gly Tyr Thr Phe Thr
            180                 185                 190

Ser Tyr Trp Leu His Trp Val Arg Gln Ala Pro Gly Gln Arg Leu Glu
        195                 200                 205

Trp Met Gly Tyr Ile Asn Pro Arg Asn Asp Tyr Thr Glu Tyr Asn Gln
    210                 215                 220

Asn Phe Lys Asp Arg Val Thr Leu Thr Ala Asp Lys Ser Ala Ser Thr
225                 230                 235                 240

Ala Tyr Met Glu Leu Ser Ser Leu Arg Ser Glu Asp Thr Ala Val Tyr
                245                 250                 255

Tyr Cys Ala Arg Arg Asp Ile Thr Thr Phe Tyr Trp Gly Gln Gly Thr
            260                 265                 270

Thr Leu Thr Val Ser Ser Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Arg His Gly Asp Glu Asp Thr Tyr
                565                 570                 575
```

Tyr Leu Gln Val Arg Gly Arg Glu Asn Phe Glu Ile Leu Met Lys Leu
580 585 590

Lys Glu Ser Leu Glu Leu Met Glu Leu Val Pro Gln Pro Leu Val Asp
595 600 605

Ser Tyr Arg Gln Gln Gln Gln Leu Leu Gln Arg Pro Gly Gly Ser Gly
610 615 620

Gly Ala
625

<210> SEQ ID NO 81
<211> LENGTH: 633
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 81

Met Gly Trp Ser Cys Ile Ile Leu Phe Leu Val Ala Thr Ala Thr Gly
1 5 10 15

Val His Ser Gln Val Gln Leu Val Gln Ser Gly Ala Glu Val Lys Lys
20 25 30

Pro Gly Ala Ser Val Lys Val Ser Cys Lys Ala Ser Gly Tyr Thr Phe
35 40 45

Thr Ser Tyr Trp Leu His Trp Val Arg Gln Ala Pro Gly Gln Arg Leu
50 55 60

Glu Trp Met Gly Tyr Ile Asn Pro Arg Asn Asp Tyr Thr Glu Tyr Asn
65 70 75 80

Gln Asn Phe Lys Asp Arg Val Thr Leu Thr Ala Asp Lys Ser Ala Ser
85 90 95

Thr Ala Tyr Met Glu Leu Ser Ser Leu Arg Ser Glu Asp Thr Ala Val
100 105 110

Tyr Tyr Cys Ala Arg Arg Asp Ile Thr Thr Phe Tyr Trp Gly Gln Gly
115 120 125

Thr Thr Leu Thr Val Ser Ser Gly Gly Gly Gly Ser Gly Gly Gly Gly
130 135 140

Ser Gly Gly Gly Gly Ser Gly Gly Gly Gly Ser Gly Gly Gly Gly Ser
145 150 155 160

Gly Gly Gly Gly Ser Asp Ile Val Leu Thr Gln Ser Pro Asp Ser Leu
165 170 175

Ala Val Ser Ala Gly Glu Arg Val Thr Met Asn Cys Lys Ser Ser Gln
180 185 190

Ser Val Leu Tyr Ser Ala Asn His Lys Asn Tyr Leu Ala Trp Tyr Gln
195 200 205

Gln Lys Pro Gly Gln Pro Pro Lys Leu Leu Ile Tyr Trp Ala Ser Thr
210 215 220

Arg Glu Ser Gly Val Pro Asp Arg Phe Ser Gly Ser Gly Ser Gly Thr
225 230 235 240

Asp Phe Thr Leu Thr Ile Ser Ser Val Gln Ala Glu Asp Val Ala Ile
245 250 255

Tyr Tyr Cys His Gln Tyr Leu Ser Ser Trp Thr Phe Gly Gly Gly Thr
260 265 270

Lys Leu Glu Ile Lys Arg Gly Gly Gly Gly Ser Gly Gly Gly Ser
275 280 285

Gly Gly Gly Gly Ser Gly Gly Gly Gly Ser His Val Gln Leu Val Glu
290 295 300

```
Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430

Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Arg His Gly Asp Glu Asp Thr Tyr
                565                 570                 575

Tyr Leu Gln Val Arg Gly Arg Glu Asn Phe Glu Ile Leu Met Lys Leu
            580                 585                 590

Lys Glu Ser Leu Glu Leu Met Glu Leu Val Pro Gln Pro Leu Val Asp
        595                 600                 605

Ser Tyr Arg Gln Gln Gln Gln Leu Leu Gln Arg Pro Gly Gly Ser Gly
    610                 615                 620

Gly Ala Pro His His His His His His
625                 630
```

<210> SEQ ID NO 82
<211> LENGTH: 626
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

```
Met Gly Trp Ser Cys Ile Ile Leu Phe Leu Val Ala Thr Ala Thr Gly
1               5                   10                  15
```

```
Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Leu His Trp Val Arg Gln Ala Pro Gly Gln Arg Leu
    50                  55                  60

Glu Trp Met Gly Tyr Ile Asn Pro Arg Asn Asp Tyr Thr Glu Tyr Asn
65                  70                  75                  80

Gln Asn Phe Lys Asp Arg Val Thr Leu Thr Ala Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Asp Ile Val Leu Thr Gln Ser Pro Asp Ser Leu
                165                 170                 175

Ala Val Ser Ala Gly Glu Arg Val Thr Met Asn Cys Lys Ser Ser Gln
            180                 185                 190

Ser Val Leu Tyr Ser Ala Asn His Lys Asn Tyr Leu Ala Trp Tyr Gln
        195                 200                 205

Gln Lys Pro Gly Gln Pro Pro Lys Leu Leu Ile Tyr Trp Ala Ser Thr
    210                 215                 220

Arg Glu Ser Gly Val Pro Asp Arg Phe Ser Gly Ser Gly Ser Gly Thr
225                 230                 235                 240

Asp Phe Thr Leu Thr Ile Ser Ser Val Gln Ala Glu Asp Val Ala Ile
                245                 250                 255

Tyr Tyr Cys His Gln Tyr Leu Ser Ser Trp Thr Phe Gly Gly Gly Thr
            260                 265                 270

Lys Leu Glu Ile Lys Arg Gly Gly Gly Gly Ser Gly Gly Gly Gly Ser
        275                 280                 285

Gly Gly Gly Gly Ser Gly Gly Gly Gly Ser His Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Ser Leu Thr Asp Tyr Gly Val His Trp Val Arg
                325                 330                 335

Gln Ala Pro Gly Lys Gly Leu Glu Trp Leu Gly Val Ile Trp Ser Gly
            340                 345                 350

Gly Gly Thr Ala Tyr Asn Thr Ala Leu Ile Ser Arg Phe Thr Ile Ser
        355                 360                 365

Arg Asp Asn Ser Lys Asn Thr Leu Tyr Leu Gln Met Asn Ser Leu Arg
    370                 375                 380

Ala Glu Asp Thr Ala Val Tyr Tyr Cys Ala Arg Arg Gly Ser Tyr Pro
385                 390                 395                 400

Tyr Asn Tyr Phe Asp Ala Trp Gly Cys Gly Thr Leu Val Thr Val Ser
                405                 410                 415

Ser Gly Gly Gly Gly Ser Gly Gly Gly Gly Ser Gly Gly Gly Gly Ser
            420                 425                 430
```

```
Gly Gly Gly Gly Ser Gly Gly Gly Gly Ser Gly Gly Gly Gly Ser Gln
        435                 440                 445

Ala Val Val Thr Gln Glu Pro Ser Leu Thr Val Ser Pro Gly Gly Thr
    450                 455                 460

Val Thr Leu Thr Cys Gly Ser Ser Thr Gly Ala Val Thr Ala Ser Asn
465                 470                 475                 480

Tyr Ala Asn Trp Val Gln Gln Lys Pro Gly Gln Cys Pro Arg Gly Leu
                485                 490                 495

Ile Gly Gly His Asn Asn Arg Pro Pro Gly Val Pro Ala Arg Phe Ser
            500                 505                 510

Gly Ser Leu Leu Gly Gly Lys Ala Ala Leu Thr Leu Leu Gly Ala Gln
        515                 520                 525

Pro Glu Asp Glu Ala Glu Tyr Tyr Cys Ala Leu Trp Tyr Ser Asp His
    530                 535                 540

Trp Val Ile Gly Gly Gly Thr Lys Leu Thr Val Leu Gly Thr Pro Leu
545                 550                 555                 560

Gly Asp Thr Thr His Thr Ser Gly Arg His Gly Asp Glu Asp Thr Tyr
                565                 570                 575

Tyr Leu Gln Val Arg Gly Arg Glu Asn Phe Glu Ile Leu Met Lys Leu
            580                 585                 590

Lys Glu Ser Leu Glu Leu Met Glu Leu Val Pro Gln Pro Leu Val Asp
        595                 600                 605

Ser Tyr Arg Gln Gln Gln Gln Leu Leu Gln Arg Pro Gly Gly Ser Gly
    610                 615                 620

Gly Ala
625


<210> SEQ ID NO 83
<211> LENGTH: 847
<212> TYPE: PRT
<213> ORGANISM: Homo sapiens

<400> SEQUENCE: 83

Met His Leu Leu Gly Pro Trp Leu Leu Leu Leu Val Leu Glu Tyr Leu
1               5                   10                  15

Ala Phe Ser Asp Ser Ser Lys Trp Val Phe Glu His Pro Glu Thr Leu
            20                  25                  30

Tyr Ala Trp Glu Gly Ala Cys Val Trp Ile Pro Cys Thr Tyr Arg Ala
        35                  40                  45

Leu Asp Gly Asp Leu Glu Ser Phe Ile Leu Phe His Asn Pro Glu Tyr
    50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
            100                 105                 110

Asp Ser Gly Gln Leu Gly Leu Arg Met Glu Ser Lys Thr Glu Lys Trp
        115                 120                 125

Met Glu Arg Ile His Leu Asn Val Ser Glu Arg Pro Phe Pro Pro His
    130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175
```

```
Leu Leu Glu Gly Val Pro Met Arg Gln Ala Ala Val Thr Ser Thr Ser
            180                 185                 190

Leu Thr Ile Lys Ser Val Phe Thr Arg Ser Glu Leu Lys Phe Ser Pro
        195                 200                 205

Gln Trp Ser His His Gly Lys Ile Val Thr Cys Gln Leu Gln Asp Ala
    210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                245                 250                 255

Glu Gly Asp Ser Val Thr Met Thr Cys Glu Val Ser Ser Ser Asn Pro
            260                 265                 270

Glu Tyr Thr Thr Val Ser Trp Leu Lys Asp Gly Thr Ser Leu Lys Lys
        275                 280                 285

Gln Asn Thr Phe Thr Leu Asn Leu Arg Glu Val Thr Lys Asp Gln Ser
    290                 295                 300

Gly Lys Tyr Cys Cys Gln Val Ser Asn Asp Val Gly Pro Gly Arg Ser
305                 310                 315                 320

Glu Glu Val Phe Leu Gln Val Gln Tyr Ala Pro Glu Pro Ser Thr Val
                325                 330                 335

Gln Ile Leu His Ser Pro Ala Val Glu Gly Ser Gln Val Glu Phe Leu
            340                 345                 350

Cys Met Ser Leu Ala Asn Pro Leu Pro Thr Asn Tyr Thr Trp Tyr His
        355                 360                 365

Asn Gly Lys Glu Met Gln Gly Arg Thr Glu Glu Lys Val His Ile Pro
    370                 375                 380

Lys Ile Leu Pro Trp His Ala Gly Thr Tyr Ser Cys Val Ala Glu Asn
385                 390                 395                 400

Ile Leu Gly Thr Gly Gln Arg Gly Pro Gly Ala Glu Leu Asp Val Gln
                405                 410                 415

Tyr Pro Pro Lys Lys Val Thr Thr Val Ile Gln Asn Pro Met Pro Ile
            420                 425                 430

Arg Glu Gly Asp Thr Val Thr Leu Ser Cys Asn Tyr Asn Ser Ser Asn
        435                 440                 445

Pro Ser Val Thr Arg Tyr Glu Trp Lys Pro His Gly Ala Trp Glu Glu
    450                 455                 460

Pro Ser Leu Gly Val Leu Lys Ile Gln Asn Val Gly Trp Asp Asn Thr
465                 470                 475                 480

Thr Ile Ala Cys Ala Ala Cys Asn Ser Trp Cys Ser Trp Ala Ser Pro
                485                 490                 495

Val Ala Leu Asn Val Gln Tyr Ala Pro Arg Asp Val Arg Val Arg Lys
            500                 505                 510

Ile Lys Pro Leu Ser Glu Ile His Ser Gly Asn Ser Val Ser Leu Gln
        515                 520                 525

Cys Asp Phe Ser Ser Ser His Pro Lys Glu Val Gln Phe Phe Trp Glu
    530                 535                 540

Lys Asn Gly Arg Leu Leu Gly Lys Glu Ser Gln Leu Asn Phe Asp Ser
545                 550                 555                 560

Ile Ser Pro Glu Asp Ala Gly Ser Tyr Ser Cys Trp Val Asn Asn Ser
                565                 570                 575

Ile Gly Gln Thr Ala Ser Lys Ala Trp Thr Leu Glu Val Leu Tyr Ala
            580                 585                 590
```

```
Pro Arg Arg Leu Arg Val Ser Met Ser Pro Gly Asp Gln Val Met Glu
        595                 600                 605

Gly Lys Ser Ala Thr Leu Thr Cys Glu Ser Asp Ala Asn Pro Pro Val
    610                 615                 620

Ser His Tyr Thr Trp Phe Asp Trp Asn Asn Gln Ser Leu Pro Tyr His
625                 630                 635                 640

Ser Gln Lys Leu Arg Leu Glu Pro Val Lys Val Gln His Ser Gly Ala
                645                 650                 655

Tyr Trp Cys Gln Gly Thr Asn Ser Val Gly Lys Gly Arg Ser Pro Leu
            660                 665                 670

Ser Thr Leu Thr Val Tyr Tyr Ser Pro Glu Thr Ile Gly Arg Arg Val
        675                 680                 685

Ala Val Gly Leu Gly Ser Cys Leu Ala Ile Leu Ile Leu Ala Ile Cys
    690                 695                 700

Gly Leu Lys Leu Gln Arg Arg Trp Lys Arg Thr Gln Ser Gln Gln Gly
705                 710                 715                 720

Leu Gln Glu Asn Ser Ser Gly Gln Ser Phe Phe Val Arg Asn Lys Lys
                725                 730                 735

Val Arg Arg Ala Pro Leu Ser Glu Gly Pro His Ser Leu Gly Cys Tyr
            740                 745                 750

Asn Pro Met Met Glu Asp Gly Ile Ser Tyr Thr Thr Leu Arg Phe Pro
        755                 760                 765

Glu Met Asn Ile Pro Arg Thr Gly Asp Ala Glu Ser Ser Glu Met Gln
    770                 775                 780

Arg Pro Pro Pro Asp Cys Asp Asp Thr Val Thr Tyr Ser Ala Leu His
785                 790                 795                 800

Lys Arg Gln Val Gly Asp Tyr Glu Asn Val Ile Pro Asp Phe Pro Glu
                805                 810                 815

Asp Glu Gly Ile His Tyr Ser Glu Leu Ile Gln Phe Gly Val Gly Glu
            820                 825                 830

Arg Pro Gln Ala Gln Glu Asn Val Asp Tyr Val Ile Leu Lys His
        835                 840                 845
```

<210> SEQ ID NO 84
<211> LENGTH: 384
<212> TYPE: PRT
<213> ORGANISM: Homo sapiens

<400> SEQUENCE: 84

```
Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125
```

```
Pro Ala Thr Thr Arg Asn Thr Gly Arg Gly Gly Glu Glu Lys Lys Lys
    130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
        195                 200                 205

Lys Val Pro Thr Gly Gly Val Glu Glu Gly Leu Leu Glu Arg His Ser
    210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
                245                 250                 255

Pro Pro Gln Arg Leu Met Ala Leu Arg Glu Pro Ala Ala Gln Ala Pro
            260                 265                 270

Val Lys Leu Ser Leu Asn Leu Leu Ala Ser Ser Asp Pro Pro Glu Ala
        275                 280                 285

Ala Ser Trp Leu Leu Cys Glu Val Ser Gly Phe Ser Pro Pro Asn Ile
    290                 295                 300

Leu Leu Met Trp Leu Glu Asp Gln Arg Glu Val Asn Thr Ser Gly Phe
305                 310                 315                 320

Ala Pro Ala Arg Pro Pro Pro Gln Pro Gly Ser Thr Thr Phe Trp Ala
                325                 330                 335

Trp Ser Val Leu Arg Val Pro Ala Pro Pro Ser Pro Gln Pro Ala Thr
            340                 345                 350

Tyr Thr Cys Val Val Ser His Glu Asp Ser Arg Thr Leu Leu Asn Ala
        355                 360                 365

Ser Arg Ser Leu Glu Val Ser Tyr Val Thr Asp His Gly Pro Met Lys
    370                 375                 380


<210> SEQ ID NO 85
<211> LENGTH: 330
<212> TYPE: PRT
<213> ORGANISM: Homo sapiens

<400> SEQUENCE: 85

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

```
Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 86
<211> LENGTH: 326
<212> TYPE: PRT
<213> ORGANISM: Homo sapiens

<400> SEQUENCE: 86

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140
```

```
Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 87
<211> LENGTH: 377
<212> TYPE: PRT
<213> ORGANISM: Homo sapiens

<400> SEQUENCE: 87

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190
```

```
Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375
```

<210> SEQ ID NO 88
<211> LENGTH: 452
<212> TYPE: PRT
<213> ORGANISM: Homo sapiens

<400> SEQUENCE: 88

```
Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175
```

```
Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
    290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
    370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
                405                 410                 415

Glu Ala Leu Pro Asn Arg Val Thr Glu Arg Thr Val Asp Lys Ser Thr
            420                 425                 430

Gly Lys Pro Thr Leu Tyr Asn Val Ser Leu Val Met Ser Asp Thr Ala
        435                 440                 445

Gly Thr Cys Tyr
    450


<210> SEQ ID NO 89
<211> LENGTH: 327
<212> TYPE: PRT
<213> ORGANISM: Homo sapiens

<400> SEQUENCE: 89

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80
```

```
Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 90
<211> LENGTH: 353
<212> TYPE: PRT
<213> ORGANISM: Homo sapiens

<400> SEQUENCE: 90

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110
```

Ser Thr Pro Pro Thr Pro Ser Pro Ser Cys Cys His Pro Arg Leu Ser
115 120 125

Leu His Arg Pro Ala Leu Glu Asp Leu Leu Leu Gly Ser Glu Ala Asn
130 135 140

Leu Thr Cys Thr Leu Thr Gly Leu Arg Asp Ala Ser Gly Val Thr Phe
145 150 155 160

Thr Trp Thr Pro Ser Ser Gly Lys Ser Ala Val Gln Gly Pro Pro Glu
165 170 175

Arg Asp Leu Cys Gly Cys Tyr Ser Val Ser Ser Val Leu Pro Gly Cys
180 185 190

Ala Glu Pro Trp Asn His Gly Lys Thr Phe Thr Cys Thr Ala Ala Tyr
195 200 205

Pro Glu Ser Lys Thr Pro Leu Thr Ala Thr Leu Ser Lys Ser Gly Asn
210 215 220

Thr Phe Arg Pro Glu Val His Leu Leu Pro Pro Pro Ser Glu Glu Leu
225 230 235 240

Ala Leu Asn Glu Leu Val Thr Leu Thr Cys Leu Ala Arg Gly Phe Ser
245 250 255

Pro Lys Asp Val Leu Val Arg Trp Leu Gln Gly Ser Gln Glu Leu Pro
260 265 270

Arg Glu Lys Tyr Leu Thr Trp Ala Ser Arg Gln Glu Pro Ser Gln Gly
275 280 285

Thr Thr Thr Phe Ala Val Thr Ser Ile Leu Arg Val Ala Ala Glu Asp
290 295 300

Trp Lys Lys Gly Asp Thr Phe Ser Cys Met Val Gly His Glu Ala Leu
305 310 315 320

Pro Leu Ala Phe Thr Gln Lys Thr Ile Asp Arg Leu Ala Gly Lys Pro
325 330 335

Thr His Val Asn Val Ser Val Val Met Ala Glu Val Asp Gly Thr Cys
340 345 350

Tyr

<210> SEQ ID NO 91
<211> LENGTH: 340
<212> TYPE: PRT
<213> ORGANISM: Homo sapiens

<400> SEQUENCE: 91

Ala Ser Pro Thr Ser Pro Lys Val Phe Pro Leu Ser Leu Asp Ser Thr
1 5 10 15

Pro Gln Asp Gly Asn Val Val Val Ala Cys Leu Val Gln Gly Phe Phe
20 25 30

Pro Gln Glu Pro Leu Ser Val Thr Trp Ser Glu Ser Gly Gln Asn Val
35 40 45

Thr Ala Arg Asn Phe Pro Pro Ser Gln Asp Ala Ser Gly Asp Leu Tyr
50 55 60

Thr Thr Ser Ser Gln Leu Thr Leu Pro Ala Thr Gln Cys Pro Asp Gly
65 70 75 80

Lys Ser Val Thr Cys His Val Lys His Tyr Thr Asn Pro Ser Gln Asp
85 90 95

Val Thr Val Pro Cys Pro Val Pro Pro Pro Pro Pro Cys Cys His Pro
100 105 110

Arg Leu Ser Leu His Arg Pro Ala Leu Glu Asp Leu Leu Leu Gly Ser
115 120 125

```
Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
        275                 280                 285

Ala Glu Asp Trp Lys Lys Gly Asp Thr Phe Ser Cys Met Val Gly His
    290                 295                 300

Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
            340


<210> SEQ ID NO 92
<211> LENGTH: 106
<212> TYPE: PRT
<213> ORGANISM: Homo sapiens

<400> SEQUENCE: 92

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105


<210> SEQ ID NO 93
<211> LENGTH: 39
<212> TYPE: PRT
<213> ORGANISM: Homo sapiens
```

<400> SEQUENCE: 93

Lys Pro Leu Asp Gly Glu Tyr Phe Thr Leu Gln Ile Arg Gly Arg Glu
1 5 10 15

Arg Phe Glu Met Phe Arg Glu Leu Asn Glu Ala Leu Glu Leu Lys Asp
20 25 30

Ala Gln Ala Gly Lys Glu Pro
35

<210> SEQ ID NO 94
<211> LENGTH: 57
<212> TYPE: PRT
<213> ORGANISM: Homo sapiens

<400> SEQUENCE: 94

Arg Ser Pro Asp Asp Glu Leu Leu Tyr Leu Pro Val Arg Gly Arg Glu
1 5 10 15

Thr Tyr Glu Met Leu Leu Lys Ile Lys Glu Ser Leu Glu Leu Met Gln
20 25 30

Tyr Leu Pro Gln His Thr Ile Glu Thr Tyr Arg Gln Gln Gln Gln Gln
35 40 45

Gln His Gln His Leu Leu Gln Lys Gln
50 55

<210> SEQ ID NO 95
<211> LENGTH: 52
<212> TYPE: PRT
<213> ORGANISM: Homo sapiens

<400> SEQUENCE: 95

Arg His Gly Asp Glu Asp Thr Tyr Tyr Leu Gln Val Arg Gly Arg Glu
1 5 10 15

Asn Phe Glu Ile Leu Met Lys Leu Lys Glu Ser Leu Glu Leu Met Glu
20 25 30

Leu Val Pro Gln Pro Leu Val Asp Ser Tyr Arg Gln Gln Gln Gln Leu
35 40 45

Leu Gln Arg Pro
50

<210> SEQ ID NO 96
<211> LENGTH: 27
<212> TYPE: PRT
<213> ORGANISM: Homo sapiens

<400> SEQUENCE: 96

Gln Ala Ile Lys Lys Glu Leu Thr Gln Ile Lys Gln Lys Val Asp Ser
1 5 10 15

Leu Leu Glu Asn Leu Glu Lys Ile Glu Lys Glu
20 25

<210> SEQ ID NO 97
<211> LENGTH: 54
<212> TYPE: PRT
<213> ORGANISM: Homo sapiens

<400> SEQUENCE: 97

Ser Thr Arg Arg Ile Leu Gly Leu Ala Ile Glu Ser Gln Asp Ala Gly
1 5 10 15

Ile Lys Thr Ile Thr Met Leu Asp Glu Gln Lys Glu Gln Leu Asn Arg
20 25 30

```
Ile Glu Glu Gly Leu Asp Gln Ile Asn Lys Asp Met Arg Glu Thr Glu
        35                  40                  45

Lys Thr Leu Thr Glu Leu
    50


<210> SEQ ID NO 98
<211> LENGTH: 97
<212> TYPE: PRT
<213> ORGANISM: Homo sapiens

<400> SEQUENCE: 98

Met Cys Gly Ala Pro Ser Ala Thr Gln Pro Ala Thr Ala Glu Thr Gln
1               5                   10                  15

His Ile Ala Asp Gln Val Arg Ser Gln Leu Glu Glu Lys Glu Asn Lys
            20                  25                  30

Lys Phe Pro Val Phe Lys Ala Val Ser Phe Lys Ser Gln Val Val Ala
        35                  40                  45

Gly Thr Asn Tyr Phe Ile Lys Val His Val Gly Asp Glu Asp Phe Val
    50                  55                  60

His Leu Arg Val Phe Gln Ser Leu Pro His Glu Asn Lys Pro Leu Thr
65                  70                  75                  80

Leu Ser Asn Tyr Gln Thr Asn Lys Ala Lys His Asp Glu Leu Thr Tyr
                85                  90                  95

Phe


<210> SEQ ID NO 99
<211> LENGTH: 30
<212> TYPE: PRT
<213> ORGANISM: Unknown
<220> FEATURE:
<223> OTHER INFORMATION: Description of Unknown:
      KCNQ4 tetramerization domain sequence

<400> SEQUENCE: 99

Asp Glu Ile Ser Met Met Gly Arg Val Val Lys Val Glu Lys Gln Val
1               5                   10                  15

Gln Ser Ile Glu His Lys Leu Asp Leu Leu Leu Gly Phe Tyr
            20                  25                  30


<210> SEQ ID NO 100
<211> LENGTH: 60
<212> TYPE: PRT
<213> ORGANISM: Unknown
<220> FEATURE:
<223> OTHER INFORMATION: Description of Unknown:
      CBFA2T1 tetramerization domain sequence

<400> SEQUENCE: 100

Thr Val Ala Glu Ala Lys Arg Gln Ala Ala Glu Asp Ala Leu Ala Val
1               5                   10                  15

Ile Asn Gln Gln Glu Asp Ser Ser Glu Ser Cys Trp Asn Cys Gly Arg
            20                  25                  30

Lys Ala Ser Glu Thr Cys Ser Gly Cys Asn Thr Ala Arg Tyr Cys Gly
        35                  40                  45

Ser Phe Cys Gln His Lys Asp Trp Glu Lys His His
    50                  55                  60


<210> SEQ ID NO 101
<211> LENGTH: 30
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 101

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30


<210> SEQ ID NO 102
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Gly Gly Gly Ser Gly Gly Gly Gly Ser Gly Gly Gly Gly Ser Gly
1               5                   10                  15

Gly Gly Gly Ser
            20


<210> SEQ ID NO 103
<211> LENGTH: 9
<212> TYPE: PRT
<213> ORGANISM: Homo sapiens

<400> SEQUENCE: 103

Thr Pro Leu Gly Asp Thr Thr His Thr
1               5


<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Gly Gly Gly Ser Gly Gly Gly Gly Ser Gly Gly Gly Gly Ser
1               5                   10                  15


<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Gly Gly Gly Ser
1               5


<210> SEQ ID NO 106
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
```

<222> LOCATION: (1)..(75)
<223> OTHER INFORMATION: This sequence may encompass 1-15 "Gly Gly Gly Gly Ser" repeating units
<220> FEATURE:
<223> OTHER INFORMATION: See specification as filed for detailed description of substitutions and preferred embodiments

<400> SEQUENCE: 106

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser
65                  70                  75
```

<210> SEQ ID NO 107
<211> LENGTH: 150
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(150)
<223> OTHER INFORMATION: This sequence may encompass 1-20, 25 or 30 "Gly Gly Gly Gly Ser" repeating units
<220> FEATURE:
<223> OTHER INFORMATION: See specification as filed for detailed description of substitutions and preferred embodiments

<400> SEQUENCE: 107

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser Gly Gly Gly Gly Ser Gly Gly Gly Gly Ser Gly Gly
            100                 105                 110

Gly Gly Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser
145                 150
```

<210> SEQ ID NO 108
<211> LENGTH: 6
<212> TYPE: PRT
<213> ORGANISM: Artificial Sequence
<220> FEATURE:

-continued

```
<223> OTHER INFORMATION: Description of Artificial Sequence: Synthetic
      6xHis tag

<400> SEQUENCE: 108

His His His His His His
1               5
```

CD22 ANTIBODIES AND METHODS OF USING THE SAME

CROSS-REFERENCE TO RELATED APPLICATIONS

This application is a U.S. National Stage Application under 35 U.S.C. § 371 of International Patent Application No. PCT/US2020/021866, filed on Mar. 10, 2020, which claims the benefit of and priority to U.S. Provisional Patent Application No. 62/816,469, filed Mar. 11, 2019, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Apr. 2, 2020, is named 115872-0657_SL.txt and is 349,391 bytes in size.

TECHNICAL FIELD

The present technology relates generally to the preparation of immunoglobulin-related compositions (e.g., antibodies or antigen binding fragments thereof) that specifically bind CD22 protein and uses of the same. In particular, the present technology relates to the preparation of CD22 binding antibodies and their use in detecting and treating CD22-associated cancers, CD22-associated autoimmune diseases, or CD22-associated allergies.

BACKGROUND

The following description of the background of the present technology is provided simply as an aid in understanding the present technology and is not admitted to describe or constitute prior art to the present technology.

Non-Hodgkin lymphoma (NHLs) is a heterogeneous disease comprising more than 30 types of B lymphocyte and T lymphocyte malignancies, and 4.3% of all cancers diagnosed in the US. B-cell malignancies include non-Hodgkin lymphomas (NHL), chronic lymphocytic leukemia (CLL), and acute lymphocytic leukemia (ALL). B-cell lymphomas constitute 85% of all NHL; 30% being diffuse large B-cell lymphoma (DLBCL) and 20% follicular lymphoma (20%), resulting in almost 19,000 deaths. In the US, CLL accounts for one third of leukemias and responsible for 4600 deaths annually. Jemal et al., *J Natl Cancer Inst* 109(9), djx030 (2017)).

SUMMARY OF THE PRESENT TECHNOLOGY

In one aspect, the present disclosure provides an antibody or antigen binding fragment thereof comprising a heavy chain immunoglobulin variable domain ($V_H$) and a light chain immunoglobulin variable domain ($V_L$), wherein: (a) the $V_H$ comprises an amino acid sequence selected from the group consisting of: SEQ ID NOs: 5, 6, 7, 8, 9, 10, 11, 12, 13, 14, 15, and 16; and/or (b) the $V_L$ comprises an amino acid sequence selected from the group consisting of: SEQ ID NO: 21, and SEQ ID NO: 22. The antibody may further comprise an Fc domain of an isotype selected from the group consisting of IgG1, IgG2, IgG3, IgG4, IgA1, IgA2, IgM, IgD, and IgE. In some embodiments, the antibody comprises an IgG1 constant region comprising one or more amino acid substitutions selected from the group consisting of N297A and K322A. Additionally or alternatively, in some embodiments, the antibody comprises an IgG4 constant region comprising a S228P mutation. In certain embodiments, the antigen binding fragment is selected from the group consisting of Fab, $F(ab')_2$, Fab', $scF_v$, and $F_v$. In some embodiments, the antibody is a monoclonal antibody, chimeric antibody, humanized antibody, or a bispecific antibody. Additionally or alternatively, in some embodiments, the antibody or antigen binding fragment binds to a CD22 polypeptide comprising an Ig-like C2-type 1 domain (amino acid residues 143-235 of CD22) and/or an Ig-like C2-type 2 domain (amino acid residues 242-326 of CD22). Additionally or alternatively, in certain embodiments, the antibody or antigen binding fragment binds to a conformational epitope spanning the second and third Ig-like domains of CD22.

In one aspect, the present disclosure provides an antibody comprising a heavy chain (HC) comprising amino acid sequence comprising SEQ ID NO: 25, SEQ ID NO: 29, SEQ ID NO: 33, SEQ ID NO: 36, SEQ ID NO: 38, SEQ ID NO: 40, SEQ ID NO: 42, SEQ ID NO: 44, SEQ ID NO: 46, or a variant thereof having one or more conservative amino acid substitutions, and/or a light chain (LC) amino acid sequence comprising SEQ ID NO: 23, SEQ ID NO: 27, SEQ ID NO: 31, SEQ ID NO: 35, SEQ ID NO: 37, SEQ ID NO: 39, SEQ ID NO: 41, SEQ ID NO: 43, SEQ ID NO: 45, or a variant thereof having one or more conservative amino acid substitutions.

In some embodiments, the antibody comprises a HC amino acid sequence and a LC amino acid sequence selected from the group consisting of: SEQ ID NO: 25 and SEQ ID NO: 23 (chLL2 x CD3 BsAb); SEQ ID NO: 29 and SEQ ID NO: 27 (BC270-hLL2 x CD3 BsAb); SEQ ID NO: 33 and SEQ ID NO: 31 (BC251-hLL2 x CD3 BsAb); SEQ ID NO: 36 and SEQ ID NO: 35 (mLL2 x mC825 BsAb); SEQ ID NO: 38 and SEQ ID NO: 37 (mLL2 x hC825 BsAb); SEQ ID NO: 40 and SEQ ID NO: 39 (VL1VH4 x mC825); SEQ ID NO: 42 and SEQ ID NO: 41 (VL1VH4 x hC825); SEQ ID NO: 44 and SEQ ID NO: 43 (VL1VH10 x mC825); and SEQ ID NO: 46 and SEQ ID NO: 45 (VL1VH10 x hC825), respectively.

In one aspect, the present disclosure provides an antibody comprising (a) a light chain immunoglobulin variable domain sequence that is at least 80%, at least 85%, at least 90%, at least 95%, or at least 99% identical to the light chain immunoglobulin variable domain sequence present in any one of SEQ ID NOs: 21 or 22; and/or (b) a heavy chain immunoglobulin variable domain sequence that is at least 80%, at least 85%, at least 90%, at least 95%, or at least 99% identical to the heavy chain immunoglobulin variable domain sequence present in any one of SEQ ID NOs: SEQ ID NOs: 5, 6, 7, 8, 9, 10, 11, 12, 13, 14, 15, or 16.

In another aspect, the present disclosure provides an antibody comprising (a) a LC sequence that is at least 80%, at least 85%, at least 90%, at least 95%, or at least 99% identical to the LC sequence present in any one of SEQ ID NOs: 23, 27, 31, 35, 37, 39, 41, 43, or 45; and/or (b) a HC sequence that is at least 80%, at least 85%, at least 90%, at least 95%, or at least 99% identical to the HC sequence present in any one of SEQ ID NO: 25, 29, 33, 36, 38, 40, 42, 44, or 46.

In any of the above embodiments, the antibody is a chimeric antibody, a humanized antibody, or a bispecific antibody. Additionally or alternatively, in some embodiments, the antibody comprises an IgG1 constant region comprising one or more amino acid substitutions selected from the group consisting of N297A and K322A. In certain embodiments, the antibody of the present technology comprises an IgG4 constant region comprising a S228P mutation. In any of the above embodiments, the antibody or antigen binding fragment binds to the Ig-like C2-type 1 domain, and/or Ig-like C2-type 2 of CD22. In any of the above embodiments, the antibody or antigen binding fragment binds to a conformational epitope spanning the second and third Ig-like domains of CD22. Additionally or alternatively, in some embodiments, the antibody of the present technology lacks α-1,6-fucose modifications.

In one aspect, the present disclosure provides a bispecific antibody or antigen binding fragment comprising an amino acid sequence that is at least 95% identical to an amino acid sequence selected from any one of SEQ ID NOs:47-82. In certain embodiments, the bispecific antibody or antigen binding fragment comprises an amino acid sequence selected from any one of SEQ ID NOs:47-82.

In one aspect, the present disclosure provides a bispecific antigen binding fragment comprising a first polypeptide chain, wherein: the first polypeptide chain comprises in the N-terminal to C-terminal direction: (i) a heavy chain variable domain of a first immunoglobulin that is capable of specifically binding to a first epitope; (ii) a flexible peptide linker comprising the amino acid sequence $(GGGGS)_6$ (SEQ ID NO: 101); (iii) a light chain variable domain of the first immunoglobulin; (iv) a flexible peptide linker comprising the amino acid sequence $(GGGGS)_4$ (SEQ ID NO: 102); (v) a heavy chain variable domain of a second immunoglobulin that is capable of specifically binding to a second epitope; (vi) a flexible peptide linker comprising the amino acid sequence $(GGGGS)_6$ (SEQ ID NO: 101); (vii) a light chain variable domain of the second immunoglobulin; (viii) a flexible peptide linker sequence comprising the amino acid sequence TPLGDTTHT (SEQ ID NO: 103); and (ix) a self-assembly disassembly (SADA) polypeptide, wherein the heavy chain variable domain of the first immunoglobulin is selected from the group consisting of: SEQ ID NOs: 5, 6, 7, 8, 9, 10, 11, 12, 13, 14, 15, and 16; and/or the light chain variable domain of the first immunoglobulin is selected from the group consisting of: SEQ ID NO: 21 and SEQ ID NO: 22.

In another aspect, the present disclosure provides a bispecific antigen binding fragment comprising a first polypeptide chain, wherein: the first polypeptide chain comprises in the N-terminal to C-terminal direction: (i) a light chain variable domain of a first immunoglobulin that is capable of specifically binding to a first epitope; (ii) a flexible peptide linker comprising the amino acid sequence $(GGGGS)_6$ (SEQ ID NO: 101); (iii) a heavy chain variable domain of the first immunoglobulin; (iv) a flexible peptide linker comprising the amino acid sequence $(GGGGS)_4$ (SEQ ID NO: 102); (v) a heavy chain variable domain of a second immunoglobulin that is capable of specifically binding to a second epitope; (vi) a flexible peptide linker comprising the amino acid sequence $(GGGGS)_6$ (SEQ ID NO: 101); (vii) a light chain variable domain of the second immunoglobulin; (viii) a flexible peptide linker sequence comprising the amino acid sequence TPLGDTTHT (SEQ ID NO: 103); and (ix) a self-assembly disassembly (SADA) polypeptide, wherein the heavy chain variable domain of the first immunoglobulin is selected from the group consisting of: SEQ ID NOs: 5, 6, 7, 8, 9, 10, 11, 12, 13, 14, 15, and 16; and/or the light chain variable domain of the first immunoglobulin is selected from the group consisting of: SEQ ID NO: 21 and SEQ ID NO: 22.

In certain embodiments of the bispecific antigen binding fragments disclosed herein, the SADA polypeptide comprises a tetramerization, pentamerization, or hexamerization domain. In some embodiments, the SADA polypeptide comprises a tetramerization domain of any one of p53, p63, p73, hnRNPC, SNA-23, Stefin B, KCNQ4, and CBFA2T1. Additionally or alternatively, in some embodiments, the bispecific antigen binding fragment comprises an amino acid sequence selected from SEQ ID NOs: 47-82.

In one aspect, the present disclosure provides a bispecific antibody comprising a first polypeptide chain, a second polypeptide chain, a third polypeptide chain and a fourth polypeptide chain, wherein the first and second polypeptide chains are covalently bonded to one another, the second and third polypeptide chains are covalently bonded to one another, and the third and fourth polypeptide chain are covalently bonded to one another, and wherein: (a) each of the first polypeptide chain and the fourth polypeptide chain comprises in the N-terminal to C-terminal direction: (i) a light chain variable domain of a first immunoglobulin that is capable of specifically binding to a first epitope; (ii) a light chain constant domain of the first immunoglobulin; (iii) a flexible peptide linker comprising the amino acid sequence $(GGGGS)_3$ (SEQ ID NO: 104); and (iv) a light chain variable domain of a second immunoglobulin that is linked to a complementary heavy chain variable domain of the second immunoglobulin, or a heavy chain variable domain of a second immunoglobulin that is linked to a complementary light chain variable domain of the second immunoglobulin, wherein the light chain and heavy chain variable domains of the second immunoglobulin are capable of specifically binding to a second epitope, and are linked together via a flexible peptide linker comprising the amino acid sequence $(GGGGS)_6$ (SEQ ID NO: 101) to form a single-chain variable fragment; and (b) each of the second polypeptide chain and the third polypeptide chain comprises in the N-terminal to C-terminal direction: (i) a heavy chain variable domain of the first immunoglobulin that is capable of specifically binding to the first epitope; and (ii) a heavy chain constant domain of the first immunoglobulin; and wherein the heavy chain variable domain of the first immunoglobulin is selected from the group consisting of: SEQ ID NOs: 5, 6, 7, 8, 9, 10, 11, 12, 13, 14, 15, and 16; and/or the light chain variable domain of the first immunoglobulin is selected from the group consisting of: SEQ ID NO: 21 and SEQ ID NO: 22. In certain embodiments, the second immunoglobulin binds to CD3, CD4, CD8, CD20, CD19, CD21, CD23, CD46, CD80, HLA-DR, CD74, CD22, CD14, CD15, CD16, CD123, TCR gamma/delta, NKp46, KIR, or a small molecule DOTA hapten.

In one aspect, the present disclosure provides a recombinant nucleic acid sequence encoding any of the antibodies or antigen binding fragments described herein. In some embodiments, the recombinant nucleic acid sequence is selected from the group consisting of: SEQ ID NOs: 24, 26, 28, 30, 32, and 34.

In another aspect, the present disclosure provides a host cell or vector comprising any of the recombinant nucleic acid sequences disclosed herein.

In one aspect, the present disclosure provides a composition comprising an antibody or antigen binding fragment of the present technology and a pharmaceutically-acceptable carrier, wherein the antibody or antigen binding fragment is optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof.

In some embodiments of the bispecific antibody or antigen binding fragment of the present technology, the bispecific antibody binds to T cells, B-cells, myeloid cells, plasma cells, or mast-cells. Additionally or alternatively, in some embodiments, the bispecific antibody or antigen binding fragment binds to CD3, CD4, CD8, CD20, CD19, CD21, CD23, CD46, CD80, HLA-DR, CD74, CD22, CD14, CD15, CD16, CD123, TCR gamma/delta, NKp46, KIR, or a small molecule DOTA hapten. The small molecule DOTA hapten may be selected from the group consisting of DOTA, DOTA-Bn, DOTA-desferrioxamine, DOTA-Phe-Lys(HSG)-D-Tyr-Lys(HSG)-$NH_2$, Ac-Lys(HSG)D-Tyr-Lys(HSG)-Lys(Tscg-Cys)-$NH_2$, DOTA-D-Asp-D-Lys(HSG)-D-Asp-D-Lys(HSG)-$NH_2$; DOTA-D-Glu-D-Lys(HSG)-D-Glu-D-Lys(HSG)-$NH_2$, DOTA-D-Tyr-D-Lys(HSG)-D-Glu-D-Lys(HSG)-$NH_2$, DOTA-D-Ala-D-Lys(HSG)-D-Glu-D-Lys(HSG)-$NH_2$, DOTA-D-Phe-D-Lys(HSG)-D-Tyr-D-Lys(HSG)-$NH_2$, Ac-D-Phe-D-Lys(DOTA)-D-Tyr-D-Lys(DOTA)-$NH_2$, Ac-D-Phe-D-Lys(DTPA)-D-Tyr-D-Lys(DTPA)-$NH_2$, Ac-D-Phe-D-Lys(Bz-DTPA)-D-Tyr-D-Lys(Bz-DTPA)-$NH_2$, Ac-D-Lys(HSG)-D-Tyr-D-Lys(HSG)-D-Lys(Tscg-Cys)-$NH_2$, DOTA-D-Phe-D-Lys(HSG)-D-Tyr-D-Lys(HSG)-D-Lys(Tscg-Cys)-$NH_2$, (Tscg-Cys)-D-Phe-D-Lys(HSG)-D-Tyr-D-Lys(HSG)-D-Lys(DOTA)-$NH_2$, Tscg-D-Cys-D-Glu-D-Lys(HSG)-D-Glu-D-Lys(HSG)-$NH_2$, (Tscg-Cys)-D-Glu-D-Lys(HSG)-D-Glu-D-Lys(HSG)-$NH_2$, Ac-D-Cys-D-Lys(DOTA)-D-Tyr-D-Ala-D-Lys(DOTA)-D-Cys-$NH_2$, Ac-D-Cys-D-Lys(DTPA)-D-Tyr-D-Lys(DTPA)-$NH_2$, Ac-D-Lys(DTPA)-D-Tyr-D-Lys(DTPA)-D-Lys(Tscg-Cys)-$NH_2$, and Ac-D-Lys(DOTA)-D-Tyr-D-Lys(DOTA)-D-Lys(Tscg-Cys)-$NH_2$.

In another aspect, the present disclosure provides a method for treating a CD22-associated cancer, a CD22-associated autoimmune disease, or a CD22-associated allergy in a subject in need thereof, comprising administering to the subject an effective amount of any one of the antibodies or antigen binding fragments disclosed herein. In certain embodiments, the antibody comprises a HC amino acid sequence and a LC amino acid sequence selected from the group consisting of: SEQ ID NO: 25 and SEQ ID NO: 23 (chLL2 x CD3 BsAb); SEQ ID NO: 29 and SEQ ID NO: 27 (BC270-hLL2 x CD3 BsAb); SEQ ID NO: 33 and SEQ ID NO: 31 (BC251-hLL2 x CD3 BsAb); SEQ ID NO: 36 and SEQ ID NO: 35 (mLL2 x mC825 BsAb); SEQ ID NO: 38 and SEQ ID NO: 37 (mLL2 x hC825 BsAb); SEQ ID NO: 40 and SEQ ID NO: 39 (VL1VH4 x mC825); SEQ ID NO: 42 and SEQ ID NO: 41 (VL1VH4 x hC825); SEQ ID NO: 44 and SEQ ID NO: 43 (VL1VH10 x mC825); and SEQ ID NO: 46 and SEQ ID NO: 45 (VL1VH10 x hC825), respectively, wherein the antibody specifically binds to CD22. In some embodiments, the antibody or antigen binding fragment comprises an amino acid sequence selected from any one of SEQ ID NOs: 47-82.

In some embodiments, the CD22-associated cancer is acute myeloid leukemia, myelodysplastic syndrome, chronic Myeloid Leukemia, Chronic Lymphocytic Leukemia, Non-Hodgkin Lymphoma, multiple myeloma, Plasmacytoma, Monoclonal gammopathy of undetermined significance, Waldenström's macroglobulinemia (lymphoplasmacytic lymphoma), Heavy chain disease, primary amyloidosis, Post-transplant lymphoproliferative disorder, Hodgkin lymphoma, MALT lymphoma, B cell Lymphoma, mantle cell lymphoma, (germinal center-like) diffuse large cell lymphoma, Burkitt's lymphoma, Bilineage leukemia, biphenotypic leukemia, Hairy cell leukemia, Precursor B acute lymphoblastic leukemia/lymphoma, Primary cutaneous follicle center lymphoma, follicular lymphoma, or Marginal Zone B-cell Non-Hodgkin's Lymphoma.

In some embodiments, the CD22-associated autoimmune disease is multiple sclerosis (MS), rheumatoid arthritis (RA), systemic lupus erythematosus, paraneoplastic syndromes, Pemphigus Vulgaris, type 2 diabetes, or graft-versus-host disease.

Additionally or alternatively, in some embodiments of the method, the antibody or antigen binding fragment is administered to the subject separately, sequentially or simultaneously with an additional therapeutic agent. Examples of additional therapeutic agents for treating cancer include one or more of alkylating agents, platinum agents, taxanes, *vinca* agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents. Examples of additional therapeutic agents for treating autoimmune disease include one or more of non-steroidal anti-inflammatory drugs (NSAIDs), glucocorticoids, disease-modifying antirheumatic drugs (DMARDs), anti-TNF biologics, abatacept, tocilizumab, anakinra, and rituximab.

In another aspect, the present disclosure provides a method for detecting a tumor in a subject in vivo comprising (a) administering to the subject an effective amount of an antibody or antigen binding fragment of the present technology, wherein the antibody or antigen binding fragment is configured to localize to a tumor expressing CD22 and is labeled with a radioisotope; and (b) detecting the presence of a tumor in the subject by detecting radioactive levels emitted by the antibody or antigen binding fragment that are higher than a reference value. In some embodiments, the subject is diagnosed with or is suspected of having cancer. Radioactive levels emitted by the antibody or antigen binding fragment may be detected using positron emission tomography or single photon emission computed tomography.

Additionally or alternatively, in some embodiments, the method further comprises administering to the subject an effective amount of an immunoconjugate comprising an antibody or antigen binding fragment of the present technology conjugated to a radionuclide. In some embodiments, the radionuclide is an alpha particle-emitting isotope, a beta particle-emitting isotope, an Auger-emitter, or any combination thereof. Examples of beta particle-emitting isotopes include $^{86}Y$, $^{90}Y$, $^{89}Sr$, $^{165}Dy$, $^{186}Re$, $^{188}Re$, $^{177}Lu$, and $^{67}Cu$. In some embodiments of the method, nonspecific FcR-dependent binding in normal tissues is eliminated or reduced (e.g., via N297A mutation in Fc region, which results in aglycosylation).

Also disclosed herein are kits for the detection and/or treatment of CD22-associated cancers, CD22-associated autoimmune diseases, or CD22-associated allergies, comprising at least one immunoglobulin-related composition of the present technology (e.g., any antibody or antigen binding fragment described herein), or a functional variant (e.g., substitutional variant) thereof and instructions for use. In certain embodiments, the immunoglobulin-related composition is coupled to one or more detectable labels. In one embodiment, the one or more detectable labels comprise a radioactive label, a fluorescent label, or a chromogenic label.

Additionally or alternatively, in some embodiments, the kit further comprises a secondary antibody that specifically binds to an anti-CD22 immunoglobulin-related composition described herein. In some embodiments, the secondary antibody is coupled to at least one detectable label selected from the group consisting of a radioactive label, a fluorescent label, or a chromogenic label.

In another aspect, the present disclosure provides a method for selecting a subject for pretargeted radioimmunotherapy comprising (a) administering to the subject an effective amount of a complex comprising a radiolabeled DOTA hapten and a bispecific antibody or antigen binding fragment of the present technology that binds to the radiolabeled DOTA hapten and a CD22 antigen, wherein the complex is configured to localize to a tumor expressing the CD22 antigen recognized by the bispecific antibody or antigen binding fragment of the complex; (b) detecting radioactive levels emitted by the complex; and (c) selecting the subject for pretargeted radioimmunotherapy when the radioactive levels emitted by the complex are higher than a reference value.

In one aspect, the present disclosure provides a method for increasing tumor sensitivity to radiation therapy in a subject diagnosed with a CD22-associated cancer comprising administering to the subject an effective amount of a complex comprising a radiolabeled-DOTA hapten and a bispecific antibody or antigen binding fragment of the present technology that recognizes and binds to the radiolabeled-DOTA hapten and a CD22 antigen target, wherein the complex is configured to localize to a tumor expressing the CD22 antigen target recognized by the bispecific antibody or antigen binding fragment of the complex.

In another aspect, the present disclosure provides a method for treating cancer in a subject in need thereof comprising administering to the subject an effective amount of a complex comprising a radiolabeled-DOTA hapten and a bispecific antibody or antigen binding fragment of the present technology that recognizes and binds to the radiolabeled-DOTA hapten and a CD22 antigen target, wherein the complex is configured to localize to a tumor expressing the CD22 antigen target recognized by the bispecific antibody or antigen binding fragment of the complex.

In any of the above embodiments of the methods disclosed herein, the complex is administered intravenously, intramuscularly, intraarterially, intrathecally, intracapsularly, intraorbitally, intradermally, intraperitoneally, transtracheally, subcutaneously, intracerebroventricularly, orally, intratumorally, or intranasally. In some embodiments of the methods disclosed herein, the subject is human. Additionally or alternatively, in any of the above embodiments of the methods disclosed herein, the radiolabeled-DOTA hapten comprises $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, $^{255}$Fm, $^{86}$Y, $^{90}$Y, $^{89}$Sr, $^{165}$Dy, $^{186}$Re, $^{188}$Re, $^{177}$Lu, $^{67}$Cu, $^{51}$In, $^{67}$Ga, $^{51}$Cr, $^{58}$Co, $^{99m}$Tc, $^{103m}$Rh, $^{195m}$Pt, $^{119}$Sb, $^{161}$Ho, $^{189m}$Os, $^{192}$Ir, $^{201}$Tl, $^{203}$Pb, $^{68}$Ga, $^{227}$Th, or $^{64}$Cu, and optionally comprises an alpha particle-emitting isotope, a beta particle-emitting isotope, or an Auger-emitter.

In one aspect, the present disclosure provides a method for increasing tumor sensitivity to radiation therapy in a subject diagnosed with a CD22-associated cancer comprising (a) administering an effective amount of an anti-DOTA bispecific antibody or antigen binding fragment of the present technology to the subject, wherein the anti-DOTA bispecific antibody or antigen binding fragment is configured to localize to a tumor expressing a CD22 antigen target; and (b) administering an effective amount of a radiolabeled-DOTA hapten to the subject, wherein the radiolabeled-DOTA hapten is configured to bind to the anti-DOTA bispecific antibody or antigen binding fragment. In another aspect, the present disclosure provides a method for treating cancer in a subject in need thereof comprising (a) administering an effective amount of an anti-DOTA bispecific antibody or antigen binding fragment of the present technology to the subject, wherein the anti-DOTA bispecific antibody or antigen binding fragment is configured to localize to a tumor expressing a CD22 antigen target; and (b) administering an effective amount of a radiolabeled-DOTA hapten to the subject, wherein the radiolabeled-DOTA hapten is configured to bind to the anti-DOTA bispecific antibody or antigen binding fragment. In some embodiments, the methods of the present technology further comprise administering an effective amount of a clearing agent to the subject prior to administration of the radiolabeled-DOTA hapten.

Additionally or alternatively, in any of the above embodiments of the methods disclosed herein, the radiolabeled-DOTA hapten comprises $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{22}$Fr, $^{217}$At, $^{255}$Fm, $^{86}$Y, $^{90}$Y, $^{89}$Sr, $^{165}$Dy, $^{186}$Re, $^{188}$Re, $^{177}$Lu, $^{67}$Cu, $^{111}$In, $^{67}$Ga, $^{51}$Cr, $^{58}$Co, $^{99m}$Tc, $^{103m}$Rh, $^{195m}$Pt, $^{119}$Sb, $^{161}$Ho, $^{189m}$Os, $^{192}$Ir, $^{201}$Tl, $^{203}$Pb, $^{68}$Ga, $^{227}$Th, or $^{64}$Cu, and optionally comprises an alpha particle-emitting isotope, a beta particle-emitting isotope, or an Auger-emitter. In any of the above embodiments of the methods disclosed herein, the subject is human.

Figure 5A:
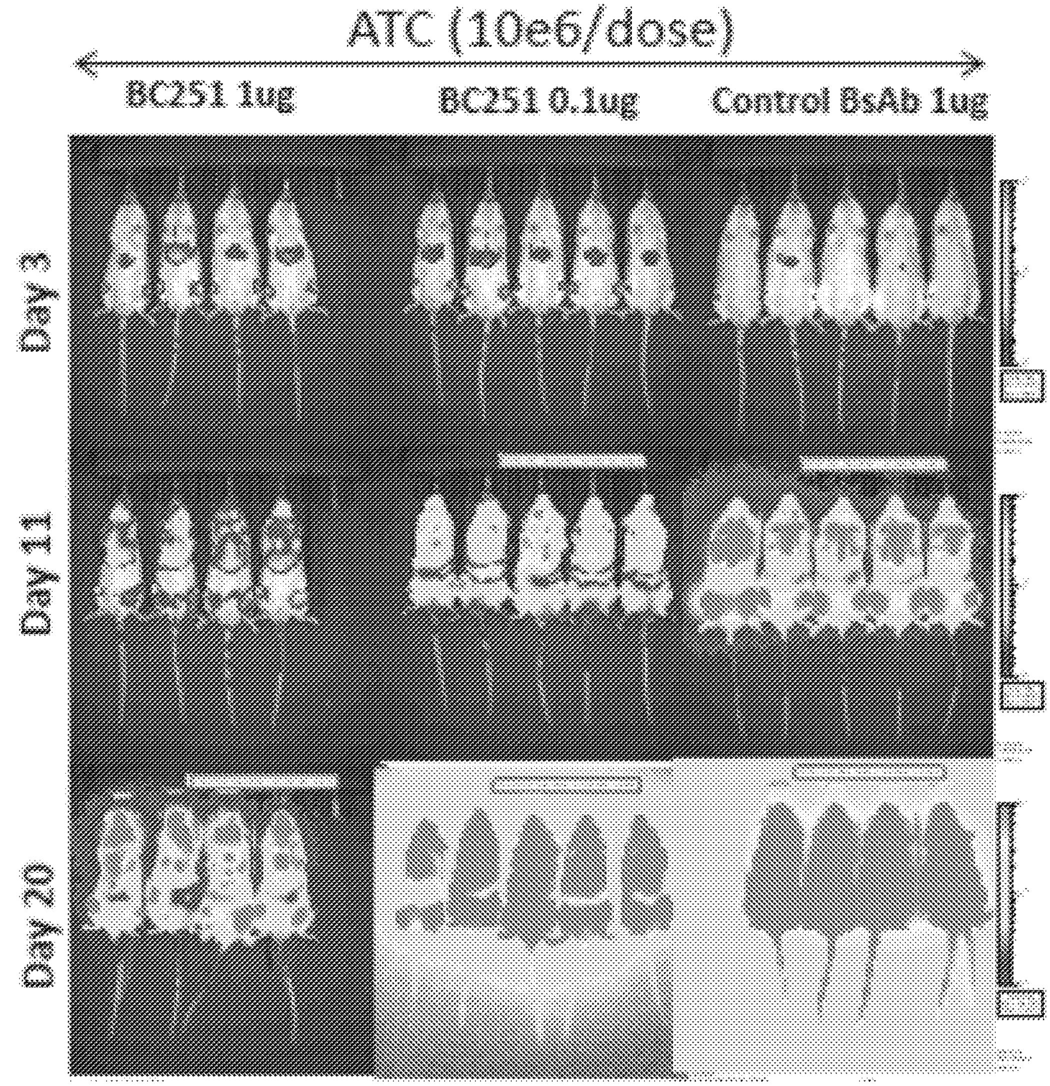
FIG. 5A shows the therapeutic effects of BsAbs BC251 on NSG mice harboring CD22(+) NALM6 human xenografts.
Figure 5B:
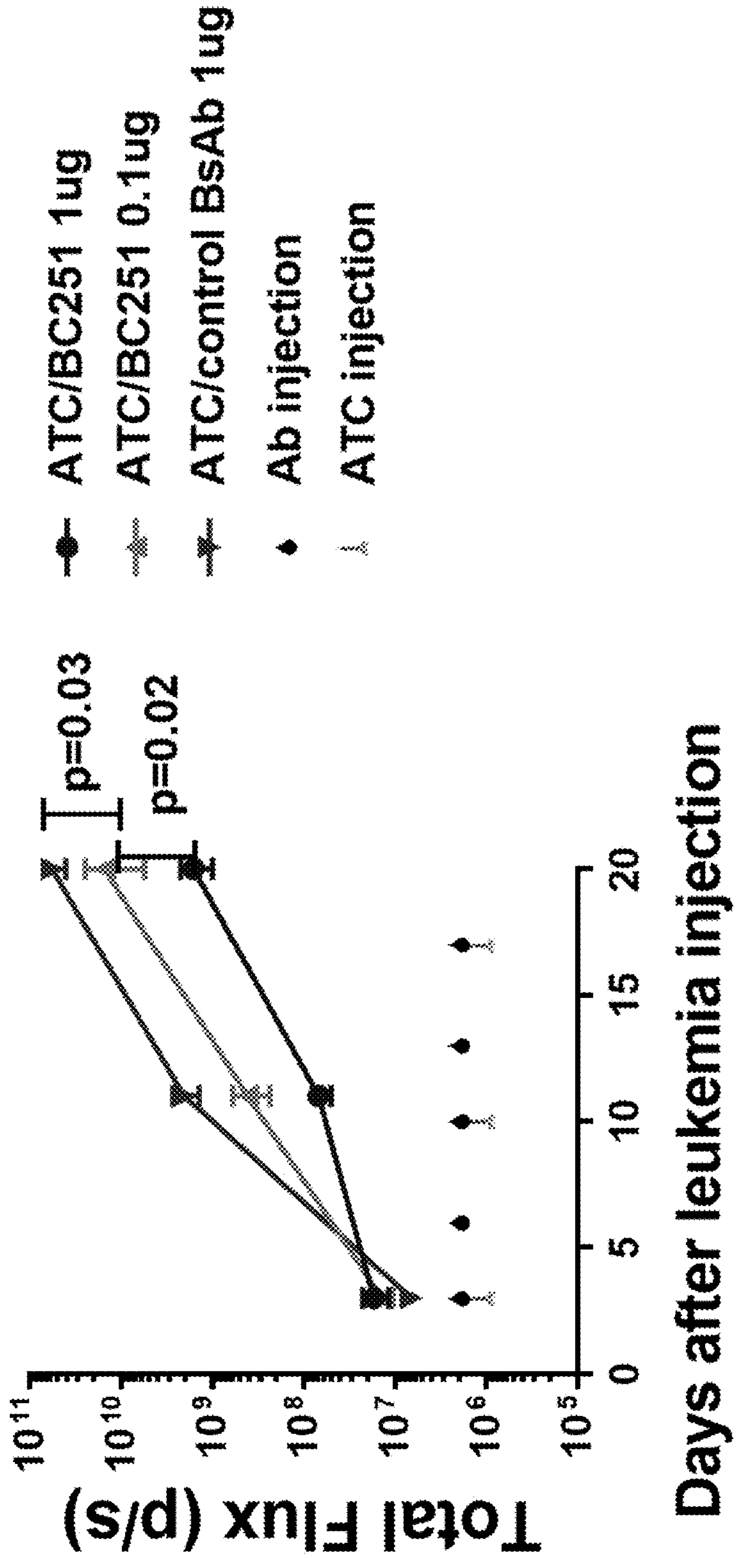
FIG. 5B shows the therapeutic effects of BsAbs BC251 on NSG mice harboring CD22(+) NALM6 human xenografts. The Y-axis represents the total flux value derived from experiments similar to those shown in FIG. 5A.
Figure 5C:
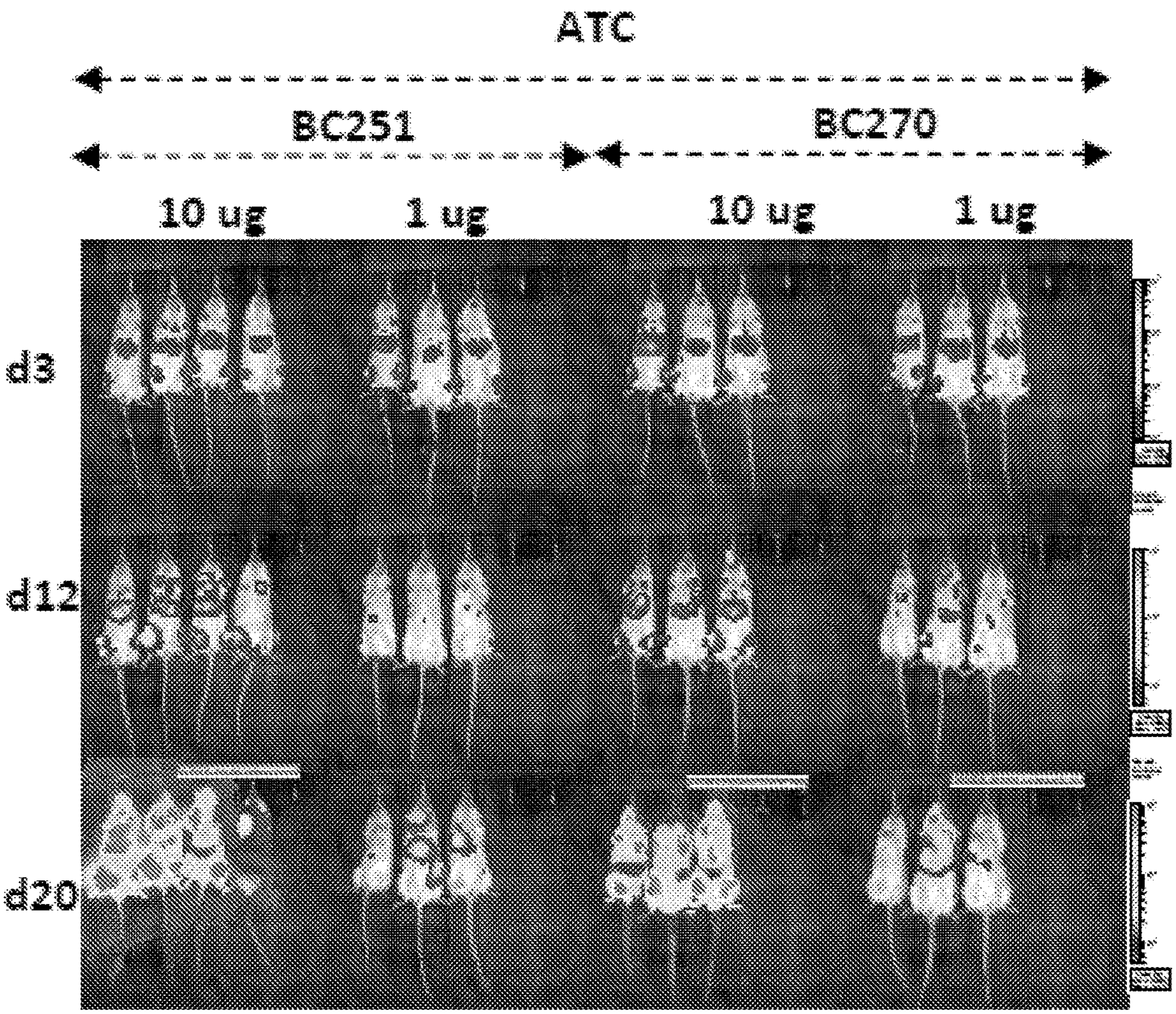
FIG. 5C shows potent anti-leukemia effect of CD22-CD3 BsAbs BC251 and BC270. NSG mice were injected with CD22(+) NALM6 human xenograft. Treatment was initiated after three days (once the tumor was established), which included weekly injections of 10 million activated T cells (ATC) as well as different doses of BC251 or BC270 twice weekly, as indicated. Injection of 10 μg BC251 or BC270 reduced leukemia growth, whereas a lower dose (1 μg) of the BsAbs unexpectedly resulted in more potent anti-leukemia effects.
Figure 5D:
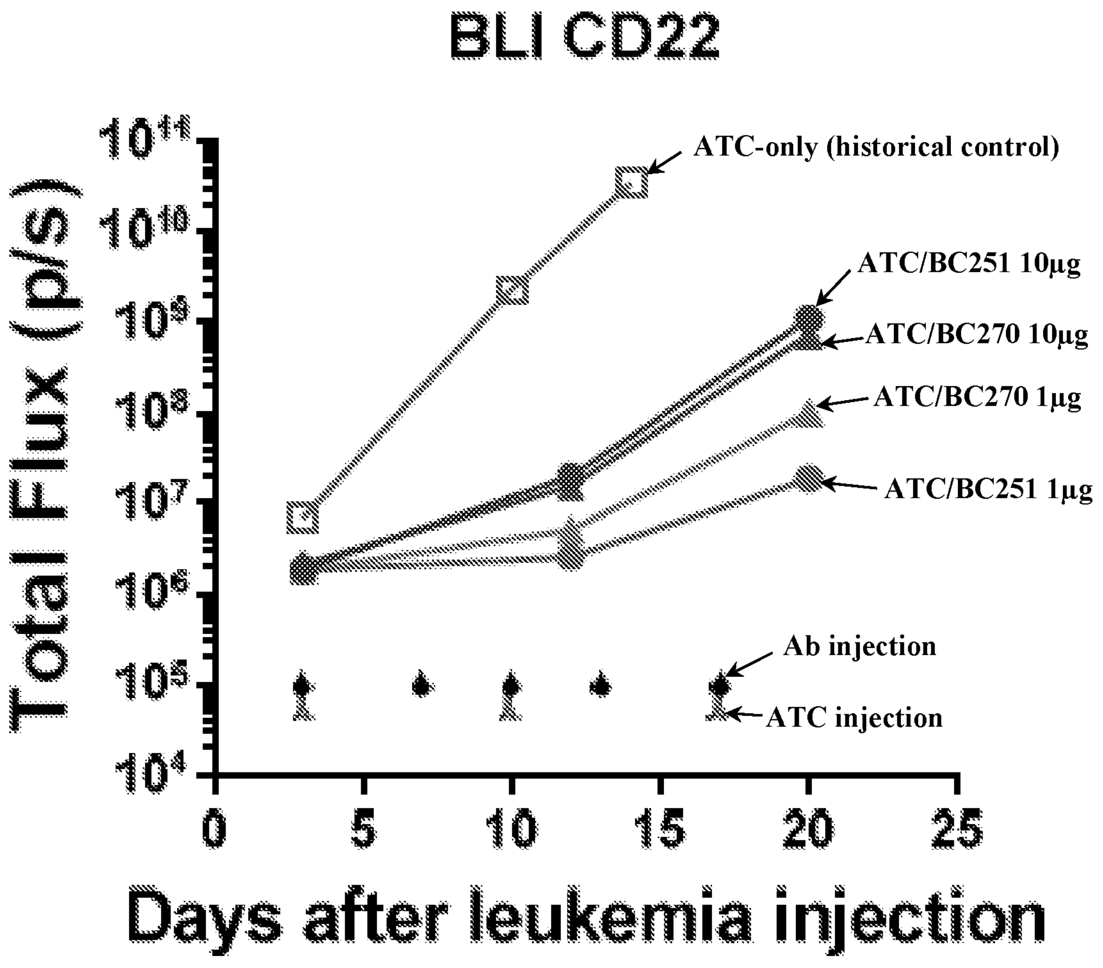

FIG. 5D shows the potent anti-leukemia effect of CD22-CD3 BsAbs BC251 and BC270. The Y-axis represents the total flux value derived from experiments similar to those shown in FIG. 5C.

FIG. 6 shows the amino acid sequences of the murine and humanized LL2 heavy chain variable domain sequences. CDR sequences are indicated by underlined, and boldface font. LL2_$V_H$ (SEQ ID NO: 1) is the sequence of murine LL2 $V_H$ domain. The amino acid sequences of the VHCDR1, VHCDR2, and VHCDR3 regions of murine LL2 $V_H$ domain are GYTFTSYW (SEQ ID NO: 2), INPRNDYT (SEQ ID NO: 3), and ARRDITTFY (SEQ ID NO: 4), respectively. VH-1 through VH-12 (SEQ ID NOs: 5, 6, 7, 8, 9, 10, 11, 12, 13, 14, 15, and 16) are humanized versions of the murine LL2 $V_H$ domain.

FIG. 7 shows the amino acid sequences of the murine and humanized LL2 light chain variable domain sequences. CDR sequences are indicated by underlined, and boldface font. LL2_$V_L$ (SEQ ID NO: 17) is the sequence of murine LL2 $V_L$ domain. The amino acid sequences of the VLCDR1, VLCDR2, and VLCDR3 regions of murine LL2 $V_L$ domain are QSVLYSANHKNY (SEQ ID NO: 18), WAS (SEQ ID NO: 19), and HQYLSSWT (SEQ ID NO: 20), respectively. VL-1 and VL-2 (SEQ ID NOs: 21, and 22) are humanized versions of the murine LL2 $V_L$ domain.

FIG. 8 shows the amino acid sequence of the light chain of chimeric anti-CD22-CD3 BsAb (chLL2) (SEQ ID NO:23). The signal peptide is underlined, the variable domains of the BsAb are indicated in italic font, and linker sequences in underlined and boldface font.

FIG. 9 shows the nucleotide sequence of the light chain of chimeric anti-CD22-CD3 BsAb (chLL2) (SEQ ID NO:24).

FIG. 10 shows the amino acid sequence of the heavy chain of chimeric anti-CD22-CD3 BsAb (chLL2) (SEQ ID NO: 25). The signal peptide is underlined, and the variable domains are indicated in italic font.

FIG. 11 shows the nucleotide sequence of the heavy chain of chimeric anti-CD22-CD3 BsAb (chLL2) (SEQ ID NO: 26).

FIG. 12 shows the amino acid sequence of the light chain of humanized anti-CD22-CD3 BsAb BC270 (SEQ ID NO: 27). The signal peptide is underlined, the variable domains of the BsAb are indicated in italic font, and linker sequences in underlined and boldface font.

FIG. 13 shows the nucleotide sequence of the light chain of humanized BsAb BC270 (SEQ ID NO: 28).

FIG. 14 shows the amino acid sequence of the heavy chain of humanized anti-CD22-CD3 BsAb BC270 (SEQ ID NO: 29). The signal peptide is underlined, and the variable domains are indicated in italic font.

FIG. 15 shows the nucleotide sequence of the heavy chain of humanized BsAb BC270 (SEQ ID NO: 30).

FIG. 16 shows the amino acid sequence of the light chain of humanized anti-CD22-CD3 BsAb BC251 (SEQ ID NO: 31). The signal peptide is underlined, the variable domains of the BsAb are indicated in italic font, and linker sequences in underlined and boldface font.

FIG. 17 shows the nucleotide sequence of the light chain of humanized BsAb BC251 (SEQ ID NO: 32).

FIG. 18 shows the amino acid sequence of the heavy chain of humanized anti-CD22-CD3 BsAb BC251 (SEQ ID NO: 33). The signal peptide is underlined, and the variable domains are indicated in italic font.

FIG. 19 shows the nucleotide sequence of the heavy chain of humanized BsAb BC251 (SEQ ID NO: 34).

FIG. 20 shows the amino acid sequence of the light chain of one embodiment of anti-CD22-DOTA BsAb (SEQ ID NO: 35). The signal peptide is underlined, the variable domains of the BsAb are indicated in italic font, and linker sequences in underlined and boldface font.

FIG. 21 shows the amino acid sequence of the heavy chain of one embodiment of anti-CD22-DOTA BsAb (SEQ ID NO: 36). The signal peptide is underlined, and the variable domains are indicated in italic font.

FIG. 22 shows the amino acid sequence of the light chain of another embodiment of anti-CD22-DOTA BsAb (SEQ ID NO: 37). The signal peptide is underlined, the variable domains of the BsAb are indicated in italic font, and linker sequences in underlined and boldface font.

FIG. 23 shows the amino acid sequence of the heavy chain of another embodiment of anti-CD22-DOTA BsAb (SEQ ID NO: 38). The signal peptide is underlined, and the variable domains are indicated in italic font.

FIG. 24 shows the amino acid sequence of the light chain of another embodiment of anti-CD22-DOTA BsAb (SEQ ID NO: 39). The signal peptide is underlined, the variable domains of the BsAb are indicated in italic font, and linker sequences in underlined and boldface font.

FIG. 25 shows the amino acid sequence of the heavy chain of another embodiment of anti-CD22-DOTA BsAb (SEQ ID NO: 40). The signal peptide is underlined, and the variable domains are indicated in italic font.

FIG. 26 shows the amino acid sequence of the light chain of another embodiment of anti-CD22-DOTA BsAb (SEQ ID NO: 41). The signal peptide is underlined, the variable domains of the BsAb are indicated in italic font, and linker sequences in underlined and boldface font.

FIG. 27 shows the amino acid sequence of the heavy chain of another embodiment of anti-CD22-DOTA BsAb (SEQ ID NO: 42). The signal peptide is underlined, and the variable domains are indicated in italic font.

FIG. 28 shows the amino acid sequence of the light chain of another embodiment of anti-CD22-DOTA BsAb (SEQ ID NO: 43). The signal peptide is underlined, the variable domains of the BsAb are indicated in italic font, and linker sequences in underlined and boldface font.

FIG. 29 shows the amino acid sequence of the heavy chain of another embodiment of anti-CD22-DOTA BsAb (SEQ ID NO: 44). The signal peptide is underlined, and the variable domains are indicated in italic font.

FIG. 30 shows the amino acid sequence of the light chain of another embodiment of anti-CD22-DOTA BsAb (SEQ ID NO: 45). The signal peptide is underlined, the variable domains of the BsAb are indicated in italic font, and linker sequences in underlined and boldface font.

FIG. 31 shows the amino acid sequence of the heavy chain of another embodiment of anti-CD22-DOTA BsAb (SEQ ID NO: 46). The signal peptide is underlined, and the variable domains are indicated in italic font.

FIG. 32 shows the amino acid sequence of one embodiment of anti-CD22-DOTA BsAb antigen binding fragment (SEQ ID NO: 47). This embodiment comprises $V_H$ and $V_L$ sequences of anti-CD22 mouse LL2, and $V_H$ and $V_L$ sequences of humanized anti-DOTA C825 antibody. The signal peptide is underlined, the variable domains of the BsAb are indicated in italic font, and linker sequences in underlined and boldface font. p53 tetramerization domain is displayed in boldface font.

FIG. 33 shows the amino acid sequence of another embodiment of anti-CD22-DOTA BsAb antigen binding fragment (SEQ ID NO: 48). This embodiment comprises $V_H$ and $V_L$ sequences of anti-CD22 mouse LL2, and $V_H$ and $V_L$ sequences of humanized anti-DOTA C825 antibody. The signal peptide is underlined, the variable domains of the BsAb are indicated in italic font, and linker sequences in underlined and boldface font. p53 tetramerization domain is displayed in boldface font.

FIG. 34 shows the amino acid sequence of another embodiment of anti-CD22-DOTA BsAb antigen binding fragment (SEQ ID NO: 49). This embodiment comprises $V_H$ and $V_L$ sequences of anti-CD22 mouse LL2, and $V_H$ and $V_L$ sequences of humanized anti-DOTA C825 antibody. The signal peptide is underlined, the variable domains of the BsAb are indicated in italic font, and linker sequences in underlined and boldface font. p53 tetramerization domain is displayed in boldface font.

FIG. 35 shows the amino acid sequence of another embodiment of anti-CD22-DOTA BsAb antigen binding fragment (SEQ ID NO: 50). This embodiment comprises $V_H$ and $V_L$ sequences of anti-CD22 mouse LL2, and $V_H$ and $V_L$ sequences of humanized anti-DOTA C825 antibody. The signal peptide is underlined, the variable domains of the BsAb are indicated in italic font, and linker sequences in underlined and boldface font. p53 tetramerization domain is displayed in boldface font.

FIG. 36 shows the amino acid sequence of one embodiment of anti-CD22-DOTA BsAb antigen binding fragment (SEQ ID NO: 51). This embodiment comprises $V_H$ and $V_L$ sequences of anti-CD22 mouse LL2, and $V_H$ and $V_L$ sequences of humanized anti-DOTA C825 antibody. The signal peptide is underlined, the variable domains of the BsAb are indicated in italic font, and linker sequences in underlined and boldface font. p63 tetramerization domain is displayed in boldface font.

FIG. 37 shows the amino acid sequence of another embodiment of anti-CD22-DOTA BsAb antigen binding fragment (SEQ ID NO: 52). This embodiment comprises $V_H$ and $V_L$ sequences of anti-CD22 mouse LL2, and $V_H$ and $V_L$ sequences of humanized anti-DOTA C825 antibody. The signal peptide is underlined, the variable domains of the BsAb are indicated in italic font, and linker sequences in underlined and boldface font. p63 tetramerization domain is displayed in boldface font.

FIG. 38 shows the amino acid sequence of another embodiment of anti-CD22-DOTA BsAb antigen binding fragment (SEQ ID NO: 53). This embodiment comprises $V_H$ and $V_L$ sequences of anti-CD22 mouse LL2, and $V_H$ and $V_L$ sequences of humanized anti-DOTA C825 antibody. The signal peptide is underlined, the variable domains of the BsAb are indicated in italic font, and linker sequences in underlined and boldface font. p63 tetramerization domain is displayed in boldface font.

FIG. 39 shows the amino acid sequence of another embodiment of anti-CD22-DOTA BsAb antigen binding fragment (SEQ ID NO: 54). This embodiment comprises $V_H$ and $V_L$ sequences of anti-CD22 mouse LL2, and $V_H$ and $V_L$ sequences of humanized anti-DOTA C825 antibody. The signal peptide is underlined, the variable domains of the BsAb are indicated in italic font, and linker sequences in underlined and boldface font. p63 tetramerization domain is displayed in boldface font.

FIG. 40 shows the amino acid sequence of one embodiment of anti-CD22-DOTA BsAb antigen binding fragment (SEQ ID NO: 55). This embodiment comprises $V_H$ and $V_L$ sequences of anti-CD22 mouse LL2, and $V_H$ and $V_L$ sequences of humanized anti-DOTA C825 antibody. The signal peptide is underlined, the variable domains of the BsAb are indicated in italic font, and linker sequences in underlined and boldface font. p73 tetramerization domain is displayed in boldface font.

FIG. 41 shows the amino acid sequence of another embodiment of anti-CD22-DOTA BsAb antigen binding fragment (SEQ ID NO: 56). This embodiment comprises $V_H$ and $V_L$ sequences of anti-CD22 mouse LL2, and $V_H$ and $V_L$ sequences of humanized anti-DOTA C825 antibody. The signal peptide is underlined, the variable domains of the BsAb are indicated in italic font, and linker sequences in underlined and boldface font. p73 tetramerization domain is displayed in boldface font.

FIG. 42 shows the amino acid sequence of another embodiment of anti-CD22-DOTA BsAb antigen binding fragment (SEQ ID NO: 57). This embodiment comprises $V_H$ and $V_L$ sequences of anti-CD22 mouse LL2, and $V_H$ and $V_L$ sequences of humanized anti-DOTA C825 antibody. The signal peptide is underlined, the variable domains of the BsAb are indicated in italic font, and linker sequences in underlined and boldface font. p73 tetramerization domain is displayed in boldface font.

FIG. 43 shows the amino acid sequence of another embodiment of anti-CD22-DOTA BsAb antigen binding fragment (SEQ ID NO: 58). This embodiment comprises $V_H$ and $V_L$ sequences of anti-CD22 mouse LL2, and $V_H$ and $V_L$ sequences of humanized anti-DOTA C825 antibody. The signal peptide is underlined, the variable domains of the BsAb are indicated in italic font, and linker sequences in underlined and boldface font. p73 tetramerization domain is displayed in boldface font.

FIG. 44 shows the amino acid sequence of one embodiment of anti-CD22-DOTA BsAb antigen binding fragment (SEQ ID NO: 59). This embodiment comprises humanized anti-CD22 sequences VL-1 and VH-4, and $V_H$ and $V_L$ sequences of humanized anti-DOTA C825 antibody. The signal peptide is underlined, the variable domains of the BsAb are indicated in italic font, and linker sequences in underlined and boldface font. p53 tetramerization domain is displayed in boldface font.

FIG. 45 shows the amino acid sequence of another embodiment of anti-CD22-DOTA BsAb antigen binding fragment (SEQ ID NO: 60). This embodiment comprises humanized anti-CD22 sequences VL-1 and VH-4, and $V_H$ and $V_L$ sequences of humanized anti-DOTA C825 antibody. The signal peptide is underlined, the variable domains of the BsAb are indicated in italic font, and linker sequences in underlined and boldface font. p53 tetramerization domain is displayed in boldface font.

FIG. 46 shows the amino acid sequence of another embodiment of anti-CD22-DOTA BsAb antigen binding fragment (SEQ ID NO: 61). This embodiment comprises humanized anti-CD22 sequences VL-1 and VH-4, and $V_H$ and $V_L$ sequences of humanized anti-DOTA C825 antibody. The signal peptide is underlined, the variable domains of the BsAb are indicated in italic font, and linker sequences in underlined and boldface font. p53 tetramerization domain is displayed in boldface font.

FIG. 47 shows the amino acid sequence of another embodiment of anti-CD22-DOTA BsAb antigen binding fragment (SEQ ID NO: 62). This embodiment comprises humanized anti-CD22 sequences VL-1 and VH-4, and $V_H$ and $V_L$ sequences of humanized anti-DOTA C825 antibody. The signal peptide is underlined, the variable domains of the BsAb are indicated in italic font, and linker sequences in underlined and boldface font. p53 tetramerization domain is displayed in boldface font.

FIG. 48 shows the amino acid sequence of one embodiment of anti-CD22-DOTA BsAb antigen binding fragment (SEQ ID NO: 63). This embodiment comprises humanized anti-CD22 sequences VL-1 and VH-4, and $V_H$ and $V_L$ sequences of humanized anti-DOTA C825 antibody. The signal peptide is underlined, the variable domains of the BsAb are indicated in italic font, and linker sequences in underlined and boldface font. p63 tetramerization domain is displayed in boldface font.

FIG. 49 shows the amino acid sequence of another embodiment of anti-CD22-DOTA BsAb antigen binding fragment (SEQ ID NO: 64). This embodiment comprises humanized anti-CD22 sequences VL-1 and VH-4, and $V_H$ and $V_L$ sequences of humanized anti-DOTA C825 antibody. The signal peptide is underlined, the variable domains of the BsAb are indicated in italic font, and linker sequences in underlined and boldface font. p63 tetramerization domain is displayed in boldface font.

FIG. 50 shows the amino acid sequence of another embodiment of anti-CD22-DOTA BsAb antigen binding fragment (SEQ ID NO: 65). This embodiment comprises humanized anti-CD22 sequences VL-1 and VH-4, and $V_H$ and $V_L$ sequences of humanized anti-DOTA C825 antibody. The signal peptide is underlined, the variable domains of the BsAb are indicated in italic font, and linker sequences in underlined and boldface font. p63 tetramerization domain is displayed in boldface font.

FIG. 51 shows the amino acid sequence of another embodiment of anti-CD22-DOTA BsAb antigen binding fragment (SEQ ID NO: 66). This embodiment comprises humanized anti-CD22 sequences VL-1 and VH-4, and $V_H$ and $V_L$ sequences of humanized anti-DOTA C825 antibody. The signal peptide is underlined, the variable domains of the BsAb are indicated in italic font, and linker sequences in underlined and boldface font. p63 tetramerization domain is displayed in boldface font.

FIG. 52 shows the amino acid sequence of one embodiment of anti-CD22-DOTA BsAb antigen binding fragment (SEQ ID NO: 67). This embodiment comprises humanized anti-CD22 sequences VL-1 and VH-4, and $V_H$ and $V_L$ sequences of humanized anti-DOTA C825 antibody. The signal peptide is underlined, the variable domains of the BsAb are indicated in italic font, and linker sequences in underlined and boldface font. p73 tetramerization domain is displayed in boldface font.

FIG. 53 shows the amino acid sequence of another embodiment of anti-CD22-DOTA BsAb antigen binding fragment (SEQ ID NO: 68). This embodiment comprises humanized anti-CD22 sequences VL-1 and VH-4, and $V_H$ and $V_L$ sequences of humanized anti-DOTA C825 antibody. The signal peptide is underlined, the variable domains of the BsAb are indicated in italic font, and linker sequences in underlined and boldface font. p73 tetramerization domain is displayed in boldface font.

FIG. 54 shows the amino acid sequence of another embodiment of anti-CD22-DOTA BsAb antigen binding fragment (SEQ ID NO: 69). This embodiment comprises humanized anti-CD22 sequences VL-1 and VH-4, and $V_H$ and $V_L$ sequences of humanized anti-DOTA C825 antibody. The signal peptide is underlined, the variable domains of the BsAb are indicated in italic font, and linker sequences in underlined and boldface font. p73 tetramerization domain is displayed in boldface font.

FIG. 55 shows the amino acid sequence of another embodiment of anti-CD22-DOTA BsAb antigen binding fragment (SEQ ID NO: 70). This embodiment comprises humanized anti-CD22 sequences VL-1 and VH-4, and $V_H$ and $V_L$ sequences of humanized anti-DOTA C825 antibody. The signal peptide is underlined, the variable domains of the BsAb are indicated in italic font, and linker sequences in underlined and boldface font. p73 tetramerization domain is displayed in boldface font.

FIG. 56 shows the amino acid sequence of one embodiment of anti-CD22-DOTA BsAb antigen binding fragment (SEQ ID NO: 71). This embodiment comprises humanized anti-CD22 sequences VL-1 and VH-10, and $V_H$ and $V_L$ sequences of humanized anti-DOTA C825 antibody. The signal peptide is underlined, the variable domains of the BsAb are indicated in italic font, and linker sequences in underlined and boldface font. p53 tetramerization domain is displayed in boldface font.

FIG. 57 shows the amino acid sequence of another embodiment of anti-CD22-DOTA BsAb antigen binding fragment (SEQ ID NO: 72). This embodiment comprises humanized anti-CD22 sequences VL-1 and VH-10, and $V_H$ and $V_L$ sequences of humanized anti-DOTA C825 antibody. The signal peptide is underlined, the variable domains of the BsAb are indicated in italic font, and linker sequences in underlined and boldface font. p53 tetramerization domain is displayed in boldface font.

FIG. 58 shows the amino acid sequence of another embodiment of anti-CD22-DOTA BsAb antigen binding fragment (SEQ ID NO: 73). This embodiment comprises humanized anti-CD22 sequences VL-1 and VH-10, and $V_H$ and $V_L$ sequences of humanized anti-DOTA C825 antibody. The signal peptide is underlined, the variable domains of the BsAb are indicated in italic font, and linker sequences in underlined and boldface font. p53 tetramerization domain is displayed in boldface font.

FIG. 59 shows the amino acid sequence of another embodiment of anti-CD22-DOTA BsAb antigen binding fragment (SEQ ID NO: 74). This embodiment comprises humanized anti-CD22 sequences VL-1 and VH-10, and $V_H$ and $V_L$ sequences of humanized anti-DOTA C825 antibody. The signal peptide is underlined, the variable domains of the BsAb are indicated in italic font, and linker sequences in underlined and boldface font. p53 tetramerization domain is displayed in boldface font.

FIG. 60 shows the amino acid sequence of one embodiment of anti-CD22-DOTA BsAb antigen binding fragment (SEQ ID NO: 75). This embodiment comprises humanized anti-CD22 sequences VL-1 and VH-10, and $V_H$ and $V_L$ sequences of humanized anti-DOTA C825 antibody. The signal peptide is underlined, the variable domains of the BsAb are indicated in italic font, and linker sequences in underlined and boldface font. p63 tetramerization domain is displayed in boldface font.

FIG. 61 shows the amino acid sequence of another embodiment of anti-CD22-DOTA BsAb antigen binding fragment (SEQ ID NO: 76). This embodiment comprises humanized anti-CD22 sequences VL-1 and VH-10, and $V_H$ and $V_L$ sequences of humanized anti-DOTA C825 antibody. The signal peptide is underlined, the variable domains of the BsAb are indicated in italic font, and linker sequences in underlined and boldface font. p63 tetramerization domain is displayed in boldface font.

FIG. 62 shows the amino acid sequence of another embodiment of anti-CD22-DOTA BsAb antigen binding fragment (SEQ ID NO: 77). This embodiment comprises humanized anti-CD22 sequences VL-1 and VH-10, and $V_H$ and $V_L$ sequences of humanized anti-DOTA C825 antibody. The signal peptide is underlined, the variable domains of the BsAb are indicated in italic font, and linker sequences in underlined and boldface font. p63 tetramerization domain is displayed in boldface font.

FIG. 63 shows the amino acid sequence of another embodiment of anti-CD22-DOTA BsAb antigen binding fragment (SEQ ID NO: 78). This embodiment comprises humanized anti-CD22 sequences VL-1 and VH-10, and $V_H$ and $V_L$ sequences of humanized anti-DOTA C825 antibody. The signal peptide is underlined, the variable domains of the BsAb are indicated in italic font, and linker sequences in underlined and boldface font. p63 tetramerization domain is displayed in boldface font.

FIG. 64 shows the amino acid sequence of one embodiment of anti-CD22-DOTA BsAb antigen binding fragment (SEQ ID NO: 79). This embodiment comprises humanized anti-CD22 sequences VL-1 and VH-10, and $V_H$ and $V_L$ sequences of humanized anti-DOTA C825 antibody. The signal peptide is underlined, the variable domains of the BsAb are indicated in italic font, and linker sequences in underlined and boldface font. p73 tetramerization domain is displayed in boldface font.

FIG. 65 shows the amino acid sequence of another embodiment of anti-CD22-DOTA BsAb antigen binding fragment (SEQ ID NO: 80). This embodiment comprises humanized anti-CD22 sequences VL-1 and VH-10, and $V_H$ and $V_L$ sequences of humanized anti-DOTA C825 antibody. The signal peptide is underlined, the variable domains of the BsAb are indicated in italic font, and linker sequences in underlined and boldface font. p73 tetramerization domain is displayed in boldface font.

FIG. 66 shows the amino acid sequence of another embodiment of anti-CD22-DOTA BsAb antigen binding fragment (SEQ ID NO: 81). This embodiment comprises humanized anti-CD22 sequences VL-1 and VH-10, and $V_H$ and $V_L$ sequences of humanized anti-DOTA C825 antibody. The signal peptide is underlined, the variable domains of the BsAb are indicated in italic font, and linker sequences in underlined and boldface font. p73 tetramerization domain is displayed in boldface font.

FIG. 67 shows the amino acid sequence of another embodiment of anti-CD22-DOTA BsAb antigen binding fragment (SEQ ID NO: 82). This embodiment comprises humanized anti-CD22 sequences VL-1 and VH-10, and $V_H$ and $V_L$ sequences of humanized anti-DOTA C825 antibody. The signal peptide is underlined, the variable domains of the BsAb are indicated in italic font, and linker sequences in underlined and boldface font. p73 tetramerization domain is displayed in boldface font.

DETAILED DESCRIPTION

It is to be appreciated that certain aspects, modes, embodiments, variations and features of the present methods are described below in various levels of detail in order to provide a substantial understanding of the present technology.

The present disclosure generally provides immunoglobulin-related compositions (e.g., antibodies or antigen binding fragments thereof), which can specifically bind to CD22 polypeptides. The immunoglobulin-related compositions of the present technology are useful in methods for detecting and/or treating CD22-associated cancers, CD22-associated autoimmune diseases, or CD22-associated allergies in a subject in need thereof. Accordingly, the various aspects of the present methods relate to the preparation, characterization, and manipulation of anti-CD22 antibodies. The immunoglobulin-related compositions of the present technology are useful alone or in combination with additional therapeutic agents for treating cancer. In some embodiments, the immunoglobulin-related composition is a humanized antibody, a chimeric antibody, or a bispecific antibody. The Examples of the present disclosure demonstrate that although the antigen-binding and cytotoxic properties of the anti-CD22 immunoglobulin-related compositions of the present technology increase in a dose-dependent manner, lower doses of such compositions yield superior therapeutic effects in vivo compared to higher doses. See FIGS. 5C-5D.

In practicing the present methods, many conventional techniques in molecular biology, protein biochemistry, cell biology, immunology, microbiology and recombinant DNA are used. See, e.g., Sambrook and Russell eds. (2001) *Molecular Cloning: A Laboratory Manual,* 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique,* 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*. Methods to detect and measure levels of polypeptide gene expression products (i.e., gene translation level) are well-known in the art and include the use of polypeptide detection methods such as antibody detection and quantification techniques. (See also, Strachan & Read, Human Molecular Genetics, Second Edition. (John Wiley and Sons, Inc., NY, 1999)).

DEFINITIONS

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function.

Administration can be carried out by any suitable route, including but not limited to, orally, intranasally, parenterally (intravenously, intramuscularly, intraperitoneally, or subcutaneously), rectally, intrathecally, intratumorally or topically. Administration includes self-administration and the administration by another.

An "adjuvant" refers to one or more substances that cause stimulation of the immune system. In this context, an adjuvant is used to enhance an immune response to one or more vaccine antigens or antibodies. An adjuvant may be administered to a subject before, in combination with, or after administration of the vaccine. Examples of chemical compounds used as adjuvants include aluminum compounds, oils, block polymers, immune stimulating complexes, vitamins and minerals (e.g., vitamin E, vitamin A, selenium, and vitamin B12), Quil A (saponins), bacterial and fungal cell wall components (e.g., lipopolysaccharides, lipoproteins, and glycoproteins), hormones, cytokines, and co-stimulatory factors.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. As used herein, "antibodies" (includes intact immunoglobulins) and "antigen binding fragments" specifically bind to a molecule of interest (or a group of highly similar molecules of interest) to the substantial exclusion of binding to other molecules (for example, antibodies and antibody fragments that have a binding constant for the molecule of interest that is at least $10^3$ $M^{-1}$ greater, at least $10^4$ $M^{-1}$ greater or at least $10^5$ $M^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., *Immunology,* 3$^{rd}$ Ed., W.H. Freeman & Co., New York, 1997.

More particularly, antibody refers to a polypeptide ligand comprising at least a light chain immunoglobulin variable region or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Typically, an immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds CD22 protein will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs). "Immunoglobulin-related compositions" as used herein, refers to antibodies (including monoclonal antibodies, polyclonal antibodies, humanized antibodies, chimeric antibodies, recombinant antibodies, multispecific antibodies, bispecific antibodies, etc.) as well as antibody fragments. An antibody or antigen binding fragment thereof specifically binds to an antigen.

As used herein, the term "antibody-related polypeptide" means antigen-binding antibody fragments, including single-chain antibodies, that can comprise the variable region(s) alone, or in combination, with all or part of the following polypeptide elements: hinge region, $CH_1$, $CH_2$, and $CH_3$ domains of an antibody molecule. Also included in the technology are any combinations of variable region(s) and hinge region, $CH_1$, $CH_2$, and $CH_3$ domains. Antibody-related molecules useful in the present methods, e.g., but are not limited to, Fab, Fab' and $F(ab')_2$, Fd, single-chain Fvs (scFv), single-chain antibodies, disulfide-linked Fvs (sdFv) and fragments comprising either a $V_L$ or $V_H$ domain. Examples include: (i) a Fab fragment, a monovalent fragment consisting of the $V_L$, $V_H$, $C_L$ and $CH_1$ domains; (ii) a $F(ab')_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., *Nature* 341: 544-546, 1989), which consists of a $V_H$ domain; and (vi) an isolated complementarity determining region (CDR). As such "antibody fragments" or "antigen binding fragments" can comprise a portion of a full length antibody, generally the antigen binding or variable region thereof. Examples of antibody fragments or antigen binding fragments include Fab, Fab', $F(ab')_2$, and Fv fragments; diabodies; linear antibodies; single-chain antibody molecules; and multispecific antibodies formed from antibody fragments.

"Bispecific antibody" or "BsAb", as used herein, refers to an antibody that can bind simultaneously to two targets that have a distinct structure, e.g., two different target antigens, two different epitopes on the same target antigen, or a hapten and a target antigen or epitope on a target antigen. A variety of different bispecific antibody structures are known in the art. In some embodiments, each antigen binding moiety in a bispecific antibody includes $V_H$ and/or $V_L$ regions; in some such embodiments, the $V_H$ and/or $V_L$ regions are those found in a particular monoclonal antibody. In some embodiments, the bispecific antibody contains two antigen binding moieties, each including $V_H$ and/or $V_L$ regions from different monoclonal antibodies. In some embodiments, the bispecific antibody contains two antigen binding moieties, wherein one of the two antigen binding moieties includes an immunoglobulin molecule having $V_H$ and/or $V_L$ regions that contain CDRs from a first monoclonal antibody, and the other antigen binding moiety includes an antibody fragment (e.g., Fab, F(ab'), $F(ab')_2$, Fd, Fv, dAB, scFv, etc.) having $V_H$ and/or $V_L$ regions that contain CDRs from a second monoclonal antibody.

As used herein, a "clearing agent" is an agent that binds to excess bispecific antibody that is present in the blood compartment of a subject to facilitate rapid clearance via kidneys. The use of the clearing agent prior to hapten administration (e.g., DOTA) facilitates better tumor-to-background ratios in pretargeted radioimmunotherapy (PRIT) systems. Examples of clearing agents include 500 kD-dextran-DOTA-Bn(Y) (Orcutt et al., *Mol Cancer Ther.* 11(6): 1365-1372 (2012)), 500 kD aminodextran-DOTA conjugate, antibodies against the pretargeting antibody, etc.

As used herein, the term "conjugated" refers to the association of two molecules by any method known to those in the art. Suitable types of associations include chemical bonds and physical bonds. Chemical bonds include, for example, covalent bonds and coordinate bonds. Physical bonds include, for instance, hydrogen bonds, dipolar interactions, van der Waal forces, electrostatic interactions, hydrophobic interactions and aromatic stacking.

As used herein, the term "diabodies" refers to small antibody fragments with two antigen-binding sites, which fragments comprise a heavy-chain variable domain ($V_H$) connected to a light-chain variable domain ($V_L$) in the same polypeptide chain ($V_H V_L$). By using a linker that is too short to allow pairing between the two domains on the same chain, the domains are forced to pair with the complementary domains of another chain and create two antigen binding sites. Diabodies are described more fully in, e.g., EP 404, 097; WO 93/11161; and Hollinger et al., *Proc. Natl. Acad. Sci. USA,* 90: 6444-6448 (1993).

As used herein, the terms "single-chain antibodies" or "single-chain Fv (scFv)" refer to an antibody fusion molecule of the two domains of the Fv fragment, $V_L$ and $V_H$. Single-chain antibody molecules may comprise a polymer with a number of individual molecules, for example, dimer, trimer or other polymers. Furthermore, although the two domains of the $F_v$ fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single-chain $F_v$ ($scF_v$)). Bird et al. (1988) *Science* 242:423-426 and Huston et al. (1988) *Proc. Natl. Acad Sci. USA* 85:5879-5883. Such single-chain antibodies can be prepared by recombinant techniques or enzymatic or chemical cleavage of intact antibodies.

Any of the above-noted antibody fragments are obtained using conventional techniques known to those of skill in the art, and the fragments are screened for binding specificity and neutralization activity in the same manner as are intact antibodies.

As used herein, an "antigen" refers to a molecule to which an antibody (or antigen binding fragment thereof) can selectively bind. The target antigen may be a protein, carbohydrate, nucleic acid, lipid, hapten, or other naturally occurring or synthetic compound. In some embodiments, the target antigen may be a polypeptide (e.g., a CD22 polypeptide). An antigen may also be administered to an animal to generate an immune response in the animal.

The term "antigen binding fragment" refers to a fragment of the whole immunoglobulin structure which possesses a part of a polypeptide responsible for binding to antigen. Examples of the antigen binding fragment useful in the present technology include scFv, $(scFv)_2$, scFvFc, Fab, Fab' and $F(ab')_2$, but are not limited thereto.

By "binding affinity" is meant the strength of the total noncovalent interactions between a single binding site of a molecule (e.g., an antibody) and its binding partner (e.g., an antigen or antigenic peptide). The affinity of a molecule X for its partner Y can generally be represented by the dissociation constant ($K_D$). Affinity can be measured by standard methods known in the art, including those described herein. A low-affinity complex contains an antibody that generally tends to dissociate readily from the antigen, whereas a high-affinity complex contains an antibody that generally tends to remain bound to the antigen for a longer duration.

As used herein, the term "biological sample" means sample material derived from living cells. Biological samples may include tissues, cells, protein or membrane extracts of cells, and biological fluids (e.g., ascites fluid or cerebrospinal fluid (CSF)) isolated from a subject, as well as tissues, cells and fluids present within a subject. Biological samples of the present technology include, but are not limited to, samples taken from breast tissue, renal tissue, the uterine cervix, the endometrium, the head or neck, the gallbladder, parotid tissue, the prostate, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, thymus, blood, hair, buccal, skin, serum, plasma, CSF, semen, prostate fluid, seminal fluid, urine, feces, sweat, saliva, sputum, mucus, bone marrow, lymph, and tears. Biological samples can also be obtained from biopsies of internal organs or from cancers. Biological samples can be obtained from subjects for diagnosis or research or can be obtained from non-diseased individuals, as controls or for basic research. Samples may be obtained by standard methods including, e.g., venous puncture and surgical biopsy. In certain embodiments, the biological sample is a blood sample or a sample derived from bone marrow aspiration and biopsy. In certain embodiments, the biological sample is a liver sample, a muscle sample, a lung sample, a skin sample, a sinus/upper respiratory tract sample, an ocular sample, a musculoskeletal sample, an abdominal sample, a hematological sample, a salivary/parotid sample, a cardiac sample, a neurological sample or a renal sample obtained by needle biopsy.

As used herein, the term "CDR-grafted antibody" means an antibody in which at least one CDR of an "acceptor" antibody is replaced by a CDR "graft" from a "donor" antibody possessing a desirable antigen specificity.

As used herein, the term "chimeric antibody" means an antibody in which the Fc constant region of a monoclonal antibody from one species (e.g., a mouse Fc constant region) is replaced, using recombinant DNA techniques, with an Fc constant region from an antibody of another species (e.g., a human Fc constant region). See generally, Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 0125, 023; Better et al., *Science* 240: 1041-1043, 1988; Liu et al., *Proc. Natl. Acad. Sci. USA* 84: 3439-3443, 1987; Liu et al., *J. Immunol* 139: 3521-3526, 1987; Sun et al., *Proc. Natl. Acad. Sci. USA* 84: 214-218, 1987; Nishimura et al., *Cancer Res* 47: 999-1005, 1987; Wood et al., *Nature* 314: 446-449, 1885; and Shaw et al., *J. Natl. Cancer Inst.* 80: 1553-1559, 1988.

As used herein, the term "consensus FR" means a framework (FR) antibody region in a consensus immunoglobulin sequence. The FR regions of an antibody do not contact the antigen.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of a disease or condition described herein. As used herein, a "therapeutically effective amount" of a composition refers to composition levels in which the physiological effects of a disease or condition are ameliorated or eliminated. A therapeutically effective amount can be given in one or more administrations.

As used herein, the term "effector cell" means an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Effector cells express specific Fc receptors and carry out specific immune functions. An effector cell can induce antibody-dependent cell-mediated cytotoxicity (ADCC), e.g., a neutrophil capable of inducing ADCC. For example, monocytes, macrophages, neutrophils, eosinophils, and lymphocytes which express FcαR are involved in specific killing of target cells and presenting antigens to other components of the immune system, or binding to cells that present antigens.

As used herein, the term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. In some embodiments, an "epitope" of the CD22 protein is a region of the protein to which the anti-CD22 antibodies of the present technology specifically bind. In some embodiments, the epitope is a conformational epitope or a non-conformational epitope. To screen for anti-CD22 antibodies which bind to an epitope, a routine cross-blocking assay such as that described in Antibodies, *A Laboratory Manual*, Cold Spring Harbor Laboratory, Ed Harlow and David Lane (1988), can be performed. This assay can be used to determine if an anti-CD22 antibody binds the same site or epitope as an anti-CD22 antibody of the present technology. Alternatively, or additionally, epitope mapping can be performed by methods known in the art. For example, the antibody sequence can be mutagenized such as by alanine scanning, to identify contact residues. In a different method, peptides corresponding to different regions of CD22 protein can be used in competition assays with the test antibodies or with a test antibody and an antibody with a characterized or known epitope.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "gene" means a segment of DNA that contains all the information for the regulated biosynthesis of an RNA product, including promoters, exons, introns, and other untranslated regions that control expression.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

As used herein, "humanized" forms of non-human (e.g., murine) antibodies are chimeric antibodies which contain minimal sequence derived from non-human immunoglobulin. For the most part, humanized antibodies are human immunoglobulins in which hypervariable region residues of the recipient are replaced by hypervariable region residues from a non-human species (donor antibody) such as mouse, rat, rabbit or nonhuman primate having the desired specificity, affinity, and capacity. In some embodiments, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains (e.g., Fab, Fab', $F(ab')_2$, or Fv), in which all or substantially all of the hypervariable loops correspond to those of a non-human immunoglobulin and all or substantially all of the FR regions are those of a human immunoglobulin consensus FR sequence although the FR regions may include one or more amino acid substitutions that improve binding affinity. The number of these amino acid substitutions in the FR are typically no more than 6 in the H chain, and in the L chain, no more than 3. The humanized antibody optionally may also comprise at least a portion of an immunoglobulin constant region (Fc), typically that of a human immunoglobulin. For further details, see Jones et al., *Nature* 321: 522-525 (1986); Reichmann et al., *Nature* 332:323-329 (1988); and Presta, *Curr. Op. Struct. Biol.* 2:593-596 (1992). See e.g., Ahmed & Cheung, *FEBS Letters* 588(2):288-297 (2014).

As used herein, the term "hypervariable region" refers to the amino acid residues of an antibody which are responsible for antigen-binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35B (H1), 50-65 (H2) and 95-102 (H3) in the $V_H$ (Kabat et al., *Sequences of Proteins of Immunological Interest,* 5th Ed. Public Health Service, National Institutes of Health, Bethesda, MD (1991)) and/or those residues from a "hypervariable loop" (e.g., residues 26-32 (L1), 50-52 (L2) and 91-96 (L3) in the $V_L$, and 26-32 (H1), 52A-55 (H2) and 96-101 (H3) in the $V_H$ (Chothia and Lesk *J. Mol. Biol.* 196:901-917 (1987)).

As used herein, the terms "identical" or percent "identity", when used in the context of two or more nucleic acids or polypeptide sequences, refer to two or more sequences or subsequences that are the same or have a specified percentage of amino acid residues or nucleotides that are the same (i.e., about 60%, 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein)), when compared and aligned for maximum correspondence over a comparison window or designated region as measured using a BLAST or BLAST 2.0 sequence comparison algorithms with default parameters described below, or by manual alignment and visual inspection (e.g., NCBI web site). Such sequences are then said to be "substantially identical." This term also refers to, or can be applied to, the complement of a test sequence. The term also includes sequences that have deletions and/or additions, as well as those that have substitutions. In some embodiments, identity exists over a region that is at least about 25 amino acids or nucleotides in length, or 50-100 amino acids or nucleotides in length.

As used herein, the term "intact antibody" or "intact immunoglobulin" means an antibody that has at least two heavy (H) chain polypeptides and two light (L) chain polypeptides interconnected by disulfide bonds. Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: $FR_1$, $CDR_1$, $FR_2$, $CDR_2$, $FR_3$, $CDR_3$, $FR_4$. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

As used herein, the terms "individual", "patient", or "subject" can be an individual organism, a vertebrate, a mammal, or a human. In some embodiments, the individual, patient or subject is a human.

The term "monoclonal antibody" as used herein refers to an antibody obtained from a population of substantially homogeneous antibodies, i.e., the individual antibodies comprising the population are identical except for possible naturally occurring mutations that may be present in minor amounts. For example, a monoclonal antibody can be an antibody that is derived from a single clone, including any eukaryotic, prokaryotic, or phage clone, and not the method by which it is produced. A monoclonal antibody composition displays a single binding specificity and affinity for a particular epitope. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. Monoclonal antibodies can be prepared using a wide variety of techniques known in the art including, e.g., but not limited to, hybridoma, recombinant, and phage display technologies. For example, the monoclonal antibodies to be used in accordance with the present methods may be made by the hybridoma method first described by Kohler et al., *Nature* 256:495 (1975), or may be made by recombinant DNA methods (See, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration. Pharmaceutically-acceptable carriers and their formulations are known to one skilled in the art and are described, for example, in Remington's Pharmaceutical Sciences ($20^{th}$ edition, ed. A. Gennaro, 2000, Lippincott, Williams & Wilkins, Philadelphia, Pa.).

As used herein, the term "polyclonal antibody" means a preparation of antibodies derived from at least two (2) different antibody-producing cell lines. The use of this term includes preparations of at least two (2) antibodies that contain antibodies that specifically bind to different epitopes or regions of an antigen.

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, the terms "polypeptide," "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature.

As used herein, "PRIT" or "pretargeted radioimmunotherapy" refers to a multistep process that resolves the slow blood clearance of tumor targeting antibodies, which contributes to undesirable toxicity to normal tissues such as bone marrow. In pre-targeting, a radionuclide or other diagnostic or therapeutic agent is attached to a small hapten. A pre-targeting bispecific antibody, which has binding sites for the hapten as well as a target antigen, is administered first. Unbound antibody is then allowed to clear from circulation and the hapten is subsequently administered.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, for example, recombinant cells express genes that are not found within the native (non-recombinant) form of the cell or express native genes that are otherwise abnormally expressed, under expressed or not expressed at all.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, "specifically binds" refers to a molecule (e.g., an antibody or antigen binding fragment thereof) which recognizes and binds another molecule (e.g., an antigen), but that does not substantially recognize and bind other molecules. The terms "specific binding," "specifically binds to," or is "specific for" a particular molecule (e.g., a polypeptide, or an epitope on a polypeptide), as used herein, can be exhibited, for example, by a molecule having a $K_D$ for the molecule to which it binds to of about $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M. The term "specifically binds" may also refer to binding where a molecule (e.g., an antibody or antigen binding fragment thereof) binds to a particular polypeptide (e.g., a CD22 polypeptide), or an epitope on a particular polypeptide, without substantially binding to any other polypeptide, or polypeptide epitope.

As used herein, the term "simultaneous" therapeutic use refers to the administration of at least two active ingredients by the same route and at the same time or at substantially the same time.

As used herein, the term "therapeutic agent" is intended to mean a compound that, when present in an effective amount, produces a desired therapeutic effect on a subject in need thereof.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment of disorders as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

Amino acid sequence modification(s) of the anti-CD22 antibodies described herein are contemplated. For example, it may be desirable to improve the binding affinity and/or other biological properties of the antibody. Amino acid sequence variants of an anti-CD22 antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to obtain the antibody of interest, as long as the obtained antibody possesses the desired properties. The modification also includes the change of the pattern of glycosylation of the protein. The sites of greatest interest for substitutional mutagenesis include the hypervariable regions, but FR alterations are also contemplated. “Conservative substitutions” are shown in the Table below.

TABLE 1

Amino Acid Substitutions

| Original Residue | Exemplary Substitutions | Conservative Substitutions |
|---|---|---|
| Ala (A) | Val, Leu, Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Tyr |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

One type of substitutional variant involves substituting one or more hypervariable region residues of a parent antibody. A convenient way for generating such substitutional variants involves affinity maturation using phage display. Specifically, several hypervariable region sites (e.g., 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen. Such contact residues and neighboring residues are candidates for substitution according to the techniques elaborated herein. Once such variants are generated, the panel of variants is subjected to screening as described herein and antibodies with similar or superior properties in one or more relevant assays may be selected for further development.

CD22

CD22 or cluster of differentiation-22 (also known as SIGLEC-2, SIGLEC2, Sialic Acid-Binding Ig-Like Lectin 2, BL-CAM, B-Lymphocyte Cell Adhesion Molecule, T-Cell Surface Antigen Leu-14B-Cell Receptor CD22) is an inhibitory coreceptor of the B-cell receptor (BCR) and, like other coreceptors, is required to modulate the antigen receptor signal in response to cues from the local microenvironment. CD22 (UniProtKB—P20273) is a 140 kDa glycoprotein that binds to sialic acid and is a member of the sialic acid-binding Ig-related lectin (SIGLEC) family of proteins (α2,6Sia ligands). Siglec proteins are thought to be involved in diverse biological processes such as hematopoiesis, neuronal development and immunity (Vinson et al., *J. Biol. Chem.* 271:9267-9272 (1996)). Studies also suggest that Siglec proteins mediate cell adhesion/cell signaling through recognition of sialyated cell surface glycans (Kelm et al., *Glycoconj. J.* 13:913-926 (1996); Kelm et al., *Eur. J. Biochem.* 255:663-672 (1998); Vinson et al., *J. Biol. Chem.* 271:9267-9272 (1996)). The amino acid sequence of CD22 (UniProtKB—P20273; SEQ ID NO: 83) is provided below:

```
        10         20         30         40
MHLLGPWLLL LVLEYLAFSD SSKWVFEHPE TLYAWEGACV

        50         60         70         80
WIPCTYRALD GDLESFILFH NPEYNKNTSK FDGTRLYEST

        90        100        110        120
KDGKVPSEQK RVQFLGDKNK NCTLSIHPVH LNDSGQLGLR

       130        140        150        160
MESKTEKWME RIHLNVSERP FPPHIQLPPE IQESQEVTLT

       170        180        190        200
CLLNFSCYGY PIQLQWLLEG VPMRQAAVTS TSLTIKSVFT

       210        220        230        240
RSELKFSPQW SHHGKIVTCQ LQDADGKFLS NDTVQLNVKH

       250        260        270        280
TPKLEIKVTP SDAIVREGDS VTMTCEVSSS NPEYTTVSWL

       290        300        310        320
KDGTSLKKQN TFTLNLREVT KDQSGKYCCQ VSNDVGPGRS

       330        340        350        360
EEVFLQVQYA PEPSTVQILH SPAVEGSQVE FLCMSLANPL

       370        380        390        400
PTNYTWYHNG KEMQGRTEEK VHIPKILPWH AGTYSCVAEN

       410        420        430        440
ILGTGQRGPG AELDVQYPPK KVTTVIQNPM PIREGDTVTL

       450        460        470        480
SCNYNSSNPS VTRYEWKPHG AWEEPSLGVL KIQNVGWDNT

       490        500        510        520
TIACAACNSW CSWASPVALN VQYAPRDVRV RKIKPLSEIH

       530        540        550        560
SGNSVSLQCD FSSSHPKEVQ FFWEKNGRLL GKESQLNFDS

       570        580        590        600
ISPEDAGSYS CWVNNSIGQT ASKAWTLEVL YAPRRLRVSM

       610        620        630        640
SPGDQVMEGK SATLTCESDA NPPVSHYTWF DWNNQSLPYH

       650        660        670        680
SQKLRLEPVK VQHSGAYWCQ GTNSVGKGRS PLSTLTVYYS

       690        700        710        720
PETIGRRVAV GLGSCLAILI LAICGLKLQR RWKRTQSQQG

       730        740        750        760
LQENSSGQSF FVRNKKVRRA PLSEGPHSLG CYNPMMEDGI

       770        780        790        800
SYTTLRFPEM NIPRTGDAES SEMQRPPPDC DDTVTYSALH
```

-continued

```
      810         820         830         840
KRQVGDYENV IPDFPEDEGI HYSELIQFGV GERPQAQENV

DYVILKH
```

CD22 is a single-spanning membrane glycoprotein that contains a large extracellular portion comprising seven immunoglobulin-like domains. The most distal immunoglobulin-like domain is known as a V-type immunoglobulin domain, which is responsible for binding α2,6Sia ligands, and contains two arginine residues (for example, mouse R130 and R137) that are essential for α2,6Sia-binding.

CD22 is an inhibitory coreceptor of the B-cell receptor (BCR), and plays a critical role in establishing signaling thresholds for B-cell activation. The BCR-associated CD22 undergoes rapid tyrosine-phosphorylation upon cross-linking of the BCR by antigen. The phosphorylation leads to formation of docking sites for a number of SH2-domain-containing proteins, including the protein tyrosine phosphatase SUP-1. Dephosphorylation activity of SHP-1 leads to dampening of the BCR signal. Through this mechanism, CD22 participates in ensuring that an appropriate humoral response is mounted against pathogens, but that reactivity to self antigens and autoimmunity is avoided. Given its role as a negative regulator of BCR signaling, it seems likely that defects in CD22 might predispose a subject to autoimmunity. CD22 also possesses two immunoreceptor tyrosine-based activation (ITAM) motifs in its cytoplasmic tail, and it has been suggested that CD22 may provide positive signals and promote B-cell survival.

CD22 maps to chromosome 19q13.1, with spliced variants CD22α, and the dominant form CD220. CD220 contains seven extracellular IgSF domains, one N-terminal N type and six C type. CD22α lacks the IgSF 3$^{rd}$ and 4$^{th}$ domains with unknown significance. The ectodomain of CD22 is homologous to CEA subfamily of adhesion molecules, which includes the myelin-associated glycoprotein (MAG) and CD33. As a Siglec subfamily of the IgSF, CD22 also functions as an adhesion molecule. The two N-terminal IgSF domains mediate adhesion to both B and T lymphocytes via the binding of structures carrying α2,6 sialic acids. CD22 is also capable of modulating BCR signaling. CD22 becomes tyrosine-phosphorylated upon mIgM engagement. Tyrosine-phosphorylated CD22 complexes with SH2-containing proteins (e.g., LYN and SYK tyrosine kinases, PI3-kinase, phospholipase C-γ, and SUP-1). The 140-amino acid cytoplasmic domain of CD22 contains six conserved tyrosine residues, three of which (for example, mouse Y762, Y822 and Y842) are located within conserved consensus ITIM sequences that can bind to the SH2 domain of the SUP-1 phosphatase. The presence of the multiple ITIMs and association with SUP-1 suggest the negative role of CD22 on BCR signaling. CD22-deficient B cells exhibit hyperactive B-cell responses upon BCR triggering and an increased incidence of autoantibodies. CD22 inhibits B cell receptor signaling via its alpha-2,6-sialic acid ligand binding activity. Elevated CD22 is present in hairy cell leukemia, pre-B ALL, blastic plasmacytoid dendritic cell neoplasm, B cell leukemias and lymphomas. CD22 expression can be variable among NHLs.

CD22 is known to be expressed at low levels on pre- and immature B cells, maximally on mature B cells and is downregulated on plasma cells. CD22 is restricted to the B lineage, and limited to the cytoplasm of progenitor and pre-B cells in early B-cell development. CD22 is also found on dendritic cells and basophils. The appearance of CD22 on B cells coincides with surface IgD. Following B-cell activation, CD22 is upregulated initially and then downregulated with terminal differentiation to plasma cells. CD22 expression has also been reported on a number of malignant cells. CD22 has also been implicated in autoimmune disease as well as allergies. See Orgel et al., *J Allergy Clin Immunol.* 139(1):366-369 (2017); Nakashima et al., *J Immunol.* 184 (9): 4637-4645 (2010).

Anti-CD22 agents are generally allocated in four groups: naked antibodies, antibody toxin conjugates, radionuclide conjugates, and bispecific antibodies. Existing anti-CD22 agents suffer from, inter alia, inferior tumor antigen binding avidity, short in vivo half-life, and toxicity. Wayne et al, *Blood* 130(14):1620-1627 (2017); George et al., *Immunotherapy* 135-43 (2016); Besponsa: EPAR Product Information, in *European Medicines Agency*).

Immunoglobulin-Related Compositions of the Present Technology

The anti-CD22 immunoglobulin-related compositions of the present disclosure may be useful in the diagnosis, or treatment of CD22-associated cancers, CD22-associated autoimmune diseases, and CD22-associated allergies. Anti-CD22 immunoglobulin-related compositions within the scope of the present technology include, e.g., but are not limited to, monoclonal, chimeric, humanized, bispecific antibodies and diabodies that specifically bind the target polypeptide, a homolog, derivative or a fragment thereof. The present disclosure also provides antigen binding fragments of any of the anti-CD22 antibodies disclosed herein, wherein the antigen binding fragment is selected from the group consisting of Fab, F(ab)'2, Fab', $scF_v$, and $F_v$. The present technology discloses anti-CD22 bispecific antibody formats that address existing issues of inferior tumor antigen binding avidity, short in vivo half-life and toxicity. In one aspect, the present technology provides chimeric and humanized variants of LL2, including multispecific immunoglobulin-related compositions (e.g., bispecific antibody agents).

In one aspect, the present disclosure provides an antibody or antigen binding fragment thereof comprising a heavy chain immunoglobulin variable domain ($V_H$) and a light chain immunoglobulin variable domain ($V_L$), wherein: (a) the $V_H$ comprises an amino acid sequence selected from the group consisting of: SEQ ID NOs: 5, 6, 7, 8, 9, 10, 11, 12, 13, 14, 15, and 16; and/or (b) the $V_L$ comprises an amino acid sequence selected from the group consisting of: SEQ ID NO: 21, and SEQ ID NO: 22. In some embodiments, the antibody further comprises a Fc domain of any isotype, e.g., but are not limited to, IgG (including IgG1, IgG2, IgG3, and IgG4), IgA (including $IgA_1$ and IgA2), IgD, IgE, or IgM, and IgY. Non-limiting examples of constant region sequences include:

```
Human IgD constant region, Uniprot: P01880
                                    (SEQ ID NO: 84)
APTKAPDVFPIISGCRHPKDNSPVVLACLITGYHPTSVTVTWYMGT

QSQPQRTFPEIQRRDSYYMTSSQLSTPLQQWRQGEYKCVVQHTASK

SKKEIFRWPESPKAQASSVPTAQPQAEGSLAKATTAPATTRNTGRG

GEEKKKEKEKEEQEERETKTPECPSHTQPLGVYLLTPAVQDLWLRD

KATFTCFVVGSDLKDAHLTWEVAGKVPTGGVEEGLLERHSNGSQSQ

HSRLTLPRSLWNAGTSVTCTLNHPSLPPQRLMALREPAAQAPVKLS

LNLLASSDPPEAASWLLCEVSGFSPPNILLMWLEDQREVNTSGFAP
```

-continued

ARPPPQPGSTTFWAWSVLRVPAPPSPQPATYTCVVSHEDSRTLLNA

SRSLEVSYVTDHGPMK

Human IgG1 constant region, Uniprot: P01857
(SEQ ID NO: 85)

ASTKGPSVFPLAPSSKSTSGGTAALGCLVKDYFPEPVTVSWNSGAL

TSGVHTFPAVLQSSGLYSLSSVVTVPSSSLGTQTYICNVNHKPSNT

KVDKKVEPKSCDKTHTCPPCPAPELLGGPSVFLFPPKPKDTLMISR

TPEVTCVVVDVSHEDPEVKFNWYVDGVEVHNAKTKPREEQYNSTYR

VVSVLTVLHQDWLNGKEYKCKVSNKALPAPIEKTISKAKGQPREPQ

VYTLPPSRDELTKNQVSLTCLVKGFYPSDIAVEWESNGQPENNYKT

TPPVLDSDGSFFLYSKLTVDKSRWQQGNVFSCSVMHEALHNHYTQK

SLSLSPGK

Human IgG2 constant region, Uniprot: P01859
(SEQ ID NO: 86)

ASTKGPSVFPLAPCSRSTSESTAALGCLVKDYFPEPVTVSWNSGAL

TSGVHTFPAVLQSSGLYSLSSVVTVPSSNFGTQTYTCNVDHKPSNT

KVDKTVERKCCVECPPCPAPPVAGPSVFLFPPKPKDTLMISRTPEV

TCVVVDVSHEDPEVQFNWYVDGVEVHNAKTKPREEQFNSTFRVVSV

LTVVHQDWLNGKEYKCKVSNKGLPAPIEKTISKTKGQPREPQVYTL

PPSREEMTKNQVSLTCLVKGFYPSDISVEWESNGQPENNYKTTPPM

LDSDGSFFLYSKLTVDKSRWQQGNVFSCSVMHEALHNHYTQKSLSL

SPGK

Human IgG3 constant region, Uniprot: P01860
(SEQ ID NO: 87)

ASTKGPSVFPLAPCSRSTSGGTAALGCLVKDYFPEPVTVSWNSGAL

TSGVHTFPAVLQSSGLYSLSSVVTVPSSSLGTQTYTCNVNHKPSNT

KVDKRVELKTPLGDTTHTCPRCPEPKSCDTPPPCPRCPEPKSCDTP

PPCPRCPEPKSCDTPPPCPRCPAPELLGGPSVFLFPPKPKDTLMIS

RTPEVTCVVVDVSHEDPEVQFKWYVDGVEVHNAKTKPREEQYNSTF

RVVSVLTVLHQDWLNGKEYKCKVSNKALPAPIEKTISKTKGQPREP

QVYTLPPSREEMTKNQVSLTCLVKGFYPSDIAVEWESSGQPENNYN

TTPPMLDSDGSFFLYSKLTVDKSRWQQGNIFSCSVMHEALHNRFTQ

KSLSLSPGK

Human IgM constant region, Uniprot: P01871
(SEQ ID NO: 88)

GSASAPTLFPLVSCENSPSDTSSVAVGCLAQDFLPDSITLSWKYKN

NSDISSTRGFPSVLRGGKYAATSQVLLPSKDVMQGTDEHVVCKVQH

PNGNKEKNVPLPVIAELPPKVSVFVPPRDGFFGNPRKSKLICQATG

FSPRQIQVSWLREGKQVGSGVTTDQVQAEAKESGPTTYKVTSTLTI

KESDWLGQSMFTCRVDHRGLTFQQNASSMCVPDQDTAIRVFAIPPS

FASIFLTKSTKLTCLVTDLTTYDSVTISWTRQNGEAVKTHTNISES

HPNATFSAVGEASICEDDWNSGERFTCTVTHTDLPSPLKQTISRPK

GVALHRPDVYLLPPAREQLNLRESATITCLVTGFSPADVFVQWMQR

-continued

GQPLSPEKYVTSAPMPEPQAPGRYFAHSILTVSEEEWNTGETYTCV

AHEALPNRVTERTVDKSTGKPTLYNVSLVMSDTAGTCY

Human IgG4 constant region, Uniprot: P01861
(SEQ ID NO: 89)

ASTKGPSVFPLAPCSRSTSESTAALGCLVKDYFPEPVTVSWNSGAL

TSGVHTFPAVLQSSGLYSLSSVVTVPSSSLGTKTYTCNVDHKPSNT

KVDKRVESKYGPPCPSCPAPEFLGGPSVFLFPPKPKDTLMISRTPE

VTCVVVDVSQEDPEVQFNWYVDGVEVHNAKTKPREEQFNSTYRVVS

VLTVLHQDWLNGKEYKCKVSNKGLPSSIEKTISKAKGQPREPQVYT

LPPSQEEMTKNQVSLTCLVKGFYPSDIAVEWESNGQPENNYKTTPP

VLDSDGSFFLYSRLTVDKSRWQEGNVFSCSVMHEALHNHYTQKSLS

LSLGK

Human IgA1 constant region, Uniprot: P01876
(SEQ ID NO: 90)

ASPTSPKVFPLSLCSTQPDGNVVIACLVQGFFPQEPLSVTWSESGQ

GVTARNFPPSQDASGDLYTTSSQLTLPATQCLAGKSVTCHVKHYTN

PSQDVTVPCPVPSTPPTPSPSTPPTPSPSCCHPRLSLHRPALEDLL

LGSEANLTCTLTGLRDASGVTFTWTPSSGKSAVQGPPERDLCGCYS

VSSVLPGCAEPWNHGKTFTCTAAYPESKTPLTATLSKSGNTFRPEV

HLLPPPSEELALNELVTLTCLARGFSPKDVLVRWLQGSQELPREKY

LTWASRQEPSQGTTTFAVTSILRVAAEDWKKGDTFSCMVGHEALPL

AFTQKTIDRLAGKPTHVNVSVVMAEVDGTCY

Human IgA2 constant region, Uniprot: P01877
(SEQ ID NO: 91)

ASPTSPKVFPLSLDSTPQDGNVVVACLVQGFFPQEPLSVTWSESGQ

NVTARNFPPSQDASGDLYTTSSQLTLPATQCPDGKSVTCHVKHYTN

PSQDVTVPCPVPPPPPCCHPRLSLHRPALEDLLLGSEANLTCTLTG

LRDASGATFTWTPSSGKSAVQGPPERDLCGCYSVSSVLPGCAQPWN

HGETFTCTAAHPELKTPLTANITKSGNTFRPEVHLLPPPSEELALN

ELVTLTCLARGFSPKDVLVRWLQGSQELPREKYLTWASRQEPSQGT

TTFAVTSILRVAAEDWKKGDTFSCMVGHEALPLAFTQKTIDRMAGK

PTHVNVSVVMAEVDGTCY

Human Ig kappa constant region, Uniprot: P01834
(SEQ ID NO: 92)

TVAAPSVFIFPPSDEQLKSGTASVVCLLNNFYPREAKVQWKVDNAL

QSGNSQESVTEQDSKDSTYSLSSTLTLSKADYEKHKVYACEVTHQG

LSSPVTKSFNRGEC

In some embodiments, the immunoglobulin-related compositions of the present technology comprise a heavy chain constant region that is at least 80%, at least 85%, at least 90%, at least 95%, at least 99%, or is 100% identical to SEQ ID NOS: 84-91. Additionally or alternatively, in some embodiments, the immunoglobulin-related compositions of the present technology comprise a light chain constant region that is at least 80%, at least 85%, at least 90%, at least 95%, at least 99%, or is 100% identical to SEQ ID NO: 92. In some embodiments, the antibody or antigen binding fragment binds to the Ig-like C2-type 1 domain, (amino acid residues 143-235 of CD22) and/or Ig-like C2-type 2 domain (amino acid residues 242-326 of CD22). In any of the above embodiments, the antibody or antigen binding fragment binds to a conformational epitope spanning the second and third Ig-like domains of CD22.

In another aspect, the present disclosure provides an isolated immunoglobulin-related composition (e.g., an antibody or antigen binding fragment thereof) comprising a heavy chain (HC) amino acid sequence comprising SEQ ID NO: 25, SEQ ID NO: 29, SEQ ID NO: 33, SEQ ID NO: 36, SEQ ID NO: 38, SEQ ID NO: 40, SEQ ID NO: 42, SEQ ID NO: 44, SEQ ID NO: 46, or a variant thereof having one or more conservative amino acid substitutions.

Additionally or alternatively, in some embodiments, the immunoglobulin-related compositions of the present technology comprise a light chain (LC) amino acid sequence comprising SEQ ID NO: 23, SEQ ID NO: 27, SEQ ID NO: 31, SEQ ID NO: 35, SEQ ID NO: 37, SEQ ID NO: 39, SEQ ID NO: 41, SEQ ID NO: 43, SEQ ID NO: 45, or a variant thereof having one or more conservative amino acid substitutions.

In some embodiments, the immunoglobulin-related compositions of the present technology comprise a HC amino acid sequence and a LC amino acid sequence selected from the group consisting of: SEQ ID NO: 25 and SEQ ID NO: 23 (chLL2 x CD3 BsAb); SEQ ID NO: 29 and SEQ ID NO: 27 (BC270-hLL2 x CD3 BsAb); SEQ ID NO: 33 and SEQ ID NO: 31 (BC251-hLL2 x CD3 BsAb); SEQ ID NO: 36 and SEQ ID NO: 35 (mLL2 x mC825 BsAb); SEQ ID NO: 38 and SEQ ID NO: 37 (mLL2 x hC825 BsAb); SEQ ID NO: 40 and SEQ ID NO: 39 (VL1VH4 x mC825); SEQ ID NO: 42 and SEQ ID NO: 41 (VL1VH4 x hC825); SEQ ID NO: 44 and SEQ ID NO: 43 (VL1VH10 x mC825); and SEQ ID NO: 46 and SEQ ID NO: 45 (VL1VH10 x hC825), respectively.

In any of the above embodiments of the immunoglobulin-related compositions, the HC and LC immunoglobulin variable domain sequences form an antigen binding site that binds to the Ig-like C2-type 1 domain and/or Ig-like C2-type 2 domain of CD22. In some embodiments, the epitope is a conformational epitope.

In some embodiments, the HC and LC immunoglobulin variable domain sequences are components of the same polypeptide chain. In other embodiments, the HC and LC immunoglobulin variable domain sequences are components of different polypeptide chains. In certain embodiments, the antibody is a full-length antibody.

In some embodiments, the immunoglobulin-related compositions of the present technology bind specifically to at least one CD22 polypeptide. In some embodiments, the immunoglobulin-related compositions of the present technology bind at least one CD22 polypeptide with a dissociation constant ($K_D$) of about $10^{-3}$M, $10^{-4}$ M, $10^{-5}$ M, $10^{-6}$ M, $10^{-7}$ M, $10^{-8}$ M, $10^{-9}$ M, $10^{-10}$ M, $10^{-11}$ M, or $10^{-12}$ M. In certain embodiments, the immunoglobulin-related compositions are monoclonal antibodies, chimeric antibodies, humanized antibodies, or bispecific antibodies. In some embodiments, the antibodies comprise a human antibody framework region.

In certain embodiments, the immunoglobulin-related composition includes one or more of the following characteristics: (a) a light chain immunoglobulin variable domain sequence that is at least 80%, at least 85%, at least 90%, at least 95%, or at least 99% identical to the light chain immunoglobulin variable domain sequence present in any one of SEQ ID NOs: 21 or 22; and/or (b) a heavy chain immunoglobulin variable domain sequence that is at least 80%, at least 85%, at least 90%, at least 95%, or at least 99% identical to the heavy chain immunoglobulin variable domain sequence present in any one of SEQ ID NOs: SEQ ID NOs: 5, 6, 7, 8, 9, 10, 11, 12, 13, 14, 15, or 16. In another aspect, one or more amino acid residues in the immunoglobulin-related compositions provided herein are substituted with another amino acid. The substitution may be a "conservative substitution" as defined herein.

In some embodiments, the immunoglobulin-related composition comprises (a) a LC sequence that is at least 80%, at least 85%, at least 90%, at least 95%, or at least 99% identical to the LC sequence present in any one of SEQ ID NOs: 23, 27, 31, 35, 37, 39, 41, 43, or 45; and/or (b) a HC sequence that is at least 80%, at least 85%, at least 90%, at least 95%, or at least 99% identical to the HC sequence present in any one of SEQ ID NO: 25, 29, 33, 36, 38, 40, 42, 44, or 46.

In one aspect, the present disclosure provides an immunoglobulin-related composition comprising an amino acid sequence that is at least 80%, at least 85%, at least 90%, at least 95%, or at least 99% identical to an amino acid sequence selected from SEQ ID NOs:47-82. In certain embodiments, an immunoglobulin-related composition of the present disclosure comprises an amino acid sequence selected from SEQ ID NOs:47-82.

In one aspect, the present disclosure provides a bispecific antigen binding fragment comprising a first polypeptide chain, wherein: the first polypeptide chain comprises in the N-terminal to C-terminal direction: (i) a heavy chain variable domain of a first immunoglobulin that is capable of specifically binding to a first epitope; (ii) a flexible peptide linker comprising the amino acid sequence $(GGGGS)_6$ (SEQ ID NO: 101); (iii) a light chain variable domain of the first immunoglobulin; (iv) a flexible peptide linker comprising the amino acid sequence $(GGGGS)_4$ (SEQ ID NO: 102); (v) a heavy chain variable domain of a second immunoglobulin that is capable of specifically binding to a second epitope; (vi) a flexible peptide linker comprising the amino acid sequence $(GGGGS)_6$ (SEQ ID NO: 101); (vii) a light chain variable domain of the second immunoglobulin; (viii) a flexible peptide linker sequence comprising the amino acid sequence TPLGDTTHT (SEQ ID NO: 103); and (ix) a self-assembly disassembly (SADA) polypeptide, wherein the heavy chain variable domain of the first immunoglobulin is selected from the group consisting of: SEQ ID NOs: 5, 6, 7, 8, 9, 10, 11, 12, 13, 14, 15, and 16; and/or the light chain variable domain of the first immunoglobulin is selected from the group consisting of: SEQ ID NO: 21 and SEQ ID NO: 22.

In another aspect, the present disclosure provides a bispecific antigen binding fragment comprising a first polypeptide chain, wherein: the first polypeptide chain comprises in the N-terminal to C-terminal direction: (i) a light chain variable domain of a first immunoglobulin that is capable of specifically binding to a first epitope; (ii) a flexible peptide linker comprising the amino acid sequence $(GGGGS)_6$ (SEQ ID NO: 101); (iii) a heavy chain variable domain of the first immunoglobulin; (iv) a flexible peptide linker comprising the amino acid sequence $(GGGGS)_4$ (SEQ ID NO: 102); (v) a heavy chain variable domain of a second immunoglobulin that is capable of specifically binding to a second epitope; (vi) a flexible peptide linker comprising the amino acid sequence $(GGGGS)_6$ (SEQ ID NO: 101); (vii) a light chain variable domain of the second immunoglobulin; (viii) a flexible peptide linker sequence comprising the amino acid sequence TPLGDTTHT (SEQ ID NO: 103); and (ix) a self-assembly disassembly (SADA) polypeptide, wherein the heavy chain variable domain of the first immunoglobulin is selected from the group consisting of: SEQ ID NOs: 5, 6, 7, 8, 9, 10, 11, 12, 13, 14, 15, and 16; and/or the light chain variable domain of the first immunoglobulin is selected from the group consisting of: SEQ ID NO: 21 and SEQ ID NO: 22.

In certain embodiments of the bispecific antigen binding fragments disclosed herein, the SADA polypeptide comprises a tetramerization, pentamerization, or hexamerization domain. In some embodiments, the SADA polypeptide comprises a tetramerization domain of any one of p53, p63, p73, hnRNPC, SNA-23, Stefin B, KCNQ4, and CBFA2T1. Additionally or alternatively, in some embodiments, the bispecific antigen binding fragment comprises an amino acid sequence selected from SEQ ID NOs: 47-82.

In one aspect, the present disclosure provides a bispecific antibody comprising a first polypeptide chain, a second polypeptide chain, a third polypeptide chain and a fourth polypeptide chain, wherein the first and second polypeptide chains are covalently bonded to one another, the second and third polypeptide chains are covalently bonded to one another, and the third and fourth polypeptide chain are covalently bonded to one another, and wherein: (a) each of the first polypeptide chain and the fourth polypeptide chain comprises in the N-terminal to C-terminal direction: (i) a light chain variable domain of a first immunoglobulin that is capable of specifically binding to a first epitope; (ii) a light chain constant domain of the first immunoglobulin; (iii) a flexible peptide linker comprising the amino acid sequence $(GGGGS)_3$ (SEQ ID NO: 104); and (iv) a light chain variable domain of a second immunoglobulin that is linked to a complementary heavy chain variable domain of the second immunoglobulin, or a heavy chain variable domain of a second immunoglobulin that is linked to a complementary light chain variable domain of the second immunoglobulin, wherein the light chain and heavy chain variable domains of the second immunoglobulin are capable of specifically binding to a second epitope, and are linked together via a flexible peptide linker comprising the amino acid sequence $(GGGGS)_6$ (SEQ ID NO: 101) to form a single-chain variable fragment; and (b) each of the second polypeptide chain and the third polypeptide chain comprises in the N-terminal to C-terminal direction: (i) a heavy chain variable domain of the first immunoglobulin that is capable of specifically binding to the first epitope; and (ii) a heavy chain constant domain of the first immunoglobulin; and wherein the heavy chain variable domain of the first immunoglobulin is selected from the group consisting of: SEQ ID NOs: 5, 6, 7, 8, 9, 10, 11, 12, 13, 14, 15, and 16; and/or the light chain variable domain of the first immunoglobulin is selected from the group consisting of: SEQ ID NO: 21 and SEQ ID NO: 22. In certain embodiments, the second immunoglobulin binds to CD3, CD4, CD8, CD20, CD19, CD21, CD23, CD46, CD80, HLA-DR, CD74, CD22, CD14, CD15, CD16, CD123, TCR gamma/delta, NKp46, KIR, or a small molecule DOTA hapten.

In certain embodiments, the immunoglobulin-related compositions contain an IgG1 constant region comprising one or more amino acid substitutions selected from the group consisting of N297A and K322A. Additionally or alternatively, in some embodiments, the immunoglobulin-related compositions contain an IgG4 constant region comprising a S228P mutation.

In some aspects, the anti-CD22 immunoglobulin-related compositions described herein contain structural modifications to facilitate rapid binding and cell uptake and/or slow release. In some aspects, the anti-CD22 immunoglobulin-related composition of the present technology (e.g., an antibody) may contain a deletion in the $CH_2$ constant heavy chain region to facilitate rapid binding and cell uptake and/or slow release. In some aspects, a Fab fragment is used to facilitate rapid binding and cell uptake and/or slow release. In some aspects, a $F(ab)'_2$ fragment is used to facilitate rapid binding and cell uptake and/or slow release.

In one aspect, the present technology provides a recombinant nucleic acid sequence encoding any of the immunoglobulin-related compositions described herein. In some embodiments, the nucleic acid sequence is selected from the group consisting of SEQ ID NOs: 24, 26, 28, 30, 32, and 34.

In another aspect, the present technology provides a host cell or vector expressing any nucleic acid sequence encoding any of the immunoglobulin-related compositions described herein.

The immunoglobulin-related compositions of the present technology (e.g., an anti-CD22 antibody) can be monospecific, bispecific, trispecific or of greater multispecificity. Multispecific antibodies can be specific for different epitopes of one or more CD22 polypeptides or can be specific for both the CD22 polypeptide(s) as well as for heterologous compositions, such as a heterologous polypeptide or solid support material. See, e.g., WO 93/17715; WO 92/08802; WO 91/00360; WO 92/05793; Tutt et al., *J. Immunol.* 147: 60-69 (1991); U.S. Pat. Nos. 5,573,920, 4,474,893, 5,601,819, 4,714,681, 4,925,648; 6,106,835; Kostelny et al., *J. Immunol.* 148: 1547-1553 (1992). In some embodiments, the immunoglobulin-related compositions are chimeric. In certain embodiments, the immunoglobulin-related compositions are humanized.

The immunoglobulin-related compositions of the present technology can further be recombinantly fused to a heterologous polypeptide at the N- or C-terminus or chemically conjugated (including covalently and non-covalently conjugations) to polypeptides or other compositions. For example, the immunoglobulin-related compositions of the present technology can be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

In any of the above embodiments of the immunoglobulin-related compositions of the present technology, the antibody or antigen binding fragment may be optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof. For a chemical bond or physical bond, a functional group on the immunoglobulin-related composition typically associates with a functional group on the agent. Alternatively, a functional group on the agent associates with a functional group on the immunoglobulin-related composition.

The functional groups on the agent and immunoglobulin-related composition can associate directly. For example, a functional group (e.g., a sulfhydryl group) on an agent can associate with a functional group (e.g., sulfhydryl group) on an immunoglobulin-related composition to form a disulfide. Alternatively, the functional groups can associate through a cross-linking agent (i.e., linker). Some examples of cross-linking agents are described below. The cross-linker can be attached to either the agent or the immunoglobulin-related composition. The number of agents or immunoglobulin-related compositions in a conjugate is also limited by the number of functional groups present on the other. For example, the maximum number of agents associated with a conjugate depends on the number of functional groups present on the immunoglobulin-related composition. Alternatively, the maximum number of immunoglobulin-related compositions associated with an agent depends on the number of functional groups present on the agent.

In yet another embodiment, the conjugate comprises one immunoglobulin-related composition associated to one agent. In one embodiment, a conjugate comprises at least one agent chemically bonded (e.g., conjugated) to at least one immunoglobulin-related composition. The agent can be chemically bonded to an immunoglobulin-related composition by any method known to those in the art. For example, a functional group on the agent may be directly attached to a functional group on the immunoglobulin-related composition. Some examples of suitable functional groups include, for example, amino, carboxyl, sulfhydryl, maleimide, isocyanate, isothiocyanate and hydroxyl.

The agent may also be chemically bonded to the immunoglobulin-related composition by means of cross-linking agents, such as dialdehydes, carbodiimides, dimaleimides, and the like. Cross-linking agents can, for example, be obtained from Pierce Biotechnology, Inc., Rockford, Ill. The Pierce Biotechnology, Inc. web-site can provide assistance. Additional cross-linking agents include the platinum cross-linking agents described in U.S. Pat. Nos. 5,580,990; 5,985,566; and 6,133,038 of Kreatech Biotechnology, B.V., Amsterdam, The Netherlands.

Alternatively, the functional group on the agent and immunoglobulin-related composition can be the same. Homobifunctional cross-linkers are typically used to cross-link identical functional groups. Examples of homobifunctional cross-linkers include EGS (i.e., ethylene glycol bis [succinimidylsuccinate]), DSS (i.e., disuccinimidyl suberate), DMA (i.e., dimethyl adipimidate.2HCl), DTSSP (i.e., 3,3'-dithiobis[sulfosuccinimidylpropionate])), DPDPB (i.e., 1,4-di-[3'-(2'-pyridyldithio)-propionamido]butane), and BMH (i.e., bis-maleimidohexane). Such homobifunctional cross-linkers are also available from Pierce Biotechnology, Inc.

In other instances, it may be beneficial to cleave the agent from the immunoglobulin-related composition. The web-site of Pierce Biotechnology, Inc. described above can also provide assistance to one skilled in the art in choosing suitable cross-linkers which can be cleaved by, for example, enzymes in the cell. Thus the agent can be separated from the immunoglobulin-related composition. Examples of cleavable linkers include SMPT (i.e., 4-succinimidyloxycarbonyl-methyl-a-[2-pyridyldithio]toluene), Sulfo-LC-SPDP (i.e., sulfosuccinimidyl 6-(3-[2-pyridyldithio]-propionamido)hexanoate), LC-SPDP (i.e., succinimidyl 6-(3-[2-pyridyldithio]-propionamido)hexanoate), Sulfo-LC-SPDP (i.e., sulfosuccinimidyl 6-(3-[2-pyridyldithio]-propionamido)hexanoate), SPDP (i.e., N-succinimidyl 3-[2-pyridyldithio]-propionamidohexanoate), and AEDP (i.e., 3-[(2-aminoethyl)dithio]propionic acid HCl).

In another embodiment, a conjugate comprises at least one agent physically bonded with at least one immunoglobulin-related composition. Any method known to those in the art can be employed to physically bond the agents with the immunoglobulin-related compositions. For example, the immunoglobulin-related compositions and agents can be mixed together by any method known to those in the art. The order of mixing is not important. For instance, agents can be physically mixed with immunoglobulin-related compositions by any method known to those in the art. For example, the immunoglobulin-related compositions and agents can be placed in a container and agitated, by for example, shaking the container, to mix the immunoglobulin-related compositions and agents.

The immunoglobulin-related compositions can be modified by any method known to those in the art. For instance, the immunoglobulin-related composition may be modified by means of cross-linking agents or functional groups, as described above.

A. Methods of Preparing Anti-CD22 Antibodies of the Present Technology

General Overview. Initially, a target polypeptide is chosen to which an antibody of the present technology can be raised. For example, an antibody may be raised against the full-length CD22 protein, a CD22 protein lacking the intracellular domain, or to a portion of the extracellular domain of the CD22 protein (e.g., the Ig-like C2-type 1 domain (amino acid residues 143-235 of CD22) and/or Ig-like C2-type 2 (amino acid residues 242-326 of CD22)), or a synthetic peptide (e.g. a synthetic phospho-peptide comprising phospho-Tyr 807 of human CD22). Techniques for generating antibodies directed to such target polypeptides are well known to those skilled in the art. Examples of such techniques include, for example, but are not limited to, those involving display libraries, xeno or human mice, hybridomas, and the like. Target polypeptides within the scope of the present technology include any polypeptide derived from CD22 protein containing the extracellular domain which is capable of eliciting an immune response (e.g., an epitope spanning the second and third Ig-like domains of CD22).

It should be understood that recombinantly engineered antibodies and antibody fragments, e.g., antibody-related polypeptides, which are directed to CD22 protein and fragments thereof are suitable for use in accordance with the present disclosure.

Anti-CD22 antibodies that can be subjected to the techniques set forth herein include monoclonal and polyclonal antibodies, and antibody fragments such as Fab, Fab', F(ab')$_2$, Fd, scFv, diabodies, antibody light chains, antibody heavy chains and/or antibody fragments. Methods useful for the high yield production of antibody Fv-containing polypeptides, e.g., Fab' and F(ab')$_2$ antibody fragments have been described. See U.S. Pat. No. 5,648,237.

Generally, an antibody is obtained from an originating species. More particularly, the nucleic acid or amino acid sequence of the variable portion of the light chain, heavy chain or both, of an originating species antibody having specificity for a target polypeptide antigen is obtained. An originating species is any species which was useful to generate the antibody of the present technology or library of antibodies, e.g., rat, mouse, rabbit, chicken, monkey, human, and the like.

Phage or phagemid display technologies are useful techniques to derive the antibodies of the present technology. Techniques for generating and cloning monoclonal antibodies are well known to those skilled in the art. Expression of sequences encoding antibodies of the present technology, can be carried out in *E. coli.*

Due to the degeneracy of nucleic acid coding sequences, other sequences which encode substantially the same amino acid sequences as those of the naturally occurring proteins may be used in the practice of the present technology These include, but are not limited to, nucleic acid sequences including all or portions of the nucleic acid sequences encoding the above polypeptides, which are altered by the substitution of different codons that encode a functionally equivalent amino acid residue within the sequence, thus producing a silent change. It is appreciated that the nucleotide sequence of an immunoglobulin according to the present technology tolerates sequence homology variations of up to 25% as calculated by standard methods ("Current Methods in Sequence Comparison and Analysis," *Macromolecule Sequencing and Synthesis, Selected Methods and Applications*, pp. 127-149, 1998, Alan R. Liss, Inc.) so long as such a variant forms an operative antibody which recognizes CD22 proteins. For example, one or more amino acid residues within a polypeptide sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the present technology are proteins or fragments or derivatives thereof which are differentially modified during or after translation, e.g., by glycosylation, proteolytic cleavage, linkage to an antibody molecule or other cellular ligands, etc. Additionally, an immunoglobulin encoding nucleic acid sequence can be mutated in vitro or in vivo to create and/or destroy translation, initiation, and/or termination sequences or to create variations in coding regions and/or form new restriction endonuclease sites or destroy pre-existing ones, to facilitate further in vitro modification. Any technique for mutagenesis known in the art can be used, including but not limited to in vitro site directed mutagenesis, *J. Biol. Chem.* 253:6551, use of Tab linkers (Pharmacia), and the like.

Preparation of Polyclonal Antisera and Immunogens. Methods of generating antibodies or antibody fragments of the present technology typically include immunizing a subject (generally a non-human subject such as a mouse or rabbit) with a purified CD22 protein or fragment thereof or with a cell expressing the CD22 protein or fragment thereof. An appropriate immunogenic preparation can contain, e.g., a recombinantly-expressed CD22 protein or a chemically-synthesized CD22 peptide. The extracellular domain of the CD22 protein, or a portion or fragment thereof (e.g., the Ig-like C2-type 1 domain and/or Ig-like C2-type 2 domain), can be used as an immunogen to generate an anti-CD22 antibody that binds to the CD22 protein, or a portion or fragment thereof using standard techniques for polyclonal and monoclonal antibody preparation.

The full-length CD22 protein or fragments thereof, are useful as fragments as immunogens. In some embodiments, a CD22 fragment comprises the Ig-like C2-type 1 domain and/or Ig-like C2-type 2 domain of CD22 such that an antibody raised against the peptide forms a specific immune complex with CD22 protein, including a CD22 variant lacking the Ig-like V-type domain (e.g., residues 20-138 of CD22 polypeptide)

In some embodiments, the antigenic CD22 peptide comprises at least 5, 8, 10, 15, 20, 30, 40, 50, 60, 70, 80, 90, 100, 110, 120, 130, 140, 150, 160, 170 or 180 amino acid residues. In some embodiments, the CD22 peptide comprises a modification, such as phosphorylation. Longer antigenic peptides are sometimes desirable over shorter antigenic peptides, depending on use and according to methods well known to those skilled in the art. Multimers of a given epitope are sometimes more effective than a monomer.

If needed, the immunogenicity of the CD22 protein (or fragment thereof) can be increased by fusion or conjugation to a hapten such as keyhole limpet hemocyanin (KLH) or ovalbumin (OVA). Many such haptens are known in the art. One can also combine the CD22 protein with a conventional adjuvant such as Freund's complete or incomplete adjuvant to increase the subject's immune reaction to the polypeptide. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and *Corynebacterium parvum*, or similar immunostimulatory compounds. These techniques are standard in the art.

In describing the present technology, immune responses may be described as either "primary" or "secondary" immune responses. A primary immune response, which is also described as a "protective" immune response, refers to an immune response produced in an individual as a result of some initial exposure (e.g., the initial "immunization") to a particular antigen, e.g., CD22 protein. In some embodiments, the immunization can occur as a result of vaccinating the individual with a vaccine containing the antigen. For example, the vaccine can be a CD22 vaccine comprising one or more CD22 protein-derived antigens. A primary immune response can become weakened or attenuated over time and can even disappear or at least become so attenuated that it cannot be detected. Accordingly, the present technology also relates to a "secondary" immune response, which is also described here as a "memory immune response." The term secondary immune response refers to an immune response elicited in an individual after a primary immune response has already been produced.

Thus, a secondary immune response can be elicited, e.g., to enhance an existing immune response that has become weakened or attenuated, or to recreate a previous immune response that has either disappeared or can no longer be detected. The secondary or memory immune response can be either a humoral (antibody) response or a cellular response. A secondary or memory humoral response occurs upon stimulation of memory B cells that were generated at the first presentation of the antigen. Delayed type hypersensitivity (DTH) reactions are a type of cellular secondary or memory immune response that are mediated by $CD4^+$ T cells. A first exposure to an antigen primes the immune system and additional exposure(s) results in a DTH.

Following appropriate immunization, the anti-CD22 antibody can be prepared from the subject's serum. If desired, the antibody molecules directed against the CD22 protein can be isolated from the mammal (e.g., from the blood) and further purified by well-known techniques, such as polypeptide A chromatography to obtain the IgG fraction.

Monoclonal Antibody. In one embodiment of the present technology, the antibody is an anti-CD22 monoclonal antibody. For example, in some embodiments, the anti-CD22 monoclonal antibody may be a human or a mouse anti-CD22 monoclonal antibody. For preparation of monoclonal antibodies directed towards the CD22 protein, or derivatives, fragments, analogs or homologs thereof, any technique that provides for the production of antibody molecules by continuous cell line culture can be utilized. Such techniques include, but are not limited to, the hybridoma technique (See, e.g., Kohler & Milstein, 1975. *Nature* 256: 495-497); the trioma technique; the human B-cell hybridoma technique (See, e.g., Kozbor, et al., 1983. *Immunol. Today* 4: 72) and the EBV hybridoma technique to produce human monoclonal antibodies (See, e.g., Cole, et al., 1985. In: MONOCLONAL ANTIBODIES AND CANCER THERAPY, Alan R. Liss, Inc., pp. 77-96). Human monoclonal antibodies can be utilized in the practice of the present technology and can be produced by using human hybridomas (See, e.g., Cote, et al., 1983. *Proc. Natl. Acad. Sci. USA* 80: 2026-2030) or by transforming human B-cells with Epstein Barr Virus in vitro (See, e.g., Cole, et al., 1985. In: MONOCLONAL ANTIBODIES AND CANCER THERAPY, Alan R. Liss, Inc., pp. 77-96). For example, a population of nucleic acids that encode regions of antibodies can be isolated. PCR utilizing primers derived from sequences encoding conserved regions of antibodies is used to amplify sequences encoding portions of antibodies from the population and then DNAs encoding antibodies or fragments thereof, such as variable domains, are reconstructed from the amplified sequences. Such amplified sequences also can be fused to DNAs encoding other proteins—e.g., a bacteriophage coat, or a bacterial cell surface protein—for expression and display of the fusion polypeptides on phage or bacteria. Amplified sequences can then be expressed and further selected or isolated based, e.g., on the affinity of the expressed antibody or fragment thereof for an antigen or epitope present on the CD22 protein. Alternatively, hybridomas expressing anti-CD22 monoclonal antibodies can be prepared by immunizing a subject and then isolating hybridomas from the subject's spleen using routine methods. See, e.g., Milstein et al., (Galfre and Milstein, *Methods Enzymol* (1981) 73: 3-46). Screening the hybridomas using standard methods will produce monoclonal antibodies of varying specificity (i.e., for different epitopes) and affinity. A selected monoclonal antibody with the desired properties, e.g., CD22 binding, can be used as expressed by the hybridoma, it can be bound to a molecule such as polyethylene glycol (PEG) to alter its properties, or a cDNA encoding it can be isolated, sequenced and manipulated in various ways. Synthetic dendromeric trees can be added to reactive amino acid side chains, e.g., lysine, to enhance the immunogenic properties of CD22 protein. Also, CPG-dinucleotide techniques can be used to enhance the immunogenic properties of the CD22 protein. Other manipulations include substituting or deleting particular amino acyl residues that contribute to instability of the antibody during storage or after administration to a subject, and affinity maturation techniques to improve affinity of the antibody of the CD22 protein.

Hybridoma Technique. In some embodiments, the antibody of the present technology is an anti-CD22 monoclonal antibody produced by a hybridoma which includes a B cell obtained from a transgenic non-human animal, e.g., a transgenic mouse, having a genome comprising a human heavy chain transgene and a light chain transgene fused to an immortalized cell. Hybridoma techniques include those known in the art and taught in Harlow et al., *Antibodies: A Laboratory Manual* Cold Spring Harbor Laboratory, Cold Spring Harbor, NY, 349 (1988); Hammerling et al., *Monoclonal Antibodies And T-Cell Hybridomas,* 563-681 (1981). Other methods for producing hybridomas and monoclonal antibodies are well known to those of skill in the art.

Phage Display Technique. As noted above, the antibodies of the present technology can be produced through the application of recombinant DNA and phage display technology. For example, anti-CD22 antibodies, can be prepared using various phage display methods known in the art. In phage display methods, functional antibody domains are displayed on the surface of a phage particle which carries polynucleotide sequences encoding them. Phages with a desired binding property are selected from a repertoire or combinatorial antibody library (e.g., human or murine) by selecting directly with an antigen, typically an antigen bound or captured to a solid surface or bead. Phages used in these methods are typically filamentous phage including fd and M13 with Fab, Fv or disulfide stabilized Fv antibody domains that are recombinantly fused to either the phage gene III or gene VIII protein. In addition, methods can be adapted for the construction of Fab expression libraries (See, e.g., Huse, et al., *Science* 246: 1275-1281, 1989) to allow rapid and effective identification of monoclonal Fab fragments with the desired specificity for a CD22 polypeptide, e.g., a polypeptide or derivatives, fragments, analogs or homologs thereof. Other examples of phage display methods that can be used to make the antibodies of the present technology include those disclosed in Huston et al., *Proc. Natl. Acad. Sci U.S.A.,* 85: 5879-5883, 1988; Chaudhary et al., *Proc. Natl. Acad. Sci U.S.A.,* 87: 1066-1070, 1990; Brinkman et al., *J. Immunol. Methods* 182: 41-50, 1995; Ames et al., *J. Immunol. Methods* 184: 177-186, 1995; Kettleborough et al., *Eur. J. Immunol.* 24: 952-958, 1994; Persic et al., *Gene* 187: 9-18, 1997; Burton et al., *Advances in Immunology* 57: 191-280, 1994; PCT/GB91/01134; WO 90/02809; WO 91/10737; WO 92/01047; WO 92/18619; WO 93/11236; WO 95/15982; WO 95/20401; WO 96/06213; WO 92/01047 (Medical Research Council et al.); WO 97/08320 (Morphosys); WO 92/01047 (CAT/MRC); WO 91/17271 (Affymax); and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743. Methods useful for displaying polypeptides on the surface of bacteriophage particles by attaching the polypeptides via disulfide bonds have been described by Lohning, U.S. Pat. No. 6,753,136. As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and $F(ab')_2$ fragments can also be employed using methods known in the art such as those disclosed in WO 92/22324; Mullinax et al., *BioTechniques* 12: 864-869, 1992; and Sawai et al., *AJRI* 34: 26-34, 1995; and Better et al., *Science* 240: 1041-1043, 1988.

Generally, hybrid antibodies or hybrid antibody fragments that are cloned into a display vector can be selected against the appropriate antigen in order to identify variants that maintain good binding activity, because the antibody or antibody fragment will be present on the surface of the phage or phagemid particle. See, e.g., Barbas III et al., *Phage Display, A Laboratory Manual* (Cold Spring Harbor Laboratory Press, Cold Spring Harbor, N.Y., 2001). However, other vector formats could be used for this process, such as cloning the antibody fragment library into a lytic phage vector (modified T7 or Lambda Zap systems) for selection and/or screening.

Expression of Recombinant Anti-CD22 Antibodies. As noted above, the antibodies of the present technology can be produced through the application of recombinant DNA technology. Recombinant polynucleotide constructs encoding an anti-CD22 antibody of the present technology typically include an expression control sequence operably-linked to the coding sequences of anti-CD22 antibody chains, including naturally-associated or heterologous promoter regions. As such, another aspect of the technology includes vectors containing one or more nucleic acid sequences encoding an anti-CD22 antibody of the present technology. For recombinant expression of one or more of the polypeptides of the present technology, the nucleic acid containing all or a portion of the nucleotide sequence encoding the anti-CD22 antibody is inserted into an appropriate cloning vector, or an expression vector (i.e., a vector that contains the necessary elements for the transcription and translation of the inserted polypeptide coding sequence) by recombinant DNA techniques well known in the art and as detailed below. Methods for producing diverse populations of vectors have been described by Lerner et al., U.S. Pat. Nos. 6,291,160 and 6,680,192.

In general, expression vectors useful in recombinant DNA techniques are often in the form of plasmids. In the present disclosure, "plasmid" and "vector" can be used interchangeably as the plasmid is the most commonly used form of vector. However, the present technology is intended to include such other forms of expression vectors that are not technically plasmids, such as viral vectors (e.g., replication defective retroviruses, adenoviruses and adeno-associated viruses), which serve equivalent functions. Such viral vectors permit infection of a subject and expression of a construct in that subject. In some embodiments, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences encoding the anti-CD22 antibody, and the collection and purification of the anti-CD22 antibody, e.g., cross-reacting anti-CD22 antibodies. See generally, U.S. 2002/0199213. These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences. Vectors can also encode signal peptide, e.g., pectate lyase, useful to direct the secretion of extracellular antibody fragments. See U.S. Pat. No. 5,576,195.

The recombinant expression vectors of the present technology comprise a nucleic acid encoding a protein with CD22 binding properties in a form suitable for expression of the nucleic acid in a host cell, which means that the recombinant expression vectors include one or more regulatory sequences, selected on the basis of the host cells to be used for expression that is operably-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, e.g., in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, etc. Typical regulatory sequences useful as promoters of recombinant polypeptide expression (e.g., anti-CD22 antibody), include, e.g., but are not limited to, promoters of 3-phosphoglycerate kinase and other glycolytic enzymes. Inducible yeast promoters include, among others, promoters from alcohol dehydrogenase, isocytochrome C, and enzymes responsible for maltose and galactose utilization. In one embodiment, a polynucleotide encoding an anti-CD22 antibody of the present technology is operably-linked to an ara B promoter and expressible in a host cell. See U.S. Pat. No. 5,028,530. The expression vectors of the present technology can be introduced into host cells to thereby produce polypeptides or peptides, including fusion polypeptides, encoded by nucleic acids as described herein (e.g., anti-CD22 antibody, etc.).

Another aspect of the present technology pertains to anti-CD22 antibody-expressing host cells, which contain a nucleic acid encoding one or more anti-CD22 antibodies. The recombinant expression vectors of the present technology can be designed for expression of an anti-CD22 antibody in prokaryotic or eukaryotic cells. For example, an anti-CD22 antibody can be expressed in bacterial cells such as *Escherichia coli*, insect cells (using baculovirus expression vectors), fungal cells, e.g., yeast, yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, e.g., using T7 promoter regulatory sequences and T7 polymerase. Methods useful for the preparation and screening of polypeptides having a predetermined property, e.g., anti-CD22 antibody, via expression of stochastically generated polynucleotide sequences has been previously described. See U.S. Pat. Nos. 5,763,192; 5,723,323; 5,814,476; 5,817,483; 5,824,514; 5,976,862; 6,492,107; 6,569,641.

Expression of polypeptides in prokaryotes is most often carried out in *E. coli* with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (i) to increase expression of recombinant polypeptide; (ii) to increase the solubility of the recombinant polypeptide; and (iii) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding polypeptide, or polypeptide A, respectively, to the target recombinant polypeptide.

Examples of suitable inducible non-fusion *E. coli* expression vectors include pTrc (Amrann et al., (1988) *Gene* 69: 301-315) and pET 11d (Studier et al., GENE EXPRESSION TECHNOLOGY: METHODS IN ENZYMOLOGY 185, Academic Press, San Diego, Calif. (1990) 60-89). Methods for targeted assembly of distinct active peptide or protein domains to yield multifunctional polypeptides via polypeptide fusion has been described by Pack et al., U.S. Pat. Nos.

6,294,353; 6,692,935. One strategy to maximize recombinant polypeptide expression, e.g., an anti-CD22 antibody, in *E. coli* is to express the polypeptide in host bacteria with an impaired capacity to proteolytically cleave the recombinant polypeptide. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in the expression host, e.g., *E. coli* (See, e.g., Wada, et al., 1992. *Nucl. Acids Res.* 20: 2111-2118). Such alteration of nucleic acid sequences of the present technology can be carried out by standard DNA synthesis techniques.

In another embodiment, the anti-CD22 antibody expression vector is a yeast expression vector. Examples of vectors for expression in yeast *Saccharomyces cerevisiae* include pYepSec1 (Baldari, et al., 1987. *EMBO J.* 6: 229-234), pMFa (Kurjan and Herskowitz, *Cell* 30: 933-943, 1982), pJRY88 (Schultz et al., *Gene* 54: 113-123, 1987), pYES2 (Invitrogen Corporation, San Diego, Calif.), and picZ (Invitrogen Corp, San Diego, Calif.). Alternatively, an anti-CD22 antibody can be expressed in insect cells using baculovirus expression vectors. Baculovirus vectors available for expression of polypeptides, e.g., anti-CD22 antibody, in cultured insect cells (e.g., SF9 cells) include the pAc series (Smith, et al., *Mol. Cell. Biol.* 3: 2156-2165, 1983) and the pVL series (Lucklow and Summers, 1989. *Virology* 170: 31-39).

In yet another embodiment, a nucleic acid encoding an anti-CD22 antibody of the present technology is expressed in mammalian cells using a mammalian expression vector. Examples of mammalian expression vectors include, e.g., but are not limited to, pCDM8 (Seed, *Nature* 329: 840, 1987) and pMT2PC (Kaufman, et al., *EMBO J.* 6: 187-195, 1987). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells that are useful for expression of the anti-CD22 antibody of the present technology, see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid in a particular cell type (e.g., tissue-specific regulatory elements). Tissue-specific regulatory elements are known in the art. Non-limiting examples of suitable tissue-specific promoters include the albumin promoter (liver-specific; Pinkert, et al., *Genes Dev.* 1: 268-277, 1987), lymphoid-specific promoters (Calame and Eaton, *Adv. Immunol.* 43: 235-275, 1988), promoters of T cell receptors (Winoto and Baltimore, *EMBO J.* 8: 729-733, 1989) and immunoglobulins (Banerji, et al., 1983. *Cell* 33: 729-740; Queen and Baltimore, *Cell* 33: 741-748, 1983.), neuron-specific promoters (e.g., the neurofilament promoter; Byrne and Ruddle, *Proc. Natl. Acad. Sci. USA* 86: 5473-5477, 1989), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, *Science* 249: 374-379, 1990) and the α-fetoprotein promoter (Campes and Tilghman, *Genes Dev.* 3: 537-546, 1989).

Another aspect of the present methods pertains to host cells into which a recombinant expression vector of the present technology has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an anti-CD22 antibody can be expressed in bacterial cells such as *E. coli*, insect cells, yeast or mammalian cells. Mammalian cells are a suitable host for expressing nucleotide segments encoding immunoglobulins or fragments thereof. See Winnacker, *From Genes To Clones*, (VCH Publishers, N Y, 1987). A number of suitable host cell lines capable of secreting intact heterologous proteins have been developed in the art, and include Chinese hamster ovary (CHO) cell lines, various COS cell lines, HeLa cells, L cells and myeloma cell lines. In some embodiments, the cells are non-human. Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Queen et al., *Immunol. Rev.* 89: 49, 1986. Illustrative expression control sequences are promoters derived from endogenous genes, cytomegalovirus, SV40, adenovirus, bovine papillomavirus, and the like. Co et al., *J Immunol.* 148: 1149, 1992. Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, electroporation, biolistics or viral-based transfection. Other methods used to transform mammalian cells include the use of polybrene, protoplast fusion, liposomes, electroporation, and microinjection (See generally, Sambrook et al., *Molecular Cloning*). Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals. The vectors containing the DNA segments of interest can be transferred into the host cell by well-known methods, depending on the type of cellular host.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the anti-CD22 antibody or can be introduced on a separate vector. Cells stably transfected with the introduced nucleic acid can be identified by drug selection (e.g., cells that have incorporated the selectable marker gene will survive, while the other cells die).

A host cell that includes an anti-CD22 antibody of the present technology, such as a prokaryotic or eukaryotic host cell in culture, can be used to produce (i.e., express) recombinant anti-CD22 antibody. In one embodiment, the method comprises culturing the host cell (into which a recombinant expression vector encoding the anti-CD22 antibody has been introduced) in a suitable medium such that the anti-CD22 antibody is produced. In another embodiment, the method further comprises the step of isolating the anti-CD22 antibody from the medium or the host cell. Once expressed, collections of the anti-CD22 antibody, e.g., the anti-CD22 antibodies or the anti-CD22 antibody-related polypeptides are purified from culture media and host cells. The anti-CD22 antibody can be purified according to standard procedures of the art, including HPLC purification, column chromatography, gel electrophoresis and the like. In one embodiment, the anti-CD22 antibody is produced in a host organism by the method of Boss et al., U.S. Pat. No. 4,816,397. Usually, anti-CD22 antibody chains are expressed with signal sequences and are thus released to the culture media. However, if the anti-CD22 antibody chains are not naturally secreted by host cells, the anti-CD22 antibody chains can be released by treatment with mild detergent. Purification of recombinant polypeptides is well known in the art and includes ammonium sulfate precipitation, affinity chromatography purification technique, column chromatography, ion exchange purification technique, gel electrophoresis and the like (See generally Scopes, Protein Purification (Springer-Verlag, N.Y., 1982).

Polynucleotides encoding anti-CD22 antibodies, e.g., the anti-CD22 antibody coding sequences, can be incorporated in transgenes for introduction into the genome of a transgenic animal and subsequent expression in the milk of the transgenic animal. See, e.g., U.S. Pat. Nos. 5,741,957, 5,304,489, and 5,849,992. Suitable transgenes include coding sequences for light and/or heavy chains in operable linkage with a promoter and enhancer from a mammary gland specific gene, such as casein or β-lactoglobulin. For production of transgenic animals, transgenes can be microinjected into fertilized oocytes, or can be incorporated into the genome of embryonic stem cells, and the nuclei of such cells transferred into enucleated oocytes.

Single-Chain Antibodies. In one embodiment, the anti-CD22 antibody of the present technology is a single-chain anti-CD22 antibody. According to the present technology, techniques can be adapted for the production of single-chain antibodies specific to a CD22 protein (See, e.g., U.S. Pat. No. 4,946,778). Examples of techniques which can be used to produce single-chain Fvs and antibodies of the present technology include those described in U.S. Pat. Nos. 4,946,778 and 5,258,498; Huston et al., *Methods in Enzymology,* 203: 46-88, 1991; Shu, L. et al., *Proc. Natl. Acad. Sci. USA,* 90: 7995-7999, 1993; and Skerra et al., *Science* 240: 1038-1040, 1988.

Chimeric and Humanized Antibodies. In one embodiment, the anti-CD22 antibody of the present technology is a chimeric anti-CD22 antibody. In one embodiment, the anti-CD22 antibody of the present technology is a humanized anti-CD22 antibody. In one embodiment of the present technology, the donor and acceptor antibodies are monoclonal antibodies from different species. For example, the acceptor antibody is a human antibody (to minimize its antigenicity in a human), in which case the resulting CDR-grafted antibody is termed a "humanized" antibody.

Recombinant anti-CD22 antibodies, such as chimeric and humanized monoclonal antibodies, comprising both human and non-human portions, can be made using standard recombinant DNA techniques, and are within the scope of the present technology. For some uses, including in vivo use of the anti-CD22 antibody of the present technology in humans as well as use of these agents in in vitro detection assays, it is possible to use chimeric or humanized anti-CD22 antibodies. Such chimeric and humanized monoclonal antibodies can be produced by recombinant DNA techniques known in the art. Such useful methods include, e.g., but are not limited to, methods described in International Application No. PCT/US86/02269; U.S. Pat. No. 5,225,539; European Patent No. 184187; European Patent No. 171496; European Patent No. 173494; PCT International Publication No. WO 86/01533; U.S. Pat. Nos. 4,816,567; 5,225,539; European Patent No. 125023; Better, et al., 1988. *Science* 240: 1041-1043; Liu, et al., 1987. *Proc. Natl. Acad. Sci. USA* 84: 3439-3443; Liu, et al., 1987. *J. Immunol.* 139: 3521-3526; Sun, et al., 1987. *Proc. Natl. Acad. Sci. USA* 84: 214-218; Nishimura, et al., 1987. *Cancer Res.* 47: 999-1005; Wood, et al., 1985. *Nature* 314: 446-449; Shaw, et al., 1988. *J. Natl. Cancer Inst.* 80: 1553-1559; Morrison (1985) *Science* 229: 1202-1207; Oi, et al. (1986) *BioTechniques* 4: 214; Jones, et al., 1986. *Nature* 321: 552-525; Verhoeyan, et al., 1988. *Science* 239: 1534; Morrison, *Science* 229: 1202, 1985; Oi et al., *BioTechniques* 4: 214, 1986; Gillies et al., *J. Immunol. Methods,* 125: 191-202, 1989; U.S. Pat. No. 5,807,715; and Beidler, et al., 1988. *J. Immunol.* 141: 4053-4060. For example, antibodies can be humanized using a variety of techniques including CDR-grafting (EP 0 239 400; WO 91/09967; U.S. Pat. Nos. 5,530,101; 5,585,089; 5,859,205; 6,248,516; EP460167), veneering or resurfacing (EP 0 592 106; EP 0 519 596; Padlan E. A., *Molecular Immunology,* 28: 489-498, 1991; Studnicka et al., *Protein Engineering* 7: 805-814, 1994; Roguska et al., *PNAS* 91: 969-973, 1994), and chain shuffling (U.S. Pat. No. 5,565,332). In one embodiment, a cDNA encoding a murine anti-CD22 monoclonal antibody is digested with a restriction enzyme selected specifically to remove the sequence encoding the Fc constant region, and the equivalent portion of a cDNA encoding a human Fc constant region is substituted (See Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 125,023; Better et al. (1988) *Science* 240: 1041-1043; Liu et al. (1987) *Proc. Natl. Acad. Sci. USA* 84: 3439-3443; Liu et al. (1987) *J Immunol* 139: 3521-3526; Sun et al. (1987) *Proc. Natl. Acad. Sci. USA* 84: 214-218; Nishimura et al. (1987) *Cancer Res* 47: 999-1005; Wood et al. (1985) *Nature* 314: 446-449; and Shaw et al. (1988) *J. Natl. Cancer Inst.* 80: 1553-1559; U.S. Pat. Nos. 6,180,370; 6,300,064; 6,696,248; 6,706,484; 6,828,422.

In one embodiment, the present technology provides the construction of humanized anti-CD22 antibodies that are unlikely to induce a human anti-mouse antibody (hereinafter referred to as "HAMA") response, while still having an effective antibody effector function. As used herein, the terms "human" and "humanized", in relation to antibodies, relate to any antibody which is expected to elicit a therapeutically tolerable weak immunogenic response in a human subject. In one embodiment, the present technology provides for a humanized anti-CD22 antibodies, heavy and light chain immunoglobulins.

CDR Antibodies. In some embodiments, the anti-CD22 antibody of the present technology is an anti-CD22 CDR antibody. Generally, the donor and acceptor antibodies used to generate the anti-CD22 CDR antibody are monoclonal antibodies from different species; typically, the acceptor antibody is a human antibody (to minimize its antigenicity in a human), in which case the resulting CDR-grafted antibody is termed a "humanized" antibody. The graft may be of a single CDR (or even a portion of a single CDR) within a single $V_H$ or $V_L$ of the acceptor antibody, or can be of multiple CDRs (or portions thereof) within one or both of the $V_H$ and $V_L$. Frequently, all three CDRs in all variable domains of the acceptor antibody will be replaced with the corresponding donor CDRs, though one needs to replace only as many as necessary to permit adequate binding of the resulting CDR-grafted antibody to CD22 protein. Methods for generating CDR-grafted and humanized antibodies are taught by Queen et al. U.S. Pat. Nos. 5,585,089; 5,693,761; 5,693,762; and Winter U.S. Pat. No. 5,225,539; and EP 0682040. Methods useful to prepare $V_H$ and $V_L$ polypeptides are taught by Winter et al., U.S. Pat. Nos. 4,816,397; 6,291,158; 6,291,159; 6,291,161; 6,545,142; EP 0368684; EP0451216; and EP0120694.

After selecting suitable framework region candidates from the same family and/or the same family member, either or both the heavy and light chain variable regions are produced by grafting the CDRs from the originating species into the hybrid framework regions. Assembly of hybrid antibodies or hybrid antibody fragments having hybrid variable chain regions with regard to either of the above aspects can be accomplished using conventional methods known to those skilled in the art. For example, DNA sequences encoding the hybrid variable domains described herein (i.e., frameworks based on the target species and CDRs from the originating species) can be produced by oligonucleotide synthesis and/or PCR. The nucleic acid encoding CDR regions can also be isolated from the originating species antibodies using suitable restriction enzymes and ligated into the target species framework by ligating with suitable ligation enzymes. Alternatively, the framework regions of the variable chains of the originating species antibody can be changed by site-directed mutagenesis.

Since the hybrids are constructed from choices among multiple candidates corresponding to each framework region, there exist many combinations of sequences which are amenable to construction in accordance with the principles described herein. Accordingly, libraries of hybrids can be assembled having members with different combinations of individual framework regions. Such libraries can be electronic database collections of sequences or physical collections of hybrids.

This process typically does not alter the acceptor antibody's FRs flanking the grafted CDRs. However, one skilled in the art can sometimes improve antigen binding affinity of the resulting anti-CD22 CDR-grafted antibody by replacing certain residues of a given FR to make the FR more similar to the corresponding FR of the donor antibody. Suitable locations of the substitutions include amino acid residues adjacent to the CDR, or which are capable of interacting with a CDR (See, e.g., U.S. Pat. No. 5,585,089, especially columns 12-16). Or one skilled in the art can start with the donor FR and modify it to be more similar to the acceptor FR or a human consensus FR. Techniques for making these modifications are known in the art. Particularly if the resulting FR fits a human consensus FR for that position, or is at least 90% or more identical to such a consensus FR, doing so may not increase the antigenicity of the resulting modified anti-CD22 CDR-grafted antibody significantly compared to the same antibody with a fully human FR.

Bispecific Antibodies (BsAbs). A bispecific antibody is an antibody that can bind simultaneously to two targets that have a distinct structure, e.g., two different target antigens, two different epitopes on the same target antigen, or a hapten and a target antigen or epitope on a target antigen. BsAbs can be made, for example, by combining heavy chains and/or light chains that recognize different epitopes of the same or different antigen. In some embodiments, by molecular function, a bispecific binding agent binds one antigen (or epitope) on one of its two binding arms (one $V_H/V_L$ pair), and binds a different antigen (or epitope) on its second arm (a different $V_H/V_L$ pair). By this definition, a bispecific binding agent has two distinct antigen binding arms (in both specificity and CDR sequences), and is monovalent for each antigen to which it binds.

Bispecific antibodies (BsAb) and bispecific antibody fragments (BsFab) of the present technology have at least one arm that specifically binds to, for example, CD22 and at least one other arm that specifically binds to a second target antigen. In some embodiments, the second target antigen is an antigen or epitope of a B-cell, a T-cell, a myeloid cell, a plasma cell, or a mast-cell. Additionally or alternatively, in certain embodiments, the second target antigen is selected from the group consisting of CD3, CD4, CD8, CD20, CD19, CD21, CD23, CD46, CD80, HLA-DR, CD74, CD22, CD14, CD15, CD16, CD123, TCR gamma/delta, NKp46 and KIR. In certain embodiments, the BsAbs are capable of binding to tumor cells that express CD22 antigen on the cell surface. In some embodiments, the BsAbs have been engineered to facilitate killing of tumor cells by directing (or recruiting) cytotoxic T cells to a tumor site. Other exemplary BsAbs include those with a first antigen binding site specific for CD22 and a second antigen binding site specific for a small molecule hapten (e.g., DTP A, IMP288, DOTA, DOTA-Bn, DOTA-desferrioxamine, other DOTA-chelates described herein, Biotin, fluorescein, or those disclosed in Goodwin, D A. et al, 1994, *Cancer Res.* 54(22):5937-5946).

A variety of bispecific fusion proteins can be produced using molecular engineering. For example, BsAbs have been constructed that either utilize the full immunoglobulin framework (e.g., IgG), single chain variable fragment (scFv), or combinations thereof. In some embodiments, the bispecific fusion protein is divalent, comprising, for example, a scFv with a single binding site for one antigen and a Fab fragment with a single binding site for a second antigen. In some embodiments, the bispecific fusion protein is divalent, comprising, for example, an scFv with a single binding site for one antigen and another scFv fragment with a single binding site for a second antigen. In other embodiments, the bispecific fusion protein is tetravalent, comprising, for example, an immunoglobulin (e.g., IgG) with two binding sites for one antigen and two identical scFvs for a second antigen. BsAbs composed of two scFv units in tandem have been shown to be a clinically successful bispecific antibody format. In some embodiments, BsAbs comprise two single chain variable fragments (scFvs) in tandem have been designed such that an scFv that binds a tumor antigen (e.g., CD22) is linked with an scFv that engages T cells (e.g., by binding CD3). In this way, T cells are recruited to a tumor site such that they can mediate cytotoxic killing of the tumor cells. See e.g., Dreier et al., *J. Immunol.* 170:4397-4402 (2003); Bargou et al., *Science*

321:974-977 (2008)). In some embodiments, BsAbs of the present technology comprise two single chain variable fragments (scFvs) in tandem have been designed such that an scFv that binds a tumor antigen (e.g., CD22) is linked with an scFv that engages a small molecule DOTA hapten.

Recent methods for producing BsAbs include engineered recombinant monoclonal antibodies which have additional cysteine residues so that they crosslink more strongly than the more common immunoglobulin isotypes. See, e.g., FitzGerald et al., *Protein Eng.* 10(10):1221-1225 (1997). Another approach is to engineer recombinant fusion proteins linking two or more different single-chain antibody or antibody fragment segments with the needed dual specificities. See, e.g., Coloma et al., *Nature Biotech.* 15:159-163 (1997). A variety of bispecific fusion proteins can be produced using molecular engineering.

Bispecific fusion proteins linking two or more different single-chain antibodies or antibody fragments are produced in a similar manner. Recombinant methods can be used to produce a variety of fusion proteins. In some certain embodiments, a BsAb according to the present technology comprises an immunoglobulin, which immunoglobulin comprises a heavy chain and a light chain, and an scFv. In some certain embodiments, the scFv is linked to the C-terminal end of the heavy chain of any CD22 immunoglobulin disclosed herein. In some certain embodiments, scFvs are linked to the C-terminal end of the light chain of any CD22 immunoglobulin disclosed herein. In various embodiments, scFvs are linked to heavy or light chains via a linker sequence. Appropriate linker sequences necessary for the in-frame connection of the heavy chain Fd to the scFv are introduced into the $V_L$ and $V_{kappa}$ domains through PCR reactions. The DNA fragment encoding the scFv is then ligated into a staging vector containing a DNA sequence encoding the $CH_1$ domain. The resulting scFv-$CH_1$ construct is excised and ligated into a vector containing a DNA sequence encoding the $V_H$ region of a CD22 antibody. The resulting vector can be used to transfect an appropriate host cell, such as a mammalian cell for the expression of the bispecific fusion protein.

In some embodiments, a linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide (e.g., first and/or second antigen binding sites). In some embodiments, a linker is employed in a BsAb described herein based on specific properties imparted to the BsAb such as, for example, an increase in stability. In some embodiments, a BsAb of the present technology comprises a $G_4S$ linker (SEQ ID NO: 105). In some certain embodiments, a BsAb of the present technology comprises a $(G_4S)_n$ linker (SEQ ID NO: 106), wherein n is 1, 2, 3, 4, 5, 6, 7, 8, 9, 10, 11, 12, 13, 14, 15 or more.

Self assembly disassembly (SADA) Conjugates. In some embodiments, the anti-CD22 antibodies of the present technology comprise one or more SADA domains. SADA domains can be designed and/or tailored to achieve environmentally-dependent multimerization with beneficial kinetic, thermodynamic, and/or pharmacologic properties. For example, it is recognized that SADA domains may be part of a conjugate that permit effective delivery of a payload to a target site of interest while minimizing the risk of off-target interactions. The anti-CD22 antibodies of the present technology may comprise a SADA domain linked to one or more binding domains. In some embodiments, such conjugates are characterized in that they multimerize to form a complex of a desired size under relevant conditions (e.g., in a solution in which the conjugate is present above a threshold concentration or pH and/or when present at a target site characterized by a relevant level or density of receptors for the payload), and disassemble to a smaller form under other conditions (e.g., absent the relevant environmental multimerization trigger).

A SADA conjugate may have improved characteristics compared to a conjugate without a SADA domain. In some embodiments, improved characteristics of a multimeric conjugate include: increased avidity/binding to a target, increased specificity for target cells or tissues, and/or extended initial serum half-life. In some embodiments, improved characteristics include that through dissociation to smaller states (e.g., dimeric or monomeric), a SADA conjugate exhibits reduced non-specific binding, decreased toxicity, and/or improved renal clearance. In some embodiments, a SADA conjugate comprises a SADA polypeptide having an amino acid sequence that shows at least 75% identity with that of a human homo-multimerizing polypeptide and is characterized by one or more multimerization dissociation constants ($K_D$).

In some embodiments, a SADA conjugate is constructed and arranged so that it adopts a first multimerization state and one or more higher-order multimerization states. In some embodiments, a first multimerization state is less than about ~70 kDa in size. In some embodiments, a first multimerization state is an unmultimerized state (e.g., a monomer or a dimer). In some embodiments, a first multimerization state is a monomer. In some embodiments, a first multimerization state is a dimer. In some embodiments, a first multimerization state is a multimerized state (e.g., a trimer or a tetramer). In some embodiments, a higher-order multimerization states is a homo-tetramer or higher-order homo-multimer greater than 150 kDa in size. In some embodiments, a higher-order homo-multimerized conjugate is stable in aqueous solution when the conjugate is present at a concentration above the SADA polypeptide $K_D$. In some embodiments, a SADA conjugate transitions from a higher-order multimerization state(s) to a first multimerization state under physiological conditions when the concentration of the conjugate is below the SADA polypeptide $K_D$.

In some embodiments, a SADA polypeptide is covalently linked to a binding domain via a linker. Any suitable linker known in the art can be used. In some embodiments, a SADA polypeptide is linked to a binding domain via a polypeptide linker. In some embodiments, a polypeptide linker is a Gly-Ser linker. In some embodiments, a polypeptide linker is or comprises a sequence of (GGGGS)n (SEQ ID NO: 107), where n represents the number of repeating GGGGS (SEQ ID NO: 105) units and is 1, 2, 3, 4, 5, 6, 7, 8, 9, 10, 11, 12, 13, 14, 15, 16, 17, 18, 19, 20, 25, 30 or more. In some embodiments, a binding domain is directly fused to a SADA polypeptide.

In some embodiments, a SADA domain is a human polypeptide or a fragment and/or derivative thereof. In some embodiments, a SADA domain is substantially non-immunogenic in a human. In some embodiments, a SADA polypeptide is stable as a multimer. In some embodiments, a SADA polypeptide lacks unpaired cysteine residues. In some embodiments, a SADA polypeptide does not have large exposed hydrophobic surfaces. In some embodiments, a SADA domain has or is predicted to have a structure comprising helical bundles that can associate in a parallel or anti-parallel orientation. In some embodiments, a SADA polypeptide is capable of reversible multimerization. In some embodiments, a SADA domain is a tetramerization domain, a heptamerization domain, a hexamerization domain or an octamerization domain. In certain embodiments, a SADA domain is a tetramerization domain. In some embodiments, a SADA domain is composed of a multimerization domains which are each composed of helical bundles that associate in a parallel or anti-parallel orientation. In some embodiments, a SADA domain is selected from the group of one of the following human proteins: p53, p63, p73, heterogeneous nuclear Ribonucleoprotein C (hnRNPC), N-terminal domain of Synaptosomal-associated protein 23 (SNAP-23), Stefin B (Cystatin B), Potassium voltage-gated channel subfamily KQT member 4 (KCNQ4), or Cyclin-D-related protein (CBFA2T1). Examples of suitable SADA domains are described in PCT/US2018/031235, which is hereby incorporated by reference in its entirety. Provided below are polypeptide sequences for exemplary SADA domains.

Human p53 tetramerization domain amino acid sequence (321-359)

(SEQ ID NO: 93)

KPLDGEYFTLQIRGRERFEMFRELNEALELKDAQAGKEP

Human p63 tetramerization domain amino acid sequence (396-450)

(SEQ ID NO: 94)

RSPDDELLYLPVRGRETYEMLLKIKESLELMQYLPQHTIETYRQQQQQHQ

HLLQKQ

Human p73 tetramerization domain amino acid sequence (348-399)

(SEQ ID NO: 95)

RHGDEDTYYLQVRGRENFEILMKLKESLELMELVPQPLVDSYRQQQQLLQR

P.

Human HNRNPC tetramerization domain amino acid sequence (194-220)

(SEQ ID NO: 96)

QAIKKELTQIKQKVDSLLENLEKIEKE

Human SNAP-23 tetramerization domain amino acid sequence (23-76)

(SEQ ID NO: 97)

STRRILGLAIESQDAGIKTITMLDEQKEQLNRIEEGLDQINKDMRETEKTL

TEL

Human Stefin B tetramerization domain amino acid sequence (2-98)

(SEQ ID NO: 98)

MCGAPSATQPATAETQHIADQVRSQLEEKENKKFPVFKAVSFKSQVVAGTN

YFIKVHVGDEDFVHLRVFQSLPHENKPLTLSNYQTNKAKHDELTYF

KCNQ4 tetramerization domain amino acid sequence (611-640)

(SEQ ID NO: 99)

DEISMMGRVVKVEKQVQSIEHKLDLLLGFY

CBFA2T1 tetramerization domain amino acid sequence (462-521)

(SEQ ID NO: 100)

TVAEAKRQAAEDALAVINQQEDSSESCWNCGRKASETCSGCNTARYCGSFC

QHKDWEKHH

In some embodiments, a SADA polypeptide is or comprises a tetramerization domain of p53, p63, p73, heterogeneous nuclear Ribonucleoprotein C (hnRNPC), N-terminal domain of Synaptosomal-associated protein 23 (SNAP-23), Stefin B (Cystatin B), Potassium voltage-gated channel subfamily KQT member 4 (KCNQ4), or Cyclin-D-related protein (CBFA2T1). In some embodiments, a SADA polypeptide is or comprises a sequence that is at least 75%, 80%, 85%, 90%, 91%, 92%, 93%, 94%, 95%, 96%, 97%, 98%, 99% or 100% identical to a sequence as set forth in any one of SEQ ID NOs: 93-100.

Fc Modifications. In some embodiments, the anti-CD22 antibodies of the present technology comprise a variant Fc region, wherein said variant Fc region comprises at least one amino acid modification relative to a wild-type Fc region (or the parental Fc region), such that said molecule has an altered affinity for an Fc receptor (e.g., an FcγR), provided that said variant Fc region does not have a substitution at positions that make a direct contact with Fc receptor based on crystallographic and structural analysis of Fc-Fc receptor interactions such as those disclosed by Sondermann et al., *Nature,* 406:267-273 (2000). Examples of positions within the Fc region that make a direct contact with an Fc receptor such as an FcγR, include amino acids 234-239 (hinge region), amino acids 265-269 (B/C loop), amino acids 297-299 (C7E loop), and amino acids 327-332 (F/G) loop.

In some embodiments, an anti-CD22 antibody of the present technology has an altered affinity for activating and/or inhibitory receptors, having a variant Fc region with one or more amino acid modifications, wherein said one or more amino acid modification is a N297 substitution with alanine, or a K322 substitution with alanine.

Glycosylation Modifications. In some embodiments, anti-CD22 antibodies of the present technology have an Fc region with variant glycosylation as compared to a parent Fc region. In some embodiments, variant glycosylation includes the absence of fucose; in some embodiments, variant glycosylation results from expression in GnT1-deficient CHO cells.

In some embodiments, the antibodies of the present technology, may have a modified glycosylation site relative to an appropriate reference antibody that binds to an antigen of interest (e.g., CD22), without altering the functionality of the antibody, e.g., binding activity to the antigen. As used herein, "glycosylation sites" include any specific amino acid sequence in an antibody to which an oligosaccharide (i.e., carbohydrates containing two or more simple sugars linked together) will specifically and covalently attach.

Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. For example, an Fc-glycoform (hCD22-IgGln) that lacks certain oligosaccharides including fucose and terminal N-acetylglucosamine may be produced in special CHO cells and exhibit enhanced ADCC effector function.

In some embodiments, the carbohydrate content of an immunoglobulin-related composition disclosed herein is modified by adding or deleting a glycosylation site. Methods for modifying the carbohydrate content of antibodies are well known in the art and are included within the present technology, see, e.g., U.S. Pat. No. 6,218,149; EP 0359096B1; U.S. Patent Publication No. US 2002/0028486; International Patent Application Publication WO 03/035835; U.S. Patent Publication No. 2003/0115614; U.S. Pat. Nos. 6,218,149; 6,472,511; all of which are incorporated herein by reference in their entirety. In some embodiments, the carbohydrate content of an antibody (or relevant portion or component thereof) is modified by deleting one or more endogenous carbohydrate moieties of the antibody. In some certain embodiments, the present technology includes deleting the glycosylation site of the Fc region of an antibody, by modifying position 297 from asparagine to alanine.

Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example N-acetylglucosaminyltransferase III (GnTIII), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al., 1999, *Nat. Biotechnol.* 17: 176-180; Davies et al., 2001, *Biotechnol. Bioeng.* 74:288-294; Shields et al., 2002, *J. Biol. Chem.* 277:26733-26740; Shinkawa et al., 2003, *J. Biol. Chem.* 278:3466-3473; U.S. Pat. No. 6,602,684; U.S. patent application Ser. No. 10/277,370; U.S. patent application Ser. No. 10/113,929; International Patent Application Publications WO 00/61739A1; WO 01/292246A1; WO 02/311140A1; WO 02/30954A1; POTILLEGENT™ technology (Biowa, Inc. Princeton, N.J.); GLYCOMAB™ glycosylation engineering technology (GLYCART biotechnology AG, Zurich, Switzerland); each of which is incorporated herein by reference in its entirety. See, e.g., International Patent Application Publication WO 00/061739; U.S. Patent Application Publication No. 2003/0115614; Okazaki et al., 2004, *JMB*, 336: 1239-49.

Fusion Proteins. In one embodiment, the anti-CD22 antibody of the present technology is a fusion protein. The anti-CD22 antibodies of the present technology, when fused to a second protein, can be used as an antigenic tag. Examples of domains that can be fused to polypeptides include not only heterologous signal sequences, but also other heterologous functional regions. The fusion does not necessarily need to be direct, but can occur through linker sequences. Moreover, fusion proteins of the present technology can also be engineered to improve characteristics of the anti-CD22 antibodies. For instance, a region of additional amino acids, particularly charged amino acids, can be added to the N-terminus of the anti-CD22 antibody to improve stability and persistence during purification from the host cell or subsequent handling and storage. Also, peptide moieties can be added to an anti-CD22 antibody to facilitate purification. Such regions can be removed prior to final preparation of the anti-CD22 antibody. The addition of peptide moieties to facilitate handling of polypeptides are familiar and routine techniques in the art. The anti-CD22 antibody of the present technology can be fused to marker sequences, such as a peptide which facilitates purification of the fused polypeptide. In select embodiments, the marker amino acid sequence is a hexa-histidine peptide (SEQ ID NO: 108), such as the tag provided in a pQE vector (QIAGEN, Inc., Chatsworth, Calif.), among others, many of which are commercially available. As described in Gentz et al., *Proc. Natl. Acad. Sci. USA* 86: 821-824, 1989, for instance, hexa-histidine (SEQ ID NO: 108) provides for convenient purification of the fusion protein. Another peptide tag useful for purification, the "HA" tag, corresponds to an epitope derived from the influenza hemagglutinin protein. Wilson et al., *Cell* 37: 767, 1984.

Thus, any of these above fusion proteins can be engineered using the polynucleotides or the polypeptides of the present technology. Also, in some embodiments, the fusion proteins described herein show an increased half-life in vivo.

Fusion proteins having disulfide-linked dimeric structures (due to the IgG) can be more efficient in binding and neutralizing other molecules compared to the monomeric secreted protein or protein fragment alone. Fountoulakis et al., *J. Biochem.* 270: 3958-3964, 1995.

Similarly, EP-A-O 464 533 (Canadian counterpart 2045869) discloses fusion proteins comprising various portions of constant region of immunoglobulin molecules together with another human protein or a fragment thereof. In many cases, the Fc part in a fusion protein is beneficial in therapy and diagnosis, and thus can result in, e.g., improved pharmacokinetic properties. See EP-A 0232 262. Alternatively, deleting or modifying the Fc part after the fusion protein has been expressed, detected, and purified, may be desired. For example, the Fc portion can hinder therapy and diagnosis if the fusion protein is used as an antigen for immunizations. In drug discovery, e.g., human proteins, such as hIL-5, have been fused with Fc portions for the purpose of high-throughput screening assays to identify antagonists of hIL-5. Bennett et al., *J. Molecular Recognition* 8: 52-58, 1995; Johanson et al., *J. Biol. Chem.,* 270: 9459-9471, 1995.

Labeled Anti-CD22 antibodies. In one embodiment, the anti-CD22 antibody of the present technology is coupled with a label moiety, i.e., detectable group. The particular label or detectable group conjugated to the anti-CD22 antibody is not a critical aspect of the technology, so long as it does not significantly interfere with the specific binding of the anti-CD22 antibody of the present technology to the CD22 protein. The detectable group can be any material having a detectable physical or chemical property. Such detectable labels have been well-developed in the field of immunoassays and imaging. In general, almost any label useful in such methods can be applied to the present technology. Thus, a label is any composition detectable by spectroscopic, photochemical, biochemical, immunochemical, electrical, optical or chemical means. Labels useful in the practice of the present technology include magnetic beads (e.g., Dynabeads™), fluorescent dyes (e.g., fluorescein isothiocyanate, Texas red, rhodamine, and the like), radiolabels (e.g., $^{3}$H, $^{14}$C, $^{35}$S, $^{125}$I, $^{121}$I, $^{131}$I, $^{112}$In, $^{99}$mTc), other imaging agents such as microbubbles (for ultrasound imaging), $^{18}$F, $^{11}$C, $^{15}$O, (for Positron emission tomography), $^{99m}$TC, $^{111}$In (for Single photon emission tomography), enzymes (e.g., horse radish peroxidase, alkaline phosphatase and others commonly used in an ELISA), and calorimetric labels such as colloidal gold or colored glass or plastic (e.g., polystyrene, polypropylene, latex, and the like) beads. Patents that describe the use of such labels include U.S. Pat. Nos. 3,817,837; 3,850,752; 3,939,350; 3,996,345; 4,277,437; 4,275,149; and 4,366,241, each incorporated herein by reference in their entirety and for all purposes. See also Handbook of Fluorescent Probes and Research Chemicals ($6^{th}$ Ed., Molecular Probes, Inc., Eugene OR).

The label can be coupled directly or indirectly to the desired component of an assay according to methods well known in the art. As indicated above, a wide variety of labels can be used, with the choice of label depending on factors such as required sensitivity, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, e.g., biotin, thyroxine, and cortisol, it can be used in conjunction with the labeled, naturally-occurring anti-ligands. Alternatively, any haptenic or antigenic compound can be used in combination with an antibody, e.g., an anti-CD22 antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds useful as labeling moieties, include, but are not limited to, e.g., fluorescein and its derivatives, rhodamine and its derivatives, dansyl, umbelliferone, and the like. Chemiluminescent compounds useful as labeling moieties, include, but are not limited to, e.g., luciferin, and 2,3-dihydrophthalazinediones, e.g., luminol. For a review of various labeling or signal-producing systems which can be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels can be detected by providing the appropriate substrates for the enzyme and detecting the resulting reaction product. Finally, simple colorimetric labels can be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies, e.g., the anti-CD22 antibodies. In this case, antigen-coated particles are agglutinated by samples comprising the target antibodies. In this format, none of the components need be labeled and the presence of the target antibody is detected by simple visual inspection.

B. Identifying and Characterizing the Anti-CD22 Antibodies of the Present Technology Methods for identifying and/or screening the anti-CD22 antibodies of the present technology. Methods useful to identify and screen antibodies against CD22 polypeptides for those that possess the desired specificity to CD22 protein (e.g., those that bind an epitope spanning the second and third Ig-like domains of CD22) include any immunologically-mediated techniques known within the art. Components of an immune response can be detected in vitro by various methods that are well known to those of ordinary skill in the art. For example, (1) cytotoxic T lymphocytes can be incubated with radioactively labeled target cells and the lysis of these target cells detected by the release of radioactivity; (2) helper T lymphocytes can be incubated with antigens and antigen presenting cells and the synthesis and secretion of cytokines measured by standard methods (Windhagen A et al., *Immunity,* 2: 373-80, 1995); (3) antigen presenting cells can be incubated with whole protein antigen and the presentation of that antigen on MHC detected by either T lymphocyte activation assays or biophysical methods (Harding et al., *Proc. Natl. Acad. Sci.,* 86: 4230-4, 1989); (4) mast cells can be incubated with reagents that cross-link their Fc-epsilon receptors and histamine release measured by enzyme immunoassay (Siraganian et al., *TIPS,* 4: 432-437, 1983); and (5) enzyme-linked immunosorbent assay (ELISA).

Similarly, products of an immune response in either a model organism (e.g., mouse) or a human subject can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., *Blood,* 72: 1310-5, 1988); (3) the proliferation of peripheral blood mononuclear cells (PBMCs) in response to mitogens or mixed lymphocyte reaction can be measured using $^{3}$H-thymidine; (4) the phagocytic capacity of granulocytes, macrophages, and other phagocytes in PBMCs can be measured by placing PBMCs in wells together with labeled particles (Peters et al., *Blood,* 72: 1310-5, 1988); and (5) the differentiation of immune system cells can be measured by labeling PBMCs with antibodies to CD molecules such as CD4 and CD8 and measuring the fraction of the PBMCs expressing these markers.

In one embodiment, anti-CD22 antibodies of the present technology are selected using display of CD22 peptides on the surface of replicable genetic packages. See, e.g., U.S. Pat. Nos. 5,514,548; 5,837,500; 5,871,907; 5,885,793; 5,969,108; 6,225,447; 6,291,650; 6,492,160; EP 585 287; EP 605522; EP 616640; EP 1024191; EP 589 877; EP 774 511; EP 844 306. Methods useful for producing/selecting a filamentous bacteriophage particle containing a phagemid genome encoding for a binding molecule with a desired specificity has been described. See, e.g., EP 774 511; U.S. Pat. Nos. 5,871,907; 5,969,108; 6,225,447; 6,291,650; 6,492,160.

In some embodiments, anti-CD22 antibodies of the present technology are selected using display of CD22 peptides on the surface of a yeast host cell. Methods useful for the isolation of scFv polypeptides by yeast surface display have been described by Kieke et al., *Protein Eng.* 1997 November; 10(11): 1303-10.

In some embodiments, anti-CD22 antibodies of the present technology are selected using ribosome display. Methods useful for identifying ligands in peptide libraries using ribosome display have been described by Mattheakis et al., *Proc. Natl. Acad. Sci. USA* 91: 9022-26, 1994; and Hanes et al., *Proc. Natl. Acad. Sci. USA* 94: 4937-42, 1997.

In certain embodiments, anti-CD22 antibodies of the present technology are selected using tRNA display of CD22 peptides. Methods useful for in vitro selection of ligands using tRNA display have been described by Merryman et al., *Chem. Biol.,* 9: 741-46, 2002.

In one embodiment, anti-CD22 antibodies of the present technology are selected using RNA display. Methods useful for selecting peptides and proteins using RNA display libraries have been described by Roberts et al. *Proc. Natl. Acad. Sci. USA,* 94: 12297-302, 1997; and Nemoto et al., *FEBS Lett.,* 414: 405-8, 1997. Methods useful for selecting peptides and proteins using unnatural RNA display libraries have been described by Frankel et al., *Curr. Opin. Struct. Biol.,* 13: 506-12, 2003.

In some embodiments, anti-CD22 antibodies of the present technology are expressed in the periplasm of gram negative bacteria and mixed with labeled CD22 protein. See WO 02/34886. In clones expressing recombinant polypeptides with affinity for CD22 protein, the concentration of the labeled CD22 protein bound to the anti-CD22 antibodies is increased and allows the cells to be isolated from the rest of the library as described in Harvey et al., *Proc. Natl. Acad. Sci.* 22: 9193-98 2004 and U.S. Pat. Publication No. 2004/0058403.

After selection of the desired anti-CD22 antibodies, it is contemplated that said antibodies can be produced in large volume by any technique known to those skilled in the art, e.g., prokaryotic or eukaryotic cell expression and the like. The anti-CD22 antibodies which are, e.g., but not limited to, anti-CD22 hybrid antibodies or fragments can be produced by using conventional techniques to construct an expression vector that encodes an antibody heavy chain in which the CDRs and, if necessary, a minimal portion of the variable region framework, that are required to retain original species antibody binding specificity (as engineered according to the techniques described herein) are derived from the originating species antibody and the remainder of the antibody is derived from a target species immunoglobulin which can be manipulated as described herein, thereby producing a vector for the expression of a hybrid antibody heavy chain.

Measurement of CD22 Binding. In some embodiments, a CD22 binding assay refers to an assay format wherein CD22 protein and an anti-CD22 antibody are mixed under conditions suitable for binding between the CD22 protein and the anti-CD22 antibody and assessing the amount of binding between the CD22 protein and the anti-CD22 antibody. The amount of binding is compared with a suitable control, which can be the amount of binding in the absence of the CD22 protein, the amount of the binding in the presence of a non-specific immunoglobulin composition, or both. The amount of binding can be assessed by any suitable method. Binding assay methods include, e.g., ELISA, radioimmunoassays, scintillation proximity assays, fluorescence energy transfer assays, liquid chromatography, membrane filtration assays, and the like. Biophysical assays for the direct measurement of CD22 protein binding to anti-CD22 antibody are, e.g., nuclear magnetic resonance, fluorescence, fluorescence polarization, surface plasmon resonance (BIACORE chips) and the like. Specific binding is determined by standard assays known in the art, e.g., radioligand binding assays, ELISA, FRET, immunoprecipitation, SPR, NMR (2D-NMR), mass spectroscopy and the like. If the specific binding of a candidate anti-CD22 antibody is at least 1 percent greater than the binding observed in the absence of the candidate anti-CD22 antibody, the candidate anti-CD22 antibody is useful as an anti-CD22 antibody of the present technology. In some embodiments, the CD22 protein is a variant that lacks the Ig-like V-type domain (e.g., residues 20-138 of CD22 polypeptide).

Measurement of CD22 Neutralization. As used here, "CD22 neutralization" refers to reduction of the activity and/or expression of CD22 protein through the binding of an anti-CD22 antibody. The capacity of anti-CD22 antibodies of the present technology to neutralize CD22 activity/expression may be assessed in vitro or in vivo using methods known in the art.

Uses of the Anti-CD22 Antibodies of the Present Technology

General. The anti-CD22 antibodies of the present technology are useful in methods known in the art relating to the localization and/or quantitation of CD22 protein (e.g., for use in measuring levels of the CD22 protein within appropriate physiological samples, for use in diagnostic methods, for use in imaging the polypeptide, and the like). Antibodies of the present technology are useful to isolate a CD22 protein by standard techniques, such as affinity chromatography, immunohistochemistry, immunofluorescence or immunoprecipitation. An anti-CD22 antibody of the present technology can facilitate the purification of natural immunoreactive CD22 proteins from biological samples, e.g., mammalian sera or cells as well as recombinantly-produced immunoreactive CD22 proteins expressed in a host system. Moreover, anti-CD22 antibodies can be used to detect an immunoreactive CD22 protein (e.g., in plasma, a cellular lysate or cell supernatant) in order to evaluate the abundance and pattern of expression of the immunoreactive polypeptide. The anti-CD22 antibodies of the present technology can be used diagnostically to monitor immunoreactive CD22 protein levels in tissue as part of a clinical testing procedure, e.g., to determine the efficacy of a given treatment regimen. As noted above, the detection can be facilitated by coupling (i.e., physically linking) the anti-CD22 antibodies of the present technology to a detectable substance.

Detection of CD22 protein. An exemplary method for detecting the presence or absence of an immunoreactive CD22 protein in a biological sample involves obtaining a biological sample from a test subject and contacting the biological sample with an anti-CD22 antibody of the present technology capable of detecting an immunoreactive CD22 protein such that the presence of an immunoreactive CD22 protein is detected in the biological sample. Detection may be accomplished by means of a detectable label attached to the antibody.

The term "labeled" with regard to the anti-CD22 antibody is intended to encompass direct labeling of the antibody by coupling (i.e., physically linking) a detectable substance to the antibody, as well as indirect labeling of the antibody by reactivity with another compound that is directly labeled, such as a secondary antibody. Examples of indirect labeling include detection of a primary antibody using a fluorescently-labeled secondary antibody and end-labeling of a DNA probe with biotin such that it can be detected with fluorescently-labeled streptavidin.

In some embodiments, the anti-CD22 antibodies disclosed herein are conjugated to one or more detectable labels. For such uses, anti-CD22 antibodies may be detectably labeled by covalent or non-covalent attachment of a chromogenic, enzymatic, radioisotopic, isotopic, fluorescent, toxic, chemiluminescent, nuclear magnetic resonance contrast agent or other label.

Examples of suitable chromogenic labels include diaminobenzidine and 4-hydroxyazo-benzene-2-carboxylic acid. Examples of suitable enzyme labels include malate dehydrogenase, staphylococcal nuclease, Δ-5-steroid isomerase, yeast-alcohol dehydrogenase, α-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is an exemplary isotope where in vivo imaging is used since its avoids the problem of dehalogenation of the $^{125}$I or $^{131}$I-labeled CD22-binding antibodies by the liver. In addition, this isotope has a more favorable gamma emission energy for imaging (Perkins et al, *Eur. J. Nucl. Med.* 70:296-301 (1985); Carasquillo et al., *J. Nucl. Med.* 25:281-287 (1987)). For example, $^{111}$In coupled to monoclonal antibodies with 1-(P-isothiocyanatobenzyl)-DPTA exhibits little uptake in non-tumorous tissues, particularly the liver, and enhances specificity of tumor localization (Esteban et al., *J. Nucl. Med.* 28:861-870 (1987)). Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, a Green Fluorescent Protein (GFP) label, an o-phthaldehyde label, and a fluorescamine label. Examples of suitable toxin labels include diphtheria toxin, ricin, and cholera toxin.

Examples of chemiluminescent labels include a luminol label, an isoluminol label, an aromatic acridinium ester label, an imidazole label, an acridinium salt label, an oxalate ester label, a luciferin label, a luciferase label, and an aequorin label. Examples of nuclear magnetic resonance contrasting agents include heavy metal nuclei such as Gd, Mn, and iron.

The detection method of the present technology can be used to detect an immunoreactive CD22 protein in a biological sample in vitro as well as in vivo. In vitro techniques for detection of an immunoreactive CD22 protein include enzyme linked immunosorbent assays (ELISAs), Western blots, immunoprecipitations, radioimmunoassay, and immunofluorescence. Furthermore, in vivo techniques for detection of an immunoreactive CD22 protein include introducing into a subject a labeled anti-CD22 antibody. For example, the anti-CD22 antibody can be labeled with a radioactive marker whose presence and location in a subject can be detected by standard imaging techniques. In one embodiment, the biological sample contains CD22 protein molecules from the test subject.

Immunoassay and Imaging. An anti-CD22 antibody of the present technology can be used to assay immunoreactive CD22 protein levels in a biological sample (e.g., human plasma) using antibody-based techniques. For example, protein expression in tissues can be studied with classical immunohistological methods. Jalkanen, M. et al., *J. Cell. Biol.* 101: 976-985, 1985; Jalkanen, M. et al., *J. Cell. Biol.* 105: 3087-3096, 1987. Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes or other radioactive agent, such as iodine ($^{125}$I, $^{121}$I $^{131}$I), carbon ($^{14}$C), sulfur ($^{35}$S), tritium ($^{3}$H), indium ($^{112}$In), and technetium ($^{99}$mTc), and fluorescent labels, such as fluorescein, rhodamine, and green fluorescent protein (GFP), as well as biotin.

In addition to assaying immunoreactive CD22 protein levels in a biological sample, anti-CD22 antibodies of the present technology may be used for in vivo imaging of CD22. Antibodies useful for this method include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which can be incorporated into the anti-CD22 antibodies by labeling of nutrients for the relevant scFv clone.

An anti-CD22 antibody which has been labeled with an appropriate detectable imaging moiety, such as a radioisotope (e.g., $^{131}$I, $^{112}$In, $^{99}$mTc), a radio-opaque substance, or a material detectable by nuclear magnetic resonance, is introduced (e.g., parenterally, subcutaneously, or intraperitoneally) into the subject. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled anti-CD22 antibody will then accumulate at the location of cells which contain the specific target polypeptide. For example, labeled anti-CD22 antibodies of the present technology will accumulate within the subject in cells and tissues in which the CD22 protein has localized.

Thus, the present technology provides a diagnostic method of a medical condition, which involves: (a) assaying the expression of immunoreactive CD22 protein by measuring binding of an anti-CD22 antibody of the present technology in cells or body fluid of an individual; (b) comparing the amount of immunoreactive CD22 protein present in the sample with a standard reference, wherein an increase or decrease in immunoreactive CD22 protein levels compared to the standard is indicative of a medical condition.

Affinity Purification. The anti-CD22 antibodies of the present technology may be used to purify immunoreactive CD22 protein from a sample. In some embodiments, the antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10 (1986); Jacoby et al., *Meth. Enzym.* 34 Academic Press, N.Y. (1974)).

The simplest method to bind the antigen to the antibody-support matrix is to collect the beads in a column and pass the antigen solution down the column. The efficiency of this method depends on the contact time between the immobilized antibody and the antigen, which can be extended by using low flow rates. The immobilized antibody captures the antigen as it flows past. Alternatively, an antigen can be contacted with the antibody-support matrix by mixing the antigen solution with the support (e.g., beads) and rotating or rocking the slurry, allowing maximum contact between the antigen and the immobilized antibody. After the binding reaction has been completed, the slurry is passed into a column for collection of the beads. The beads are washed using a suitable washing buffer and then the pure or substantially pure antigen is eluted.

An antibody or polypeptide of interest can be conjugated to a solid support, such as a bead. In addition, a first solid support such as a bead can also be conjugated, if desired, to a second solid support, which can be a second bead or other support, by any suitable means, including those disclosed herein for conjugation of a polypeptide to a support. Accordingly, any of the conjugation methods and means disclosed herein with reference to conjugation of a polypeptide to a solid support can also be applied for conjugation of a first support to a second support, where the first and second solid support can be the same or different.

Appropriate linkers, which can be cross-linking agents, for use for conjugating a polypeptide to a solid support include a variety of agents that can react with a functional group present on a surface of the support, or with the polypeptide, or both. Reagents useful as cross-linking agents include homo-bi-functional and, in particular, hetero-bi-functional reagents. Useful bi-functional cross-linking agents include, but are not limited to, N-SIAB, dimaleimide, DTNB, N-SATA, N-SPDP, SMCC and 6-HYNIC. A cross-linking agent can be selected to provide a selectively cleavable bond between a polypeptide and the solid support. For example, a photolabile cross-linker, such as 3-amino-(2-nitrophenyl)propionic acid can be employed as a means for cleaving a polypeptide from a solid support. (Brown et al., *Mol. Divers*, pp, 4-12 (1995); Rothschild et al., *Nucl. Acids Res.,* 24:351-66 (1996); and U.S. Pat. No. 5,643,722). Other cross-linking reagents are well-known in the art. (See, e.g., Wong (1991), supra; and Hermanson (1996), supra).

An antibody or polypeptide can be immobilized on a solid support, such as a bead, through a covalent amide bond formed between a carboxyl group functionalized bead and the amino terminus of the polypeptide or, conversely, through a covalent amide bond formed between an amino group functionalized bead and the carboxyl terminus of the polypeptide. In addition, a bi-functional trityl linker can be attached to the support, e.g., to the 4-nitrophenyl active ester on a resin, such as a Wang resin, through an amino group or a carboxyl group on the resin via an amino resin. Using a bi-functional trityl approach, the solid support can require treatment with a volatile acid, such as formic acid or trifluoroacetic acid to ensure that the polypeptide is cleaved and can be removed. In such a case, the polypeptide can be deposited as a beadless patch at the bottom of a well of a solid support or on the flat surface of a solid support. After addition of a matrix solution, the polypeptide can be desorbed into a MS.

Hydrophobic trityl linkers can also be exploited as acid-labile linkers by using a volatile acid or an appropriate matrix solution, e.g., a matrix solution containing 3-HPA, to cleave an amino linked trityl group from the polypeptide. Acid lability can also be changed. For example, trityl, monomethoxytrityl, dimethoxytrityl or trimethoxytrityl can be changed to the appropriate p-substituted, or more acid-labile tritylamine derivatives, of the polypeptide, i.e., trityl ether and tritylamine bonds can be made to the polypeptide. Accordingly, a polypeptide can be removed from a hydrophobic linker, e.g., by disrupting the hydrophobic attraction or by cleaving tritylether or tritylamine bonds under acidic conditions, including, if desired, under typical MS conditions, where a matrix, such as 3-HPA acts as an acid.

Orthogonally cleavable linkers can also be useful for binding a first solid support, e.g., a bead to a second solid support, or for binding a polypeptide of interest to a solid support. Using such linkers, a first solid support, e.g., a bead, can be selectively cleaved from a second solid support, without cleaving the polypeptide from the support; the polypeptide then can be cleaved from the bead at a later time. For example, a disulfide linker, which can be cleaved using a reducing agent, such as DTT, can be employed to bind a bead to a second solid support, and an acid cleavable bi-functional trityl group could be used to immobilize a polypeptide to the support. As desired, the linkage of the polypeptide to the solid support can be cleaved first, e.g., leaving the linkage between the first and second support intact. Trityl linkers can provide a covalent or hydrophobic conjugation and, regardless of the nature of the conjugation, the trityl group is readily cleaved in acidic conditions.

For example, a bead can be bound to a second support through a linking group which can be selected to have a length and a chemical nature such that high density binding of the beads to the solid support, or high density binding of the polypeptides to the beads, is promoted. Such a linking group can have, e.g., "tree-like" structure, thereby providing a multiplicity of functional groups per attachment site on a solid support. Examples of such linking group; include polylysine, polyglutamic acid, penta-erythrole and tris-hydroxy-aminomethane.

Noncovalent Binding Association. An antibody or polypeptide can be conjugated to a solid support, or a first solid support can also be conjugated to a second solid support, through a noncovalent interaction. For example, a magnetic bead made of a ferromagnetic material, which is capable of being magnetized, can be attracted to a magnetic solid support, and can be released from the support by removal of the magnetic field. Alternatively, the solid support can be provided with an ionic or hydrophobic moiety, which can allow the interaction of an ionic or hydrophobic moiety, respectively, with a polypeptide, e.g., a polypeptide containing an attached trityl group or with a second solid support having hydrophobic character.

A solid support can also be provided with a member of a specific binding pair and, therefore, can be conjugated to a polypeptide or a second solid support containing a complementary binding moiety. For example, a bead coated with avidin or with streptavidin can be bound to a polypeptide having a biotin moiety incorporated therein, or to a second solid support coated with biotin or derivative of biotin, such as iminobiotin.

It should be recognized that any of the binding members disclosed herein or otherwise known in the art can be reversed. Thus, biotin, e.g., can be incorporated into either a polypeptide or a solid support and, conversely, avidin or other biotin binding moiety would be incorporated into the support or the polypeptide, respectively. Other specific binding pairs contemplated for use herein include, but are not limited to, hormones and their receptors, enzyme, and their substrates, a nucleotide sequence and its complementary sequence, an antibody and the antigen to which it interacts specifically, and other such pairs knows to those skilled in the art.

A. Diagnostic Uses of Anti-CD22 Antibodies of the Present Technology

General. The anti-CD22 antibodies of the present technology are useful in diagnostic methods. As such, the present technology provides methods using the antibodies in the diagnosis of CD22 activity in a subject. Anti-CD22 antibodies of the present technology may be selected such that they have any level of epitope binding specificity and very high binding affinity to a CD22 protein. In general, the higher the binding affinity of an antibody the more stringent wash conditions can be performed in an immunoassay to remove nonspecifically bound material without removing target polypeptide. Accordingly, anti-CD22 antibodies of the present technology useful in diagnostic assays usually have binding affinities of about $10^8$ $M^{-1}$, $10^9$ $M^{-1}$, $10^{10}$ $M^{-1}$, $10^{-11}$ $M^{-1}$ or $10^{12}$ $M^{-1}$. Further, it is desirable that anti-CD22 antibodies used as diagnostic reagents have a sufficient kinetic on-rate to reach equilibrium under standard conditions in at least 12 h, at least five (5) h, or at least one (1) hour.

Anti-CD22 antibodies can be used to detect an immunoreactive CD22 protein in a variety of standard assay formats. Such formats include immunoprecipitation, Western blotting, ELISA, radioimmunoassay, and immunometric assays. See Harlow & Lane, *Antibodies, A Laboratory Manual* (Cold Spring Harbor Publications, New York, 1988); U.S. Pat. Nos. 3,791,932; 3,839,153; 3,850,752; 3,879,262; 4,034,074, 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Biological samples can be obtained from any tissue or body fluid of a subject. In certain embodiments, the subject is at an early stage of cancer. In one embodiment, the early stage of cancer is determined by the level or expression pattern of CD22 protein in a sample obtained from the subject. In certain embodiments, the sample is selected from the group consisting of urine, blood, serum, plasma, saliva, amniotic fluid, cerebrospinal fluid (CSF), and biopsied body tissue.

Immunometric or sandwich assays are one format for the diagnostic methods of the present technology. See U.S. Pat. Nos. 4,376,110, 4,486,530, 5,914,241, and 5,965,375. Such assays use one antibody, e.g., an anti-CD22 antibody or a population of anti-CD22 antibodies immobilized to a solid phase, and another anti-CD22 antibody or a population of anti-CD22 antibodies in solution. Typically, the solution anti-CD22 antibody or population of anti-CD22 antibodies is labeled. If an antibody population is used, the population can contain antibodies binding to different epitope specificities within the target polypeptide. Accordingly, the same population can be used for both solid phase and solution antibody. If anti-CD22 monoclonal antibodies are used, first and second CD22 monoclonal antibodies having different binding specificities are used for the solid and solution phase. Solid phase (also referred to as "capture") and solution (also referred to as "detection") antibodies can be contacted with target antigen in either order or simultaneously. If the solid phase antibody is contacted first, the assay is referred to as being a forward assay. Conversely, if the solution antibody is contacted first, the assay is referred to as being a reverse assay. If the target is contacted with both antibodies simultaneously, the assay is referred to as a simultaneous assay. After contacting the CD22 protein with the anti-CD22 antibody, a sample is incubated for a period that usually varies from about 10 min to about 24 hr and is usually about 1 hr. A wash step is then performed to remove components of the sample not specifically bound to the anti-CD22 antibody being used as a diagnostic reagent. When solid phase and solution antibodies are bound in separate steps, a wash can be performed after either or both binding steps. After washing, binding is quantified, typically by detecting a label linked to the solid phase through binding of labeled solution antibody. Usually for a given pair of antibodies or populations of antibodies and given reaction conditions, a calibration curve is prepared from samples containing known concentrations of target antigen. Concentrations of the immunoreactive CD22 protein in samples being tested are then read by interpolation from the calibration curve (i.e., standard curve). Analyte can be measured either from the amount of labeled solution antibody bound at equilibrium or by kinetic measurements of bound labeled solution antibody at a series of time points before equilibrium is reached. The slope of such a curve is a measure of the concentration of the CD22 protein in a sample.

Suitable supports for use in the above methods include, e.g., nitrocellulose membranes, nylon membranes, and derivatized nylon membranes, and also particles, such as agarose, a dextran-based gel, dipsticks, particulates, microspheres, magnetic particles, test tubes, microtiter wells, SEPHADEX™ (Amersham Pharmacia Biotech, Piscataway N.J.), and the like. Immobilization can be by absorption or by covalent attachment. Optionally, anti-CD22 antibodies can be joined to a linker molecule, such as biotin for attachment to a surface bound linker, such as avidin.

In some embodiments, the present disclosure provides an anti-CD22 antibody of the present technology conjugated to a diagnostic agent. The diagnostic agent may comprise a radioactive or non-radioactive label, a contrast agent (such as for magnetic resonance imaging, computed tomography or ultrasound), and the radioactive label can be a gamma-, beta-, alpha-, Auger electron-, or positron-emitting isotope. A diagnostic agent is a molecule which is administered conjugated to an antibody moiety, i.e., antibody or antibody fragment, or subfragment, and is useful in diagnosing or detecting a disease by locating the cells containing the antigen.

Useful diagnostic agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MRI). U.S. Pat. No. 6,331,175 describes MRI technique and the preparation of antibodies conjugated to a MRI enhancing agent and is incorporated in its entirety by reference. In some embodiments, the diagnostic agents are selected from the group consisting of radioisotopes, enhancing agents for use in magnetic resonance imaging, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates may be coupled to the antibodies of the present technology using standard chemistries. The chelate is normally linked to the antibody by a group which enables formation of a bond to the molecule with minimal loss of immunoreactivity and minimal aggregation and/or internal cross-linking. Other methods and reagents for conjugating chelates to antibodies are disclosed in U.S. Pat. No. 4,824,659. Particularly useful metal-chelate combinations include 2-benzyl-DTPA and its monomethyl and cyclohexyl analogs, used with diagnostic isotopes for radio-imaging. The same chelates, when complexed with non-radioactive metals, such as manganese, iron and gadolinium are useful for MRI, when used along with the CD22 antibodies of the present technology.

Macrocyclic chelates such as NOTA (1,4,7-triaza-cyclononane-N,N',N"-triacetic acid), DOTA, and TETA (p-bromoacetamido-benzyl-tetraethylaminetetraacetic acid) are of use with a variety of metals and radiometals, such as radionuclides of gallium, yttrium and copper, respectively. Such metal-chelate complexes can be stabilized by tailoring the ring size to the metal of interest. Examples of other DOTA chelates include (i) DOTA-Phe-Lys(HSG)-D-Tyr-Lys(HSG)-$NH_2$; (ii) Ac-Lys(HSG)D-Tyr-Lys(HSG)-Lys(Tscg-Cys)-$NH_2$; (iii) DOTA-D-Asp-D-Lys(HSG)-D-Asp-D-Lys(HSG)-$NH_2$; (iv) DOTA-D-Glu-D-Lys(HSG)-D-Glu-D-Lys(HSG)-$NH_2$; (v) DOTA-D-Tyr-D-Lys(HSG)-D-Glu-D-Lys(HSG)-$NH_2$; (vi) DOTA-D-Ala-D-Lys(HSG)-D-Glu-D-Lys(HSG)-$NH_2$; (vii) DOTA-D-Phe-D-Lys(HSG)-D-Tyr-D-Lys(HSG)-$NH_2$; (viii) Ac-D-Phe-D-Lys(DOTA)-D-Tyr-D-Lys(DOTA)-$NH_2$; (ix) Ac-D-Phe-D-Lys(DTPA)-D-Tyr-D-Lys(DTPA)-$NH_2$; (x) Ac-D-Phe-D-Lys(Bz-DTPA)-D-Tyr-D-Lys(Bz-DTPA)-$NH_2$; (xi) Ac-D-Lys(HSG)-D-Tyr-D-Lys(HSG)-D-Lys(Tscg-Cys)-$NH_2$; (xii) DOTA-D-Phe-D-Lys(HSG)-D-Tyr-D-Lys(HSG)-D-Lys(Tscg-Cys)-$NH_2$; (xiii) (Tscg-Cys)-D-Phe-D-Lys(HSG)-D-Tyr-D-Lys(HSG)-D-Lys(DOTA)-$NH_2$; (xiv) Tscg-D-Cys-D-Glu-D-Lys(HSG)-D-Glu-D-Lys(HSG)-$NH_2$; (xv) (Tscg-Cys)-D-Glu-D-Lys(HSG)-D-Glu-D-Lys(HSG)-$NH_2$; (xvi) Ac-D-Cys-D-

Lys(DOTA)-D-Tyr-D-Ala-D-Lys(DOTA)-D-Cys-$NH_2$; (xvii) Ac-D-Cys-D-Lys(DTPA)-D-Tyr-D-Lys(DTPA)-$NH_2$; (xviii) Ac-D-Lys(DTPA)-D-Tyr-D-Lys(DTPA)-D-Lys(Tscg-Cys)-$NH_2$; and (xix) Ac-D-Lys(DOTA)-D-Tyr-D-Lys (DOTA)-D-Lys(Tscg-Cys)-$NH_2$.

Other ring-type chelates such as macrocyclic polyethers, which are of interest for stably binding nuclides, such as $^{223}$Ra for RAIT are also contemplated.

B. Therapeutic Use of Anti-CD22 Antibodies of the Present Technology

The immunoglobulin-related compositions (e.g., antibodies or antigen binding fragments thereof) of the present technology are useful for the treatment of CD22-associated cancers, CD22-associated autoimmune diseases, or CD22-associated allergies. Such treatment can be used in patients identified as having pathologically high levels of the CD22 (e.g., those diagnosed by the methods described herein) or in patients diagnosed with a disease known to be associated with such pathological levels. In one aspect, the present disclosure provides a method for treating a CD22-associated cancer, a CD22-associated autoimmune disease, or a CD22-associated allergy in a subject in need thereof, comprising administering to the subject an effective amount of an antibody (or antigen binding fragment thereof) of the present technology. Examples of cancers that can be treated by the antibodies of the present technology include, but are not limited to: acute myeloid leukemia, myelodysplastic syndrome, chronic myeloid leukemia, chronic lymphocytic leukemia, Non-Hodgkin Lymphoma, multiple myeloma, Plasmacytoma, Monoclonal gammopathy of undetermined significance, Waldenström's macroglobulinemia (lymphoplasmacytic lymphoma), Heavy chain disease, primary amyloidosis, Post-transplant lymphoproliferative disorder, Hodgkin lymphoma, MALT lymphoma, B cell Lymphoma, mantle cell lymphoma, (germinal center-like) diffuse large cell lymphoma, Burkitt's lymphoma, Bilineage leukemia, biphenotypic leukemia, Hairy cell leukemia, Precursor B acute lymphoblastic leukemia/lymphoma, Primary cutaneous follicle center lymphoma, follicular lymphoma, or Marginal Zone B-cell Non-Hodgkin's Lymphoma.

The compositions of the present technology may be employed in conjunction with other therapeutic agents useful in the treatment of CD22-associated cancers. For example, the antibodies of the present technology may be separately, sequentially or simultaneously administered with at least one additional therapeutic agent-selected from the group consisting of alkylating agents, platinum agents, taxanes, vinca agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents and targeted biological therapy agents (e.g., therapeutic peptides described in U.S. Pat. No. 6,306,832, WO 2012007137, WO 2005000889, WO 2010096603 etc.). In some embodiments, the at least one additional therapeutic agent is a chemotherapeutic agent. Specific chemotherapeutic agents include, but are not limited to, cyclophosphamide, fluorouracil (or 5-fluorouracil or 5-FU), methotrexate, edatrexate (10-ethyl-10-deaza-aminopterin), thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb, anthracyclines (e.g., daunorubicin and doxorubicin), bevacizumab, oxaliplatin, melphalan, etoposide, mechlorethamine, bleomycin, microtubule poisons, annonaceous acetogenins, or combinations thereof.

The compositions of the present technology may optionally be administered as a single bolus to a subject in need thereof. Alternatively, the dosing regimen may comprise multiple administrations performed at various times after the appearance of tumors.

Examples of autoimmune diseases that can be treated by the antibodies of the present technology include, but are not limited to: multiple sclerosis (MS), rheumatoid arthritis (RA), systemic lupus erythematosus, paraneoplastic syndromes, Pemphigus Vulgaris, type 2 diabetes, and graft-versus-host diseases.

Methods for treating autoimmune diseases may further comprise sequentially, separately, or simultaneously administering to the subject at least one additional therapy selected from among non-steroidal anti-inflammatory drugs (NSAIDs), glucocorticoids, disease-modifying antirheumatic drugs (DMARDs), anti-TNF biologics, abatacept, tocilizumab, anakinra, and rituximab. Examples of NSAIDs include (1) salicylic acid derivatives such as acetylsalicylic acid (aspirin), diflunisal and sulfasalazine; (2) para-aminophenol derivatives such as acetaminophen; (3) fenamates such as mefenamic acid, meclofenamate, flufenamic acid; (4) propionic acid derivatives such as ibuprofen, naproxen, fenoprofen, ketoprofen, flurbiprofen, oxaprozin; (5) enolic acid (oxicam) derivatives such as piroxicam, tenoxicam; (6) selective COX-2 inhibitors such as meloxicam, salicylate, and nimesulide; and (7) highly selective COX-2 inhibitors such as celecoxib, rofecoxib, valdecoxib, lumiracoxib, parecoxib, and etoricoxib. Examples of glucocorticoids include prednisone/prednisolone, methylprednisolone, and fluorinated glucocorticoids such as dexamethasone and betamethasone. Examples of DMARDs include methotrexate, leflunomide, gold compounds, sulfasalazine, azathioprine, cyclophosphamide, antimalarials, D-penicillamine, cyclosporine, hydroxychloroquine, and chloroquine. Examples of anti-TNF biologics include infliximab, etanercept, adalimumab, golimumab, and certolizumab pegol.

Administration can be carried out by any suitable route, including orally, intranasally, parenterally (intravenously, intramuscularly, intraperitoneally, or subcutaneously), rectally, intracranially, intratumorally, intrathecally, or topically. Administration includes self-administration and the administration by another. It is also to be appreciated that the various modes of treatment of medical conditions as described are intended to mean "substantial", which includes total but also less than total treatment, and wherein some biologically or medically relevant result is achieved.

In some embodiments, the antibodies of the present technology comprise pharmaceutical formulations which may be administered to subjects in need thereof in one or more doses. Dosage regimens can be adjusted to provide the desired response (e.g., a therapeutic response).

Typically, an effective amount of the antibody compositions of the present technology, sufficient for achieving a therapeutic effect, range from about 0.000001 mg per kilogram body weight per day to about 10,000 mg per kilogram body weight per day. Typically, the dosage ranges are from about 0.0001 mg per kilogram body weight per day to about 100 mg per kilogram body weight per day. For administration of anti-CD22 antibodies, the dosage ranges from about 0.0001 to 100 mg/kg, and more usually 0.01 to 5 mg/kg every week, every two weeks or every three weeks, of the subject body weight. For example, dosages can be 1 mg/kg body weight or 10 mg/kg body weight every week, every two weeks or every three weeks or within the range of 1-10 mg/kg every week, every two weeks or every three weeks. In one embodiment, a single dosage of antibody ranges from 0.1-10,000 micrograms per kg body weight. In one embodiment, antibody concentrations in a carrier range from 0.2 to 2000 micrograms per delivered milliliter. An exemplary treatment regime entails administration once per every two weeks or once a month or once every 3 to 6 months. Anti-CD22 antibodies may be administered on multiple occasions. Intervals between single dosages can be hourly, daily, weekly, monthly or yearly. Intervals can also be irregular as indicated by measuring blood levels of the antibody in the subject. In some methods, dosage is adjusted to achieve a serum antibody concentration in the subject of from about 75 μg/mL to about 125 μg/mL, 100 μg/mL to about 150 μg/mL, from about 125 μg/mL to about 175 μg/mL, or from about 150 μg/mL to about 200 g/mL. Alternatively, anti-CD22 antibodies can be administered as a sustained release formulation, in which case less frequent administration is required. Dosage and frequency vary depending on the half-life of the antibody in the subject. The dosage and frequency of administration can vary depending on whether the treatment is prophylactic or therapeutic. In prophylactic applications, a relatively low dosage is administered at relatively infrequent intervals over a long period of time. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

In another aspect, the present disclosure provides a method for detecting a tumor in a subject in vivo comprising (a) administering to the subject an effective amount of an antibody (or antigen binding fragment thereof) of the present technology, wherein the antibody is configured to localize to a tumor expressing CD22 and is labeled with a radioisotope; and (b) detecting the presence of a tumor in the subject by detecting radioactive levels emitted by the antibody that are higher than a reference value. In some embodiments, the reference value is expressed as injected dose per gram (% ID/g). The reference value may be calculated by measuring the radioactive levels present in non-tumor (normal) tissues, and computing the average radioactive levels present in non-tumor (normal) tissues±standard deviation. In some embodiments, the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

In some embodiments, the subject is diagnosed with or is suspected of having cancer. Radioactive levels emitted by the antibody may be detected using positron emission tomography or single photon emission computed tomography.

Additionally or alternatively, in some embodiments, the method further comprises administering to the subject an effective amount of an immunoconjugate comprising an antibody of the present technology conjugated to a radionuclide. In some embodiments, the radionuclide is an alpha particle-emitting isotope, a beta particle-emitting isotope, an Auger-emitter, or any combination thereof. Examples of beta particle-emitting isotopes include $^{86}$Y, $^{90}$Y, $^{89}$Sr, $^{165}$Dy, $^{186}$Re, $^{188}$Re, $^{177}$Lu, and $^{67}$Cu. Examples of alpha particle-emitting isotopes include $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, and $^{255}$Fm. Examples of Auger-emitters include $^{111}$In, $^{67}$Ga, $^{51}$Cr, $^{58}$Co, $^{99m}$Tc, $^{103m}$Rh, $^{195m}$Pt, $^{119}$Sb, $^{161}$Ho, $^{189m}$Os, $^{192}$Ir, $^{201}$Tl, and $^{203}$Pb. In some embodiments of the method, nonspecific FcR-dependent binding in normal tissues is eliminated or reduced (e.g., via N297A mutation in Fc region, which results in aglycosylation). The therapeutic effectiveness of such an immunoconjugate may be determined by computing the area under the curve (AUC) tumor: AUC normal tissue ratio. In some embodiments, the immunoconjugate has a AUC tumor: AUC normal tissue ratio of about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

PRIT. In one aspect, the present disclosure provides a method for detecting tumors in a subject in need thereof comprising (a) administering to the subject an effective amount of a complex comprising a radiolabeled DOTA hapten and a bispecific antibody of the present technology that binds to the radiolabeled DOTA hapten and a CD22 antigen, wherein the complex is configured to localize to a tumor expressing the CD22 antigen recognized by the bispecific antibody of the complex; and (b) detecting the presence of solid tumors in the subject by detecting radioactive levels emitted by the complex that are higher than a reference value. In some embodiments, the subject is human.

In another aspect, the present disclosure provides a method for selecting a subject for pretargeted radioimmunotherapy comprising (a) administering to the subject an effective amount of a complex comprising a radiolabeled DOTA hapten and a bispecific antibody of the present technology that binds to the radiolabeled DOTA hapten and a CD22 antigen, wherein the complex is configured to localize to a tumor expressing the CD22 antigen recognized by the bispecific antibody of the complex; (b) detecting radioactive levels emitted by the complex; and (c) selecting the subject for pretargeted radioimmunotherapy when the radioactive levels emitted by the complex are higher than a reference value. In some embodiments, the subject is human.

Examples of DOTA haptens include (i) DOTA-Phe-Lys(HSG)-D-Tyr-Lys(HSG)-$NH_2$; (ii) Ac-Lys(HSG)D-Tyr-Lys(HSG)-Lys(Tscg-Cys)-$NH_2$; (iii) DOTA-D-Asp-D-Lys(HSG)-D-Asp-D-Lys(HSG)-$NH_2$; (iv) DOTA-D-Glu-D-Lys(HSG)-D-Glu-D-Lys(HSG)-$NH_2$; (v) DOTA-D-Tyr-D-Lys(HSG)-D-Glu-D-Lys(HSG)-$NH_2$; (vi) DOTA-D-Ala-D-Lys(HSG)-D-Glu-D-Lys(HSG)-$NH_2$; (vii) DOTA-D-Phe-D-Lys(HSG)-D-Tyr-D-Lys(HSG)-$NH_2$; (viii) Ac-D-Phe-D-Lys(DOTA)-D-Tyr-D-Lys(DOTA)-$NH_2$; (ix) Ac-D-Phe-D-Lys(DTPA)-D-Tyr-D-Lys(DTPA)-$NH_2$; (x) Ac-D-Phe-D-Lys(Bz-DTPA)-D-Tyr-D-Lys(Bz-DTPA)-$NH_2$; (xi) Ac-D-Lys(HSG)-D-Tyr-D-Lys(HSG)-D-Lys(Tscg-Cys)-$NH_2$; (xii) DOTA-D-Phe-D-Lys(HSG)-D-Tyr-D-Lys(HSG)-D-Lys(Tscg-Cys)-$NH_2$; (xiii) (Tscg-Cys)-D-Phe-D-Lys(HSG)-D-Tyr-D-Lys(HSG)-D-Lys(DOTA)-$NH_2$; (xiv) Tscg-D-Cys-D-Glu-D-Lys(HSG)-D-Glu-D-Lys(HSG)-$NH_2$; (xv) (Tscg-Cys)-D-Glu-D-Lys(HSG)-D-Glu-D-Lys(HSG)-$NH_2$; (xvi) Ac-D-Cys-D-Lys(DOTA)-D-Tyr-D-Ala-D-Lys(DOTA)-D-Cys-$NH_2$; (xvii) Ac-D-Cys-D-Lys(DTPA)-D-Tyr-D-Lys(DTPA)-$NH_2$; (xviii) Ac-D-Lys(DTPA)-D-Tyr-D-Lys(DTPA)-D-Lys(Tscg-Cys)-$NH_2$; (xix) Ac-D-Lys(DOTA)-D-Tyr-D-Lys(DOTA)-D-Lys(Tscg-Cys)-$NH_2$ and (xx) DOTA. The radiolabel may be an alpha particle-emitting isotope, a beta particle-emitting isotope, or an Auger-emitter. Examples of radiolabels include $^{213}$Bi, $^{211}$At, $^{225}$Ac, $^{152}$Dy, $^{212}$Bi, $^{223}$Ra, $^{219}$Rn, $^{215}$Po, $^{211}$Bi, $^{221}$Fr, $^{217}$At, $^{255}$Fm, $^{86}$Y $^{90}$Y, $^{89}$Sr, $^{165}$Dy, $^{186}$Re, $^{188}$Re, $^{177}$Lu, $^{67}$Cu, $^{111}$In, $^{67}$Ga, $^{51}Cr$, $^{58}Co$, $^{99m}Tc$, $^{103m}Rh$, $^{195m}Pt$, $^{119}Sb$, $^{161}Ho$, $^{189m}Os$, $^{192}Ir$, $^{201}Tl$, $^{203}Pb$, $^{68}Ga$, $^{227}Th$, or $^{64}Cu$.

In some embodiments of the methods disclosed herein, the radioactive levels emitted by the complex are detected using positron emission tomography or single photon emission computed tomography. Additionally or alternatively, in some embodiments of the methods disclosed herein, the subject is diagnosed with, or is suspected of having a CD22-associated autoimmune disease or a CD22-associated cancer such as acute myeloid leukemia, myelodysplastic syndrome, chronic Myeloid Leukemia, Chronic Lymphocytic Leukemia, Non-Hodgkin Lymphoma, multiple myeloma, Plasmacytoma, Monoclonal gammopathy of undetermined significance, Waldenström's macroglobulinemia (lymphoplasmacytic lymphoma), Heavy chain disease, primary amyloidosis, Post-transplant lymphoproliferative disorder, Hodgkin lymphoma, MALT lymphoma, B cell Lymphoma, mantle cell lymphoma, (germinal center-like) diffuse large cell lymphoma, Burkitt's lymphoma, Bilineage leukemia, biphenotypic leukemia, Hairy cell leukemia, Precursor B acute lymphoblastic leukemia/lymphoma, Primary cutaneous follicle center lymphoma, follicular lymphoma, or Marginal Zone B-cell Non-Hodgkin's Lymphoma.

Additionally or alternatively, in some embodiments of the methods disclosed herein, the complex is administered intravenously, intramuscularly, intraarterially, intrathecally, intracapsularly, intraorbitally, intradermally, intraperitoneally, transtracheally, subcutaneously, intracerebroventricularly, orally, intratumorally, or intranasally. In certain embodiments, the complex is administered into the cerebral spinal fluid or blood of the subject.

In some embodiments of the methods disclosed herein, the radioactive levels emitted by the complex are detected between 2 to 120 hours after the complex is administered. In certain embodiments of the methods disclosed herein, the radioactive levels emitted by the complex are expressed as the percentage injected dose per gram tissue (% ID/g). The reference value may be calculated by measuring the radioactive levels present in non-tumor (normal) tissues, and computing the average radioactive levels present in non-tumor (normal) tissues±standard deviation. In some embodiments, the reference value is the standard uptake value (SUV). See Thie J A, *J Nucl Med.* 45(9):1431-4 (2004). In some embodiments, the ratio of radioactive levels between a tumor and normal tissue is about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

In another aspect, the present disclosure provides a method for increasing tumor sensitivity to radiation therapy in a subject diagnosed with a CD22-associated cancer comprising (a) administering an effective amount of an anti-DOTA bispecific antibody of the present technology to the subject, wherein the anti-DOTA bispecific antibody is configured to localize to a tumor expressing a CD22 antigen target; and (b) administering an effective amount of a radiolabeled-DOTA hapten to the subject, wherein the radiolabeled-DOTA hapten is configured to bind to the anti-DOTA bispecific antibody. In some embodiments, the subject is human.

The anti-DOTA bispecific antibody is administered under conditions and for a period of time (e.g., according to a dosing regimen) sufficient for it to saturate tumor cells. In some embodiments, unbound anti-DOTA bispecific antibody is removed from the blood stream after administration of the anti-DOTA bispecific antibody. In some embodiments, the radiolabeled-DOTA hapten is administered after a time period that may be sufficient to permit clearance of unbound anti-DOTA bispecific antibody.

The radiolabeled-DOTA hapten may be administered at any time between 1 minute to 4 or more days following administration of the anti-DOTA bispecific antibody. For example, in some embodiments, the radiolabeled-DOTA hapten is administered 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour, 1.25 hours, 1.5 hours, 1.75 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 48 hours, 72 hours, 96 hours, or any range therein, following administration of the anti-DOTA bispecific antibody. Alternatively, the radiolabeled-DOTA hapten may be administered at any time after 4 or more days following administration of the anti-DOTA bispecific antibody.

Additionally or alternatively, in some embodiments, the method further comprises administering an effective amount of a clearing agent to the subject prior to administration of the radiolabeled-DOTA hapten. A clearing agent can be any molecule (dextran or dendrimer or polymer) that can be conjugated with C825-hapten. In some embodiments, the clearing agent is no more than 2000 kD, 1500 kD, 1000 kD, 900 kD, 800 kD, 700 kD, 600 kD, 500 kD, 400 kD, 300 kD, 200 kD, 100 kD, 90 kD, 80 kD, 70 kD, 60 kD, 50 kD, 40 kD, 30 kD, 20 kD, 10 kD, or 5 kD. In some embodiments, the clearing agent is a 500 kD aminodextran-DOTA conjugate (e.g., 500 kD dextran-DOTA-Bn (Y), 500 kD dextran-DOTA-Bn (Lu), or 500 kD dextran-DOTA-Bn (In) etc.).

In some embodiments, the clearing agent and the radiolabeled-DOTA hapten are administered without further administration of the anti-DOTA bispecific antibody of the present technology. For example, in some embodiments, an anti-DOTA bispecific antibody of the present technology is administered according to a regimen that includes at least one cycle of: (i) administration of the anti-DOTA bispecific antibody of the present technology (optionally so that relevant tumor cells are saturated); (ii) administration of a radiolabeled-DOTA hapten and, optionally a clearing agent; (iii) optional additional administration of the radiolabeled-DOTA hapten and/or the clearing agent, without additional administration of the anti-DOTA bispecific antibody. In some embodiments, the method may comprise multiple such cycles (e.g., 1, 2, 3, 4, 5, 6, 7, 8, 9, 10 or more cycles).

Additionally or alternatively, in some embodiments of the method, the anti-DOTA bispecific antibody and/or the radiolabeled-DOTA hapten is administered intravenously, intramuscularly, intraarterially, intrathecally, intracapsularly, intraorbitally, intradermally, intraperitoneally, transtracheally, subcutaneously, intracerebroventricularly, intratumorally, orally or intranasally.

In one aspect, the present disclosure provides a method for increasing tumor sensitivity to radiation therapy in a subject diagnosed with a CD22-associated cancer comprising administering to the subject an effective amount of a complex comprising a radiolabeled-DOTA hapten and a bispecific antibody of the present technology that recognizes and binds to the radiolabeled-DOTA hapten and a CD22 antigen target, wherein the complex is configured to localize to a tumor expressing the CD22 antigen target recognized by the bispecific antibody of the complex. The complex may be administered intravenously, intramuscularly, intraarterially, intrathecally, intracapsularly, intraorbitally, intradermally, intraperitoneally, transtracheally, subcutaneously, intracerebroventricularly, orally, intratumorally, or intranasally. In some embodiments, the subject is human.

In another aspect, the present disclosure provides a method for treating cancer in a subject in need thereof comprising (a) administering an effective amount of an anti-DOTA bispecific antibody of the present technology to the subject, wherein the anti-DOTA bispecific antibody is configured to localize to a tumor expressing a CD22 antigen target; and (b) administering an effective amount of a radiolabeled-DOTA hapten to the subject, wherein the radiolabeled-DOTA hapten is configured to bind to the anti-DOTA bispecific antibody. The anti-DOTA bispecific antibody is administered under conditions and for a period of time (e.g., according to a dosing regimen) sufficient for it to saturate tumor cells. In some embodiments, unbound anti-DOTA bispecific antibody is removed from the blood stream after administration of the anti-DOTA bispecific antibody. In some embodiments, the radiolabeled-DOTA hapten is administered after a time period that may be sufficient to permit clearance of unbound anti-DOTA bispecific antibody. In some embodiments, the subject is human.

Accordingly, in some embodiments, the method further comprises administering an effective amount of a clearing agent to the subject prior to administration of the radiolabeled-DOTA hapten. The radiolabeled-DOTA hapten may be administered at any time between 1 minute to 4 or more days following administration of the anti-DOTA bispecific antibody. For example, in some embodiments, the radiolabeled-DOTA hapten is administered 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour, 1.25 hours, 1.5 hours, 1.75 hours, 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 48 hours, 72 hours, 96 hours, or any range therein, following administration of the anti-DOTA bispecific antibody. Alternatively, the radiolabeled-DOTA hapten may be administered at any time after 4 or more days following administration of the anti-DOTA bispecific antibody.

The clearing agent may be a 500 kD aminodextran-DOTA conjugate (e.g., 500 kD dextran-DOTA-Bn (Y), 500 kD dextran-DOTA-Bn (Lu), or 500 kD dextran-DOTA-Bn (In) etc.). In some embodiments, the clearing agent and the radiolabeled-DOTA hapten are administered without further administration of the anti-DOTA bispecific antibody. For example, in some embodiments, an anti-DOTA bispecific antibody is administered according to a regimen that includes at least one cycle of: (i) administration of the an anti-DOTA bispecific antibody of the present technology (optionally so that relevant tumor cells are saturated); (ii) administration of a radiolabeled-DOTA hapten and, optionally a clearing agent; (iii) optional additional administration of the radiolabeled-DOTA hapten and/or the clearing agent, without additional administration of the anti-DOTA bispecific antibody. In some embodiments, the method may comprise multiple such cycles (e.g., 1, 2, 3, 4, 5, 6, 7, 8, 9, 10 or more cycles).

Also provided herein are methods for treating cancer in a subject in need thereof comprising administering to the subject an effective amount of a complex comprising a radiolabeled-DOTA hapten and a bispecific antibody of the present technology that recognizes and binds to the radiolabeled-DOTA hapten and a CD22 antigen target, wherein the complex is configured to localize to a tumor expressing the CD22 antigen target recognized by the bispecific antibody of the complex. The therapeutic effectiveness of such a complex may be determined by computing the area under the curve (AUC) tumor: AUC normal tissue ratio. In some embodiments, the complex has a AUC tumor: AUC normal tissue ratio of about 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1 or 100:1.

Toxicity. Optimally, an effective amount (e.g., dose) of an anti-CD22 antibody described herein will provide therapeutic benefit without causing substantial toxicity to the subject. Toxicity of the anti-CD22 antibody described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the anti-CD22 antibody described herein lies within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: *The Pharmacological Basis of Therapeutics*, Ch. 1 (1975).

Formulations of Pharmaceutical Compositions. According to the methods of the present technology, the anti-CD22 antibody can be incorporated into pharmaceutical compositions suitable for administration. The pharmaceutical compositions generally comprise recombinant or substantially purified antibody and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions for administering the antibody compositions (See, e.g., *Remington's Pharmaceutical Sciences*, Mack Publishing Co., Easton, PA $18^{th}$ ed., 1990). The pharmaceutical compositions are generally formulated as sterile, substantially isotonic and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. "Pharmaceutically-acceptable salts and esters" means salts and esters that are pharmaceutically-acceptable and have the desired pharmacological properties. Such salts include salts that can be formed where acidic protons present in the composition are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically-acceptable esters include esters formed from carboxy, sulfonyloxy, and phosphonoxy groups present in the anti-CD22 antibody, e.g., $C_{1-6}$ alkyl esters. When there are two acidic groups present, a pharmaceutically-acceptable salt or ester can be a mono-acid-mono-salt or ester or a di-salt or ester; and similarly where there are more than two acidic groups present, some or all of such groups can be salified or esterified. An anti-CD22 antibody named in this technology can be present in unsalified or unesterified form, or in salified and/or esterified form, and the naming of such anti-CD22 antibody is intended to include both the original (unsalified and unesterified) compound and its pharmaceutically-acceptable salts and esters. Also, certain embodiments of the present technology can be present in more than one stereoisomeric form, and the naming of such anti-CD22 antibody is intended to include all single stereoisomers and all mixtures (whether racemic or otherwise) of such stereoisomers. A person of ordinary skill in the art, would have no difficulty determining the appropriate timing, sequence and dosages of administration for particular drugs and compositions of the present technology.

Examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the anti-CD22 antibody, use thereof in the compositions is contemplated. Supplementary active compounds can also be incorporated into the compositions.

A pharmaceutical composition of the present technology is formulated to be compatible with its intended route of administration. The anti-CD22 antibody compositions of the present technology can be administered by parenteral, topical, intravenous, oral, subcutaneous, intraarterial, intradermal, transdermal, rectal, intracranial, intrathecal, intraperitoneal, intranasal; or intramuscular routes, or as inhalants. The anti-CD22 antibody can optionally be administered in combination with other agents that are at least partly effective in treating various CD22-associated cancers, CD22-associated autoimmune diseases, or CD22-associated allergies.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be desirable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating an anti-CD22 antibody of the present technology in the required amount in an appropriate solvent with one or a combination of ingredients enumerated above, as required, followed by filtered sterilization. Generally, dispersions are prepared by incorporating the anti-CD22 antibody into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The antibodies of the present technology can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the anti-CD22 antibody can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the anti-CD22 antibody is delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the anti-CD22 antibody is formulated into ointments, salves, gels, or creams as generally known in the art.

The anti-CD22 antibody can also be prepared as pharmaceutical compositions in the form of suppositories (e.g., with conventional suppository bases such as cocoa butter and other glycerides) or retention enemas for rectal delivery.

In one embodiment, the anti-CD22 antibody is prepared with carriers that will protect the anti-CD22 antibody against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art, e.g., as described in U.S. Pat. No. 4,522,811.

C. Kits

The present technology provides kits for the detection and/or treatment of CD22-associated cancers, CD22-associated autoimmune diseases, or CD22-associated allergies, comprising at least one immunoglobulin-related composition of the present technology (e.g., any antibody or antigen binding fragment described herein), or a functional variant (e.g., substitutional variant) thereof. Optionally, the above described components of the kits of the present technology are packed in suitable containers and labeled for diagnosis and/or treatment of CD22-associated cancers, CD22-associated autoimmune diseases, or CD22-associated allergies. The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic or diagnostic products, that contain information about, for example, the indications, usage, dosage, manufacture, administration, contraindications and/or warnings concerning the use of such therapeutic or diagnostic products.

The kits are useful for detecting the presence of an immunoreactive CD22 protein in a biological sample, e.g., any body fluid including, but not limited to, e.g., serum, plasma, lymph, cystic fluid, urine, stool, cerebrospinal fluid, ascitic fluid or blood and including biopsy samples of body tissue. For example, the kit can comprise: one or more humanized, chimeric, or bispecific anti-CD22 antibodies of the present technology (or antigen binding fragments thereof) capable of binding a CD22 protein in a biological sample; means for determining the amount of the CD22 protein in the sample; and means for comparing the amount of the immunoreactive CD22 protein in the sample with a standard. One or more of the anti-CD22 antibodies may be labeled. The kit components, (e.g., reagents) can be packaged in a suitable container. The kit can further comprise instructions for using the kit to detect the immunoreactive CD22 protein.

For antibody-based kits, the kit can comprise, e.g., 1) a first antibody, e.g. a humanized, chimeric or bispecific CD22 antibody of the present technology (or an antigen binding fragment thereof), attached to a solid support, which binds to a CD22 protein; and, optionally; 2) a second, different antibody which binds to either the CD22 protein or to the first antibody, and is conjugated to a detectable label.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit, e.g., for detection of a CD22 protein in vitro or in vivo, or for treatment of CD22-associated cancers, CD22-associated autoimmune diseases, or CD22-associated allergies in a subject in need thereof. In certain embodiments, the use of the reagents can be according to the methods of the present technology.

EXAMPLES

The present technology is further illustrated by the following Examples, which should not be construed as limiting in any way. The following Examples demonstrate the preparation characterization, and use of the CD22 immunoglobulin-related compositions of the present technology.

Example 1: Sequences and Construction of CD22-CD3 Bispecific Antibodies

Figure 1:
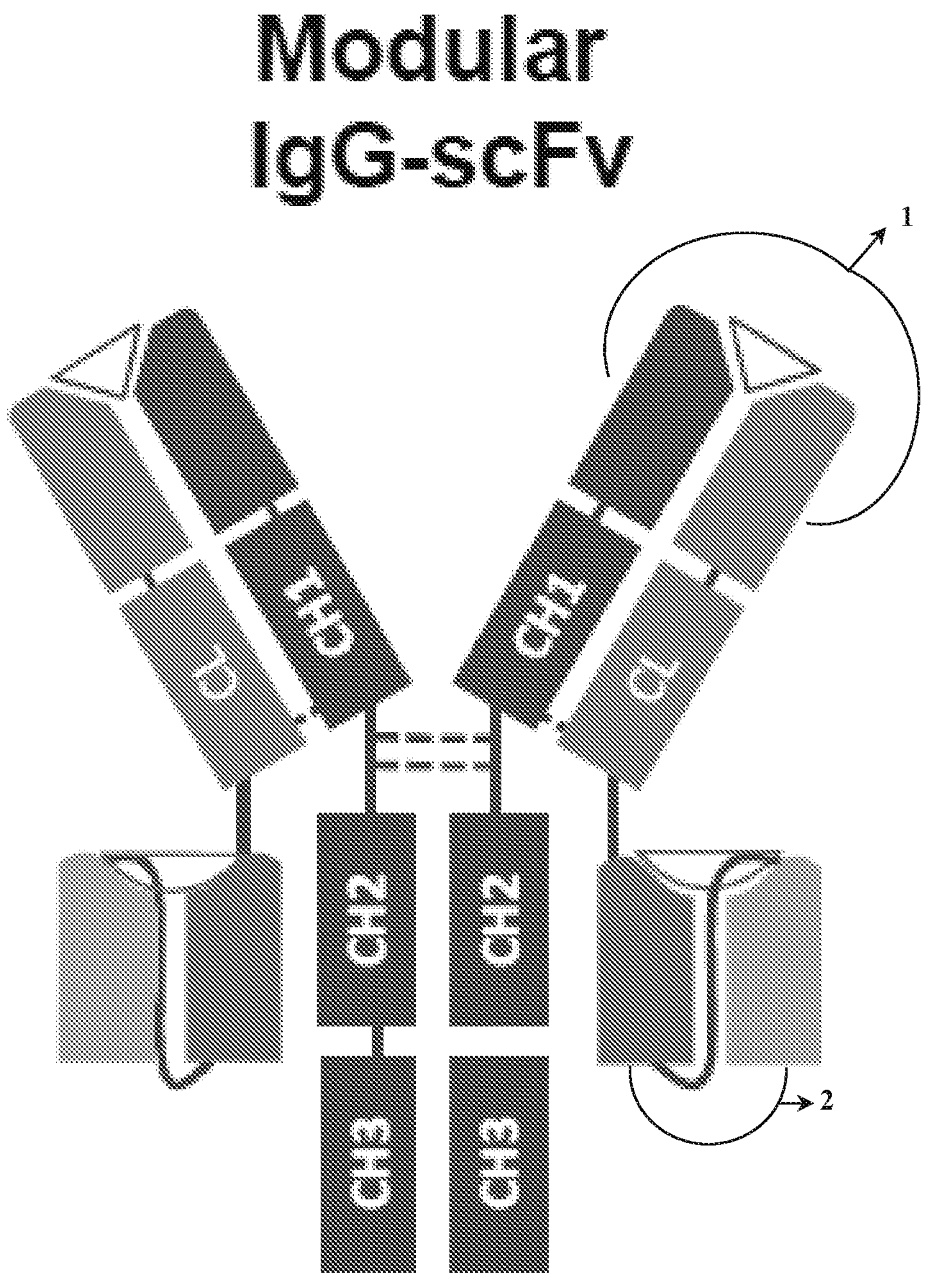
FIG. 1 shows a schematic diagram showing the structure of modular IgG-scFv. CH1 through CH3 are constant domains of the heavy chain of a first antibody. CL is the constant domain of the light chain of the first antibody. Heavy chain and light chain variable regions of the first antibody, are denoted by numerical 1. The C-terminus of the CL is fused to a single chain Fv fragment (scFv) derived from a second antibody. The single chain Fv fragment (scFv) is denoted by numerical 2.

CD22-BsAbs were designed using the IgG-scFv format shown in FIG. 1. The IgG-scFv modular platform was used to build CD22-CD3 bispecific antibody (BsAb). An anti- CD3 humanized OKT3 (huOKT3) single chain Fv fragment (scFv) was genetically fused to the carboxyl end of the LL2 IgG1 light chain. Humanized versions of the murine LL2 antibody were also created. These sequences were modular in that certain sequences may be easily substituted with other equivalent sequences. Sequence elements were joined using various linkers, spacers, and the like. The sequences disclosed herein show some examples of modular sequence elements, linkers, spacers, and the like. While selecting the antibody, the scFv fragment and exact mechanics of joining them together, the following factors were given consideration, among various other factors:

(1) an optimal size (100-200 kD) to maximize tumor uptake. See e.g., Wittrup K D, Thurber G M, Schmidt M M, et al., *Methods Enzymol* 503:255-68 (2012);

(2) bivalency towards the tumor target to maintain avidity;

(3) a scaffold that is naturally assembled like any IgG (heavy chain and light chain) in CHO cells, purifiable by standard protein A affinity chromatography;

(4) structural arrangement to render the anti-CD3 component functionally monovalent, hence reducing non-specific activation of T cells; and (5) a platform with proven tumor targeting efficiency in animal models.

The CDRs of the heavy and light chains of LL2 were grafted onto human IgG1 frameworks based on their homology with human frameworks IGHV1-3*01 and IGHJ6*01 for $V_H$, and IGKV4-1*01-IGKJ4*01 for $V_L$, respectively. From 12 heavy chain and 2 light chain designs, 24 four versions of huLL2 were gene synthesized and expressed in DG44 cells. The amino acid sequences of these humanized human $V_H$ and $V_L$ domains are shown in FIGS. 6-7.

CD22-CD3 bispecific antibody expression in CHO-S cells. CD22-BsAb (hLL2) were designed using the IgG-scFv format (FIG. 1). Briefly, two peptides were designed: The first peptide, encoding the light chain of BsAb, comprised, sequentially from N-terminus to C-terminus: (1) signal peptide; (2) $V_L$ domain of murine anti-CD22 antibody (LL2) (or a humanized version thereof); (3) human $C_L$ domain; (4) $(G4S)_3$ linker (SEQ ID NO: 104) (5) $V_H$ domain of a humanized anti-CD3 antibody (OKT3); (6) $(G4S)_6$ linker (SEQ ID NO: 101); and p(7) $V_L$ domain of OKT3. The second peptide, encoding the heavy chain of BsAb, comprised, sequentially from N-terminus to C-terminus: (1) signal peptide; (2) $V_H$ domain of murine LL2 (or a humanized version thereof); and (3) human $CH_1$-3 domains. See FIGS. 8-19.

Following design of the two peptides, genes encoding those peptides were synthesized and purified. This resulted in chimeric version of anti-CD22-Cd3-BsAb, and its humanized versions. Two such clones were named BC270, and BC251.

Additional anti-CD22 BsAbs for pretargeted radioimmunotherapy. Most currently available BsAbs recruit T cells to inhibit cancer cells. However, certain classes of BsAbs have specificity to tumor cells and incorporate an additional specificity for a radioactive metal that can be used for theranostic purposes. These antibodies are not limited by the low therapeutic index of directly radiolabeled antibodies. Two categories of these novel BsAbs are: (a) IgG(L)-scFv platform for 3-step pretargeted radioimmunotherapy (PRIT) (PCT/US2018/040911); and (b) the multimeric antibody platform for two-step targeting (SADA) (PCT/US2018/031235).

Both platforms are versatile options even for endocytosing antigens such as HER2. See, e.g., Cheal S M, Xu H, Guo H F, et al., *Eur J Nucl Med Mol Imaging* 43:925-37 (2016) and can be used with different radionuclides such as the alpha emitter lanthanides (PCT/2018/0409011). Exemplary amino acid sequences of CD22-specific DOTA-engaging bispecific antibodies or antigen binding fragments are shown in FIGS. 20-67.

Example 2: The Humanness of the Bispecific CD22-CD3 IgG-scFv Antibodies of the Present Technology The CDRs and the surrounding framework regions were analyzed to calculate a humanness score of the variable region sequences of the bispecific antibodies of the present technology. As shown in Table 2 the humanness scores of BC251 are higher compared to anti-CD22 antibodies Inotuzumab, epratuzumab, and moxetumomab.

TABLE 2

| | $V_H$ humanness % | $V_L$ humanness % |
|---|---|---|
| Inotuzumab | 82.7 | 73.7 |
| epratuzumab | 76.5 | 79.4 |
| moxetumomab | 79.6 | 74.7 |
| BC251 | 84.7 | 89 |
| BC270 | 84.7 | 89 |
| VL1-VH11 | 84.7 | 89 |
| VL1-VH12 | 84.7 | 89 |

Example 3. Biophysical Properties of the Humanized LL2 Antibodies of the Present Technology Some of the antibodies described in Example 1 were expressed, purified and characterized. As shown in Table 3, the yield of the antibodies ranged from 0.1 to 23.9 mg.

TABLE 3

| | | Stability at 40° C. (HPLC) | | | | | | | |
|---|---|---|---|---|---|---|---|---|---|
| Protein Name | Yield (mg) | d0 | HPLC after 10-times Freeze thaw | d5 | d12 | d20 | d33 | Stability | MFI (FACS NALM6) |
| chimeric | 5.6 | 98.9 | 95.9 | 95.8 | 93.2 | 89.9 | 69.6 | 89.9 | 33.4 |
| L1 + H7 | 0.2 | 100.0 | 97.4 | 97.9 | 96.0 | 96.0 | 90.5 | 96.0 | 21.8 |
| L1 + H1 | 17.4 | 99.2 | 96.5 | 95.4 | 94.0 | 92.4 | 89.4 | 92.4 | 26.4 |
| L1 + H2 | 0.5 | 99.1 | 96.0 | 95.5 | 93.9 | 92.3 | 87.2 | 92.3 | 32.8 |
| L1 + H3 | 19.5 | 99.3 | 96.4 | 96.3 | 95.0 | 91.8 | 68.6 | 91.8 | 31.9 |
| L1 + H4 | 23.9 | 99.2 | 95.6 | 95.9 | 94.8 | 93.3 | 89.6 | 93.3 | 33.6 |
| L1 + H5 | 2.1 | 99.0 | 96.0 | 96.5 | 95.7 | 94.8 | 91.4 | 94.8 | 35.2 |

TABLE 3-continued

| | | | | Stability at 40° C. (HPLC) | | | | | |
|---|---|---|---|---|---|---|---|---|---|
| Protein Name | Yield (mg) | d0 | HPLC after 10-times Freeze thaw | d5 | d12 | d20 | d33 | Stability | MFI (FACS NALM6) |
| L1 + H6 | 6.8 | 99.1 | 95.7 | 96.3 | 95.2 | 94.5 | 89.9 | 94.5 | 33.5 |
| L1 + H8 | 0.1 | 100.0 | 97.1 | 97.0 | 97.3 | 95.6 | 30.8 | 95.6 | 23.3 |
| L1 + H9 | 19.5 | 99.3 | 96.6 | 95.6 | 95.6 | 94.5 | 89.7 | 94.5 | 34.5 |
| L1 + H10 | 21.8 | 99.5 | 96.0 | 95.8 | 96.0 | 94.9 | 90.2 | 94.9 | 32.7 |
| L1 + H11 | 20.6 | 99.3 | 95.3 | 95.9 | 95.6 | 93.9 | 90.3 | 93.9 | 33.6 |
| L1 + H12 | 19.6 | 99.2 | 96.0 | 96.0 | 95.2 | 93.3 | 89.9 | 93.3 | 39.2 |
| L2 + H1 | 16.3 | 99.2 | 96.5 | 96.0 | 94.9 | 93.7 | 89.1 | 93.7 | 40 |
| L2 + H2 | 2.9 | 99.3 | 96.5 | 96.5 | 85.8 | 94.1 | 87.4 | 94.1 | 28.1 |
| L2 + H3 | 15.9 | 99.6 | 96.6 | 93.4 | 86.0 | 80.0 | 69.5 | 80.0 | 36.8 |
| L2 + H4 | 16.9 | 99.5 | 96.6 | 93.4 | 84.4 | 78.2 | 67.5 | 78.2 | 35.9 |
| L2 + H5 | 11.2 | 99.6 | 96.5 | 93.5 | 85.2 | 79.0 | 65.0 | 79.0 | 40.4 |
| L2 + H6 | 8.7 | 100.0 | 96.7 | 94.6 | 86.9 | 81.4 | 7.0 | 81.4 | 36.1 |
| L2 + H7 | 0.1 | 100.0 | 95.9 | 96.0 | 95.1 | 94.8 | 89.5 | 94.8 | 27.3 |
| L2 + H8 | 0.2 | 100.0 | 96.9 | 97.2 | 95.2 | 94.8 | 65.1 | 94.8 | 26.7 |
| L2 + H9 | 17.2 | 99.6 | 96.3 | 94.0 | 86.3 | 80.5 | 24.7 | 80.5 | 34.3 |
| L2 + H10 | 16.4 | 99.6 | 97.2 | 93.4 | 84.7 | 78.0 | 68.3 | 78.0 | 37 |
| L2 + H11 | 14.9 | 99.5 | 96.1 | 91.4 | 80.6 | 75.0 | 64.4 | 75.0 | 36.3 |
| L2 + H12 | 9.95 | 99.6 | 96.8 | 91.7 | 83.7 | 77.9 | 70.5 | 77.9 | 31.7 |

To evaluate the long-term stability of the antibodies at accelerated storage conditions, antibody solutions were stored in a temperature-controlled incubator at 40° C. Samples were withdrawn at various times and analyzed for integrity by HPLC. As shown in Table 3, most of the antibodies were 65 to 9000 intact after thirty-three days at 40° C. These antibodies showed corresponding levels of binding activity at those times (data not shown). Further, the antibodies were subjected to stability studies and HPLC after repeated freezing and thawing. Both these assays showed that the anti-CD22 antibodies disclosed herein had excellent stability. Binding of the various antibodies of the present technology to NALM6 CD22(+) leukemic cells was assayed using flow cytometry. Table 3 shows the mean fluorescence intensity (MFI) of the anti-CD22 antibodies of the present technology. Affinity values of the anti-CD22 antibodies were measured via Biacore (SPR) at 37° C. The results of these assays are shown in Table 4:

TABLE 4

| Binding properties of the humanized LL2 antibodies | | | |
|---|---|---|---|
| antibody | ka (1/Ms) | kd (1/s) | KD (M) |
| chimeric | 1.69E+05 | 2.31E−07 | 1.37E−12 |
| H2L1 | 2.77E+06 | 4.78E−03 | 1.72E−09 |
| H3L1 | 8.98E+04 | 3.09E−06 | 3.44E−11 |
| H4L1 | 1.54E+05 | 2.94E−10 | 1.91E−15 |
| H5L1 | 1.02E+05 | 4.19E−06 | 4.10E−11 |
| H6L1 | 1.71E+05 | 2.91E−08 | 1.70E−13 |
| H9L1 | 1.33E+05 | 3.30E−06 | 2.48E−11 |
| H10L1 | 1.76E+05 | 7.67E−09 | 4.35E−14 |
| H11L1 | 1.64E+05 | 1.71E−09 | 1.04E−14 |
| H12L1 | 2.87E+05 | 5.88E−07 | 2.05E−12 |
| H1L2 | 5.43E+06 | 2.19E−03 | 4.03E−10 |

As shown in Table 4, the anti-CD22 antibodies of the present technology have femtomolar to picomolar affinities for CD22, whereas the affinity of bespona (innotuzumab) for CD22 is in the subnanomolar range (George et al., *Immunotherapy* 135-43 (2016)).

These results demonstrate that the anti-CD22 antibodies or antigen binding fragments of the present technology are useful in methods for detecting CD22 polypeptides in a biological sample.

Figure 2:
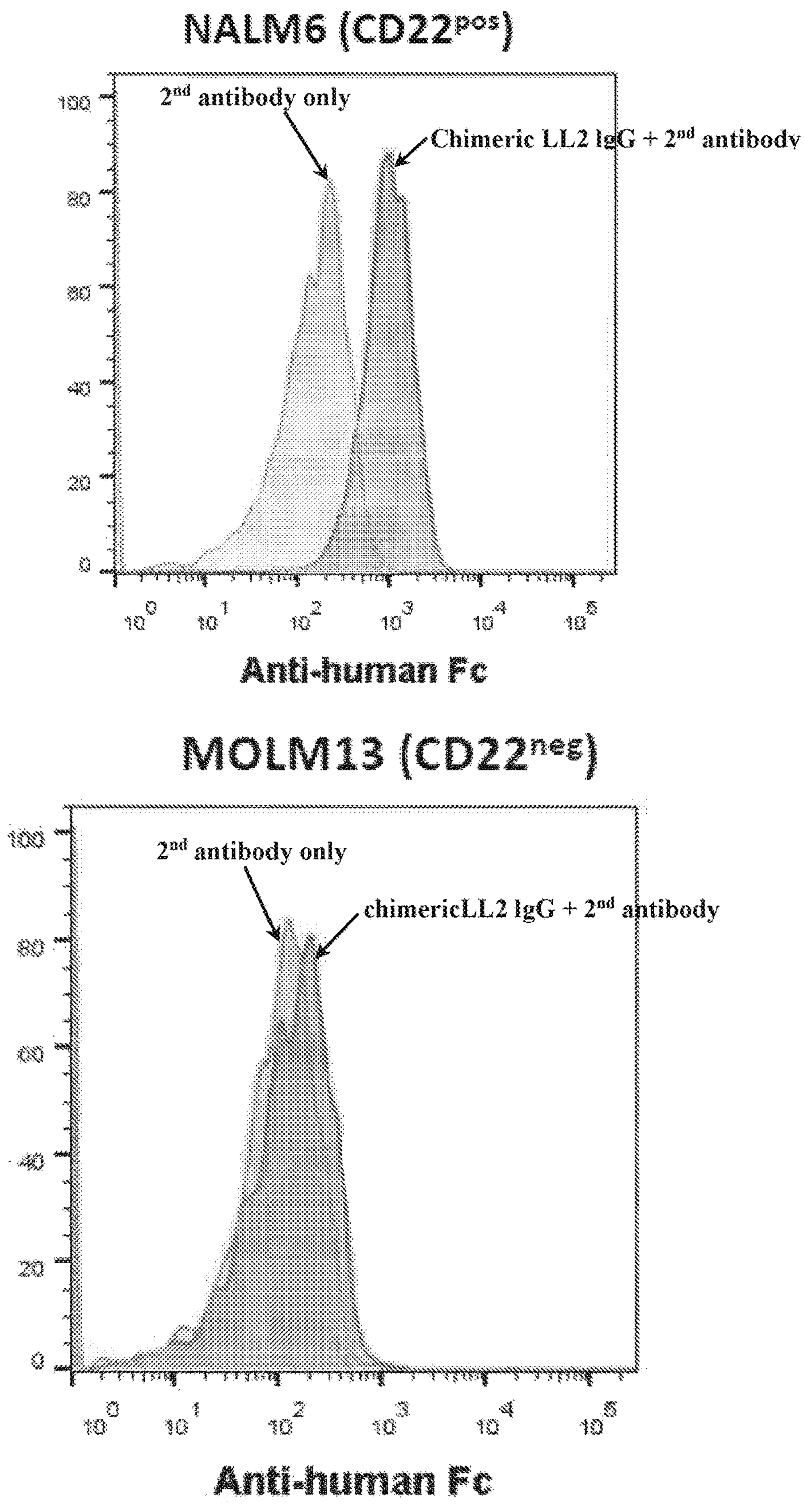
FIG. 2 shows FACS analysis of CD22(+) ALL cell line NALM6 and CD22(−) MOLM13 AML cells stained with (1) a bispecific IgG-scFv antibody comprising CD22-specific LL2 IgG, and a single chain Fv fragment (scFv) version of anti-CD3 humanized OKT3 (huOKT3), or (2) anti-CD3 humanized OKT3 (huOKT3).

Example 4: Antigen Binding Properties of Bispecific CD22-CD3 Antibodies of the Present Technology The binding of bispecific CD22-CD3 IgG-scFv antibodies to NALM6 CD22(+) leukemic cells was assayed using FACS. CD22(−) MOLM13 AML cells were used as a negative control for CD22 expression, and anti-CD3 humanized OKT3 (huOKT3) was used as a negative antibody control. As shown in FIG. 2, unlike the huOKT3 antibody, the chimeric LL2 IgG+huOKT3 scFv specifically stained the CD22(+) NALM6 leukemic cells. In contrast, neither the chimeric LL2 IgG+huOKT3 scFv nor the huOKT3 antibody stained the CD22(−) MOLM13 AML cells.

Figure 3:
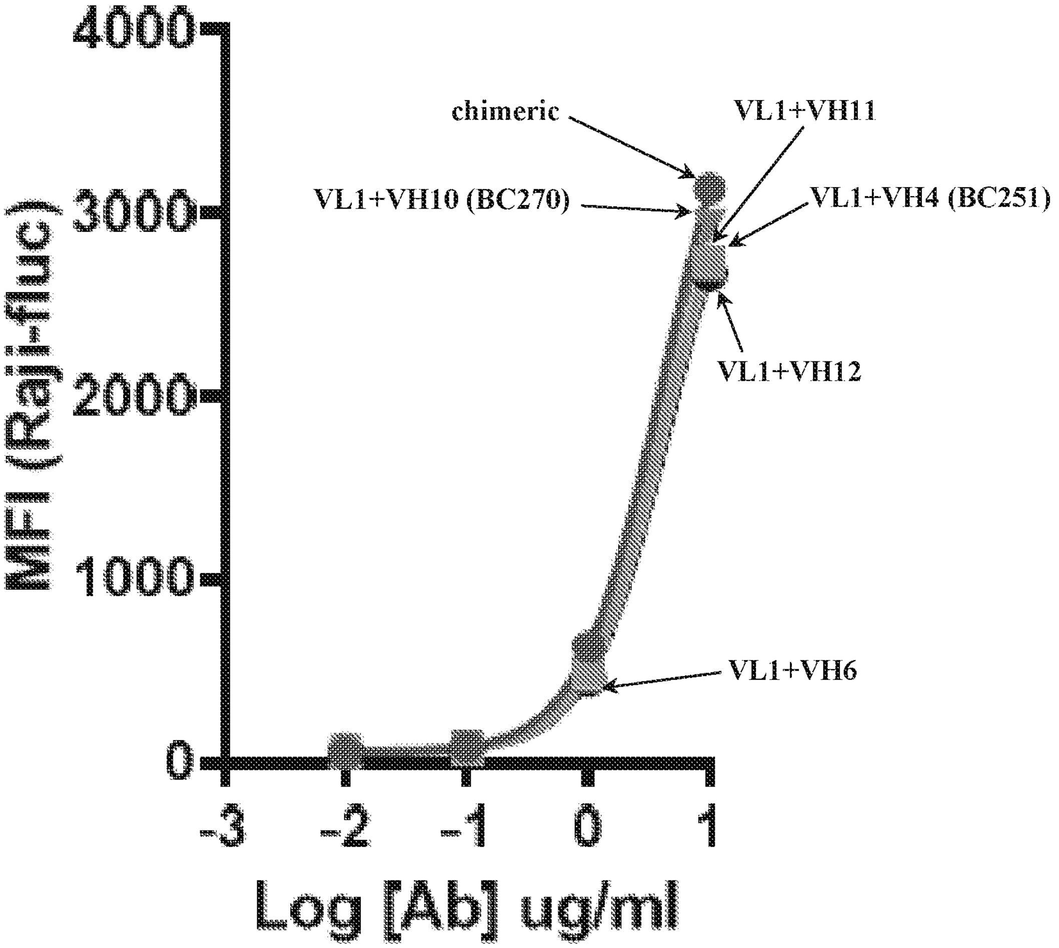
FIG. 3 shows binding of humanized CD22-CD3 BsAbs of the present technology to CD22(+) Raji cells. Binding data was derived by flow cytometry assays using indicated concentrations of the humanized CD22-CD3 BsAb.

The binding of bispecific CD22-CD3 IgG-scFv antibodies of the present technology to Raji cells (which express elevated levels of CD22) was assayed via flow cytometry. Various concentrations of the BsAbs were tested and the mean fluorescence intensity (MFI) was calculated. The bispecific CD22-CD3 IgG-scFv antibodies of the present technology showed a dose-dependent increase in binding to CD22(+) Raji cells. See FIG. 3.

These results demonstrate that the anti-CD22 antibodies or antigen binding fragments of the present technology are useful in methods for detecting CD22 polypeptides in a biological sample.

Figure 4:
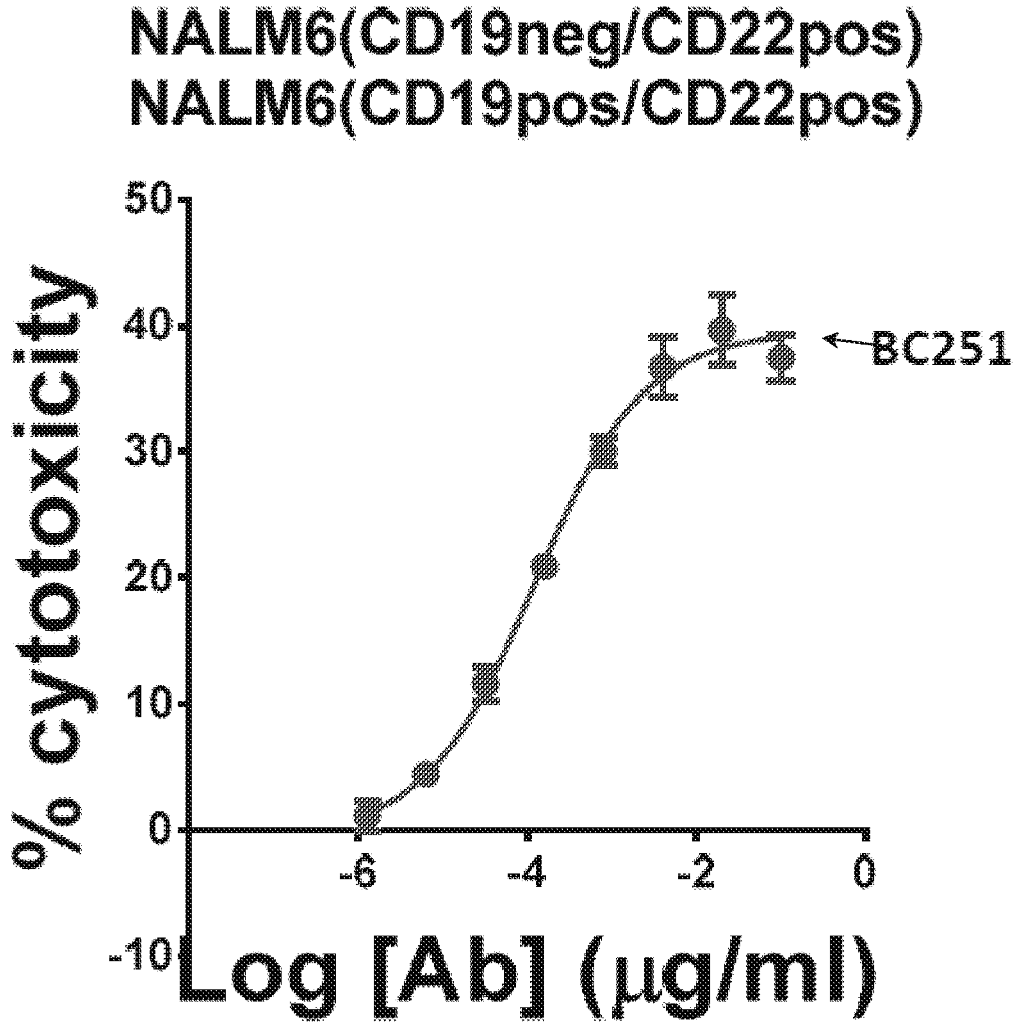
FIG. 4 shows that the cytotoxicity of CD22-CD3 BsAb clone BC251 increases in a dose-dependent manner. The potency of the BC251 antibody was tested in cytotoxicity assays where activated T cells were exposed to CD22(+) target cells (a mixture of CD19(−) CD22(+) and CD19(+) CD22(+) NALM6 cells) in the presence of the BC251 antibody. BC251 potently mediated lyses of CD22(+) target cells.

Example 5: In Vitro Therapeutic Effects of the CD22-CD3 BsAbs of the Present Technology To evaluate the potency of the bispecific CD22-CD3 IgG-scFv antibody BC251, activated T cells were incubated with target cells in the presence of different doses of the bispecific antibody. The target cells used in this assay were a mixture of CD19(−) CD22(+) and CD19(+) CD22(+) NALM6 cells. The cytotoxicity induced by the antibody was measured using standard assays. Briefly, target tumor cells were labeled with sodium $^{51}$Cr chromate (Amersham, Arlington Heights, IL) at 100 μCi/$10^6$ cells at 37° C. for 1 hour. After the cells were washed twice, 5000 target cells per well were mixed with 50 000 effector cells at an effector to target (E:T) ratio of 10:1 in the presence of serial dilutions of the BsAbs and incubated in 96-well polystyrene roundbottom plates (BD Biosciences, San Jose CA) in a final volume of 250 μL per well at 37° C. for 4 hours. After centrifugation at 400×g for 10 minutes, the released $^{51}Cr$ in the supernatant was counted in a 7-counter (Packard Bioscience Company, Downers Grove, IL). Percentage of specific lysis was calculated using the formula 100% (experimental cpm−background cpm)/(total cpm−background cpm), where cpm represented counts per minute of $^{51}Cr$ released. Total release was assessed by lysis with 10% sodium dodecyl sulfate (Sigma, St. Louis, MO), and background release was measured in the absence of effector cells. As shown in FIG. 4, increasing doses of BC251 mediated lysis of CD22(+) target cells.

These results demonstrate that the anti-CD22 antibodies or antigen binding fragments of the present technology can detect tumors and inhibit tumor growth.

Example 6: In Vivo Therapeutic Effects of the CD22-CD3 BsAbs of the Present Technology To evaluate the therapeutic effects of the CD22-CD3 BsAbs BC251 and BC270 on leukemia in vivo, female NSG mice were injected intravenously with $0.5\times10^{-6}$ NALM6 cells that express low amount of CD22 (about 7500 molecule/cell). Three days later, treatment was initiated, which included weekly injections of 10 million ATC with different concentrations of the BsAbs twice/week. Interleukin-2 1000 IU was also injected 2×/week subcutaneously. Tumor growth was monitored with the IVIS BLI imager. FIGS. 5A-5B demonstrate that animals treated with BsAb BC251 showed a significant reduction in tumor burden compared to untreated controls.

NSG mice were injected with CD22(+) NALM6 cells on day 0 to establish a human xenograft. After three days, once the tumor was established, treatment was initiated, which included weekly injections of 10 million activated T cells (ATC) as well as different doses of BC251 or BC270 twice weekly. Tumor burden was calculated based on total flux value and plotted as a function of time. As shown in FIGS. 5C-5D, BsAbs BC251 and BC270 treatment resulted in reduced leukemia compared to untreated controls. Surprisingly, while injection of 10 μg BC251 or BC270 reduced tumor growth, a lower dose of the BsAbs (1 μg) had more potent anti-leukemia effect.

These results demonstrate that the anti-CD22 antibodies or antigen binding fragments of the present technology can detect tumors and inhibit the progression of tumor growth and/or metastasis.

Example 7: Use of Anti-CD22 BsAbs of the Present Technology in PRIT

IgG-based CD22-C825 BsAbs. CD22(+) leukemic cells will be injected subcutaneously, intraperitoneally, intravenously, or via other routes into animals. After tumor establishment (depending on the type of tumor and the route of injection), treatment will be initiated. Treatment is composed of one or more cycles. Each cycle comprises administration of the test BsAb (250 μg intravenously), followed by injection of a clearing agent (DOTA dextran or DOTA dendrimer; dose is 5-15% of the BsAb dose, see Cheal S M et al., *Mol Cancer Ther* 13:1803-12, 2014) after 24 to 48 hours. After 4 hours, DOTA-$^{177}Lu$ (up to 1.5 mCi) or DOTA-$^{225}Ac$ (1 μCi) will be injected intravenously. Generally, DOTA-$^{225}Ac$ is more potent than DOTA-$^{177}Lu$ and may require fewer cycles for tumor eradication.

Tetramerized BsAbs. CD22(+) leukemic cells will be injected subcutaneously, intraperitoneally, intravenously, or via other routes into animals and after tumor establishment (depending on the type of tumor and the route of injection), treatment will be initiated. Treatment is composed of one or more cycles. Each cycle consists of administration of the BsAb (250 μg intravenously) followed by intravenous injection of DOTA-$^{177}Lu$ (up to 1.5 mCi) or DOTA-$^{225}Ac$ (1 μCi) after 24-48 hours. Generally, DOTA-$^{225}Ac$ is more potent than DOTA-$^{177}Lu$ and may require fewer cycles for tumor eradication. These results will demonstrate that the anti-CD22 antibodies or antigen binding fragments of the present technology will be effective in PRIT.

These results will demonstrate that the anti-CD22 antibodies or antigen binding fragments of the present technology can detect tumors and inhibit the progression of tumor growth and/or metastasis. Accordingly, the immunoglobulin-related compositions disclosed herein are useful in methods for detecting and treating a CD22-associated cancer in a subject in need thereof.

Example 8: Use of Anti-CD22 Antibodies of the Present Technology to Treat Autoimmune Disease Transgenic mice that express human CD3 on mouse T cells will be crossed with transgenic mice that express human CD22 on mouse B cells. The resulting offspring will be crossed to New Zealand black (NZB) mice that spontaneously develop anemia due to autoantibodies against red blood cells (RBCs). The offspring with induced anemia will express human CD3 on mouse T cells and human CD22 on mouse B cells. Animals showing anemia will be treated with anti-CD22 BsAb or a control BsAb. Development of anemia will be detected in those mice as a readout of the experiment. It is anticipated that animals receiving the anti-CD22 BsAbs will show reduced anemia compared to those receiving a placebo.

Accordingly, the immunoglobulin-related compositions disclosed herein are useful in methods for treating a CD22-associated autoimmune disease in a subject in need thereof.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. An antibody or antigen binding fragment thereof comprising a heavy chain immunoglobulin variable domain ($V_H$) and a light chain immunoglobulin variable domain ($V_L$), wherein:

(a) the $V_H$ comprises an amino acid sequence selected from the group consisting of: SEQ ID NOs: 5, 6, 7, 8, 9, 10, 11, 12, 13, 14, 15, and 16; and (b) the $V_L$ comprises an amino acid sequence selected from the group consisting of: SEQ ID NO: 21, and SEQ ID NO: 22, wherein the antibody or antigen binding fragment binds to a CD22 polypeptide comprising an Ig-like C2-type 1 domain and/or an Ig-like C2-type 2 domain, or the antibody is a monoclonal antibody, a chimeric antibody, a humanized antibody, or a bispecific antibody, or the antigen binding fragment is selected from the group consisting of Fab, F(ab')$_2$, Fab', scF$_v$, and F$_v$, or wherein the bispecific antibody binds to T cells, B-cells, myeloid cells, plasma cells, or mast-cells, or wherein the bispecific antibody or antigen binding fragment binds to CD3, CD4, CD8, CD20, CD19, CD21, CD23, CD46, CD80, HLA-DR, CD74, CD22, CD14, CD15, CD16, CD123, TCR gamma/delta, NKp46, KIR, or a small molecule DOTA hapten, or wherein the bispecific antibody or antigen binding fragment comprises an amino acid sequence selected from any one of SEQ ID NOs: 59-82.

2. The antibody or antigen binding fragment of claim 1, further comprising a Fc domain of an isotype selected from the group consisting of IgG1, IgG2, IgG3, IgG4, IgA1, IgA2, IgM, IgD, and IgE, optionally wherein IgG1 comprises one or more amino acid substitutions selected from the group consisting of N297A and K322A; or IgG4 comprises a S228P mutation, or the antibody lacks α-1,6-fucose modifications.

3. The antibody, or antigen binding fragment, of claim 1, comprising a heavy chain (HC) amino acid sequence comprising SEQ ID NO: 29, SEQ ID NO: 33, SEQ ID NO: 40, SEQ ID NO: 42, SEQ ID NO: 44, or SEQ ID NO: 46, and a light chain (LC) amino acid sequence comprising SEQ ID NO: 27, SEQ ID NO: 31, SEQ ID NO: 39, SEQ ID NO: 41, SEQ ID NO: 43, or SEQ ID NO: 45.

4. The antibody, or antigen binding fragment, of claim 1, comprising a HC amino acid sequence and a LC amino acid sequence selected from the group consisting of:

SEQ ID NO: 29 and SEQ ID NO: 27 (BC270-hLL2 x CD3 BsAb);

SEQ ID NO: 33 and SEQ ID NO: 31 (BC251-hLL2 x CD3 BsAb);

SEQ ID NO: 40 and SEQ ID NO: 39 (VL1VH4 x mC825);

SEQ ID NO: 42 and SEQ ID NO: 41 (VL1VH4 x hC825);

SEQ ID NO: 44 and SEQ ID NO: 43 (VL1VH10 x mC825); and

SEQ ID NO: 46 and SEQ ID NO: 45 (VL1VH10 x hC825), respectively.

5. The bispecific antibody or antigen binding fragment of claim 4 or a bispecific antibody or antigen binding fragment comprising an amino acid sequence selected from any one of SEQ ID NOs: 59-82, wherein the bispecific antibody binds to a radiolabeled DOTA hapten and a CD22 antigen.

6. A recombinant nucleic acid sequence encoding the antibody or antigen binding fragment of claim 3.

7. A host cell or vector comprising the recombinant nucleic acid sequence of claim 6.

8. A composition comprising the antibody or antigen binding fragment of claim 1 and a pharmaceutically-acceptable carrier, wherein the antibody or antigen binding fragment is optionally conjugated to an agent selected from the group consisting of isotopes, dyes, chromagens, contrast agents, drugs, toxins, cytokines, enzymes, enzyme inhibitors, hormones, hormone antagonists, growth factors, radionuclides, metals, liposomes, nanoparticles, RNA, DNA or any combination thereof.

9. A kit comprising the antibody or antigen binding fragment of claim 1 and instructions for use, optionally wherein the antibody or antigen binding fragment is coupled to at least one detectable label selected from the group consisting of a radioactive label, a fluorescent label, a chromogenic label and a detectably labeled secondary antibody that specifically binds to the antibody or antigen binding fragment.

10. A method for treating a CD22-associated cancer, a CD22-associated autoimmune disease, or a CD22-associated allergy in a subject in need thereof, comprising administering to the subject an effective amount of the antibody, or antigen binding fragment, of claim 4 or a bispecific antibody, or antigen binding fragment thereof, comprising an amino acid sequence selected from any one of SEQ ID NOs: 59-82.

11. The method of claim 10 wherein, the CD22-associated cancer is acute myeloid leukemia, myelodysplastic syndrome, chronic myeloid leukemia, chronic lymphocytic leukemia, Non-Hodgkin Lymphoma, multiple myeloma, Plasmacytoma, Monoclonal gammopathy of undetermined significance, Waldenstrom's macroglobulinemia (lymphoplasmacytic lymphoma), Heavy chain disease, primary amyloidosis, Post-transplant lymphoproliferative disorder, Hodgkin lymphoma, MALT lymphoma, B cell Lymphoma, mantle cell lymphoma, diffuse large cell lymphoma, Burkitt's lymphoma, Bilineage leukemia, biphenotypic leukemia, Hairy cell leukemia, Precursor B acute lymphoblastic leukemia/lymphoma, Primary cutaneous follicle center lymphoma, follicular lymphoma, or Marginal Zone B-cell Non-Hodgkin's Lymphoma, or the CD22-associated autoimmune disease is multiple sclerosis (MS), rheumatoid arthritis (RA), systemic lupus erythematosus, paraneoplastic syndromes, Pemphigus Vulgaris, type 2 diabetes, or graft-versus-host disease.

12. The method of claim 10, wherein the antibody or antigen binding fragment is administered to the subject separately, sequentially or simultaneously with an additional therapeutic agent.

13. A method for detecting a tumor in a subject in vivo comprising (a) administering to the subject an effective amount of the antibody or antigen binding fragment of claim 3, wherein the antibody is configured to localize to a tumor expressing CD22 and is labeled with a radioisotope; and (b) detecting the presence of a tumor in the subject by detecting radioactive levels emitted by the antibody or antigen binding fragment that are higher than a reference value, optionally wherein the subject is diagnosed with or is suspected of having a CD22-associated cancer, or the radioactive levels emitted by the antibody or antigen binding fragment are detected using positron emission tomography or single photon emission computed tomography.

14. The method of claim 13, further comprising administering to the subject an effective amount of an immunoconjugate comprising a radionuclide conjugated to an antibody or antigen binding fragment thereof that comprises a $V_H$ amino acid sequence selected from the group consisting of: SEQ ID NOs: 5, 6, 7, 8, 9, 10, 11, 12, 13, 14, 15, and 16; and a $V_L$ amino acid sequence selected from the group consisting of: SEQ ID NO: 21, and SEQ ID NO: 22.

15. The method of claim 14, wherein the radionuclide is an alpha particle-emitting isotope, a beta particle-emitting isotope, an Auger-emitter, or any combination thereof, optionally wherein the beta particle-emitting isotope is selected from the group consisting of $^{86}$Y, $^{90}$Y, $^{89}$Sr, $^{165}$Dy, $^{186}$Re, $^{188}$Re, $^{177}$Lu, and $^{67}$Cu.

16. A method for selecting a subject for pretargeted radioimmunotherapy comprising (a) administering to the subject an effective amount of a complex comprising a radiolabeled DOTA hapten and the bispecific antibody or antigen binding fragment of claim 5, wherein the complex is configured to localize to CD22 expressing tumor;

(b) detecting radioactive levels emitted by the complex; and (c) selecting the subject for pretargeted radioimmunotherapy when the radioactive levels emitted by the complex are higher than a reference value.

17. A method for treating cancer or increasing tumor sensitivity to radiation therapy in a subject diagnosed with a CD22-associated cancer comprising administering to the subject an effective amount of a complex comprising a radiolabeled DOTA hapten and the bispecific antibody or antigen binding fragment of claim 5, wherein the complex is configured to localize to a CD22 expressing tumor.

18. A method for treating cancer or increasing tumor sensitivity to radiation therapy in a subject diagnosed with a CD22-associated cancer comprising (a) administering an effective amount of the bispecific antibody or antigen binding fragment of claim 5, wherein the bispecific antibody or antigen binding fragment is configured to localize to a CD22 expressing tumor; and (b) administering an effective amount of a radiolabeled-DOTA hapten to the subject, wherein the radiolabeled-DOTA hapten is configured to bind to the bispecific antibody or antigen binding fragment.

19. The method of claim 18, further comprising administering an effective amount of a clearing agent to the subject prior to administration of the radiolabeled-DOTA hapten.

* * * * *